US012799492B2

(12) United States Patent
Abedi et al.

(10) Patent No.: US 12,799,492 B2
(45) Date of Patent: Nov. 17, 2026

(54) ACOUSTIC REMOTE CONTROL OF MICROBIAL IMMUNOTHERAPY

(71) Applicant: California Institute of Technology, Pasadena, CA (US)

(72) Inventors: Mohamad H. Abedi, Pasadena, CA (US); Mikhail G. Shapiro, Pasadena, CA (US); Michael S. Yao, Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 137 days.

(21) Appl. No.: 17/692,778

(22) Filed: Mar. 11, 2022

(65) Prior Publication Data

US 2022/0290162 A1 Sep. 15, 2022

Related U.S. Application Data

(60) Provisional application No. 63/160,152, filed on Mar. 12, 2021.

(51) Int. Cl.
*C12N 15/63* (2006.01)
*C12N 9/22* (2006.01)
*C12N 15/90* (2006.01)

(52) U.S. Cl.
CPC ............. *C12N 15/635* (2013.01); *C12N 9/22* (2013.01); *C12N 15/907* (2013.01); *C12N 2800/30* (2013.01); *C12N 2830/008* (2013.01)

(58) Field of Classification Search
None
See application file for complete search history.

(56) References Cited

U.S. PATENT DOCUMENTS

| | | | |
|---|---|---|---|
| 5,260,291 | A | 11/1993 | Lunt et al. |
| 5,589,168 | A | 12/1996 | Allen et al. |
| 5,747,498 | A | 5/1998 | Schnur et al. |
| 6,203,797 | B1 | 3/2001 | Perry |
| 6,326,193 | B1 | 12/2001 | Liu et al. |
| 6,703,199 | B1 | 3/2004 | Koide |
| 6,835,376 | B1 | 12/2004 | Neeser et al. |
| 2008/0139587 | A1 | 6/2008 | Huang et al. |
| 2016/0324989 | A1 | 11/2016 | Li et al. |
| 2017/0298425 | A1 | 10/2017 | Shapiro et al. |
| 2019/0055297 | A1 | 2/2019 | Zhao et al. |
| 2020/0108145 | A1 | 4/2020 | Wang et al. |
| 2021/0138066 | A1 | 5/2021 | Abundo et al. |
| 2021/0324389 | A1 | 10/2021 | Abedi et al. |

FOREIGN PATENT DOCUMENTS

| | | | |
|---|---|---|---|
| EP | 0564409 | 3/1993 | |
| EP | 0566226 | 11/1995 | |
| EP | 0520722 | 12/1996 | |
| EP | 0787722 | 8/1997 | |
| EP | 0837063 | 4/1998 | |
| WO | WO1996033980 | 10/1996 | |
| WO | WO1997002266 | 1/1997 | |
| WO | WO1997030034 | 8/1997 | |
| WO | WO1997038983 | 10/1997 | |
| WO | WO1997049688 | 12/1997 | |
| WO | WO1998010767 | 3/1998 | |
| WO | WO1999003854 | 1/1999 | |
| WO | WO2001029058 | 4/2001 | |
| WO | WO2001096584 | 12/2001 | |
| WO | WO2002022577 | 3/2002 | |
| WO | WO2003013541 | 2/2003 | |
| WO | WO2016210373 | 12/2016 | |
| WO | WO-2018098315 A1 * | 5/2018 | ......... A61K 39/0011 |
| WO | WO2021/050658 | 3/2021 | |
| WO | WO2021/211776 | 10/2021 | |

OTHER PUBLICATIONS

Morgan. Plasmids 101: The Promoter Region—Let's Go!. (accessed at: https://blog.addgene.org/plasmids-101-the-promoter-region#:~:text=Promoter%20specificity&text=Bacterial%20promoters%20only%20work%20in,there%20is%20very%20little%20crossover) (Year: 2014).*

Kelmenson. Cre Lox Breeding for Beginners, Part 1. (accessed at: https://www.jax.org/news-and-insights/jax-blog/2011/september/cre-lox-breeding)(Year: 2011).*

Federov et al. PD-1-and CTLA-4-Based Inhibitory Chimeric Antigen Receptors (iCARs) Divert Off-Target Immunotherapy ResponsesSci Transl Med. Dec. 11, 2013;5(215):215ra172. (Year: 2013).*

Bapst et al. Cre-mediated, IoxP independent sequential recombination of a tripartite transcriptional stop cassette allows for partial read-through transcription. Biochim Biophys Acta Gene Regul Mech. Aug. 2020; 1863(8):194568. Epub Apr. 25, 2020. (Year: 2020).*

Derived. Dictionary.com (accessed at: https://www.dictionary.com/browse/derived on Feb. 5, 2025) (Year: 2025).*

Nag et al. Bacteriophage Lambda Containing Two Temperature-Sensitive Mutations in the cI Gene Produces Clear Plaque at 30. Virology. Apr. 30, 1982;118(2):448-50. (Year: 1982).*

Krajewski et al. Temperature-driven differential gene expression by RNA thermosensors. Biochim Biophys Acta. Oct. 2014;1839(10):978-988. Epub Mar. 21, 2014. (Year: 2014).*

Miladi et al. MutaRNA: analysis and visualization of mutation-induced changes in RNA structure. Nucleic Acids Res. Jul. 2, 2020;48(W1):W287-W291. (Year: 2020).*

(Continued)

*Primary Examiner* — Valarie E Bertoglio
*Assistant Examiner* — Briana N Ebbinghaus
(74) *Attorney, Agent, or Firm* — Dickinson Wright PLLC

(57) ABSTRACT

Disclosed herein include methods, compositions, and kits suitable for use in spatiotemporal regulation of probiotic cells. There are provided, in some embodiments, thermal bioswitches that allow probiotic cells to sense small changes in temperature and use them as inputs for the actuation of genetic circuits. Genetic circuits capable of inducing expression of a payload upon thermal stimulation are provided. Thermally actuated probiotic cells and methods of use for the treatment of diseases or disorders are also provided.

17 Claims, 26 Drawing Sheets

Specification includes a Sequence Listing.

(56) References Cited

OTHER PUBLICATIONS

Therapeutic. Merriam-Webster. (accessed at: https://www.merriam-webster.com/dictionary/therapeutic on Feb. 5, 2025)(Year: 2025).*

Abedi et al., "Thermal Control of Engineered T-cells," ACS Synth. Biol. 2020, 9, 1941-1950.

Abedi et al., "Acoustic Remote Control of Bacterial Immunotherapy," bioRxiv 2021, in 11 pages. doi: https://doi.org/10.1101/2021.03.25.434639.

Anderson et al., "Obstacles Posed by the Tumor Microenvironment to T cell Activity: A Case for Synergistic Therapies," Cancer Cell 2017, 31, 311-325.

Arthur et al., "Intestinal inflammation targets cancer-inducing activity of the microbiota," Science 2012, 338(6103), 120-123.

Ash et al., "Effect of wavelength and beamwidth on penetration in light-tissue interaction using computational methods," Lasers Med Sci 2017, 32, 1909-1918.

Bernardes & Chakrabarty, "Engineering of bacterial strains and their products for cancer therapy," Appl Microbiol Biotechnol 2013, in 11 pages.

Bertrand et al., "Immune related adverse events associated with anti-CTLA-4 antibodies: systematic review and meta-analysis," BMC Medicine 2015, 13(211), in 14 pages.

Chavez et al., "Distinct immune signatures in directly treated and distant tumors result from TLR adjuvants and focal ablation," Theranostics 2018, 8(13), 3611-3628.

Chen et al., "Characterization of 582 natural and synthetic terminators and quantification of their design constraints," Nature Methods 2013, 10(7), 659-664.

Chien et al., "Advances in bacterial cancer therapies using synthetic biology," Curr Opin Syst Biol. 2017, 5, 1-8.

Chien et al., "Multiplexed biosensors for precision bacteria tropism in vivo," bioRxiv 2019, in 10 pages. doi: https://doi.org/10.1101/851311.

Chowdhury et al., "Programmable bacteria induce durable tumor regression and systemic antitumor immunity," Nat Med. 2019, 25(7), 1057-1063.

Clairmont et al., "Biodistribution and Genetic Stability of the Novel Antitumor Agent VNP20009, a Genetically Modified Strain of *Salmonella typhimurium*," The Journal of Infectious Diseases 2000, 181, 1996-2002.

Coley, "Contribution to the Knowledge of Sarcoma," New York Academy of Medicine 1891, 199-220.

Courbet et al., "Detection of pathological biomarkers in human clinical samples via amplifying genetic switches and logic gates," Science Translational Medicine 2015, 7(289) 1-11.

Couture et al., "Review of ultrasound mediated drug delivery for cancer treatment: updates from pre-clinical studies," Transl Cancer Res 2014, 3(5), 494-511.

Cronin et al., "Orally Administered Bifidobacteria as Vehicles for Delivery of Agents to Systemic Tumors," Molecular Therapy 2010, 18(7), 1397-1407.

Cronin et al., "High Resolution In Vivo Bioluminescent Imaging for the Study of Bacterial Tumour Targeting," PLoS ONE 2012, 7(1), e30940, in 11 pages.

Cuevas-Ramos et al., "*Escherichia coli* induces DNA damage in vivo and triggers genomic instability in mammalian cells," PNAS 2010, 107(25), 11537-11542.

Dai et al., "Construction of an Inducible Cell-Communication System That Amplifies *Salmonella* Gene Expression in Tumor Tissue,," Biotechnol. Bioeng. 2013, 110, 1769-1781.

Dang et al., "Combination bacteriolytic therapy for the treatment of experimental tumors" PNAS 2001, 98(26), 15155-15160.

Deckers & Moonen, "Ultrasound triggered, image guided, local drug delivery," Journal of Controlled Release 2010, 148, 25-33.

Dinleyici et al., "Lactobacillus reuteri DSM 17938 effectively reduces the duration of acute diarrhoea in hospitalised children," Acta Pædiatrica 2014, 103, 300-305.

Dou & Bennett, "Synthetic biology and the gut microbiome," Biotechnol J 2018, 13(5), in 22 pages.

Duong et al., "Bacteria-cancer interactions: bacteria-based cancer therapy," Experimental & Molecular Medicine 2019, 51(152), in 15 pages.

Fedorec et al., "Two New Plasmid Post-segregational Killing Mechanisms for the Implementation of Synthetic Gene Networks in *Escherichia coli*," iScience 2019, 14, 323-334.

Feigner et al., "Tumour-targeting bacteria-based cancer therapies for increased specificity and improved outcome," Microbial Biotechnology 2017, 10(5), 1074-1078.

Flynn et al., "Overlapping recognition determinants within the ssrA degradation tag allow modulation of proteolysis," PNAS 2001, 98(19), 10584-10589.

Forbes, "Profile of a bacterial tumor killer," Nat Biotechnol 2006, 24(12), 1484-1485.

Fuca et al., "Enhancing Chimeric Antigen Receptor T-Cell Efficacy in Solid Tumors," Clin Cancer Res 2020, 26, 2444-2451.

Gamboa et al., "Synthetic immunity by remote control," Theranostics 2020, 10(8), 3652-3667.

Gilbert et al., "Living materials with programmable functionalities grown from engineered microbial co-cultures," Nature Materials 2021, 20, 691-700.

Gonzalez et al., "Resilient living materials built by printing bacterial spores," Nature Chemical Biology 2019, in 14 pages.

Grady & Hayes, "Axe-Txe, a broad-spectrum proteic toxin—antitoxin system specified by a multidrug-resistant, clinical isolate of *Enterococcus faecium*," Molecular Microbiology 2003, 47(5), 1419-1432.

Groot et al., "Functional antibodies produced by oncolytic clostridia," Biochemical and Biophysical Research Communications 2007, 364, 985-989.

Gurbatri et al., "Engineered Probiotics for Local Tumor Delivery of Checkpoint Blockade Nanobodies," Sci Transl Med. 2020, 12(530), in 26 pages.

Hartsough et al., "Optogenetic control of gut bacterial metabolism to promote longevity," eLife 2020, 9(:e56849), in 16 pages.

Hollinger & Hudson, "Engineered antibody fragments and the rise of single domains," Nature Biotechnology 2005, 23(9), 1126-1136.

Hsiao et al., "A population-based temporal logic gate for timing and recording chemical events," Molecular Systems Biology 2016, 12(869), in 14 pages.

International Search Report and Written Opinion dated Oct. 24, 2022 in International Application No. PCT/US2022/020053.

Jain & Forbes, "Can engineered bacteria help control cancer?," PNAS 2001, 98(26), 14748-14750.

Jiang et al., "Inhibition of Tumor Growth and Metastasis by a Combination of *Escherichia coli*-mediated Cytolytic Therapy and Radiotherapy," Molecular Therapy 2010, 18(3), 635-642.

Kang et al., "Imaging of tumor colonization by *Escherichia coli* using 18F-FDS PET," Theranostics 2020, 10(11), 4958-4966.

Kruse et al., "Short-duration-focused ultrasound stimulation of Hsp70 expression in vivo," Phys. Med. Biol. 2008, 53, 3641-3660.

Lalwani et al., "Optogenetic control of the lac operon for bacterial chemical and protein production," Nature Chemical Biology 2019, in 26 pages.

Landry & Tabor, "Engineering Diagnostic and Therapeutic Gut Bacteria," Microbial Spectrum 2017, in 22 pages.

Lee at al., "Design and development of synthetic microbial platform cells for bioenergy," Frontiers in Microbiology 2013, 4(92), in 13 pages.

Leschner et al., "Tumor Invasion of Salmonella enterica Serovar Typhimurium Is Accompanied by Strong Hemorrhage Promoted by TNF-a," PLoS ONE 2009, 4(8), e6692. in 11 pages.

Leventhal et al., "Immunotherapy with engineered bacteria by targeting the STING pathway for anti-tumor immunity," Nature Communications 2020, 11(2739), 1-15.

Liu et al., "Programming Bacteria With Light—Sensors and Applications in Synthetic Biology," Frontiers in Microbiology 2018, 9(2692), 1-11.

Liu et al., "Tumor-targeting bacterial therapy: A potential treatment for oral cancer (Review)," Oncology Letters 2014, 8, 2359-2366.

Martins et al., "Adverse effects of immune-checkpoint inhibitors: epidemiology, management and surveillance," Nature Reviews, Clinical Oncology 2019, 16, 563-580.

(56) References Cited

OTHER PUBLICATIONS

Massa et al., "*Salmonella* engineered to express CD20-targeting antibodies and a drug-converting enzyme can eradicate human lymphomas," Blood 2013, 122(5), 705-714.
Meysman et al., "Expression Divergence between *Escherichia coli* and *Salmonella enterica* serovar Typhimurium Reflects Their Lifestyles, " Mol. Biol. Evol. 2013, 30(6), 1302-1314.
Mimee et al., "Microbiome Therapeutics—Advances and Challenges," Adv Drug Deliv Rev. 2016, 105(Pt A), 44-54.
Mirzael et al., "Chimeric Antigen Receptors T Cell Therapy in Solid Tumor: Challenges and Clinical Applications," Frontiers in Immunology 2017, 8(1850), 1-13.
Moonen, "Spatio-Temporal Control of Gene Expression and Cancer Treatment Using Magnetic Resonance Imaging—Guided Focused Ultrasound," Clin Cancer Res 2007, 13(12), 3482-3489.
Morissey et al., "Tumour targeting with systemically administered bacteria," Curr Gene Ther. 2010, 10(1), 3-14.
Nguyen et al., "Engineered Living Materials: Prospects and Challenges for Using Biological Systems to Direct the Assembly of Smart Materials," Adv Mater. 2018, 30(19), in 66 pages.
Nougayrède et al., "*Escherichia coli* induces DNA double-strand breaks in eukaryotic cells," Science 2006, 313(5788), 848-851.
Olier et al., "Genotoxicity of *Escherichia coli* Nissle 1917 strain cannot be dissociated from its probiotic activity," Gut Microbes 2012, 3(6), 501-509.
Park et al., "RGD Peptide Cell-Surface Display Enhances the Targeting and Therapeutic Efficacy of Attenuated *Salmonella*-mediated Cancer Therapy," Theranostics 2016, 6(10), 1672-1682.
Patyar et al., "Bacteria in cancer therapy: a novel experimental strategy," Journal of Biomedical Science 2010, 17(21), in 9 pages.
Piraner et al., "Tunable thermal bioswitches for in vivo control of microbial therapeutics," Nature Chemical Biology 2016, 1-8.
Riglar et al., "Engineering bacteria for diagnostic and therapeutic applications," Nature 2018, 16, 214-225.
Roßmanith et al., "Design of a Temperature-Responsive Transcription Terminator," ACS Synthetic Biology 2018, 7, 613-621.
Rome et al., "Spatial and temporal control of expression of therapeutic genes using heat shock protein promoters," Methods 2005, 35, 188-198.
Ryan et al., "Bacterial delivery of a novel cytolysin to hypoxic areas of solid tumors," Gene Therapy 2009, 16, 329-339.
Silvestrini et al., "Priming is key to effective incorporation of image-guided thermal ablation into immunotherapy protocols," JCI Insight 2017, 2(6), 1-16.
Stritzker et al., "Tumor-specific colonization, tissue distribution, and gene induction by probiotic *Escherichia coli* Nissle 1917 in live mice," International Journal of Medical Microbiology 2007, 297, 151-162.
Voight, "Synthetic biology 2020-2030: six commercially-available products that are changing our world," Nature Communications 2020, 11(6379), 1-6.
Weber et al., "The Emerging Landscape of Immune Cell Therapies," Cell 2020, 181, 46-62.
YU et l., "Cancer cell therapies: the clinical trial landscape," Nature review Drug Discovery 2020, 19, 583-584.
Zheng et al., "Two-step enhanced cancer immunotherapy with engineered *Salmonella typhimurium* secreting heterologous flagellin," Science translational Medicine 2017, 9, in 10 pages.
Zhou et al., "Tumor-targeting bacteria engineered to fight cancer," Nat Rev Cancer. 2018, 18(12), 727-743.
International Preliminary Report on Patentability for International Application No. PCT/US2022/020053, mailed on Sep. 21, 2023, 6 pages.
Abedi et al., "Ultrasound-controllable engineered bacteria for cancer immunotherapy," Nature Communications (2022), 13(1), 1-11.
Extended European Search Report for European Patent Application No. 22781843.2 dated Dec. 23, 2024.

* cited by examiner

| Rationally designed candidates | Low copy origin | Medium copy origin |
|---|---|---|
| No terminator | A | C |
| Temperature responsive terminator | B | D |

ACOUSTIC REMOTE CONTROL OF MICROBIAL IMMUNOTHERAPY

RELATED APPLICATIONS

This application claims the benefit under 35 U.S.C. § 119(e) of U.S. Provisional Patent Application Ser. No. 63/160,152, filed Mar. 12, 2021, the content of this related application is incorporated herein by reference in its entirety for all purposes.

STATEMENT REGARDING FEDERALLY SPONSORED R&D

This invention was made with government support under Grant No. W911NF-19-D-0001 awarded by the Army and under Grant No. D14AP00050 awarded by Department of Interior. The government has certain rights in the invention.

REFERENCE TO SEQUENCE LISTING

The present application is being filed along with a Sequence Listing in electronic format. The Sequence Listing is provided as a file entitled 30KJ_302441_US, created Mar. 10, 2022, which is 72.0 kilobytes in size. The information in the electronic format of the Sequence Listing is incorporated herein by reference in its entirety.

BACKGROUND

Field

The present disclosure relates generally to the field of probiotic cell therapies and more specifically to spatiotemporal control of probiotic cell activity.

Description of the Related Art

Cell therapies are rapidly emerging as an exciting and effective class of technologies for cancer treatment. Among the cell types being investigated for therapy, immune cells have excelled in the treatment of hematologic malignancies. However, their use in solid tumors has been hampered by their reduced ability to penetrate and function in the tumor's immunosuppressive environment, especially within immune-privileged hypoxic cores. Conversely, the reduced immune activity of some tumor cores creates a favorable microenvironment for the growth of certain bacteria, which can reach the tumors after systemic administration. Capitalizing on their tumor-infiltrating properties, such bacteria can be engineered to function as effective cellular therapies by secreting therapeutic payloads to directly kill tumor cells or remodel the microenvironment to stimulate anti-tumor immunity. However, the benefits of microbial therapy are often counterbalanced by safety concerns accompanying the systemic injection of microbes into patients with limited control over their biodistribution or activity. This is especially important given the well-documented engraftment of circulating bacteria into healthy tissues such as the liver, spleen, and certain hypoxic stem cell niches. To avoid damaging healthy organs, it is crucial that the therapeutic activity of microbes be targeted to tumors. There is a need for temperature-based circuits enabling spatiotemporal control of probiotic cell therapeutic activity.

SUMMARY

Disclosed herein include nucleic acid compositions. In some embodiments, the nucleic acid composition comprises:

a first promoter operably linked to a first polynucleotide comprising a recombinase gene, wherein the first promoter is capable of inducing transcription of the first polynucleotide to generate a recombinase transcript upon a thermal stimulation, and wherein the recombinase transcript is capable of being translated to generate a recombinase capable of catalyzing a recombination event; a second promoter and a second polynucleotide comprising a payload gene, wherein, in the absence of the recombination event, the second promoter and the second polynucleotide are not operably linked, and wherein the second promoter and the second polynucleotide are operably linked after the recombination event such that the second promoter is capable of inducing transcription of the second polynucleotide to generate a payload transcript.

In some embodiments, the thermal stimulation comprises heating to an activating temperature. In some embodiments, the activating temperature is above a physiological temperature. In some embodiments, thermal stimulation comprises the application of one or more of focused ultrasound (FUS), magnetic hyperthermia, microwaves, infrared irradiation, liquid-based heating (e.g., intraperitoneal chemotherapy (HIPEC)), and contact heating. In some embodiments, the activating temperature is about 37.5° C., about 38.0° C., about 38.5° C., about 39.0° C., about 39.5° C., about 40.0° C., about 40.5° C., about 41.0° C., about 41.5° C., about 42.0° C., about 42.5° C., about 43.0° C., about 43.5° C., about 44.0° C., about 44.5° C., about 45.0° C., about 45.5° C., or about 46.0° C. In some embodiments, physiological temperature is about 31.5° C., about 32.0° C., about 32.5° C., about 33.0° C., about 33.5° C., about 34.0° C., about 34.5° C., about 35.0° C., about 35.5° C., about 36.0° C., about 36.5° C., about 37.0° C., about 37.5° C., about 38.0° C., about 38.5° C., about 39.0° C., about 39.5° C., or about 40.0° C. In some embodiments, in the absence of the thermal stimulation, the recombinase reaches steady state protein levels in a probiotic cell insufficient to catalyze the recombination event.

In some embodiments, the transcriptional activity of first promoter is under the control of a temperature-sensitive transcription factor (e.g., a temperature-sensitive transcriptional repressor). In some embodiments, at the physiological temperature, the temperature-sensitive transcriptional repressor is capable of repressing transcription of the recombinase, thereby repressing expression of the payload(s).

The nucleic acid composition can comprise: a third promoter operably linked to a third polynucleotide encoding a temperature-sensitive transcription factor, wherein two temperature-sensitive transcription factors are capable of associating to generate a temperature-sensitive transcription factor homodimer in the absence of the thermal stimulation, and wherein the two temperature-sensitive transcription factors are incapable of associating to generate a temperature-sensitive transcription factor homodimer in the presence of the thermal stimulation. In some embodiments, the first promoter comprises one or more operators. In some embodiments, a temperature-sensitive transcription factor homodimer is capable of binding the one or more operators. In some embodiments, upon the temperature-sensitive transcription factor homodimer binding the one or more operators, the first promoter is incapable of inducing transcription of the first polynucleotide. In some embodiments, the first promoter is incapable of inducing transcription of the first polynucleotide in the absence of the thermal stimulation. In some embodiments, the first promoter is capable of inducing transcription of the first polynucleotide in the absence of the temperature-sensitive transcription factor homodimer.

In some embodiments, a temperature-sensitive transcription factor monomer has at least about 1.1-fold, 1.3-fold, 1.5-fold, 1.7-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, or 100-fold, less binding affinity for the one or more operators as compared to a temperature-sensitive transcription factor homodimer. In some embodiments, a temperature-sensitive transcription factor monomer is not capable of binding the one or more operators. In some embodiments, the first promoter induces transcription of the first polynucleotide at least about 1.1-fold, 1.3-fold, 1.5-fold, 1.7-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, or 100-fold, less in the presence of a temperature-sensitive transcription factor homodimer as compared to a temperature-sensitive transcription factor monomer. In some embodiments, temperature-sensitive transcription factor homodimerization occurs with a dissociation constant ($K_d$) at least about 1.1-fold, 1.3-fold, 1.5-fold, 1.7-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, or 100-fold, lower in the presence of a physiological temperature as compared to in the presence of the thermal stimulation. In some embodiments, the temperature-sensitive transcription factor is a temperature-sensitive mutant of the bacteriophage lambda cI protein. In some embodiments, the temperature-sensitive transcription factor comprises wild-type TlpA, TlpA36, TlpA39, TcI, TcI42, TcI38, derivatives thereof, or any combination thereof.

In some embodiments, the recombination event comprises removal of a sequence flanked by recombinase target sites or an inversion of a sequence flanked by recombinase target sites. In some embodiments, after the recombination event, the recombinase target sites are modified such that said modified recombinase target sites are not capable of interacting with the recombinase to yield another recombination event, thereby rendering the recombination event permanent. In some embodiments, the recombination event is an inversion event. In some embodiments, the second polynucleotide is flanked by recombinase target sites. In some embodiments, prior to the recombination event, the sequence of the payload gene is inverted relative to the second promoter. The nucleic acid composition can comprise: at least one stop cassette situated between the second promoter and the payload gene, wherein the stop cassette comprises one or more stop sequences, and wherein the one or more stop cassettes are flanked by recombinase target sites. In some embodiments, the payload transcript is capable of being translated to generate a payload protein. In some embodiments, the at least one stop cassette is configured to prevent transcription of the payload gene and/or translation of the payload transcript. In some embodiments, the one or more stop sequences comprise a polyadenylation signal, a stop codon, a frame-shifting mutation, or any combination thereof.

In some embodiments, the recombinase is or comprises Cre, Dre, Flp, KD, B2, B3, λ, HK022, HP1, γ6, ParA, Tn3, Gin, ΦC31, FimB, FimE, TP091, Bxb1, ΦBT1, phiC31, RV-1, AA118, U 153, ΦFC1, R4, derivatives thereof, or any combination thereof. In some embodiments, the recombinase is a Bxb1 and the recombinase target sites comprise attP and/or attB sites. In some embodiments, the recombinase is a Flp recombinase and the recombinase target sites are FRT sites. In some embodiments, the recombinase is a Cre recombinase and the recombinase target sites are loxP sites.

In some embodiments, the first polynucleotide, recombinase transcript, and/or recombinase comprises one or more elements capable of being tuned to modulate recombinase translation and stability. In some embodiments, the one or more elements comprise one or more of a ribosomal binding sequence (RBS), a start codon, and a degradation tag. In some embodiments, the recombinase transcript coding sequence begins with a non-canonical start codon capable of reducing ribosomal efficiency (e.g., [GUG]). In some embodiments, the recombinase transcript comprises a ribosomal binding sequence (RBS). In some embodiments, the efficiency of translation is capable of being tuned by varying the sequence of the RBS. In some embodiments, the RBS comprises a nucleotide sequence that is at least 80%, 85%, 90%, 95%, 98%, 99%, or 100% identical to SEQ ID NO: 7 [ATCCTATCGGTATG] or SEQ ID NO: 8 [CTACAATCGGTATG], or a complement thereof. In some embodiments, the recombinase comprises a degradation tag (e.g., a C-terminal degradation tag). In some embodiments, the degradation rate of the recombinase is capable of being tuned by varying the sequence of the degradation tag (e.g., the last three amino acids of the degradation tag). In some embodiments, the degradation tag comprises a ssrA degradation tag. In some embodiments, the ssrA degradation tag comprises an amino acid sequence that is at least 80%, 85%, 90%, 95%, 98%, 99%, or 100% identical to SEQ ID NO: 9 [GSAANDENYAAHR] or to SEQ ID NO: 10 [GSAANDENYAAPY], or a complement thereof. In some embodiments, the first polynucleotide and/or recombinase transcript comprises a temperature-sensitive terminator upstream of the recombinase coding sequence. In some embodiments, the temperature-sensitive terminator is a temperature-modulated structure. In some embodiments, the temperature-sensitive terminator comprises, is derived from, or is configured to mimic, an RNA thermometer. In some embodiments, the temperature-sensitive terminator comprises a temperature-sensitive secondary structure capable of terminating protein expression at a temperature below the activating temperature. In some embodiments, the temperature below the activating temperature is physiological temperature. In some embodiments, the temperature-sensitive secondary structure is lost at or above the activating temperature. In some embodiments, the temperature-sensitive terminator comprises a nucleotide sequence that is at least 80%, 85%, 90%, 95%, 98%, 99%, or 100% identical to SEQ ID NO: 11 [ATGACTTACTTGCTGAATCTCAGGAGTTTATGACCTTTTTTTTTT], or a complement thereof.

In some embodiments, the one or more operators are selected from the group comprising TlpA operator/promoter, lambda phage OR1, lambda phage OR2, lambda phage OR3, lambda phage OL1, lambda phage OL2 and lambda phage OL3. In some embodiments, the first promoter comprises the TlpA operator/promoter, lambda phage pL, lambda phage pR, lambda phage pRM, or any combination thereof.

In some embodiments, the first promoter, second promoter, and/or third promoter is a promoter selected from the group comprising: a bacteriophage promoter (e.g., Pls1con, T3, T7, SP6, or PL); a bacterial promoter (e.g., Pbad, PmgrB, Ptrc2, Plac/ara, Ptac, or Pm); and/or a bacterial-bacteriophage hybrid promoter (e.g., PLlacO or PLtetO). In some embodiments, the first promoter, second promoter, and/or third promoter is P7 promoter. In some embodiments, the first promoter, second promoter, and/or third promoter is a heat-shock promoter (e.g., pTSR, pR-pL, GrpE, HtpG, Lon, RpoH, Clp, and/or DnaK).

In some embodiments, the first promoter, second promoter, and/or third promoter is a positively regulated *E. coli* promoter selected from the group comprising: a σ70 promoter (e.g., inducible pBad/araC promoter, Lux cassette right promoter, modified lamdba Prm promoter, plac Or2-62 (positive), pBad/AraC with extra REN sites, pBad, P(Las) TetO, P(Las) CIO, P(Rhl), Pu, FecA, pRE, cadC, hns, pLas, or pLux); a σS promoter (e.g., Pdps); a σ32 promoter (e.g., heat shock); and/or a σ54 promoter (e.g., glnAp2).

In some embodiments, the first promoter, second promoter, and/or third promoter is a negatively regulated *E. coli* promoter selected from the group comprising: a σ70 promoter (e.g., Promoter (PRM+), modified lamdba Prm promoter, TetR-TetR-4C P(Las) TetO, P(Las) CIO, P(Lac) IQ, RecA_DlexO_DLacO1, dapAp, FecA, Pspac-hy, pcI, plux-cI, plux-lac, CinR, CinL, glucose controlled, modified Pr, modified Prm+, FecA, Pcya, rec A (SOS), Rec A (SOS), EmrR_regulated, BetI_regulated, pLac_lux, pTet_Lac, pLac/Mnt, pTet/Mnt, LsrA/cI, pLux/cI, Lad, LacIQ, pLacIQ1, pLas/cI, pLas/Lux, pLux/Las, pRecA with LexA binding site, reverse BBa_R0011, pLacI/ara-1, pLacIq, rrnB P1, cadC, hns, PfhuA, pBad/araC, nhaA, OmpF, or RcnR); a σS promoter (e.g., Lutz-Bujard LacO with alternative sigma factor σ38); a σ32 promoter (e.g., Lutz-Bujard LacO with alternative sigma factor σ32); and/or a σ54 promoter (e.g., glnAp2).

In some embodiments, the first promoter, second promoter, and/or third promoter is a constitutive promoter selected from the group comprising: a constitutive *Escherichia coli* σ S promoter (e.g., osmY promoter (BBa_J45993)); a constitutive *Escherichia coli* σ 32 promoter (e.g., htpG heat shock promoter (BBa_J45504)); a constitutive *Escherichia coli* σ 70 promoter (e.g., lacq promoter (BBa_J54200 or BBa_J56015), *E. coli* CreABCD phosphate sensing operon promoter (BBa_J64951), GlnRS promoter (BBa_K088007), lacZ promoter (BBa_K119000 or BBa_K119001), M13K07 gene I promoter (BBa_M13101), M13K07 gene II promoter (BBa_M13102), M13K07 gene III promoter (BBa_M13103), M13K07 gene IV promoter (BBa_M13104), M13K07 gene V promoter (BBa_M13105), M13K07 gene VI promoter (BBa_M13106), M13K07 gene VIII promoter (BBa_M13108), or M13110 (BBa_M13110)); a constitutive *Bacillus subtilis* σ A promoter (e.g., promoter veg (BBa_K143013), promoter 43 (BBa_K143013), PliaG (BBa_K823000), PlepA (BBa_K823002), or Pveg (BBa_K823003)); a constitutive *Bacillus subtilis* σ B promoter (e.g., promoter ctc (BBa_K143010) or promoter gsiB (BBa_K143011)), a *Salmonella* promoter (e.g., Pspv2 from *Salmonella* (BBa_K112706) or Pspv from *Salmonella* (BBa_K112707)); a bacteriophage T7 promoter (e.g., BBa_I712074, BBa_I719005, BBa_J34814, BBa_J64997, BBa_K113010, BBa_K113011, BBa_K113012, BBa_R0085, BBa_R0180, BBa_R0181, BBa_R0182, BBa_R0183, BBa_Z0251, BBa_Z0252, or BBa_Z0253); and/or a bacteriophage SP6 promoter (e.g., SP6 promoter (BBa_J64998)).

In some embodiments, the first promoter, second promoter, and/or third promoter comprises at least one −10 element and/or at least one −35 element. The nucleic acid composition can comprise: one or more terminators. In some embodiments, the one or more terminators are positioned upstream of the first promoter, second promoter, and/or third promoter. In some embodiments, the terminator is selected from the group comprising SV40 terminator, spy terminator, yejM terminator, secG-leuU terminator, thrLABC terminator, rrnB T1 terminator, rrnB T2 terminator, hisLGDCBHAFI terminator, metZWV terminator, Csrc terminator, rrnC terminator, xapR terminator, aspA terminator, trp terminator, arcA terminator, bacteriophage lambda terminator, derivatives thereof, or any combination thereof. In some embodiments, the terminator is a rho-independent terminator or rho-dependent terminator.

In some embodiments, upon the thermal stimulation, transcription of the recombinase gene and/or payload gene is increased by at least about 1.1-fold. In some embodiments, upon the thermal stimulation, steady-state protein levels of the recombinase and/or payload is increased by at least about 1.1-fold. In some embodiments, increased expression of the payload(s) following the thermal stimulation is permanent. In some embodiments, expression levels comprise transcript levels and/or protein levels. In some embodiments, a payload protein comprises a synthetic protein circuit component.

In some embodiments, the second polynucleotide comprises one or more supplemental payload genes. In some embodiments, the payload transcript is a polycistronic transcript capable of being translated to generate a plurality of payload proteins. In some embodiments, the payload and supplemental payload(s) are each operably connected to a ribosome binding site.

In some embodiments, a payload protein comprises fluorescence activity, polymerase activity, protease activity, phosphatase activity, kinase activity, SUMOylating activity, deSUMOylating activity, ribosylation activity, deribosylation activity, myristoylation activity demyristoylation activity, or any combination thereof. In some embodiments, a payload protein comprises nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity, glycosylase activity, acetyltransferase activity, deacetylase activity, adenylation activity, deadenylation activity, or any combination thereof. In some embodiments, a payload protein comprises a diagnostic agent or is co-expressed with a diagnostic agent (e.g., green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), TagRFP, Dronpa, Padron, mApple, mCitrine, mCherry, mruby3, rsCherry, rsCherryRev, derivatives thereof, or any combination thereof). In some embodiments, the payload protein is fused with the diagnostic agent.

In some embodiments, the payload is configured to modulate one or more of T cell simulation, T cell activation, cytokine secretion, T cell survival, T cell proliferation, CTL activity, T cell degranulation, and T cell differentiation. In some embodiments, a payload is an immune checkpoint inhibitor. In some embodiments, the payload comprises αCTLA-4 or αPD-L1 nanobodies. In some embodiments, a payload comprises a bispecific T cell engager (BiTE).

In some embodiments, a payload protein comprises a cytokine. In some embodiments, the cytokine is selected from the group consisting of interleukin-1 (IL-1), IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, interleukin-1 (IL-1), IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, granulocyte macrophage colony stimulating factor (GM-CSF), M-CSF, SCF, TSLP, oncostatin M, leukemia-inhibitory factor (LIF), CNTF, Cardiotropin-1, NNT-1/BSF-3, growth hormone, Prolactin, Erythropoietin, Thrombopoietin, Leptin, G-CSF, or receptor or ligand thereof. In some embodiments, a payload protein comprises a member of the TGF-β/BMP family selected from the group consisting of TGF-β1, TGF-β2, TGF-β3, BMP-2, BMP-3a, BMP-3b, BMP-4, BMP-5, BMP-6, BMP-7, BMP-8a, BMP-8b, BMP-9, BMP-10, BMP-11, BMP-15, BMP-16, endometrial bleeding associated factor (EBAF), growth differentiation factor-1 (GDF-1), GDF-2, GDF-3, GDF-5, GDF-6, GDF-7, GDF-8, GDF-9, GDF-12, GDF-14, mullerian inhibiting substance (MIS), activin-1, activin-2, activin-3, activin-4, and activin-5. In some embodiments, a payload protein comprises a member of the TNF family of cytokines selected from the group consisting of TNF-alpha, TNF-beta, LT-beta, CD40 ligand, Fas ligand, CD 27 ligand, CD 30 ligand, and 4-1 BBL.

In some embodiments, a payload protein comprises a member of the immunoglobulin superfamily of cytokines selected from the group consisting of B7.1 (CD80) and B7.2 (B70). In some embodiments, a payload protein comprises an interferon (e.g., interferon alpha, interferon beta, or interferon gamma). In some embodiments, a payload protein comprises a chemokine (e.g., CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13, or CXCL15). In some embodiments, a payload protein comprises an interleukin (e.g., IL-10 IL-12, IL-1, IL-6, IL-7, IL-15, IL-2, IL-18 or IL-21). In some embodiments, a payload protein comprises a tumor necrosis factor (TNF) (e.g., TNF-alpha, TNF-beta, TNF-gamma, CD252, CD154, CD178, CD70, CD153, or 4-1BBL).

In some embodiments, a payload protein comprises a factor locally down-regulating the activity of endogenous immune cells. In some embodiments, a payload protein is capable of remodeling a tumor microenvironment and/or reducing immunosuppression at a target site of a subject. In some embodiments, a payload protein comprises an agonistic or antagonistic antibody or antigen-binding fragment thereof specific to a checkpoint inhibitor or checkpoint stimulator molecule (e.g., PD1, PD-L1, PD-L2, CD27, CD28, CD40, CD137, OX40, GITR, ICOS, A2AR, B7-H3, B7-H4, BTLA, CTLA4, IDO, KIR, LAG3, PD-1, and/or TIM-3). In some embodiments, the antibody or antigen-binding fragment thereof comprises an scFv, a Fv, a Fab, a (Fab')2, a single domain antibody (SDAB), a VH or VL domain, a camelid VHH domain, a Fab, a Fab', a F(ab')2, a Fv, a scFv, a dsFv, a diabody, a triabody, a tetrabody, a multispecific antibody formed from antibody fragments, a single-domain antibody (sdAb), a single chain comprising cantiomplementary scFvs (tandem scFvs) or bispecific tandem scFvs, an Fv construct, a disulfide-linked Fv, a dual variable domain immunoglobulin (DVD-Ig) binding protein or a nanobody, an aptamer, an affibody, an affilin, an affitin, an affimer, an alphabody, an anticalin, an avimer, a DARPin, a Fynomer, a Kunitz domain peptide, a monobody, or any combination thereof.

In some embodiments, the payload is capable of rendering a target cell of a subject sensitive to a drug, a prodrug, a pharmacological compound, temperature change, or light. In some embodiments, the payload protein is capable of inducing cell death of a target cell of a subject. In some embodiments, the payload protein comprises cytosine deaminase, thymidine kinase, Bax, Bid, Bad, Bak, BCL2L11, p53, PUMA, Diablo/SMAC, S-TRAIL, Cas9, Cas9n, hSpCas9, hSpCas9n, HSVtk, cholera toxin, diphtheria toxin, alpha toxin, anthrax toxin, exotoxin, pertussis toxin, Shiga toxin, shiga-like toxin Fas, TNF, caspase 2, caspase 3, caspase 6, caspase 7, caspase 8, caspase 9, caspase 10, caspase 11, caspase 12, purine nucleoside phosphorylase, or any combination thereof. In some embodiments, a payload comprises a pro-death protein capable of halting cell growth and/or inducing cell death in the presence of a pro-death agent. In some embodiments, the pro-death protein comprises Caspase-9 and the pro-death agent comprises AP1903. In some embodiments, the pro-death protein comprises HSV thymidine kinase (TK) and the pro-death agent Ganciclovir (GCV), Ganciclovir elaidic acid ester, Penciclovir (PCV), Acyclovir (ACV), Valacyclovir (VCV), (E)-5-(2-bromovinyl)-2'-deoxyuridine (BVDU), Zidovuline (AZT), and/or 2'-exo-methanocarbathymidine (MCT). In some embodiments, the pro-death protein comprises Cytosine Deaminase (CD) and the pro-death agent comprises 5-fluorocytosine (5-FC). In some embodiments, the pro-death protein comprises Purine nucleoside phosphorylase (PNP) and the pro-death agent comprises 6-methylpurine deoxyriboside (MEP) and/or fludarabine (FAMP). In some embodiments, the pro-death protein comprises a Cytochrome p450 enzyme (CYP) and the pro-death agent comprises Cyclophosphamide (CPA), Ifosfamide (IFO), and/or 4-ipomeanol (4-IM). In some embodiments, the pro-death protein comprises a Carboxypeptidase (CP) and the pro-death agent comprises 4-[(2-chloroethyl)(2-mesyloxyethyl)amino]benzoyl-L-glutamic acid (CMDA), Hydroxy- and amino-aniline mustards, Anthracycline glutamates, and/or Methotrexate α-peptides (MTX-Phe). In some embodiments, the pro-death protein comprises Carboxylesterase (CE) and the pro-death agent comprises Irinotecan (IRT), and/or Anthracycline acetals. In some embodiments, the pro-death protein comprises Nitroreductase (NTR) and the pro-death agent comprises dinitroaziridinylbenzamide CB1954, dinitrobenzamide mustard SN23862, 4-Nitrobenzyl carbamates, and/or Quinones. In some embodiments, the pro-death protein comprises Horse radish peroxidase (HRP) and the pro-death agent comprises Indole-3-acetic acid (IAA) and/or 5-Fluoroindole-3-acetic acid (FIAA). In some embodiments, the pro-death protein comprises Guanine Ribosyltransferase (XGRTP) and the pro-death agent comprises 6-Thioxanthine (6-TX). In some embodiments, the pro-death protein comprises a glycosidase enzyme and the pro-death agent comprises HM1826 and/or Anthracycline acetals. In some embodiments, the pro-death protein comprises Methionine-α,γ-lyase (MET) and the pro-death agent comprises Selenomethionine (SeMET). In some embodiments, the pro-death protein comprises thymidine phosphorylase (TP) and the pro-death agent comprises 5'-Deoxy-5-fluorouridine (5'-DFU).

In some embodiments, a payload protein is associated with an agricultural trait of interest selected from the group consisting of increased yield, increased abiotic stress tolerance, increased drought tolerance, increased flood tolerance, increased heat tolerance, increased cold and frost tolerance, increased salt tolerance, increased heavy metal tolerance, increased low-nitrogen tolerance, increased disease resistance, increased pest resistance, increased herbicide resistance, increased biomass production, male sterility, or any combination thereof. In some embodiments, a payload protein is associated with a biological manufacturing process selected from the group comprising fermentation, distillation, biofuel production, production of a compound, production of a polypeptide, or any combination thereof.

In some embodiments, the one or more payloads comprise a secretion tag. In some embodiments, the secretion tag is selected from the group comprising AbnA, AmyE, AprE, BglC, BglS, Bpr, Csn, Epr, Ggt, GlpQ, HtrA, LipA, LytD, MntA, Mpr, NprE, OppA, PbpA, PbpX, Pel, PelB, PenP, PhoA, PhoB, PhoD, PstS, TasA, Vpr, WapA, WprA, XynA, XynD, YbdN, Ybxl, YcdH, YclQ, YdhF, YdhT, YfkN, YflE, YfmC, Yfnl, YhcR, YlqB, YncM, YnfF, YoaW, YocH, YolA, YqiX, Yqxl, YrpD, YrpE, YuaB, Yurl, YvcE, YvgO, YvpA, YwaD, YweA, YwoF, YwtD, YwtF, YxaLk, YxiA, and YxkC.

The nucleic acid composition can comprise: a polynucleotide encoding a toxin and/or an antitoxin. In some embodiments, one or more elements of the Axe-Txe type II toxin anti-toxin system. In some embodiments, the nucleic acid composition is capable of being retained in a probiotic cell without antibiotic selection for at least about 10 days, about 20 days, about 40 days, about 80 days, about 80 days, or about 100 days.

In some embodiments, the nucleic acid composition comprises one or more vectors. In some embodiments, at least one of the one or more vectors is a viral vector, a plasmid, a transposable element, a naked DNA vector, a phage, a lipid nanoparticle, or any combination thereof. In some embodiments, the nucleic acid composition is situated within a chromosome (e.g., a bacterial chromosome) or a plasmid. In some embodiments, one or more of the first promoter, first polynucleotide, second promoter, second polynucleotide, third promoter, third polynucleotide, polynucleotide encoding the toxin, and polynucleotide encoding the antitoxin are situated on the same nucleic acid and/or different nucleic acids. In some embodiments, the plasmid comprises an origin of replication (e.g., a low-copy, a medium-copy, or a high-copy origin of replication). In some embodiments, the origin of replication is selected from the group comprising a low copy number modified pSC101 origin of replication, a RK2 origin of replication, a wildtype pSC101 origin of replication, a p15a origin of replication, and a pACYC origin of replication, derivatives thereof, or any combination thereof.

Disclosed herein include compositions. In some embodiments, the composition comprises: a nucleic acid composition disclosed herein. In some embodiments, the composition comprises one or more vectors, a ribonucleoprotein (RNP) complex, a liposome, a nanoparticle, a phage, an exosome, a microvesicle, or any combination thereof. In some embodiments, the vector comprises a plasmid, and the plasmid comprises an origin of replication (e.g., a low-copy, a medium-copy, or a high-copy origin of replication). In some embodiments, the origin of replication is selected from the group comprising a low copy number modified pSC101 origin of replication, a RK2 origin of replication, a wildtype pSC101 origin of replication, a p15a origin of replication, and a pACYC origin of replication, derivatives thereof, or any combination thereof.

Disclosed herein include thermally actuated probiotic cells. In some embodiments, the thermally actuated probiotic cell comprises: a nucleic acid composition disclosed herein or a composition disclosed herein.

In some embodiments, at a physiological temperature, the expression of the recombinase is repressed, thereby preventing expression of the payload(s) in the thermally actuated probiotic cell. In some embodiments, upon the thermal stimulation of the thermally actuated probiotic cell, the recombinase is expressed and the recombination event occurs, thereby yielding expression of the payload(s). In some embodiments, the thermal stimulation of the thermally actuated probiotic cell yields constitutive expression of the payload(s) (e.g., constitutive expression of the payload(s) after the thermal stimulation ends and the thermally actuated probiotic cell have returned to a physiological temperature). In some embodiments, the recombination event occurs in less than about 0.01%, about 0.1%, about 1%, about 3%, about 5%, about 10%, about 15%, about 20%, about 25%, about 30%, about 35%, about 40%, about 45%, or about 50%, of thermally actuated probiotic cells in the absence of the thermal stimulation. In some embodiments, physiological temperature is about 31.5° C., about 32.0° C., about 32.5° C., about 33.0° C., about 33.5° C., about 34.0° C., about 34.5° C., about 35.0° C., about 35.5° C., about 36.0° C., about 36.5° C., about 37.0° C., about 37.5° C., about 38.0° C., about 38.5° C., about 39.0° C., about 39.5° C., or about 40.0° C. In some embodiments, the thermally actuated probiotic cell is robust to mutations reducing or abrogating the thermal stimulation-based control of payload expression. In some such embodiments, the thermally actuated probiotic cell is robust to said mutations for at least about 5 days, about 10 days, about 20 days, about 40 days, about 80 days, about 80 days, or about 100 days, of continuous culture and/or presence in a subject.

In some embodiments, the thermally actuated probiotic cell comprises tumor-homing bacteria. In some embodiments, the tumor-homing bacteria comprises *Bifidobacterium, Caulobacter, Clostridium, Escherichia coli, Listeria, Mycobacterium, Salmonella, Streptococcus*, and *Vibrio*, e.g., *Bifidobacterium adolescentis, Bifidobacterium bifidum, Bifidobacterium breve* UCC2003, *Bifidobacterium infantis, Bifidobacterium longum, Clostridium acetobutylicum, Clostridium butyricum, Clostridium butyricum* M-55, *Clostridium butyricum* miyairi, *Clostridium cochlearum, Clostridium felsineum, Clostridium histolyticum, Clostridium multifermentans, Clostridium novyi*-NT, *Clostridium paraputrificum, Clostridium pasteureanum, Clostridium pectinovorum, Clostridium perfringens, Clostridium roseum, Clostridium sporogenes, Clostridium tertium, Clostridium tetani, Clostridium tyrobutyricum, Corynebacterium parvum, Escherichia coli* MG1655, *Escherichia coli* Nissle 1917, *Listeria monocytogenes, Mycobacterium bovis, Salmonella choleraesuis, Salmonella typhimurium*, and *Vibrio cholera*, variants thereof, derivatives thereof, or any combination thereof. In some embodiments, thermally actuated probiotic cell is obligate anaerobic, facultative anaerobic, aerobic, Gram-positive, Gram-negative, commensal, or any combination thereof. In some embodiments, the thermally actuated probiotic cell comprises naturally pathogenic bacteria that are modified or mutated to reduce or eliminate pathogenicity.

In some embodiments, the probiotic cell chromosome comprises a polynucleotide encoding a toxin and/or anti-toxin (e.g., one or more elements of the Axe-Txe type II toxin anti-toxin system). In some embodiments, the thermally actuated probiotic cell comprises a polynucleotide conferring resistance to an antibiotic (e.g., phleomycin D1 (ZEOCIN™) kanamycin, spectinomycin, streptomycin, ampicillin, carbenicillin, bleomycin, erythromycin, polymyxin B, tetracycline and chloramphenicol). In some embodiments, the nucleic acid composition comprises said polynucleotide conferring resistance to an antibiotic.

Disclosed herein include methods for treating a disease or disorder in a subject. In some embodiments, the method comprises: introducing into one or more probiotic cells a nucleic acid composition disclosed herein or a composition disclosed herein, thereby generating one or more thermally actuated probiotic cells; and administering to the subject an effective amount of the thermally actuated probiotic cells. In some embodiments, the introducing step comprises transformation, conjugation, transduction, sexduction, infection, electroporation, or any combination thereof.

Disclosed herein include methods for treating a disease or disorder in a subject. In some embodiments, the method comprises: administering to the subject an effective amount of the thermally actuated probiotic cells disclosed herein. In some embodiments, the thermally actuated probiotic cells comprise a mixture of two or more thermally actuated probiotic cells expressing different payload(s).

The method can comprise: prior to the administering step: (a) culturing singular colonies of the one or more thermally actuated probiotic cells to saturation; (b) diluting said saturated cultures (e.g., to a OD600 of about 0.1); and (c) growing said diluted cultures to exponential phase (e.g., to a OD600 of about 0.6). In some embodiments, the method comprises selecting cells at steps (a), (b), or (c) which do not express the payload(s). In some embodiments, said selecting comprises detecting: (i) the absence of fluorescence in thermally actuated probiotic cells configured to express a fluorescent payload following the recombination event; or (ii) the presence of fluorescence in thermally actuated probiotic cells configured to express a fluorescent payload and a non-fluorescent payload, prior to, and following, the recombination event, respectively.

The method can comprise: applying thermal energy to a target site of the subject sufficient to increase the local temperature of the target site to an activating temperature, thereby inducing the expression of the payload in thermally actuated probiotic cells at the target site. In some embodiments, the activating temperature is about 37.5° C., about 38.0° C., about 38.5° C., about 39.0° C., about 39.5° C., about 40.0° C., about 40.5° C., about 41.0° C., about 41.5° C., about 42.0° C., about 42.5° C., about 43.0° C., about 43.5° C., about 44.0° C., about 44.5° C., about 45.0° C., about 45.5° C., or about 46.0° C. In some embodiments, the subject maintains a physiological temperature of about 31.5° C., about 32.0° C., about 32.5° C., about 33.0° C., about 33.5° C., about 34.0° C., about 34.5° C., about 35.0° C., about 35.5° C., about 36.0° C., about 36.5° C., about 37.0° C., about 37.5° C., about 38.0° C., about 38.5° C., about 39.0° C., about 39.5° C., or about 40.0° C. In some embodiments, applying thermal energy to a target site of the subject comprises the application of one or more of focused ultrasound (FUS), magnetic hyperthermia, microwaves, infrared irradiation, liquid-based heating, and contact heating (e.g., liquid-based heating comprises intraperitoneal chemotherapy (HIPEC)). In some embodiments, the period of time between the administering and applying thermal energy is about 14 days, about 7 days, about 3 days, about 48 hours, about 44 hours, about 40 hours, about 35 hours, about 30 hours, about 25 hours, 20 hours, 15 hours, 10 hours, about 8 hours, about 8 hours, 8 hours, about 7 hours, about 6 hours, about 5 hours, about 4 hours, about 3 hours, about 2 hours, about 1 hour, about 30 minutes, about 15 minutes, about 10 minutes, or about 5 minutes.

In some embodiments, applying thermal energy to a target site comprises a continuous application of thermal energy to the target site over a duration of time. In some embodiments, applying thermal energy to a target site comprises applying one or more pulses of thermal energy to the target site over a duration of time. In some embodiments, the duration of time is about 48 hours, about 44 hours, about 40 hours, about 35 hours, about 30 hours, about 25 hours, 20 hours, 15 hours, 10 hours, about 8 hours, about 8 hours, 8 hours, about 7 hours, about 6 hours, about 5 hours, about 4 hours, about 3 hours, about 2 hours, about 1 hour, about 30 minutes, about 15 minutes, about 10 minutes, or about 5 minutes. In some embodiments, the one or more pulses have a duty cycle of greater than about 1% and less than about 100%. In some embodiments, the duty cycle is kept constant at 50% while alternating the temperature between 37° C. and 42° C. In some embodiments, the one or more pulses each have a pulse duration of about 1 hour, about 30 minutes, about 15 minutes, about 10 minutes, about 5 minutes, about 1 minute, about 1 second, or about 1 millisecond. In some embodiments, applying thermal energy to a target site comprises application of FUS for about 1 hour at about 43° C. In some embodiments, applying thermal energy to a target site comprises application of FUS for about 1 hour at about 43° C. with an about 50% duty cycle, optionally with an about 5 minute pulse duration. The method can comprise: monitoring the temperature of the target region. In some embodiments, the monitoring is performed by magnetic resonance imaging (MRI). In some embodiments, the application of thermal energy to a target site of the subject is guided spatially by magnetic resonance imaging (MRI).

In some embodiments, less than about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% of the thermally actuated probiotic cells at the target site express the payload protein before applying thermal energy to the target site. In some embodiments, at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% of the thermally actuated probiotic cells at the target site express the payload protein after applying thermal energy to the target site. In some embodiments, less than about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%, of the thermally actuated probiotics cells at a site other than the target site express the payload protein. In some embodiments, the ratio of the concentration of payload-expressing thermally actuated probiotic cells at the subject's target site to the concentration of payload-expressing thermally actuated probiotic cells in subject's blood, serum, or plasma is at least about 2:1. In some embodiments, the ratio of the concentration of payload protein at the subject's target site to the concentration of payload protein in subject's blood, serum, or plasma is about 2:1 to about 3000:1, about 2:1 to about 2000:1, about 2:1 to about 1000:1, or about 2:1 to about 600:1. In some embodiments, the concentration of payload protein at the subject's target site is increased by at least about 2-fold after the application of thermal energy.

In some embodiments, the target site comprises target cells. In some embodiments, the target cells are tumor cells (e.g., solid tumor cells). In some embodiments, the application of thermal energy to a target site of the subject results in the death of at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, of the target cells. In some embodiments, non-target cells comprise cells of the subject other than target cells, and wherein the ratio of target cell death to non-target cell death after application of thermal energy is at least about 2:1. In some embodiments, the ratio of target cell death to non-target cell death is at least about 1.1-fold greater as compared to a method comprising probiotic cells constitutively expressing the payload protein.

In some embodiments, the target site comprises a solid tumor (e.g., a head-and-neck, liver, breast, prostate, ovarian, pancreatic or brain tumor). In some embodiments, the tumor is a metastatic tumor, and wherein the application of thermal energy causes the reduction or elimination of distant tumor lesions (e.g., via an abscopal effect). In some embodiments, the disease is an oligometastatic disease, and wherein the target site comprises one or more metastases. In some embodiments, the one or more metastases comprise defined liver metastases or brain metastases of tumors other primary tissue origin. In some embodiments, the application of thermal energy to a target site of the subject results in an at least an about 1.1-fold reduction in tumor proliferation, tumor size, tumor volume, and/or tumor weight.

In some embodiments, the application of thermal energy to a target site of the subject results in an at least an about 1.1-fold reduction in tumor proliferation, tumor size, tumor volume, and/or tumor weight as compared to a method wherein the subject is administered the payload or administered probiotic bacteria constitutively expressing the payload. In some embodiments, after applying thermal energy to the target site, thermally actuated probiotic cells at the target site express the payload protein for at least about for at least about 2 days, about 4 days, about 7 days, about 10 days, about 20 days, about 40 days, about 80 days, about 80 days, or about 100 days. In some embodiments, upon administration, the thermally actuated probiotic cells accumulate in one or more target sites of the subject (e.g., hypoxic environments and/or immunosuppressive environments (e.g., the necrotic core of a solid tumor)). In some embodiments, the target site comprises a site of disease or disorder or is proximate to a site of a disease or disorder. In some embodiments, the location of the one or more sites of a disease or disorder is predetermined, is determined during the method, or both. In some embodiments, the target site is an immunosuppressive environment.

In some embodiments, a target site of a subject comprises a site of disease or disorder or is proximate to a site of a disease or disorder, In some embodiments, the subject has a disease of the GI tract. In some embodiments, the disease of the GI tract is an inflammatory bowel disease (e.g., Crohn's disease, ulcerative colitis, irritable bowel syndrome, microscopic colitis, lymphocytic-plasmocytic enteritis, coeliac disease, collagenous colitis, lymphocytic colitis and eosinophilic enterocolitis, indeterminate colitis, infectious colitis, pseudomembranous colitis, ischemic inflammatory bowel disease or Behcet's disease). In some embodiments, the target site comprises a section or subsection of the GI tract (e.g., stomach, proximal duodenum, distal duodenum, proximal jejunum, distal jejunum, proximal ileum, distal ileum, proximal cecum, distal cecum, proximal ascending colon, distal ascending colon, proximal transverse colon, distal transverse colon, proximal descending colon and distal descending colon, or any combination thereof).

In some embodiments, the target site comprises a tissue. In some embodiments, the tissue is inflamed tissue, cancerous tissue, and/or infected tissue. In some embodiments, the tissue comprises adrenal gland tissue, appendix tissue, bladder tissue, bone, bowel tissue, brain tissue, breast tissue, bronchi, coronal tissue, ear tissue, esophagus tissue, eye tissue, gall bladder tissue, genital tissue, heart tissue, hypothalamus tissue, kidney tissue, large intestine tissue, intestinal tissue, larynx tissue, liver tissue, lung tissue, lymph nodes, mouth tissue, nose tissue, pancreatic tissue, parathyroid gland tissue, pituitary gland tissue, prostate tissue, rectal tissue, salivary gland tissue, skeletal muscle tissue, skin tissue, small intestine tissue, spinal cord, spleen tissue, stomach tissue, thymus gland tissue, trachea tissue, thyroid tissue, ureter tissue, urethra tissue, soft and connective tissue, peritoneal tissue, blood vessel tissue and/or fat tissue. In some embodiments, the tissue comprises: (i) grade I, grade II, grade III or grade IV cancerous tissue; (ii) metastatic cancerous tissue; (iii) mixed grade cancerous tissue; (iv) a sub-grade cancerous tissue; (v) healthy or normal tissue; and/or (vi) cancerous or abnormal tissue.

In some embodiments, the disease is associated with expression of a tumor antigen. In some embodiments, the disease associated with expression of a tumor antigen is selected from the group consisting of a proliferative disease, a precancerous condition, a cancer, and a non-cancer related indication associated with expression of the tumor antigen. In some embodiments, the disease or disorder is a blood disease, a solid tumor, an immune disease, a neurological disease or disorder, a cancer, an infectious disease, a genetic disease, a disorder caused by aberrant mtDNA, a metabolic disease, a disorder caused by aberrant cell cycle, a disorder caused by aberrant angiogenesis, a disorder cause by aberrant DNA damage repair, or any combination thereof.

In some embodiments, the cancer is selected from the group consisting of colon cancer, rectal cancer, renal-cell carcinoma, liver cancer, non-small cell carcinoma of the lung, cancer of the small intestine, cancer of the esophagus, melanoma, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin lymphoma, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers, combinations of said cancers, and metastatic lesions of said cancers.

In some embodiments, the cancer is a hematologic cancer chosen from one or more of chronic lymphocytic leukemia (CLL), acute leukemias, acute lymphoid leukemia (ALL), B-cell acute lymphoid leukemia (B-ALL), T-cell acute lymphoid leukemia (T-ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, myelodysplasia and myelodysplastic syndrome, non-Hodgkin's lymphoma, Hodgkin's lymphoma, plasmablastic lymphoma, plasmacytoid dendritic cell neoplasm, Waldenstrom macroglobulinemia, or preleukemia.

The method can comprise: administering to the subject an oncolytic virus, radiation, an adoptive NK therapy, a stem cell transplant (SCT) therapy, and/or a chimeric antigen receptor (CAR) T cell therapy. The method can comprise: administering one or more additional agents to the subject (e.g., a prodrug or a pro-death agent). In some embodiments, the one or more additional agents comprise a protein phosphatase inhibitor, a kinase inhibitor, a cytokine, an inhibitor of an immune inhibitory molecule, and/or or an agent that decreases the level or activity of a TREG cell. In some embodiments, the one or more additional agents comprise an immune modulator, an anti-metastatic, a chemotherapeutic, a hormone or a growth factor antagonist, an alkylating agent, a TLR agonist, a cytokine antagonist, a cytokine antagonist, or any combination thereof. In some embodiments, the one or more additional agents comprise an agonistic or antagonistic antibody, or fragment thereof, specific to a checkpoint inhibitor or checkpoint stimulator molecule (e.g., PD1, PD-L1, PD-L2, CD27, CD28, CD40, CD137, OX40, GITR, ICOS, A2AR, B7-H3, B7-H4, BTLA, CTLA4, IDO, KIR, LAG3, PD-1, TIM-3).

In some embodiments, the one or more additional agents comprise a therapeutic agent useful for treating a disease of the GI tract (e.g., the disease of the GI tract is an inflammatory bowel disease). In some embodiments, the therapeutic agent useful for treating inflammatory bowel disease comprises one of the following classes of compounds: 5-aminosalicyclic acids, corticosteroids, thiopurines, tumor necrosis factor-alpha blockers and JAK inhibitors. In some embodiments, the therapeutic agent useful for treating inflammatory bowel disease comprises one or more of Prednisone, Humira, Lialda, Imuran, Sulfasalazine, Pentasa, Mercaptopurine, Azathioprine, Apriso, Simponi, Enbrel, Humira Crohn's Disease Starter Pack, Colazal, Budesonide, Azulfidine, Purinethol, Proctosol HC, Sulfazine EC, Delzicol, Balsalazide, Hydrocortisone acetate, Infliximab, Mesalamine, Proctozone-HC, Sulfazine, Orapred ODT, Mesalamine, Azasan, Asacol HD, Dipentum, Prednisone Intensol, Anusol-HC, Rowasa, Azulfidine EN-tabs, Veripred 20, Uceris, Adalimumab, Hydrocortisone, Colocort, Pediapred, Millipred, Azathioprine injection, Prednisolone sodium phosphate, Flo-Pred, Aminosalicylic acid, Procto-Cream-HC, 5-aminosalicylic acid, Millipred DP, Golimumab, Prednisolone acetate, Rayos, Proctocort, Paser, Olsalazine, Procto-Pak, Purixan, Cortenema, Giazo, Vedolizumab, Entyvio, Micheliolide, and Parthenolide.

In some embodiments, administering comprises aerosol delivery, nasal delivery, vaginal delivery, rectal delivery, buccal delivery, ocular delivery, local delivery, topical delivery, intracisternal delivery, intraperitoneal delivery, oral delivery, intramuscular injection, intravenous injection, subcutaneous injection, intranodal injection, intratumoral injection, intraperitoneal injection, intradermal injection, or any combination thereof.

BRIEF DESCRIPTION OF THE DRAWINGS

(FIG. 1A) Illustration of the genetic circuit used to characterize the behavior of temperature-sensitive repressors in *E. coli* Nissle 1917. (FIG. 1B) Optical density ($OD_{600}$)-normalized fluorescence as a function of induction temperature for a fixed duration of 1 hour, measured 24 hours after induction. To confirm that the resulting data is not driven by temperature driven changes to OD, wildtype EcN were similarly analyzed and displayed no temperature dependent fold change. Additionally, total cell count by flow cytometry was also used as a proxy for cell number and generated similar results to the ones collected by normalizing through OD as a proxy for cell count (FIG. 5). (FIG. 1C) OD-normalized fluorescence 24 hours after a 1-hour induction at 37° C. or 42° C. for the constructs shown in FIG. 1B. Measurements with values below the bottom of the y-axis appear below the axis. Bars indicate the mean. Vertical lines indicate the difference between the 42° C. and 37° C. conditions. Numbers indicate fold-change. (FIG. 1D) OD-normalized fluorescence as a function of induction duration. Cells were stimulated at 42° C. and fluorescence measured 24 hours later. (FIG. 1E) Illustration of the pulsatile heating scheme used to optimize thermal induction and cell viability. (FIG. 1F) OD-normalized fluorescence as a function of pulse duration for the TcI42 circuit. All samples were stimulated for a total of 1 hour at 42° C. and 1 hour at 37° C. and evaluated 24 hours later. Viable cell counts at various pulse durations plotted to reflect cell viability. Where not seen, error bars (±SEM) are smaller than the symbol. N=4 biological replicates for each sample. (FIG. 1G) A non-limiting exemplary schematic of a method of thermally activated sustained release of a therapeutic payload provided herein.

(FIG. 2A) Illustration of the genetic circuit constructed to establish a temperature responsive state switch. TetR is the tetracycline resistance cassette (See also FIG. 14). (FIG. 2B) Illustration of the sites targeted in a high throughput screen to optimize circuit switching. A representative fluorescence image of replica plates used to screen for circuit variants. Plates were incubated at the indicated temperature for one hour and further incubated at 37° C. until colonies grew large enough for analysis. The orange circle indicates an example colony selected for further assay. (FIG. 2C) Circuit variants from the screen in FIG. 2B characterized for their fluorescence at 37° C. and 42° C. (FIG. 2D) Percent conversion to the on-state 24 hours after a 1-hour thermal stimulation at 42° C. or 37° C. for five of the circuit variants from (FIG. 2C). Bars indicate the mean. Vertical lines indicate the difference between the 42° C. and 37° C. conditions. Numbers indicate fold-change. (FIG. 2E) Summary of rational modifications made to reduce leakage in the circuit at 37° C. (FIG. 2F) Percent induction 24 hours after a 1-hour of thermal induction at 42° C. compared to baseline incubation at 37° C. for four circuit variants described in FIG. 2E. Measurements with values below the bottom of the y-axis appear below the axis. Bars indicate the mean. Vertical lines indicate the difference between the 42° C. and 37° C. conditions. Numbers indicate fold-change.

(FIG. 3A) Temperature responsive state switch modified to release αCTLA-4 or αPD-L1 nanobodies (See also FIG. 12). The circuit includes an Axe-Txe stability cassette. (FIG. 3B) Percent activation 24 hours after a 1-hour of thermal induction at 37° C., 42° C. or 43° C. for the circuit described in FIG. 3A. (FIG. 3C) Western blot against hexahistidine-tagged αCTLA-4 nanobodies. Cells were induced for 1 hour at 37° C., 42° C. or 43° C., then expanded in 5 ml of media for 24 hours at 37° C. before collecting the media and assaying for the release of αCTLA-4 nanobodies. The original western blot image is shown in FIG. 6. Similar staining was done to confirm αPD-L1 release.

(FIG. 4A) Illustration of the automated setup used to deliver FUS hyperthermia to tumors (left) and representative time course of tumor temperature from a mouse treated with alternating 5-min steps between 37° C. and 43° C. (FIG. 4B) Diagram illustrating the experiment performed to assess the activation of microbial antitumor immunotherapy in vivo. Mice were injected with a 1:1 mixture of EcN cells carrying the αCTLA-4 or αPD-L1 circuits, or wildtype EcN. EcN cells were washed and adjusted to 0.625 $OD_{600}$ before injecting 100 μL per mouse intravenously. Ultrasound was applied for a total of 1 hour at 43° C. with 50% duty cycle and 5-min pulse duration. (FIG. 4C) Tumor sizes measured over two weeks in mice treated with wildtype EcN, therapeutic microbes in the absence of FUS, therapeutic microbes and FUS treatment, or FUS treatment alone. Asterisk represents statistical significance calculated with two-way ANOVA analysis where the therapy was compared to each of the controls with a Dunnett's multiple comparisons test. * plotted, p=[0.004(**), 0.0384(*), 0.0083()] when compared to [Wildtype, Therapeutic, FUS];  plotted, p=[<0.0001 for all]. (FIG. 4D) Percent activation of therapeutic EcN isolated from FUS-treated and non-FUS-treated tumors two weeks after FUS treatment One of the FUS-activated tumors disappeared after treatment and bacterial activation inside it could not be quantified. Results in (FIGS. 4C-4D) were collected from four independent experiments conducted on separate days with new cells transformed for each. Where not seen, error bars (±SEM) are smaller than the symbol. At least eight mice were analyzed for each control condition. Ten mice were analyzed for therapeutic condition, where three failed to activate. Data from nine therapeutic mice is displayed in panel (FIG. 4D) since the tenth disappeared and could not be analyzed. Asterisk represents statistical significance calculated with the Mann-Whitney test. (FIG. 4**E) Background activation in bystander tissues following FUS activation of tumors. Percent activation of therapeutic EcN isolated from FUS-treated tumors and bystander organs (liver, spleen). *, p=0.0286 (Tumor vs Liver) and 0.286 (Tumor vs Spleen). Statistical analysis was done with a Mann Whitney test.

(FIG. 5A) EcN cells carrying the TcI42 plasmid evaluated in FIG. 1B were analysed again, and their signal was normalized either with OD measurements or flow cytometry cell counts. (FIG. 5B) Raw measurement of $OD_{600}$ and cell count by flow cytometry. These results indicate that the fold changes observed is circuit activation are not a consequence of different OD measurements at different temperatures. Furthermore, normalizing by flow cytometry counts provided comparable results to OD normalization, validating that OD serves as a reasonable surrogate for total cells count.

(FIG. 10A) Results of testing the thermal switching circuit in *Salmonella* with wildtype lambda (cI) and TcI-42 using the same method as used in FIG. 1B. Cells were either stimulated for 1 hour or 12 hours. (FIG. 10B) Results of testing the thermal switching circuit in *Salmonella* using the same method as used in FIG. 2D. Optimal performance was observed when Tci-44 (a new variant with a higher switching threshold at around 44° C. in Nissle cells but around 42° C. in *Salmonella*) was used.

DETAILED DESCRIPTION

Figure 1A:
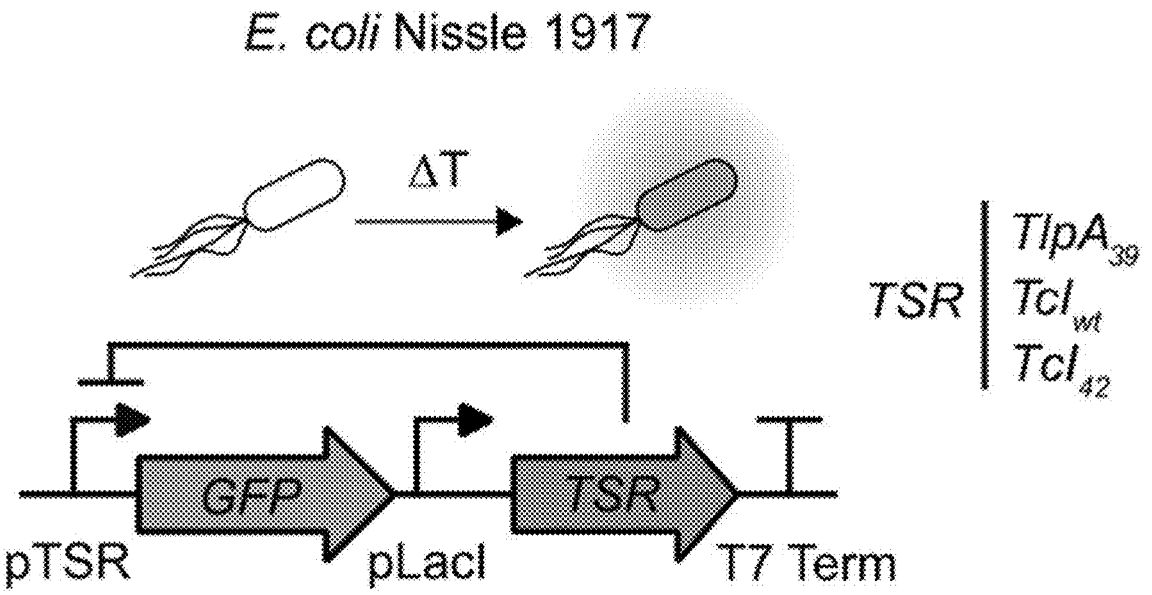
FIGS. 1A-1G depict data related to the evaluation of temperature-sensitive transcriptional repressors in *E. coli* Nissle 1917.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Disclosed herein include nucleic acid compositions. In some embodiments, the nucleic acid composition comprises:

a first promoter operably linked to a first polynucleotide comprising a recombinase gene, wherein the first promoter is capable of inducing transcription of the first polynucleotide to generate a recombinase transcript upon a thermal stimulation, and wherein the recombinase transcript is capable of being translated to generate a recombinase capable of catalyzing a recombination event; a second promoter and a second polynucleotide comprising a payload gene, wherein, in the absence of the recombination event, the second promoter and the second polynucleotide are not operably linked, and wherein the second promoter and the second polynucleotide are operably linked after the recombination event such that the second promoter is capable of inducing transcription of the second polynucleotide to generate a payload transcript.

Disclosed herein include compositions. In some embodiments, the composition comprises: a nucleic acid composition disclosed herein. Disclosed herein include thermally actuated probiotic cells. In some embodiments, the thermally actuated probiotic cell comprises: a nucleic acid composition disclosed herein or a composition disclosed herein.

Disclosed herein include methods for treating a disease or disorder in a subject. In some embodiments, the method comprises: introducing into one or more probiotic cells a nucleic acid composition disclosed herein or a composition disclosed herein, thereby generating one or more thermally actuated probiotic cells; and administering to the subject an effective amount of the thermally actuated probiotic cells.

Disclosed herein include methods for treating a disease or disorder in a subject. In some embodiments, the method comprises: administering to the subject an effective amount of the thermally actuated probiotic cells disclosed herein.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, NY 1994); Sambrook et al., Molecular Cloning, A Laboratory Manual, Cold Spring Harbor Press (Cold Spring Harbor, NY 1989). For purposes of the present disclosure, the following terms are defined below.

As used herein, the terms "nucleic acid" and "polynucleotide" are interchangeable and refer to any nucleic acid, whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sultone linkages, and combinations of such linkages. The terms "nucleic acid" and "polynucleotide" also specifically include nucleic acids composed of bases other than the five biologically occurring bases (adenine, guanine, thymine, cytosine and uracil).

The term "vector" as used herein, can refer to a vehicle for carrying or transferring a nucleic acid. Non-limiting examples of vectors include plasmids and viruses (for example, AAV viruses).

The term "construct," as used herein, refers to a recombinant nucleic acid that has been generated for the purpose of the expression of a specific nucleotide sequence(s), or that is to be used in the construction of other recombinant nucleotide sequences.

As used herein, the term "plasmid" refers to a nucleic acid that can be used to replicate recombinant DNA sequences within a host organism. The sequence can be a double stranded DNA.

The term "element" refers to a separate or distinct part of something, for example, a nucleic acid sequence with a separate function within a longer nucleic acid sequence. The term "regulatory element" and "expression control element" are used interchangeably herein and refer to nucleic acid molecules that can influence the expression of an operably linked coding sequence in a particular host organism. These terms are used broadly to and cover all elements that promote or regulate transcription, including promoters, core elements required for basic interaction of RNA polymerase and transcription factors, upstream elements, enhancers, and response elements (see, e.g., Lewin, "Genes V" (Oxford University Press, Oxford) pages 847-873). Exemplary regulatory elements in prokaryotes include promoters, operator sequences and a ribosome binding sites. Regulatory elements that are used in eukaryotic cells can include, without limitation, transcriptional and translational control sequences, such as promoters, enhancers, splicing signals, polyadenylation signals, terminators, protein degradation signals, internal ribosome-entry element (IRES), 2A sequences, and the like, that provide for and/or regulate expression of a coding sequence and/or production of an encoded polypeptide in a host cell.

As used herein, the term "promoter" is a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and mammals (including humans). A promoter can be inducible, repressible, and/or constitutive. Inducible promoters initiate increased levels of transcription from DNA under their control in response to some change in culture conditions, such as a change in temperature.

As used herein, the term "enhancer" refers to a type of regulatory element that can increase the efficiency of transcription, regardless of the distance or orientation of the enhancer relative to the start site of transcription.

As used herein, the term "operably linked" is used to describe the connection between regulatory elements and a gene or its coding region. Typically, gene expression is placed under the control of one or more regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element. For instance, a promoter is operably linked to a coding sequence if the promoter effects transcription or expression of the coding sequence.

The term "construct," as used herein, refers to a recombinant nucleic acid that has been generated for the purpose of the expression of a specific nucleotide sequence(s), or that is to be used in the construction of other recombinant nucleotide sequences.

As used herein, a "subject" refers to an animal that is the object of treatment, observation or experiment. "Animal" includes cold- and warm-blooded vertebrates and invertebrates such as fish, shellfish, reptiles, and in particular, mammals. "Mammal," as used herein, refers to an individual belonging to the class Mammalia and includes, but not limited to, humans, domestic and farm animals, zoo animals, sports and pet animals. Non-limiting examples of mammals include mice; rats; rabbits; guinea pigs; dogs; cats; sheep; goats; cows; horses; primates, such as monkeys, chimpanzees and apes, and, in particular, humans. In some embodiments, the mammal is a human. However, in some embodiments, the mammal is not a human.

As used herein, the term "treatment" refers to an intervention made in response to a disease, disorder or physiological condition manifested by a patient. The aim of treatment may include, but is not limited to, one or more of the alleviation or prevention of symptoms, slowing or stopping the progression or worsening of a disease, disorder, or condition and the remission of the disease, disorder or condition. The term "treat" and "treatment" includes, for example, therapeutic treatments, prophylactic treatments, and applications in which one reduces the risk that a subject will develop a disorder or other risk factor. Treatment does not require the complete curing of a disorder and encompasses embodiments in which one reduces symptoms or underlying risk factors. In some embodiments, "treatment" refers to both therapeutic treatment and prophylactic or preventative measures. Those in need of treatment include those already affected by a disease or disorder or undesired physiological condition as well as those in which the disease or disorder or undesired physiological condition is to be prevented. As used herein, the term "prevention" refers to any activity that reduces the burden of the individual later expressing those symptoms. This can take place at primary, secondary and/or tertiary prevention levels, wherein: a) primary prevention avoids the development of symptoms/disorder/condition; b) secondary prevention activities are aimed at early stages of the condition/disorder/symptom treatment, thereby increasing opportunities for interventions to prevent progression of the condition/disorder/symptom and emergence of symptoms; and c) tertiary prevention reduces the negative impact of an already established condition/disorder/symptom by, for example, restoring function and/or reducing any condition/disorder/symptom or related complications. The term "prevent" does not require the 100% elimination of the possibility of an event. Rather, it denotes that the likelihood of the occurrence of the event has been reduced in the presence of the compound or method.

As used herein, the term "effective amount" refers to an amount sufficient to effect beneficial or desirable biological and/or clinical results.

"Pharmaceutically acceptable" carriers are ones which are nontoxic to the cell or mammal being exposed thereto at the dosages and concentrations employed. "Pharmaceutically acceptable" carriers can be, but not limited to, organic or inorganic, solid or liquid excipients which is suitable for the selected mode of application such as oral application or injection, and administered in the form of a conventional pharmaceutical preparation, such as solid such as tablets, granules, powders, capsules, and liquid such as solution, emulsion, suspension and the like. Often the physiologically acceptable carrier is an aqueous pH buffered solution such as phosphate buffer or citrate buffer. The physiologically acceptable carrier may also comprise one or more of the following: antioxidants including ascorbic acid, low molecular weight (less than about 10 residues) polypeptides, proteins, such as serum albumin, gelatin, immunoglobulins; hydrophilic polymers such as polyvinylpyrrolidone, amino acids, carbohydrates including glucose, mannose, or dextrins, chelating agents such as EDTA, sugar alcohols such as mannitol or sorbitol, salt-forming counterions such as sodium, and nonionic surfactants such as Tween™, polyethylene glycol (PEG), and Pluronics™. Auxiliary, stabilizer, emulsifier, lubricant, binder, pH adjustor controller, isotonic agent and other conventional additives may also be added to the carriers.

The term "antibody fragment" shall be given its ordinary meaning, and shall also refers to at least one portion of an antibody, that retains the ability to specifically interact with (e.g., by binding, steric hindrance, stabilizing/destabilizing, spatial distribution) an epitope of an antigen. Examples of antibody fragments include, but are not limited to, Fab, Fab', $F(ab')_2$, Fv fragments, scFv antibody fragments, disulfide-linked Fvs (sdFv), a Fd fragment consisting of the VH and CH1 domains, linear antibodies, single domain antibodies such as sdAb (either VL or VH), camelid VHH domains, multi-specific antibodies formed from antibody fragments such as a bivalent fragment comprising two Fab fragments linked by a disulfide bridge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can also be grafted into scaffolds based on polypeptides such as a fibronectin type III (Fn3) (see U.S. Pat. No. 6,703,199, which describes fibronectin polypeptide minibodies).

Acoustic Remote Control of Microbial Immunotherapy

Cell therapies are rapidly emerging as one of the most exciting and effective technologies for cancer treatment. Among the cell types being investigated for therapy, immune cells have excelled in the treatment of hematologic malignancies. Unfortunately, these remarkable results have been challenging to reproduce in solid tumors where immune cells have reduced ability to penetrate and function due to an immunosuppressive environment, especially within immune-privileged hypoxic cores. Conversely, the absence of immune surveillance within the core of a subset of solid tumors creates an ideal environment for some microbes to thrive. By capitalizing on the natural tumor-homing property of certain bacterial strains, microbes can be engineered as effective cellular therapies that can home to otherwise inaccessible areas within tumors. Once deployed, engineered microbes can secrete therapeutic payloads to either directly kill tumor cells or enhance the native immune system's ability to eradicate the tumor by remodeling the tumor microenvironment. However, the benefits of microbial therapy are often counterbalanced by safety concerns accompanying the systemic injection of microbes into patients with limited control over their activity. This is especially important since microbes also engraft in healthy tissues, such as the liver, spleen, and certain hypoxic stem cell niches. To avoid damaging these tissues, it is crucial that the therapeutic activity of microbes is targeted to tumors.

Systemically administered chemical inducers are commonly used to control the function of microbes in vivo, but are incapable of targeting a particular anatomical site. Optically modulated control elements provide high spatiotemporal control over microbial activity, but are constrained by the poor penetration of light deep into tissues. Given the limitations of chemical and optical control methods, an alternative technology for spatiotemporal targeting in deep tissues is needed for optimal patient outcomes. Thermally actuated control elements are well suited to fill this technological gap since temperature can be elevated at arbitrary depth and with high spatial precision using noninvasive methods such as focused ultrasound (FUS). In recent work, it has been shown that by combining thermally responsive bioswitches with focused ultrasound hyperthermia the transcriptional activity of microbes can be spatiotemporally controlled at depth in vivo. However, these switches were implemented in cloning strains of bacteria, had non-therapeutic outputs, and resulted in a transient transcriptional activation that is not suitable for tumor treatment, which typically requires weeks of therapeutic activity.

Described herein is the development of FUS-controlled immunotherapeutic microbes in which a brief thermal stimulus activates sustained release of therapeutic payloads. The behavior of several temperature-sensitive repressors in the therapeutically relevant bacterium *E. coli* Nissle 1917 was first characterized, then the best repressor was combined with the serine integrase Bxb1 to develop a thermally activated state switch (Example 1). To improve the safety and clinical applicability of this switch, random and rationally designed libraries were screened and variants with minimal baseline activity and maximal induction upon stimulation were identified. The optimized switch from these screens was adapted to express anti-immunosuppression therapeutic proteins in a temperature-directed fashion. In a murine tumor model engineered microbes carrying this genetic circuit reliably switched states upon focal ultrasound activation and successfully suppressed the growth of tumors.

Rapid advances in synthetic biology are driving the development of genetically engineered microbes as therapeutic agents for a multitude of human diseases, including cancer. The immunosuppressive microenvironment of solid tumors, in particular, creates a favorable niche for systemically administered bacteria to engraft and release therapeutic payloads. However, such payloads can be harmful if released outside the tumor in healthy tissues where the bacteria also engraft in smaller numbers. To address this limitation, therapeutic bacteria were engineered to be controlled by focused ultrasound, a form of energy that can be applied noninvasively to specific anatomical sites such as solid tumors. This control is provided by a temperature-actuated genetic state switch that produces lasting therapeutic output in response to briefly applied focused ultrasound hyperthermia. Using a combination of rational design and high-throughput screening the switching circuits of engineered cells were optimized and connected their activity to the release of immune checkpoint inhibitors. In a clinically relevant cancer model, ultrasound-activated therapeutic microbes successfully turned on in situ and induced a marked suppression of tumor growth. This technology provides a critical tool for the spatiotemporal targeting of potent bacterial therapeutics in a variety of biological and clinical scenarios.

The systems, methods, compositions, and kits provided herein can, in some embodiments, be employed in concert with the methods, compositions, and kits suitable for use in the spatial and temporal delivery of payload molecules to a target site of a subject described in U.S. Patent Application Publication No. 2021/0138066, the content of which is incorporated herein by reference in its entirety.

The systems, methods, compositions, and kits provided herein can, in some embodiments, be employed in concert with methods, compositions, and kits suitable for use in spatiotemporal regulation of therapeutic T-cells through a combination of molecular and physical actuation described in U.S. Patent Application Publication No. 2021/0324389, the content of which is incorporated herein by reference in its entirety.

Nucleic Acid Compositions

There are provided, in some embodiments, nucleic acid compositions. In some embodiments, the nucleic acid composition comprises: a first promoter operably linked to a first polynucleotide comprising a recombinase gene, wherein the first promoter is capable of inducing transcription of the first polynucleotide to generate a recombinase transcript upon a thermal stimulation (e.g., at or above an activating temperature). The recombinase transcript can be capable of being translated to generate a recombinase capable of catalyzing a recombination event. The nucleic acid composition can comprise: a second promoter and a second polynucleotide comprising a payload gene. In some embodiments, in the absence of the recombination event, the second promoter and the second polynucleotide are not operably linked. The second promoter and the second polynucleotide can be operably linked after the recombination event such that the second promoter can be capable of inducing transcription of the second polynucleotide to generate a payload transcript.

The thermal stimulation can comprise heating to an activating temperature. The activating temperature can be above a physiological temperature. Thermal stimulation can comprise the application of one or more of focused ultrasound (FUS), magnetic hyperthermia, microwaves, infrared irradiation, liquid-based heating (e.g., intraperitoneal chemotherapy (HIPEC)), and contact heating. The activating temperature can be about 37.5° C., about 38.0° C., about 38.5° C., about 39.0° C., about 39.5° C., about 40.0° C., about 40.5° C., about 41.0° C., about 41.5° C., about 42.0° C., about 42.5° C., about 43.0° C., about 43.5° C., about 44.0° C., about 44.5° C., about 45.0° C., about 45.5° C., about 46.0° C., or a number or a range between any two of the values. The physiological temperature can be about 31.5° C., about 32.0° C., about 32.5° C., about 33.0° C., about 33.5° C., about 34.0° C., about 34.5° C., about 35.0° C., about 35.5° C., about 36.0° C., about 36.5° C., about 37.0° C., about 37.5° C., about 38.0° C., about 38.5° C., about 39.0° C., about 39.5° C., about 40.0° C., or a number or a range between any two of the values. In some embodiments, in the absence of the thermal stimulation, the recombinase reaches steady state protein levels in a probiotic cell insufficient to catalyze the recombination event.

In some embodiments, upon the thermal stimulation, transcription of the recombinase gene and/or payload gene is increased by at least about 1.1-fold (e.g., 1.1-fold, 1.3-fold, 1.5-fold, 1.7-fold, 1.9-fold, 2-fold, 3-fold, 4-fold, 5-fold, 6-fold, 7-fold, 8-fold, 9-fold, 10-fold, or a number or a range between any of these values). In some embodiments, upon the thermal stimulation, steady-state protein levels of the recombinase and/or payload is increased by at least about 1.1-fold (e.g., 1.1-fold, 1.3-fold, 1.5-fold, 1.7-fold, 1.9-fold, 2-fold, 3-fold, 4-fold, 5-fold, 6-fold, 7-fold, 8-fold, 9-fold, 10-fold, or a number or a range between any of these values). In some embodiments, increased expression of the payload(s) following the thermal stimulation is permanent. Expression levels can comprise transcript levels and/or protein levels.

Temperature-Sensitive Transcription Factors

The transcriptional activity of first promoter can be under the control of a temperature-sensitive transcription factor (e.g., a temperature-sensitive transcriptional repressor). At the physiological temperature, the temperature-sensitive transcriptional repressor can be capable of repressing transcription of the recombinase, thereby repressing expression of the payload(s). The nucleic acid composition can comprise: a third promoter operably linked to a third polynucleotide encoding a temperature-sensitive transcription factor. In some embodiments, two temperature-sensitive transcription factors are capable of associating to generate a temperature-sensitive transcription factor homodimer in the absence of the thermal stimulation. The two temperature-sensitive transcription factors can be incapable of associating to generate a temperature-sensitive transcription factor homodimer in the presence of the thermal stimulation (e.g., at or above an activating temperature).

The first promoter can comprise one or more operators. A temperature-sensitive transcription factor homodimer can be capable of binding the one or more operators. In some embodiments, upon the temperature-sensitive transcription factor homodimer binding the one or more operators, the first promoter is incapable of inducing transcription of the first polynucleotide. The first promoter can be incapable of inducing transcription of the first polynucleotide in the absence of the thermal stimulation. The first promoter can be capable of inducing transcription of the first polynucleotide in the absence of the temperature-sensitive transcription factor homodimer. A temperature-sensitive transcription factor monomer can have at least about 1.1-fold, 1.3-fold, 1.5-fold, 1.7-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, or 100-fold, or a number or a range between any two of the values, less binding affinity for the one or more operators as compared to a temperature-sensitive transcription factor homodimer. In some embodiments, a temperature-sensitive transcription factor monomer is not capable of binding the one or more operators. The first promoter can induce transcription of the first polynucleotide at least about 1.1-fold, 1.3-fold, 1.5-fold, 1.7-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, or a number or a range between any two of the values, less in the presence of a temperature-sensitive transcription factor homodimer as compared to a temperature-sensitive transcription factor monomer. In some embodiments, temperature-sensitive transcription factor homodimerization occurs with a dissociation constant ($K_d$) at least about 1.1-fold, 1.3-fold, 1.5-fold, 1.7-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, or a number or a range between any two of the values, lower in the presence of a physiological temperature as compared to in the presence of the thermal stimulation. The temperature-sensitive transcription factor can be a temperature-sensitive mutant of the bacteriophage lambda cI protein. The temperature-sensitive transcription factor can comprise wild-type TlpA, TlpA36, TlpA39, TcI, TcI42, TcI38, derivatives thereof, or any combination thereof.

In some embodiments, the circuits provided herein comprise two or more temperature-sensitive transcription factors configured to activate or repress transcription at different temperatures. In some embodiments, said two or more temperature-sensitive transcription factors can act on different promoters which regulate the expression of different recombinases (which in, turn, modulate the expression of different payload(s)).

Transcription factors in the sense of the disclosure can comprise transcription repression factor (also referred to as "repressor") and a transcription activation factor (also referred to as "activator"). The transcription repression factor binds to DNA regulatory sequence to repress the transcription of an encoded polynucleotide, thereby reducing the expression level of the encoded polynucleotide. The transcription activation factor binds to DNA regulatory sequence to promote the transcription of an encoded polynucleotide, thereby increasing the expression level of the encoded polynucleotide. In particular, a transcription regulatory factor has typically at least one DNA-binding domain that can bind to a DNA regulatory sequence such as an enhancer or a promoter. Some transcription factors bind to a DNA promoter sequence near the transcription start site to form the transcription initiation complex. Other transcription factors bind to other regulatory sequences, such as enhancer sequences, and can either stimulate or repress transcription of the related gene. Examples of transcription repression factors include TlpA, TetR, Lad, LambdaCI, PhlF, SrpR, QacI, BetR, LmrA, AmeR, LitR, met, and other identifiable by a skilled person, as well as homologues of known repression factors, that function in both prokarayotic and eukarayotic systems. Examples of transcription activation factors include AraC, LasR, LuxR, IpgC, MxiE, Gal4, GCN4, GR, SPl, CREB, etc as well as homologues of known activation factors, that function in both prokarayotic and eukarayotic systems.

"Temperature sensitive transcription factors" "thermal transcriptional bioswitches" or "transcriptional bioswitches" in the sense of the disclosure herein also indicated as "transcriptional bioswitches" are transcription factors that have a DNA-bound state or conformation in which the transcription factor is specifically bound to a corresponding DNA regulatory sequence through a DNA binding domain, and a DNA unbound state or conformation in which the transcription factor is not bound to a corresponding DNA regulatory sequence. In a temperature sensing transcription factor, the factor can convert from a DNA-bound state to a DNA-unbound state with reference to corresponding DNA regulatory sequence at an activating temperature.

In particular, temperature sensitive factors in the sense of the disclosure comprise transcriptional bioswitch dimers formed by two monomer proteins. The term "dimer" as used herein indicates a macromolecular complex formed by two polymers and in particular two polypeptides. In a dimer the two protein monomers bind to one another through covalent and/or non-covalent interactions as will be understood by a skilled person. Examples of non-covalent interactions comprise ionic bonds, Van der Waals interactions, polar interactions, salt bridges, coulombic attraction, coulombic repulsion, hydrophobic interaction, and others identifiable by a skilled person. An example of a non-covalently bound protein dimer is the enzyme reverse transcriptase. Examples of covalent interactions comprise any chemical bond that involves the sharing of electron pairs between such as disulfide bridges. Dimers in the sense of the disclosure can be homodimers and heterodimers. The term "homodimer" means a dimer consisting of two monomers with identical polymer sequence, and in particular two polypeptide or protein monomers with identical amino acid sequence.

In some embodiments herein described where the temperature sensitive transcription factor is a dimer, DNA binding domains of the temperature sensitive transcription factors can be configured to bind with a DNA regulatory sequence upon dimerization of the protein monomers, and therefore be dimerization dependent. The term "dimerization" refers to the process of forming a dimer of two monomers, for example two protein monomers. In particular, dimerization dependent DNA binding domains are configured so that dimerization of the monomer components strengthens the interactions of the domain with a corresponding DNA regulatory sequence, rendering the formation or dissociation of the dimers an intrinsic part of the regulatory mechanisms. Examples of dimerization-dependent DNA binding domains include helix-turn-helix DNA-binding domains or proteins such as tryptophan repressor, lambda Cro, lambda repressor fragment, catabolite gene activator protein (CAP) fragment. In particular, dimerization dependent DNA binding domains can bind to DNA sequences that are composed of two very similar "half-sites," typically also arranged symmetrically. This arrangement allows each protein monomer of the to make a nearly identical set of contacts and enormously increases the binding affinity. In some embodiments, dimerization dependent DNA binding domains are selected from helix-loop-helix, helix-turn-helix, zinc finger, leucine zipper, winged helix, winged helix turn helix, helix loop helix, HMG-box, Wor3 domain, OB-fold domain, immunoglobulin fold, B3 domain, TAL effector DNA-binding domain, and others recognizable by a skilled person. In some embodiments, of the transcriptional bioswitch dimers herein described, in each monomer protein the C-terminus of the dimerization dependent DNA binding domain is covalently attached to the N-terminus of the temperature sensitive domain.

The term "temperature-sensing domain" refers to a protein or a portion thereof having a sequence configured to provide structural lability in response to temperature changes.

In some embodiments, the temperature sensitive transcription factor is a coiled coil temperature interaction domain, and the temperature-sensing domain is a coiled coil temperature sensing domain comprising temperature sensing supercoiled motif of alpha-helical secondary structures. In particular, the term "coiled coil" indicates a structural motif in a protein in which two to seven alpha-helices are coiled together like the strands of a rope and interact with coiled coil structural motifs in one or more other proteins. Dimers and trimers are the most common types.

A representative example of coiled coil temperature sensitive transcription factors, is TlpA a transcriptional autorepressor from the virulence plasmid of *Salmonella typhimurium*. This protein contains an approximately 300 residue C-terminal coiled-coil domain that undergoes sharp, temperature-dependent uncoiling between 37° C. and 45° C., and an N-terminal DNA binding domain that, in its low-temperature dimeric state, blocks transcription from the ~50 bp TlpA operator/promoter. The TlpA operator is a strong promoter (88-fold stronger than $LacI^{Q}$) driven by the transcription factor $\sigma^{70}$. This promoter has bidirectional activity with identical thermal regulation in both orientations, but approximately 200-fold lower maximal expression in the reverse direction.

In some embodiments, the temperature sensitive transcription factor is a globular temperature sensitive factor, and the temperature-sensing domains contain two globular monomers forming a dimer by interactions between the C-terminal domains (CTDs) of the two monomers. The term "globular protein" indicates spherical, globe-like proteins induced by the proteins' tertiary structure, comprising a core interface and an exterior solvent-exposed face. The term "interface" as used herein in connection with globular temperature sensitive transcription factors, and in general with homodimers of the disclosure, indicates a portion of a monomer protein comprising amino acids involved in the cooperative binding of the monomer protein with the other monomer protein forming the homodimer. In particular in which the globular temperature sensing domain is a dimer of two monomers, each containing a globular structure having a core interface and exterior solvent exposed face. Each monomer interacts with the corresponding portion of the other monomer through chemical and/or physical interactions at the core interface to form a globular temperature sensitive transcription factor. In some embodiments, cooperative unfolding of the monomers results in a loss of the ability to correctly position the two halves of the DNA binding domain found at the N-termini of each protein monomer. Tuning of the thermal response curve can be achieved by modulating the affinity of the two monomers.

A representative example of a globular sensing domain is a temperature-sensitive variant of the bacteriophage λ repressor cI (mutant $cI^{857}$ containing an A67T mutations, herein referred to as TcI) acting on a tandem pR-pL operator-promoter. TcI repression has been modulated via large changes in temperature (e.g., steps from 30° C. to 42° C.), rather than a sharper switching. The cI repressor of bacteriophage λ is another example of a protein that binds to its operator sites cooperatively. The C-terminal domain of the repressor mediates dimerization as well as a dimer-dimer interaction that results in the cooperative binding of two repressor dimers to adjacent operator sites. Structural information is available for the isolated domains of the cI repressor and intact dimeric cI repressor bound to an operator sequence.

The TcI protein is composed of two structurally distinct domains that are tethered by a protease sensitive connector. The N-terminal DNA binding domain which contains a helix-turn-helix DNA-binding motif, is a compact alpha-helical domain that weakly self-associates to form a dimer. Dimers of the DNA binding domain recognize and bind to the operator sequences using this helix-turn-helix motif. The C-terminal domain, otherwise referred to as the "globular dimerization domain" or "globular domain" is a highly twisted beta-sheet structure that is responsible for establishing the essential dimer contacts and for mediating the higher-order dimer-dimer interactions that underlie cooperative binding to the DNA. In addition, the C-terminal domain performs a self-cleavage reaction, which is triggered in bacteriophage lambda when the lysogenic cell suffers DNA damage and depends upon an activated form of the bacterial RecA protein. This self-cleavage reaction inactivates the repressor by separating the N-terminal domain from the C-terminal domain. The connector which contains the cleavage site, consists of a small protease sensitive linker and the cleavage site region. Structurally the cleavage site region is an integral part of the C-terminal domain, forming a pair of antiparallel beta-strands that drapes across its surface. Cleavage occurs at a specific site (between Ala111 and Gly112) within a long loop (residues 106-126) that connects the antiparallel beta strands of the cleavage site region.

In some embodiments, a WT TcI has a threshold temperature of about 40° C. and mutating M1V, L65S, K68R, F115L, D126G, D188G in TcI ("$TcI_{38}$") generates a bioswitch with a threshold transcriptional activation centered at 38° C. In some embodiments, mutating K6N, S33T, Y61H, L119P, F122C ("$TcI_{42}$"), generates another bioswitch with a threshold transcriptional activation centered at 42° C.

The thermal transcriptional bioswitch herein described can encompass other proteins that operate on similar principles as TlpA or TcI. These include highly homologous proteins, such as the Coiled coil DNA binding protein KfrA, and engineered constructs such as a previously reported synthetic protein in which the Lambda cI binding domain is grafted onto the GCN4 coiled coil. Exemplary other temperature switches known or identifiable by a skilled person comprise cI mutant from Phage L1 (bioswitch temperature is between 35-38° C.; globular), cI mutant from Phage P1 (bioswitch temperature is ~40° C.; globular), c repressor from Phage Mu (bioswitch temperature is between 30° C.-42° C.), RheA (bioswitch temperature between 37° C.-41° C.; note: is a dimer, but switching does not seem to be caused by conversion to monomer), GmaR (bioswitch temperature between 22° C.-34° C.; structure is alpha-helical/random), Temperature Sensitive Lad variants: Gly187Ser (bioswitch temperature is 42° C.), Ala241Thr (bioswitch temperature is 40° C.), Gly265Asp (bioswitch temperature is 37° C.); alpha-helical C-terminal tetramerization domain). Temperature Sensitive TetR variants: High tetR expressors of G21E (bioswitch temperature is between 28° C. and 37° C.), A89D (bioswitch temperature is ~37° C.), I193N (bioswitch temperature is between 37° C.-42° C.). Low tetR expressors were repressed at all temperatures, and RovA (bioswitch temperature is between 25° C. and 37° C.; structure is alpha-helical/beta-sheet/random). Additional temperature sensitive switches capable of being used in temperature sensitive genetic circuit herein described, are identifiable by a skilled person.

Recombinases

The recombination event can comprise removal of a sequence flanked by recombinase target sites or an inversion of a sequence flanked by recombinase target sites. In some embodiments, after the recombination event, the recombinase target sites are modified such that said modified recombinase target sites are not capable of interacting with the recombinase to yield another recombination event, thereby rendering the recombination event permanent. The recombination event can be an inversion event. The second polynucleotide can comprise and/or be flanked by recombinase target sites. In some embodiments, prior to the recombination event, the sequence of the payload gene is inverted relative to the second promoter. The nucleic acid composition can comprise: at least one stop cassette situated between the second promoter and the payload gene, wherein the stop cassette comprises one or more stop sequences, and wherein the one or more stop cassettes are flanked by recombinase target sites. The payload transcript can be capable of being translated to generate a payload protein. The at least one stop cassette can be configured to prevent transcription of the payload gene and/or translation of the payload transcript. The one or more stop sequences can comprise a polyadenylation signal, a stop codon, a frame-shifting mutation, or any combination thereof. The recombination event can comprise removal of the stop cassette. In some embodiments, one or more payloads is expressed in the absence of a recombination event, and upon thermal stimulation, a recombination event triggers the permanent non-expression of said payloads (e.g., the recombination event generates a non-operable linkage between a promoter and said payload).

The recombinase can be or can comprise Cre, Dre, Flp, KD, B2, B3, λ, HK022, HP1, γ6, ParA, Tn3, Gin, ΦC31, FimB, FimE, TP091, Bxb1, ΦBT1, phiC31, RV-1, AA118, U 153, ΦFC1, R4, derivatives thereof, or any combination thereof. The recombinase can be a Bxb1 and the recombinase target sites can comprise attP and/or attB sites. The recombinase can be a Flp recombinase and the recombinase target sites can be FRT sites. The recombinase can be a Cre recombinase and the recombinase target sites can be loxP sites. As used herein, the term "lox site" refers to a nucleotide sequence at which the product of the ere gene of bacteriophage PI, Cre recombinase, can catalyze a site-specific recombination. A variety of lox sites are known to the art including but not limited to the naturally occurring loxP (the sequence found in the PI genome), loxB, loxL and loxR (these are found in the *E. coli* chromosome) as well as a number of mutant or variant lox sites such as loxP511, lox2272, loxA86, loxA117, loxC2, loxP2, loxP3 and loxP23. The term "frt site" as used herein refers to a nucleotide sequence at which the product of the FLP gene of the yeast 2 pm plasmid, FLP recombinase, can catalyze a site-specific recombination.

The term "recombinase," as used herein, refers to a site-specific enzyme that mediates the recombination of DNA between recombinase recognition sequences (e.g., recombinase target sites), which results in the excision, integration, inversion, or exchange (e.g., translocation) of DNA fragments between the recombinase recognition sequences. Recombinases can be classified into two distinct families: serine recombinases (e.g., resolvases and invertases) and tyrosine recombinases (e.g., integrases). Examples of serine recombinases include, without limitation, Hin, Gin, Tn3, β-six, CinH, ParA, yδ, Bxb1, ϕC31, TP901, TG1, φBT1, R4, φRV1, φFC1, MR11, A118, U153, and gp29. Examples of tyrosine recombinases include, without limitation, Cre, FLP, R, Lambda, HK101, HK022, and pSAM2. The term "recombine" or "recombination," in the context of a nucleic acid modification (e.g., a genomic modification), is used to refer to the process by which two or more nucleic acid molecules, or two or more regions of a single nucleic acid molecule, are modified by the action of a recombinase protein. Recombination can result in, inter alia, the insertion, inversion, excision, or translocation of a nucleic acid sequence, e.g., in or between one or more nucleic acid molecules. As used herein, the term "recombination site sequences" or "recombinase target sites" refers to short polynucleic acid sequences, typically palindromic, that are specifically recognized and acted upon by a DNA recombinase. DNA recombinase/recombination site sequence pairs include, but are not limited to, Cre/loxP, Dre/rox, VCre/VloxP, SCre/SloxP, Vika/vox, λ-int/attP, Flp/FRT, R/RRT, Kw/KwRT, Kd/KdRT, B2/B2RT, and B3/B3RT.

The first polynucleotide, recombinase transcript, and/or recombinase can comprise one or more elements capable of being tuned to modulate recombinase translation and stability. The one or more elements can comprise one or more of a ribosomal binding sequence (RBS), a start codon, and a degradation tag. In some embodiments, the recombinase transcript coding sequence begins with a non-canonical start codon capable of reducing ribosomal efficiency (e.g., [GUG]). The recombinase transcript can comprise a ribosomal binding sequence (RBS). The efficiency of translation can be capable of being tuned by varying the sequence of the RBS. The RBS can comprise a nucleotide sequence that is at least 80%, 85%, 90%, 95%, 98%, 99%, or 100% identical to SEQ ID NO: 7 [ATCCTATCGGTATG] or SEQ ID NO: 8 [CTACAATCGGTATG], or a complement thereof. The recombinase can comprise a degradation tag (e.g., a C-terminal degradation tag). The degradation rate of the recombinase can be capable of being tuned by varying the sequence of the degradation tag (e.g., the last three amino acids of the degradation tag). The degradation tag can comprise a ssrA degradation tag. The ssrA degradation tag can comprise an amino acid sequence that is at least 80%, 85%, 90%, 95%, 98%, 99%, or 100% identical to SEQ ID NO: 9 [GSAANDENYAAHR] or to SEQ ID NO: 10 [GSAANDENYAAPY], or a complement thereof. The first polynucleotide and/or recombinase transcript can comprise a temperature-sensitive terminator upstream of the recombinase coding sequence. The temperature-sensitive terminator can be a temperature-modulated structure. The temperature-sensitive terminator can comprise, can be derived from, or can be configured to mimic, an RNA thermometer. The temperature-sensitive terminator can comprise a temperature-sensitive secondary structure capable of terminating protein expression at a temperature below the activating temperature. The temperature below the activating temperature can be the physiological temperature. The temperature-sensitive secondary structure can be lost at or above the activating temperature. The temperature-sensitive terminator can comprise a nucleotide sequence that is at least 80%, 85%, 90%, 95%, 98%, 99%, or 100% identical to SEQ ID NO: 11 [ATGACTTACTTGCTGAATCTCAGGAGTTTATGACCTTTTTTTTTT], or a complement thereof.

In some embodiments, a circuit comprises a plurality of pairs of recombinase target sites, and upon thermal stimulation, a plurality of recombination events can occur (at each pair of recombinase target sites). This plurality of recombination events can lead to the permanent expression of payloads situated adjacent to said recombinase target sites. A plurality of payloads can accordingly be regulated via a plurality of recombination events.

Promoters

The one or more operators can be selected from the group comprising TlpA operator/promoter, lambda phage OR1, lambda phage OR2, lambda phage OR3, lambda phage OL1, lambda phage OL2 and lambda phage OL3. The first promoter can comprise the TlpA operator/promoter, lambda phage pL, lambda phage pR, lambda phage pRM, or any combination thereof. The first promoter, second promoter, and/or third promoter can comprise at least one −10 element and/or at least one −35 element.

The first promoter, second promoter, and/or third promoter can be a promoter selected from the group comprising: a bacteriophage promoter (e.g., Pls1con, T3, T7, SP6, or PL); a bacterial promoter (e.g., Pbad, PmgrB, Ptrc2, Plac/ara, Ptac, or Pm); and/or a bacterial-bacteriophage hybrid promoter (e.g., PLlacO or PLtetO).

The first promoter, second promoter, and/or third promoter can be a positively regulated *E. coli* promoter selected from the group comprising: a σ70 promoter (e.g., inducible pBad/araC promoter, Lux cassette right promoter, modified lamdba Prm promoter, plac Or2-62 (positive), pBad/AraC with extra REN sites, pBad, P(Las) TetO, P(Las) CIO, P(Rhl), Pu, FecA, pRE, cadC, hns, pLas, or pLux); a σS promoter (e.g., Pdps); a σ32 promoter (e.g., heat shock); and/or a σ54 promoter (e.g., glnAp2). The first promoter, second promoter, and/or third promoter can be a negatively regulated *E. coli* promoter selected from the group comprising: a σ70 promoter (e.g., Promoter (PRM+), modified lamdba Prm promoter, TetR-TetR-4C P(Las) TetO, P(Las) CIO, P(Lac) IQ, RecA_DlexO_DLacO1, dapAp, FecA, Pspac-hy, pcI, plux-cI, plux-lac, CinR, CinL, glucose controlled, modified Pr, modified Prm+, FecA, Pcya, rec A (SOS), Rec A (SOS), EmrR_regulated, BetI_regulated, pLac_lux, pTet_Lac, pLac/Mnt, pTet/Mnt, LsrA/cI, pLux/cI, Lad, LacIQ, pLacIQ1, pLas/cI, pLas/Lux, pLux/Las, pRecA with LexA binding site, reverse BBa_R0011, pLacI/ara-1, pLacIq, rrnB P1, cadC, hns, PfhuA, pBad/araC, nhaA, OmpF, or RcnR); a σS promoter (e.g., Lutz-Bujard LacO with alternative sigma factor σ38); a σ32 promoter (e.g., Lutz-Bujard LacO with alternative sigma factor σ32); and/or a σ54 promoter (e.g., glnAp2).

The first promoter, second promoter, and/or third promoter can be P7 promoter. The first promoter, second promoter, and/or third promoter can be a heat-shock promoter (e.g., pTSR, pR-pL, GrpE, HtpG, Lon, RpoH, Clp, and/or DnaK). The first promoter, second promoter, and/or third promoter can be a constitutive promoter selected from the group comprising: a constitutive *Escherichia coli* σ S promoter (e.g., osmY promoter (BBa_J45993)); a constitutive *Escherichia coli* σ 32 promoter (e.g., htpG heat shock promoter (BBa_J45504)); a constitutive *Escherichia coli* σ 70 promoter (e.g., lacq promoter (BBa_J54200 or BBa_J56015), *E. coli* CreABCD phosphate sensing operon promoter (BBa_J64951), GlnRS promoter (BBa_K088007), lacZ promoter (BBa_K119000 or BBa_K119001), M13K07 gene I promoter (BBa_M13101), M13K07 gene II promoter (BBa_M13102), M13K07 gene III promoter (BBa_M13103), M13K07 gene IV promoter (BBa_M13104), M13K07 gene V promoter (BBa_M13105), M13K07 gene VI promoter (BBa_M13106), M13K07 gene VIII promoter (BBa_M13108), or M13110 (BBa_M13110)); a constitutive *Bacillus subtilis* σ A promoter (e.g., promoter veg (BBa_K143013), promoter 43 (BBa_K143013), PliaG (BBa_K823000), PlepA (BBa_K823002), or Pveg (BBa_K823003)); a constitutive *Bacillus subtilis* σ B promoter (e.g., promoter ctc (BBa_K143010) or promoter gsiB (BBa_K143011)), a *Salmonella* promoter (e.g., Pspv2 from *Salmonella* (BBa_K112706) or Pspv from *Salmonella* (BBa_K112707)); a bacteriophage T7 promoter (e.g., BBa_I712074, BBa_I719005, BBa_J34814, BBa_J64997, BBa_K113010, BBa_K113011, BBa_K113012, BBa_R0085, BBa_R0180, BBa_R0181, BBa_R0182, BBa_R0183, BBa_Z0251, BBa_Z0252, or BBa_Z0253); and/or a bacteriophage SP6 promoter (e.g., SP6 promoter (BBa_J64998)).

The nucleic acid composition can comprise: one or more terminators. The one or more terminators can be positioned upstream of the first promoter, second promoter, and/or third promoter. The terminator can be selected from the group comprising SV40 terminator, spy terminator, yejM terminator, secG-leuU terminator, thrLABC terminator, rrnB T1 terminator, rrnB T2 terminator, hisLGDCBHAFI terminator, metZWV terminator, Csrc terminator, rrnC terminator, xapR terminator, aspA terminator, trp terminator, arcA terminator, bacteriophage lambda terminator, derivatives thereof, or any combination thereof. The terminator can be a rho-independent terminator or rho-dependent terminator. Terminators are sequences that usually occur at the end of a gene or operon and cause transcription to stop, and are also provided for use in the modules and digital-to-analog and analog-to-digital biological converter switches described herein to regulate transcription and prevent transcription from occurring in an unregulated fashion, i.e., a terminator sequence prevents activation of downstream modules by upstream promoters. A “terminator” or “termination signal”, as described herein, is comprised of the DNA sequences involved in specific termination of an RNA transcript by an RNA polymerase. Thus, in certain embodiments a terminator that ends the production of an RNA transcript is contemplated.

Thermal Switching Circuit Components

The nucleic acid compositions (e.g., thermal switching circuits) provided herein can comprise one or more components/features (e.g., first promoter, second promoter, third promoter, recombinase, payload, terminator, operators) of the αPD-L1 Thermal Switching Circuit (SEQ ID NO: 1), αCLTA-4 Thermal Switching Circuit (SEQ ID NO: 2), Thermal Switching Circuit Library Screen Plasmid Design (SEQ ID NO: 3), Thermal Switching Circuit Library Screen Parent Plasmid (SEQ ID NO: 4), Thermal Switching Circuit Library Screen Hit #2 (SEQ ID NO: 5), Thermal Switching Circuit Library Screen Hit #7 (SEQ ID NO: 6), which are shown in FIGS. 11-16 and listed in Tables 1-6, respectively. Provided herein are nucleic acids that are at least 80%, 85%, 90%, 95%, 98%, 99%, or 100% identical to SEQ ID NOS: 1-6, portions thereof, and/or complements thereof. Also provided herein are nucleic acids that comprise at least about 5 consecutive nucleotides (e.g., about 5 nt, about 10 nt, about 15 nt, about 20 nt, 25 nt, 30 nt, 35 nt, 40 nt, 45 nt, 50 nt, 60 nt, 70 nt, 80 nt, 90 nt, 100 nt, 110 nt, 120 nt, 128 nt, 130 nt, 140 nt, 150 nt, 160 nt, 170 nt, 180 nt, 190 nt, 200 nt, 210 nt, 220 nt, 230 nt, 240 nt, 250 nt, 260 nt, 270 nt, 280 nt, 290 nt, 300 nt, 310 nt, 320 nt, 330 nt, 340 nt, 350 nt, 360 nt, 370 nt, 380 nt, 390 nt, 400 nt, 410 nt, 420 nt, 430 nt, 440 nt, 450 nt, 460 nt, 470 nt, 480 nt, 490 nt, 500 nt, 510 nt, 520 nt, 530 nt, 540 nt, 550 nt, 560 nt, 570 nt, 580 nt, 590 nt, 600 nt, 610 nt, 620 nt, 630 nt, 640 nt, 650 nt, 660 nt, 670 nt, 680 nt, 690 nt, 700 nt, 710 nt, 720 nt, 730 nt, 740 nt, 750 nt, 760 nt, 770 nt, 780 nt, 790 nt, 800 nt, 810 nt, 820 nt, 830 nt, 840 nt, 850 nt, 860 nt, 870 nt, 880 nt, 890 nt, 900 nt, 910 nt, 920 nt, 930 nt, 940 nt, 950 nt, 960 nt, 970 nt, 980 nt, 990 nt, 10000 nt, 50000 nt, or a number or a range between any two of these values) of a sequence described by SEQ ID NOS: 1-6, or a complement thereof. The sequence identity between a component/feature (e.g., first promoter, second promoter, third promoter, recombinase, payload, terminator, operators) of the disclosed thermal switching circuits and the sequence of a feature of any one of SEQ ID NOS: 1-6 can be, or be about, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values.

TABLE 1

αPD-L1 Thermal Switching Circuit (SEQ ID NO: 1)

| Feature Name | Location | Size (bp) | Directionality | Type |
|---|---|---|---|---|
| PD-L1 | 80 . . . 535 | 456 | => | CDS |
| pelB signal sequence | 80 . . . 145 | 66 | => | sig_peptide |
| 6xHis | 515 . . . 532 | 18 | => | CDS |
| Superfolder GFP | 564 . . . 1283 | 720 | => | CDS |
| hisLGDCBHAFI term | 1326 . . . 1378 | 53 | => | misc_feature |
| T1 transcriptional terminator from rrnB operon | 1470 . . . 1574 | 105 | => | misc_feature |
| pRM Promoter | 1681 . . . 1710 | 30 | <= | promoter |
| Operator OR3 | 1681 . . . 1697 | 17 | == | misc_feature |
| −10 | 1681 . . . 1682 | 2 | == | −10_signal |
| −35 | 1700 . . . 1705 | 6 | == | −35_signal |
| Operator OR2 | 1704 . . . 1710 | 7 | == | misc_feature |
| pR promoter | 1711 . . . 1769 | 59 | => | promoter |
| Operator OR2 | 1711 . . . 1720 | 10 | == | misc_feature |
| −35 | 1718 . . . 1724 | 7 | == | −35_signal |
| Operator OR1 | 1728 . . . 1744 | 17 | == | misc_feature |
| −10 | 1740 . . . 1746 | 7 | == | −10_signal |
| 1 | 1753 . . . 1753 | 1 | == | misc_feature |
| Operator OL3 | 1899 . . . 1915 | 17 | == | misc_feature |
| Operator OL2 | 1919 . . . 1935 | 17 | == | misc_feature |
| pL Promoter | 1926 . . . 1976 | 51 | => | promoter |
| Operator OL1 | 1943 . . . 1959 | 17 | == | misc_feature |
| Temp term | 2006 . . . 2050 | 45 | == | misc_feature |
| Bxb1 Integrase | 2064 . . . 3596 | 1533 | => | CDS |
| Degradation tag | 3564 . . . 3596 | 33 | => | CDS |
| lacI promoter | 3641 . . . 3718 | 78 | => | promoter |
| RBS | 3726 . . . 3731 | 6 | == | RBS |
| lambda repressor (ts) | 3740 . . . 4453 | 714 | => | CDS |
| K6N | 3755 . . . 3757 | 3 | == | misc_feature |
| S33T | 3836 . . . 3838 | 3 | == | misc_feature |
| L51 Conservative | 3890 . . . 3890 | 1 | == | misc_feature |
| Y61H | 3920 . . . 3922 | 3 | == | misc_feature |
| L119P | 4094 . . . 4096 | 3 | == | misc_feature |
| F122C | 4103 . . . 4105 | 3 | == | misc_feature |
| T7 terminator | 4562 . . . 4609 | 48 | => | terminator |
| p15A | 4677 . . . 4678 | 2 | <= | rep_origin |
| Axe-Txe | 4679 . . . 5890 | 1212 | == | misc_feature |
| p15A | 5910 . . . 6706 | 797 | => | rep_origin |
| Csrc Term | 6824 . . . 6883 | 60 | <= | misc_feature |
| NeoR/KanR | 6914 . . . 7708 | 795 | <= | CDS |
| Bxb1 attB | 8096 . . . 8145 | 50 | == | misc_feature |
| P7 promoter | 8152 . . . 8198 | 47 | <= | promoter |
| Bxb1 AttP | 8199 . . . 8251 | 53 | == | misc_feature |
| Ribo J | 8252 . . . 30 | 75 | == | misc_feature |

TABLE 2

αCLTA-4 Thermal Switching Circuit (SEQ ID NO: 2)

| Feature Name | Location | Size (bp) | Directionality | Type |
|---|---|---|---|---|
| CTLA-4 | 80 . . . 532 | 453 | => | CDS |
| pelB signal sequence | 80 . . . 145 | 66 | => | sig_peptide |
| 6xHis | 512 . . . 529 | 18 | => | CDS |
| Superfolder GFP | 561 . . . 1280 | 720 | => | CDS |
| hisLGDCBHAFI term | 1323 . . . 1375 | 53 | => | misc_feature |
| T1 transcriptional terminator from rrnB operon | 1467 . . . 1571 | 105 | => | misc_feature |
| pRM Promoter | 1678 . . . 1707 | 30 | <= | promoter |
| Operator OR3 | 1678 . . . 1694 | 17 | == | misc_feature |
| −10 | 1678 . . . 1679 | 2 | == | −10_signal |
| −35 | 1697 . . . 1702 | 6 | == | −35_signal |
| Operator OR2 | 1701 . . . 1707 | 7 | == | misc_feature |
| pR promoter | 1708 . . . 1766 | 59 | => | promoter |
| Operator OR2 | 1708 . . . 1717 | 10 | == | misc_feature |
| −35 | 1715 . . . 1721 | 7 | == | −35_signal |
| Operator OR1 | 1725 . . . 1741 | 17 | == | misc_feature |
| −10 | 1737 . . . 1743 | 7 | == | −10_signal |
| 1 | 1750 . . . 1750 | 1 | == | misc_feature |
| Operator OL3 | 1896 . . . 1912 | 17 | == | misc_feature |
| Operator OL2 | 1916 . . . 1932 | 17 | == | misc_feature |
| pL Promoter | 1923 . . . 1973 | 51 | => | promoter |
| Operator OL1 | 1940 . . . 1956 | 17 | == | misc_feature |
| Temp term | 2003 . . . 2047 | 45 | == | misc_feature |
| Bxb1 Integrase | 2061 . . . 3593 | 1533 | => | CDS |
| Degradation tag | 3561 . . . 3593 | 33 | => | CDS |
| lacI promoter | 3638 . . . 3715 | 78 | => | promoter |
| RBS | 3723 . . . 3728 | 6 | == | RBS |
| lambda repressor (ts) | 3737 . . . 4450 | 714 | => | CDS |
| K6N | 3752 . . . 3754 | 3 | == | misc_feature |
| S33T | 3833 . . . 3835 | 3 | == | misc_feature |
| L51 Conservative | 3887 . . . 3887 | 1 | == | misc_feature |
| Y61H | 3917 . . . 3919 | 3 | == | misc_feature |
| L119P | 4091 . . . 4093 | 3 | == | misc_feature |
| F122C | 4100 . . . 4102 | 3 | == | misc_feature |
| T7 terminator | 4559 . . . 4606 | 48 | => | terminator |
| p15A | 4674 . . . 4675 | 2 | <= | rep_origin |
| Axe-Txe | 4676 . . . 5887 | 1212 | == | misc_feature |
| p15A | 5907 . . . 6703 | 797 | => | rep_origin |
| Csrc Term | 6821 . . . 6880 | 60 | <= | misc_feature |
| NeoR/KanR | 6911 . . . 7705 | 795 | <= | CDS |
| Bxb1 attB | 8093 . . . 8142 | 50 | == | misc_feature |
| P7 promoter | 8149 . . . 8195 | 47 | <= | promoter |
| Bxb1 AttP | 8196 . . . 8248 | 53 | == | misc_feature |
| Ribo J | 8249 . . . 30 | 75 | == | misc_feature |

TABLE 3

Thermal Switching Circuit Library Screen Plasmid Design (SEQ ID NO: 3)

| Feature Name | Location | Size (bp) | Directionality | Type |
|---|---|---|---|---|
| pSC101 insertion | 5 . . . 17 | 13 | <= | misc_feature |
| Csrc Term | 113 . . . 172 | 60 | <= | misc_feature |
| NeoR/KanR | 203 . . . 997 | 795 | <= | CDS |
| Bxb1 attB | 1385 . . . 1434 | 50 | == | misc_feature |
| P7 promoter | 1441 . . . 1487 | 47 | <= | promoter |
| Bxb1 AttP | 1488 . . . 1540 | 53 | == | misc_feature |
| Ribo J | 1541 . . . 1615 | 75 | == | misc_feature |
| BCD2_apFAB682 | 1616 . . . 1703 | 88 | == | misc_feature |
| Superfolder GFP | 1704 . . . 2420 | 717 | => | CDS |
| TcR | 2471 . . . 3661 | 1191 | => | CDS |
| hisLGDCBHAFI term | 3704 . . . 3756 | 53 | => | misc_feature |
| T1 transcriptional terminator from rrnB operon | 3848 . . . 3952 | 105 | => | misc_feature |
| pRM Promoter | 4059 . . . 4088 | 30 | <= | promoter |
| Operator OR3 | 4059 . . . 4075 | 17 | == | misc_feature |
| −10 | 4059 . . . 4060 | 2 | == | −10_signal |
| −35 | 4078 . . . 4083 | 6 | == | −35_signal |
| Operator OR2 | 4082 . . . 4098 | 17 | == | misc_feature |
| pR promoter | 4089 . . . 4147 | 59 | => | promoter |
| −35 | 4096 . . . 4102 | 7 | == | −35_signal |
| Operator OR1 | 4106 . . . 4122 | 17 | == | misc_feature |

TABLE 3-continued

Thermal Switching Circuit Library Screen Plasmid Design (SEQ ID NO: 3)

| Feature Name | Location | Size (bp) | Directionality | Type |
|---|---|---|---|---|
| −10 | 4118 . . . 4124 | 7 | == | −10_signal |
| 1 | 4131 . . . 4131 | 1 | == | misc_feature |
| Operator OL3 | 4277 . . . 4293 | 17 | == | misc_feature |
| Operator OL2 | 4297 . . . 4313 | 17 | == | misc_feature |
| pL Promoter | 4304 . . . 4354 | 51 | => | promoter |
| Operator OL1 | 4321 . . . 4337 | 17 | == | misc_feature |
| RBS | 4453 . . . 4454 | 2 | == | misc_feature |
| Bxb1 Integrase | 4466 . . . 5998 | 1533 | => | CDS |
| Degradation tag | 5966 . . . 5998 | 33 | => | CDS |
| lacI promoter | 6043 . . . 6120 | 78 | => | promoter |
| RBS | 6128 . . . 6133 | 6 | == | RBS |
| lambda repressor (ts) | 6142 . . . 6855 | 714 | => | CDS |
| K6N | 6157 . . . 6159 | 3 | == | misc_feature |
| S33T | 6238 . . . 6240 | 3 | == | misc_feature |
| L51 Conservative | 6292 . . . 6292 | 1 | == | misc_feature |
| Y61H | 6322 . . . 6324 | 3 | == | misc_feature |
| L119P | 6496 . . . 6498 | 3 | == | misc_feature |
| F122C | 6505 . . . 6507 | 3 | == | misc_feature |
| T7 terminator | 6964 . . . 7011 | 48 | => | terminator |
| pSC101 | 7042 . . . 17 | 2037 | == | misc_feature |
| pSC101 insertion | 5 . . . 17 | 13 | <= | misc_feature |
| Csrc Term | 113 . . . 172 | 60 | <= | misc_feature |
| NeoR/KanR | 203 . . . 997 | 795 | <= | CDS |

TABLE 4

Thermal Switching Circuit Library Screen Parent Plasmid (SEQ ID NO: 4)

| Feature Name | Location | Size (bp) | Directionality | Type |
|---|---|---|---|---|
| pSC101 insertion | 5 . . . 17 | 13 | <= | misc_feature |
| Csrc Term | 113 . . . 172 | 60 | <= | misc_feature |
| NeoR/KanR | 203 . . . 997 | 795 | <= | CDS |
| Bxb1 attB | 1385 . . . 1434 | 50 | == | misc_feature |
| P7 promoter | 1441 . . . 1487 | 47 | <= | promoter |
| Bxb1 AttP | 1488 . . . 1540 | 53 | == | misc_feature |
| Ribo J | 1541 . . . 1615 | 75 | == | misc_feature |
| BCD2_apFAB682 | 1616 . . . 1703 | 88 | == | misc_feature |
| Superfolder GFP | 1704 . . . 2420 | 717 | => | CDS |
| TcR | 2471 . . . 3661 | 1191 | => | CDS |
| hisLGDCBHAFI term | 3704 . . . 3756 | 53 | => | misc_feature |
| T1 transcriptional terminator from rrnB operon | 3848 . . . 3952 | 105 | => | misc_feature |
| pRM Promoter | 4059 . . . 4088 | 30 | <= | promoter |
| Operator OR3 | 4059 . . . 4075 | 17 | == | misc_feature |
| −10 | 4059 . . . 4060 | 2 | == | −10_signal |
| −35 | 4078 . . . 4083 | 6 | == | −35_signal |
| Operator OR2 | 4082 . . . 4098 | 17 | == | misc_feature |
| pR promoter | 4089 . . . 4147 | 59 | => | promoter |
| −35 | 4096 . . . 4102 | 7 | == | −35_signal |
| Operator OR1 | 4106 . . . 4122 | 17 | == | misc_feature |
| −10 | 4118 . . . 4124 | 7 | == | −10_signal |
| 1 | 4131 . . . 4131 | 1 | == | misc_feature |
| Operator OL3 | 4277 . . . 4293 | 17 | == | misc_feature |
| Operator OL2 | 4297 . . . 4313 | 17 | == | misc_feature |
| pL Promoter | 4304 . . . 4354 | 51 | => | promoter |
| Operator OL1 | 4321 . . . 4337 | 17 | == | misc_feature |
| RBS | 4453 . . . 4454 | 2 | == | misc_feature |
| Bxb1 Integrase | 4466 . . . 5998 | 1533 | => | CDS |
| Degradation tag | 5966 . . . 5998 | 33 | => | CDS |
| lacI promoter | 6043 . . . 6120 | 78 | => | promoter |
| RBS | 6128 . . . 6133 | 6 | == | RBS |
| lambda repressor (ts) | 6142 . . . 6855 | 714 | => | CDS |
| K6N | 6157 . . . 6159 | 3 | == | misc_feature |
| S33T | 6238 . . . 6240 | 3 | == | misc_feature |
| L51 Conservative | 6292 . . . 6292 | 1 | == | misc_feature |
| Y61H | 6322 . . . 6324 | 3 | == | misc_feature |
| L119P | 6496 . . . 6498 | 3 | == | misc_feature |
| F122C | 6505 . . . 6507 | 3 | == | misc_feature |
| T7 terminator | 6964 . . . 7011 | 48 | => | terminator |
| pSC101 | 7042 . . . 17 | 2037 | == | misc_feature |

TABLE 4-continued

| Thermal Switching Circuit Library Screen Parent Plasmid (SEQ ID NO: 4) | | | | |
|---|---|---|---|---|
| Feature Name | Location | Size (bp) | Directionality | Type |
| pSC101 insertion | 5 . . . 17 | 13 | <= | misc_feature |
| Csrc Term | 113 . . . 172 | 60 | <= | misc_feature |
| NeoR/KanR | 203 . . . 997 | 795 | <= | CDS |

TABLE 5

| Thermal Switching Circuit Library Screen Hit #2 (SEQ ID NO: 5) | | | | |
|---|---|---|---|---|
| Feature Name | Location | Size (bp) | Directionality | Type |
| pSC101 insertion | 5 . . . 17 | 13 | <= | misc_feature |
| Csrc Term | 113 . . . 172 | 60 | <= | misc_feature |
| NeoR/KanR | 203 . . . 997 | 795 | <= | CDS |
| Bxb1 attB | 1385 . . . 1434 | 50 | == | misc_feature |
| P7 promoter | 1441 . . . 1487 | 47 | <= | promoter |
| Bxb1 AttP | 1488 . . . 1540 | 53 | == | misc_feature |
| Ribo J | 1541 . . . 1615 | 75 | == | misc_feature |
| BCD2_apFAB682 | 1616 . . . 1703 | 88 | == | misc_feature |
| Superfolder GFP | 1704 . . . 2420 | 717 | => | CDS |
| TcR | 2471 . . . 3661 | 1191 | => | CDS |
| hisLGDCBHAFI term | 3704 . . . 3756 | 53 | => | misc_feature |
| T1 transcriptional terminator from rrnB operon | 3848 . . . 3952 | 105 | => | misc_feature |
| pRM Promoter | 4059 . . . 4088 | 30 | <= | promoter |
| Operator OR3 | 4059 . . . 4075 | 17 | == | misc_feature |
| −10 | 4059 . . . 4060 | 2 | == | −10_signal |
| −35 | 4078 . . . 4083 | 6 | == | −35_signal |
| Operator OR2 | 4082 . . . 4098 | 17 | == | misc_feature |
| pR promoter | 4089 . . . 4147 | 59 | => | promoter |
| −35 | 4096 . . . 4102 | 7 | == | −35_signal |
| Operator OR1 | 4106 . . . 4122 | 17 | == | misc_feature |
| −10 | 4118 . . . 4124 | 7 | == | −10_signal |
| 1 | 4131 . . . 4131 | 1 | == | misc_feature |
| Operator OL3 | 4277 . . . 4293 | 17 | == | misc_feature |
| Operator OL2 | 4297 . . . 4313 | 17 | == | misc_feature |
| pL Promoter | 4304 . . . 4354 | 51 | => | promoter |
| Operator OL1 | 4321 . . . 4337 | 17 | == | misc_feature |
| RBS | 4453 . . . 4458 | 6 | == | misc_feature |
| Bxb1 Integrase | 4466 . . . 5998 | 1533 | => | CDS |
| Degradation tag | 5966 . . . 5998 | 33 | => | CDS |
| lacI promoter | 6043 . . . 6120 | 78 | => | promoter |
| RBS | 6128 . . . 6133 | 6 | == | RBS |
| lambda repressor (ts) | 6142 . . . 6855 | 714 | => | CDS |
| K6N | 6157 . . . 6159 | 3 | == | misc_feature |
| S33T | 6238 . . . 6240 | 3 | == | misc_feature |
| L51 Conservative | 6292 . . . 6292 | 1 | == | misc_feature |
| Y61H | 6322 . . . 6324 | 3 | == | misc_feature |
| L119P | 6496 . . . 6498 | 3 | == | misc_feature |
| F122C | 6505 . . . 6507 | 3 | == | misc_feature |
| T7 terminator | 6964 . . . 7011 | 48 | => | terminator |
| pSC101 | 7042 . . . 17 | 2037 | == | misc_feature |
| pSC101 insertion | 5 . . . 17 | 13 | <= | misc_feature |
| Csrc Term | 113 . . . 172 | 60 | <= | misc_feature |
| NeoR/KanR | 203 . . . 997 | 795 | <= | CDS |

TABLE 6

| Thermal Switching Circuit Library Screen Hit #7 (SEQ ID NO: 6) | | | | |
|---|---|---|---|---|
| Feature Name | Location | Size (bp) | Directionality | Type |
| pSC101 insertion | 5 . . . 17 | 13 | <= | misc_feature |
| Csrc Term | 113 . . . 172 | 60 | <= | misc_feature |
| NeoR/KanR | 203 . . . 997 | 795 | <= | CDS |
| Bxb1 attB | 1385 . . . 1434 | 50 | == | misc_feature |

TABLE 6-continued

| Thermal Switching Circuit Library Screen Hit #7 (SEQ ID NO: 6) | | | | |
|---|---|---|---|---|
| Feature Name | Location | Size (bp) | Directionality | Type |
| P7 promoter | 1441 . . . 1487 | 47 | <= | promoter |
| Bxb1 AttP | 1488 . . . 1540 | 53 | == | misc_feature |
| Ribo J | 1541 . . . 1615 | 75 | == | misc_feature |
| BCD2_apFAB682 | 1616 . . . 1703 | 88 | == | misc_feature |
| Superfolder GFP | 1704 . . . 2420 | 717 | => | CDS |
| TcR | 2471 . . . 3661 | 1191 | => | CDS |
| hisLGDCBHAFI term | 3704 . . . 3756 | 53 | => | misc_feature |
| T1 transcriptional terminator from rrnB operon | 3848 . . . 3952 | 105 | => | misc_feature |
| pRM Promoter | 4059 . . . 4088 | 30 | <= | promoter |
| Operator OR3 | 4059 . . . 4075 | 17 | == | misc_feature |
| −10 | 4059 . . . 4060 | 2 | == | −10_signal |
| −35 | 4078 . . . 4083 | 6 | == | −35_signal |
| Operator OR2 | 4082 . . . 4098 | 17 | == | misc_feature |
| pR promoter | 4089 . . . 4147 | 59 | => | promoter |
| −35 | 4096 . . . 4102 | 7 | == | −35_signal |
| Operator OR1 | 4106 . . . 4122 | 17 | == | misc_feature |
| −10 | 4118 . . . 4124 | 7 | == | −10_signal |
| 1 | 4131 . . . 4131 | 1 | == | misc_feature |
| Operator OL3 | 4277 . . . 4293 | 17 | == | misc_feature |
| Operator OL2 | 4297 . . . 4313 | 17 | == | misc_feature |
| pL Promoter | 4304 . . . 4354 | 51 | => | promoter |
| Operator OL1 | 4321 . . . 4337 | 17 | == | misc _feature |
| RBS | 4453 . . . 4454 | 2 | == | misc_feature |
| Bxb1 Integrase | 4466 . . . 5998 | 1533 | => | CDS |
| Degradation tag | 5966 . . . 5998 | 33 | => | CDS |
| lacI promoter | 6043 . . . 6120 | 78 | => | promoter |
| RBS | 6128 . . . 6133 | 6 | == | RBS |
| lambda repressor (ts) | 6142 . . . 6855 | 714 | => | CDS |
| K6N | 6157 . . . 6159 | 3 | == | misc_feature |
| S33T | 6238 . . . 6240 | 3 | == | misc_feature |
| L51 Conservative | 6292 . . . 6292 | 1 | == | misc_feature |
| Y61H | 6322 . . . 6324 | 3 | == | misc_feature |
| L119P | 6496 . . . 6498 | 3 | == | misc_feature |
| F122C | 6505 . . . 6507 | 3 | == | misc_feature |
| T7 terminator | 6964 . . . 7011 | 48 | => | terminator |
| pSC101 | 7042 . . . 17 | 2037 | == | misc_feature |
| pSC101 insertion | 5 . . . 17 | 13 | <= | misc_feature |
| Csrc Term | 113 . . . 172 | 60 | <= | misc_feature |
| NeoR/KanR | 203 . . . 997 | 795 | <= | CDS |

The nucleic acid composition can comprise: a polynucleotide encoding a toxin and/or an antitoxin, such as one or more elements of the Axe-Txe type II toxin anti-toxin system. The nucleic acid composition can be capable of being retained in a probiotic cell without antibiotic selection for at least about 10 days, about 20 days, about 40 days, about 80 days, about 80 days, about 100 days, or a number or a range between any two of the values.

The nucleic acid composition can comprise one or more vectors. At least one of the one or more vectors can be a viral vector, a plasmid, a transposable element, a naked DNA vector, a phage, a lipid nanoparticle, or any combination thereof. The nucleic acid composition can be situated within a chromosome (e.g., a bacterial chromosome) or a plasmid. In some embodiments, one or more of the first promoter, first polynucleotide, second promoter, second polynucleotide, third promoter, third polynucleotide, polynucleotide encoding the toxin, and polynucleotide encoding the antitoxin are situated on the same nucleic acid and/or different nucleic acids. The plasmid can comprise an origin of replication (e.g., a low-copy, a medium-copy, or a high-copy origin of replication). The origin of replication can be selected from the group comprising a low copy number modified pSC101 origin of replication, a RK2 origin of replication, a wildtype pSC101 origin of replication, a p15a origin of replication, and a pACYC origin of replication, derivatives thereof, or any combination thereof.

Vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

The nucleic acid composition can be single-stranded or double-stranded. The nucleic acid composition can contain two or more nucleic acids. The two or more nucleic acids can be in the same form (e.g., a first plasmid and a second plasmid) or different in forms (e.g., a first plasmid and a first viral vector). In some embodiments, the probiotic cells described herein also comprise a kill switch. Suitable kill switches are described in International Patent Application PCT/US2016/39427, filed Jun. 24, 2016, published as WO2016/210373, the contents of which are herein incorporated by reference in their entirety. The kill switch is intended to actively kill engineered microbes in response to external stimuli. As opposed to an auxotrophic mutation where bacteria die because they lack an essential nutrient for survival, the kill switch is triggered by a particular factor in the environment that induces the production of toxic molecules within the microbe that cause cell death.

There are provided, in some embodiments, compositions. In some embodiments, the composition comprises: a nucleic acid composition disclosed herein. The composition can comprise one or more vectors, a ribonucleoprotein (RNP) complex, a liposome, a nanoparticle, a phage, an exosome, a microvesicle, or any combination thereof. The vector can comprise a plasmid, and the plasmid can comprise an origin of replication (e.g., a low-copy, a medium-copy, or a high-copy origin of replication). The origin of replication can be selected from the group comprising a low copy number modified pSC101 origin of replication, a RK2 origin of replication, a wildtype pSC101 origin of replication, a p15a origin of replication, and a pACYC origin of replication, derivatives thereof, or any combination thereof.

Payloads

In some embodiments, the payload gene encodes a payload protein. The payload transcript can be capable of being translated to generate a payload protein. The second polynucleotide can comprise one or more supplemental payload genes. The payload transcript can be a polycistronic transcript capable of being translated to generate a plurality of payload proteins. The payload and supplemental payload(s) can be each operably connected to a ribosome binding site.

The payload protein can comprise a factor locally down-regulating the activity of endogenous immune cells. The payload protein can be capable of remodeling a tumor microenvironment and/or reducing immunosuppression at a target site of a subject. The payload protein can comprise a degron. In some embodiments, the steady-state levels of the payload protein can be varied by varying the sequence of the degron. In some embodiments, the payload comprises a secreted protein. The one or more payloads can comprise a secretion tag. The secretion tag can be selected from the group comprising AbnA, AmyE, AprE, BglC, BglS, Bpr, Csn, Epr, Ggt, GlpQ, HtrA, LipA, LytD, MntA, Mpr, NprE, OppA, PbpA, PbpX, Pel, PelB, PenP, PhoA, PhoB, PhoD, PstS, TasA, Vpr, WapA, WprA, XynA, XynD, YbdN, Ybxl, YcdH, YclQ, YdhF, YdhT, YflE, YfmC, Yfnl, YhcR, YlqB, YncM, YnfF, YoaW, YocH, YolA, YqiX, Yqxl, YrpD, YrpE, YuaB, Yurl, YvcE, YvgO, YvpA, YwaD, YweA, YwoF, YwtD, YwtF, YxaLk, YxiA, and YxkC.

The payload can be configured to modulate one or more of T cell simulation, T cell activation, cytokine secretion, T cell survival, T cell proliferation, CTL activity, T cell degranulation, and T cell differentiation. A payload can be an immune checkpoint inhibitor. The payload can comprise αCTLA-4 or αPD-L1 nanobodies. A payload can comprise a bispecific T cell engager (BiTE). A payload protein can comprise a factor locally down-regulating the activity of endogenous immune cells. A payload protein can be capable of remodeling a tumor microenvironment and/or reducing immunosuppression at a target site of a subject. A payload protein can comprise an agonistic or antagonistic antibody or antigen-binding fragment thereof specific to a checkpoint inhibitor or checkpoint stimulator molecule (e.g., PD1, PD-L1, PD-L2, CD27, CD28, CD40, CD137, OX40, GITR, ICOS, A2AR, B7-H3, B7-H4, BTLA, CTLA4, KIR, LAG3, PD-1, and/or TIM-3). The antibody or antigen-binding fragment thereof can comprise an scFv, a Fv, a Fab, a (Fab')2, a single domain antibody (SDAB), a VH or VL domain, a camelid VHH domain, a Fab, a Fab', a F(ab')2, a Fv, a scFv, a dsFv, a diabody, a triabody, a tetrabody, a multispecific antibody formed from antibody fragments, a single-domain antibody (sdAb), a single chain comprising cantiomplementary scFvs (tandem scFvs) or bispecific tandem scFvs, an Fv construct, a disulfide-linked Fv, a dual variable domain immunoglobulin (DVD-Ig) binding protein or a nanobody, an aptamer, an affibody, an affilin, an affitin, an affimer, an alphabody, an anticalin, an avimer, a DARPin, a Fynomer, a Kunitz domain peptide, a monobody, or any combination thereof.

The payload protein can comprise a cytokine. The cytokine can be selected from the group consisting of interleukin-1 (IL-1), IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, interleukin-1 (IL-1), IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, granulocyte macrophage colony stimulating factor (GM-CSF), M-CSF, SCF, TSLP, oncostatin M, leukemia-inhibitory factor (LIF), CNTF, Cardiotropin-1, NNT-1/BSF-3, growth hormone, Prolactin, Erythropoietin, Thrombopoietin, Leptin, G-CSF, or receptor or ligand thereof.

The payload protein can comprise a member of the TGF-β/BMP family selected from the group consisting of TGF-β1, TGF-β2, TGF-β3, BMP-2, BMP-3a, BMP-3b, BMP-4, BMP-5, BMP-6, BMP-7, BMP-8a, BMP-8b, BMP-9, BMP-10, BMP-11, BMP-15, BMP-16, endometrial bleeding associated factor (EBAF), growth differentiation factor-1 (GDF-1), GDF-2, GDF-3, GDF-5, GDF-6, GDF-7, GDF-8, GDF-9, GDF-12, GDF-14, mullerian inhibiting substance (MIS), activin-1, activin-2, activin-3, activin-4, and activin-5. The payload protein can comprise a member of the TNF family of cytokines selected from the group consisting of TNF-alpha, TNF-beta, LT-beta, CD40 ligand, Fas ligand, CD 27 ligand, CD 30 ligand, and 4-1 BBL. The payload protein can comprise a member of the immunoglobulin superfamily of cytokines selected from the group consisting of B7.1 (CD80) and B7.2 (B70). The payload protein can comprise an interferon. The interferon can be selected from interferon alpha, interferon beta, or interferon gamma. The payload protein can comprise a chemokine. The chemokine can be selected from CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13, or CXCL15. The payload protein can comprise a interleukin. The interleukin can be selected from IL-10 IL-12, IL-1, IL-6, IL-7, IL-15, IL-2, IL-18 or IL-21. The payload protein can comprise a tumor necrosis factor (TNF). The TNF can be selected from TNF-alpha, TNF-beta, TNF-gamma, CD252, CD154, CD178, CD70, CD153, or 4-1BBL.

In some embodiments, the payload protein is an active fragment of a protein, such as any of the aforementioned proteins. In some embodiments, the payload protein is a fusion protein comprising some or all of two or more proteins. In some embodiments a fusion protein can comprise all or a portion of any of the aforementioned proteins.

In some embodiments, the payload protein is a multi-subunit protein. For examples, the payload protein can comprise two or more subunits, or two or more independent polypeptide chains. A payload protein can be associated with an agricultural trait of interest selected from the group consisting of increased yield, increased abiotic stress tolerance, increased drought tolerance, increased flood tolerance, increased heat tolerance, increased cold and frost tolerance, increased salt tolerance, increased heavy metal tolerance, increased low-nitrogen tolerance, increased disease resistance, increased pest resistance, increased herbicide resistance, increased biomass production, male sterility, or any combination thereof. A payload protein can be associated with a biological manufacturing process selected from the group comprising fermentation, distillation, biofuel production, production of a compound, production of a polypeptide, or any combination thereof.

A payload protein can comprise fluorescence activity, polymerase activity, protease activity, phosphatase activity, kinase activity, SUMOylating activity, deSUMOylating activity, ribosylation activity, deribosylation activity, myristoylation activity demyristoylation activity, or any combination thereof. A payload protein can comprise nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity, glycosylase activity, acetyltransferase activity, deacetylase activity, adenylation activity, deadenylation activity, or any combination thereof. A payload protein can comprise a synthetic protein circuit component (e.g., a protease, a transcription factor). In some embodiments, the synthetic protein circuit component payload can activate or repress one or more circuits in a temperature-dependent manner.

A payload protein can comprise a diagnostic agent or can be co-expressed with a diagnostic agent (e.g., green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), TagRFP, Dronpa, Padron, mApple, mCitrine, mCherry, mruby3, rsCherry, rsCherryRev, derivatives thereof, or any combination thereof). The payload protein can be fused with the diagnostic agent. As described herein, the presence or absence of detection of a diagnostic agent can indicate whether the recombination event has occurred.

In some embodiments, the payload gene encodes a human adjuvant protein capable of eliciting an innate immune response, such as, for example, cytokines which induce or enhance an innate immune response.

As described herein, the nucleotide sequence encoding the payload protein can be modified to improve expression efficiency of the protein. The methods that can be used to improve the transcription and/or translation of a gene herein are not particularly limited. For example, the nucleotide sequence can be modified to better reflect host codon usage to increase gene expression (e.g., protein production) in the host.

The degree of payload gene expression in the probiotic cell can vary. For example, in some embodiments, the payload gene encodes a payload protein. The amount of the payload protein expressed in the subject (e.g., the serum of the subject) can vary. For example, in some embodiments the protein can be expressed in the serum of the subject in the amount of at least about 9 μg/ml, at least about 10 μg/ml, at least about 50 μg/ml, at least about 100 μg/ml, at least about 200 μg/ml, at least about 300 μg/ml, at least about 400 μg/ml, at least about 500 μg/ml, at least about 600 μg/ml, at least about 700 μg/ml, at least about 800 μg/ml, at least about 900 μg/ml, or at least about 1000 μg/ml. In some embodiments, the payload protein is expressed in the serum of the subject in the amount of about 9 μg/ml, about 10 μg/ml, about 50 μg/ml, about 100 μg/ml, about 200 μg/ml, about 300 μg/ml, about 400 μg/ml, about 500 μg/ml, about 600 μg/ml, about 700 μg/ml, about 800 μg/ml, about 900 μg/ml, about 1000 μg/ml, about 1500 μg/ml, about 2000 μg/ml, about 2500 μg/ml, or a range between any two of these values. A skilled artisan will understand that the expression level in which a payload protein is needed for the method to be effective can vary depending on non-limiting factors such as the particular payload protein and the subject receiving the treatment, and an effective amount of the protein can be readily determined by a skilled artisan using conventional methods known in the art without undue experimentation.

A payload protein encoded by a payload gene can be of various lengths. For example, the payload protein can be at least about 200 amino acids, at least about 250 amino acids, at least about 300 amino acids, at least about 350 amino acids, at least about 400 amino acids, at least about 450 amino acids, at least about 500 amino acids, at least about 550 amino acids, at least about 600 amino acids, at least about 650 amino acids, at least about 700 amino acids, at least about 750 amino acids, at least about 800 amino acids, or longer in length. In some embodiments, the payload protein is at least about 480 amino acids in length. In some embodiments, the payload protein is at least about 500 amino acids in length. In some embodiments, the payload protein is about 750 amino acids in length.

The payload genes can have different lengths in different implementations. The number of payload genes can be different in different embodiments. In some embodiments, the number of payload genes in a nucleic acid composition can be, or can be about, 1, 2, 3, 4, 5, 6, 7, 8, 9, 10, 11, 12, 13, 14, 15, 16, 17, 18, 19, 20, 21, 22, 23, 24, 25, or a number or a range between any two of these values. In some embodiments, the number of payload genes in a nucleic acid composition can be at least, or can be at most, 1, 2, 3, 4, 5, 6, 7, 8, 9, 10, 11, 12, 13, 14, 15, 16, 17, 18, 19, 20, 21, 22, 23, 24, 25. In some embodiments, a payload genes is, or is about, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3250, 3500, 3750, 4000, 4250, 4500, 4750, 5000, 5500, 6000, 6500, 7000, 7500, 8000, 8500, 9000, 9500, 10000, or a number or a range between any two of these values, nucleotides in length. In some embodiments, a payload gene is at least, or is at most, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3250, 3500, 3750, 4000, 4250, 4500, 4750, 5000, 5500, 6000, 6500, 7000, 7500, 8000, 8500, 9000, 9500, or 10000 nucleotides in length.

A payload can comprise a pro-death protein. In some embodiments, the payload is capable of rendering a target cell of a subject sensitive to a drug, a prodrug, a pharmacological compound, temperature change, or light. In some embodiments, the payload protein is capable of inducing cell death of a target cell of a subject. In some embodiments, the pro-death protein is capable of halting cell growth and/or inducing cell death. In some embodiments, the pro-death protein comprises cytosine deaminase, thymidine kinase, Bax, Bid, Bad, Bak, BCL2L11, p53, PUMA, Diablo/SMAC, S-TRAIL, Cas9, Cas9n, hSpCas9, hSpCas9n, HSVtk, cholera toxin, diphtheria toxin, alpha toxin, anthrax toxin, exotoxin, pertussis toxin, Shiga toxin, shiga-like toxin Fas, TNF, caspase 2, caspase 3, caspase 6, caspase 7, caspase 8, caspase 9, caspase 10, caspase 11, caspase 12, purine nucleoside phosphorylase, or any combination thereof. In some embodiments, the pro-death protein is capable of halting cell growth and/or inducing cell death in the presence of a pro-death agent (e.g., a prodrug). In some embodiments, the pro-death protein comprises Caspase-9 and the pro-death agent comprises AP1903; the pro-death protein comprises HSV thymidine kinase (TK) and the pro-death agent Ganciclovir (GCV), Ganciclovir elaidic acid ester, Penciclovir (PCV), Acyclovir (ACV), Valacyclovir (VCV), (E)-5-(2-bromovinyl)-2'-deoxyuridine (BVDU), Zidovuline (AZT), and/or 2'-exo-methanocarbathymidine (MCT); the pro-death protein comprises Cytosine Deaminase (CD) and the pro-death agent comprises 5-fluorocytosine (5-FC); the pro-death protein comprises Purine nucleoside phosphorylase (PNP) and the pro-death agent comprises 6-methylpurine deoxyriboside (MEP) and/or fludarabine (FAMP); the pro-death protein comprises a Cytochrome p450 enzyme (CYP) and the pro-death agent comprises Cyclophosphamide (CPA), Ifosfamide (IFO), and/or 4-ipomeanol (4-IM); the pro-death protein comprises a Carboxypeptidase (CP) and the pro-death agent comprises 4-[(2-chloroethyl)(2-mesyloxyethyl)amino]benzoyl-L-glutamic acid (CMDA), Hydroxy- and amino-aniline mustards, Anthracycline glutamates, and/or Methotrexate α-peptides (MTX-Phe); the pro-death protein comprises Carboxylesterase (CE) and the pro-death agent comprises Irinotecan (IRT), and/or Anthracycline acetals; the pro-death protein comprises Nitroreductase (NTR) and the pro-death agent comprises dinitroaziridinylbenzamide CB1954, dinitrobenzamide mustard SN23862, 4-Nitrobenzyl carbamates, and/or Quinones; the pro-death protein comprises Horse radish peroxidase (HRP) and the pro-death agent comprises Indole-3-acetic acid (IAA) and/or 5-Fluoroindole-3-acetic acid (FIAA); the pro-death protein comprises Guanine Ribosyltransferase (XGRTP) and the pro-death agent comprises 6-Thioxanthine (6-TX); the pro-death protein comprises a glycosidase enzyme and the pro-death agent comprises HM1826 and/or Anthracycline acetals; the pro-death protein comprises Methionine-α,γ-lyase (MET) and the pro-death agent comprises Selenomethionine (SeMET); and/or the pro-death protein comprises thymidine phosphorylase (TP) and the pro-death agent comprises 5'-Deoxy-5-fluorouridine (5'-DFU).

Engineered Probiotic Cells

There are provided, in some embodiments, thermally actuated probiotic cells. In some embodiments, the thermally actuated probiotic cell comprises: a nucleic acid composition disclosed herein or a composition disclosed herein. The thermally actuated probiotic cells can comprise a mixture of two or more thermally actuated probiotic cells expressing different payload(s).

The term "Probiotic" can be used to refer to live, non-pathogenic microorganisms, e.g., bacteria, which can confer health benefits to a host organism that contains an appropriate amount of the microorganism. Some species, strains, and/or subtypes of non-pathogenic bacteria are currently recognized as probiotic bacteria. Examples of probiotic bacteria include, but are not limited to certain strains belonging to the genus Bifidobacteria, *Escherichia coli, Lactobacillus*, and *Saccharomyces*, e.g., *Bifidobacterium bifidum, Enterococcus faecium, Escherichia coli* strain Nissle, *Lactobacillus acidophilus, Lactobacillus bulgaricus, Lactobacillus paracasei, Lactobacillus plantarum*, and *Saccharomyces boulardii* (Dinleyici et al., 2014; U.S. Pat. Nos. 5,589,168; 6,203,797; 6,835,376). The probiotic may be a variant or a mutant strain of bacterium (Arthur et al., 2012; Cuevas-Ramos et al., 2010; Olier et al., 2012; Nougayrede et al., 2006). Non-pathogenic bacteria may be genetically engineered to enhance or improve desired biological properties, e.g., survivability. Non-pathogenic bacteria may be genetically engineered to provide probiotic properties. Probiotic bacteria may be genetically engineered or programmed to enhance or improve probiotic properties.

The thermally actuated probiotic cell can comprise tumor-homing bacteria (e.g., tumor-targeting bacteria). In some embodiments, the thermally actuated probiotic cell is obligate anaerobic, facultative anaerobic, aerobic, Gram-positive, Gram-negative, commensal, or any combination thereof. The thermally actuated probiotic cell can comprise naturally pathogenic bacteria that are modified or mutated to reduce or eliminate pathogenicity. "Tumor-targeting bacteria" can refer to bacteria that are capable of directing themselves to cancerous cells. Tumor-targeting bacteria may be naturally capable of directing themselves to cancerous cells, necrotic tissues, and/or hypoxic tissues. In some embodiments, bacteria that are not naturally capable of directing themselves to cancerous cells, necrotic tissues, and/or hypoxic tissues are genetically engineered to direct themselves to cancerous cells, necrotic tissues, and/or hypoxic tissues. Tumor-targeting bacteria may be further engineered to enhance or improve desired biological properties, mitigate systemic toxicity, and/or ensure clinical safety. These species, strains, and/or subtypes may be attenuated, e.g., deleted for a toxin gene. In some embodiments, tumor-targeting bacteria have low infection capabilities. In some embodiments, tumor-targeting bacteria are motile. In some embodiments, the tumor-targeting bacteria are capable of penetrating deeply into the tumor, where standard treatments do not reach. In some embodiments, tumor-targeting bacteria are capable of colonizing at least 20%, at least 30%, at least 40%, at least 50%, at least 60%, at least 70%, at least 80%, at least 90%, or at least 95% of a malignant tumor. Examples of tumor-targeting bacteria include, but are not limited to, *Bifidobacterium, Caulobacter, Clostridium, Escherichia coli, Listeria, Mycobacterium, Salmonella, Streptococcus*, and *Vibrio*, e.g., *Bifidobacterium adolescentis, Bifidobacterium bifidum, Bifidobacterium breve* UCC2003, *Bifidobacterium infantis, Bifidobacterium longum, Clostridium acetobutylicum, Clostridium butyricum, Clostridium butyricum* M-55, *Clostridium butyricum* miyairi, *Clostridium cochlearum, Clostridium felsineum, Clostridium histolyticum, Clostridium multifermentans, Clostridium novyi*-NT, *Clostridium paraputrificum, Clostridium pasteureanum, Clostridium pectinovorum, Clostridium perfringens, Clostridium roseum, Clostridium sporogenes, Clostridium tertium, Clostridium tetani,*

*Clostridium tyrobutyricum, Corynebacterium parvum, Escherichia coli* MG1655, *Escherichia coli* Nissle 1917, *Listeria monocytogenes, Mycobacterium bovis, Salmonella choleraesuis, Salmonella typhimurium*, and *Vibrio cholera* (Cronin et al., 2012; Forbes, 2006; Jain and Forbes, 2001; Liu et al., 2014; Morrissey et al., 2010; Nuno et al., 2013; Patyar et al., 2010; Cronin, et al., Mol Ther 2010; 18:1397-407). In some embodiments, the tumor-targeting bacteria are non-pathogenic bacteria.

At a physiological temperature, the expression of the recombinase can be repressed, thereby preventing expression of the payload(s) in the thermally actuated probiotic cell. In some embodiments, upon the thermal stimulation of the thermally actuated probiotic cell, the recombinase is expressed and the recombination event occurs, thereby yielding expression of the payload(s). The thermal stimulation of the thermally actuated probiotic cell can yield constitutive expression of the payload(s) (e.g., constitutive expression of the payload(s) after the thermal stimulation ends and the thermally actuated probiotic cell have returned to a physiological temperature). The recombination event can occur in less than about 0.01%, about 0.1%, about 1%, about 3%, about 5%, about 10%, about 15%, about 20%, about 25%, about 30%, about 35%, about 40%, about 45%, about 50%, or a number or a range between any two of the values, of thermally actuated probiotic cells in the absence of the thermal stimulation. In some embodiments, physiological temperature is about 31.5° C., about 32.0° C., about 32.5° C., about 33.0° C., about 33.5° C., about 34.0° C., about 34.5° C., about 35.0° C., about 35.5° C., about 36.0° C., about 36.5° C., about 37.0° C., about 37.5° C., about 38.0° C., about 38.5° C., about 39.0° C., about 39.5° C., about 40.0° C., or a number or a range between any two of the values. The thermally actuated probiotic cell can be robust to mutations reducing or abrogating the thermal stimulation-based control of payload expression. In some such embodiments, the thermally actuated probiotic cell is robust to said mutations for at least about 5 days, about 10 days, about 20 days, about 40 days, about 80 days, about 80 days, or about 100 days, or a number or a range between any two of the values, of continuous culture and/or presence in a subject.

The probiotic cell chromosome can comprise a polynucleotide encoding a toxin and/or antitoxin (e.g., one or more elements of the Axe-Txe type II toxin anti-toxin system). The thermally actuated probiotic cell can comprise a polynucleotide conferring resistance to an antibiotic (e.g., phleomycin D1 (ZEOCIN™), kanamycin, spectinomycin, streptomycin, ampicillin, carbenicillin, bleomycin, erythromycin, polymyxin B, tetracycline and chloramphenicol). The nucleic acid composition can comprise said polynucleotide conferring resistance to an antibiotic. In some embodiments, further enhance the number of activated cells, a thermally inducible antibiotic cassette can be added to the circuit. In some embodiments, the methods disclosed herein comprise administering an antibiotic to a subject. By applying antibiotic selective pressure after stimulation, non-activated cells within tumors and other organs can be eliminated, allowing the successfully activated antibiotic-resistant population to expand in tumors and achieve full colonization.

Methods of Treating a Disease or Disorder

There are provided, in some embodiments, methods for treating a disease or disorder in a subject. In some embodiments, the method comprises: introducing into one or more probiotic cells a nucleic acid composition disclosed herein or a composition disclosed herein, thereby generating one or more thermally actuated probiotic cells; and administering to the subject an effective amount of the thermally actuated probiotic cells. The introducing step can comprise transformation, conjugation, transduction, sexduction, infection, electroporation, or any combination thereof.

Disclosed herein include methods of treating a disease or disorder in a subject. In some embodiments, the method comprises: administering to the subject an effective amount of the thermally actuated probiotic cells disclosed herein. The method can further comprise: administering to the subject an oncolytic virus, radiation, an adoptive NK therapy, a stem cell transplant (SCT) therapy, and/or a chimeric antigen receptor (CAR) T cell therapy.

The thermally actuated probiotic cells can comprise a mixture of two or more thermally actuated probiotic cells expressing different payload(s). The method can comprise: prior to the administering step: (a) culturing singular colonies of the one or more thermally actuated probiotic cells to saturation; (b) diluting said saturated cultures (e.g., to a OD600 of about 0.1); and (c) growing said diluted cultures to exponential phase (e.g., to a OD600 of about 0.6). In some embodiments, the method comprises selecting cells at steps (a), (b), or (c) which do not express the payload(s). In some embodiments, said selecting comprises detecting: (i) the absence of fluorescence in thermally actuated probiotic cells configured to express a fluorescent payload following the recombination event; or (ii) the presence of fluorescence in thermally actuated probiotic cells configured to express a fluorescent payload and a non-fluorescent payload, prior to, and following, the recombination event, respectively.

The subject can be a mammal. In some embodiments, the disease is associated with expression of a tumor antigen, wherein the disease associated with expression of a tumor antigen is selected from the group consisting of a proliferative disease, a precancerous condition, a cancer, and a non-cancer related indication associated with expression of the tumor antigen. The disease or disorder can be a cancer (e.g., a solid tumor). The cancer can be selected from the group consisting of colon cancer, rectal cancer, renal-cell carcinoma, liver cancer, non-small cell carcinoma of the lung, cancer of the small intestine, cancer of the esophagus, melanoma, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin lymphoma, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers, combinations of said cancers, and metastatic lesions of said cancers.

The cancer can be a hematologic cancer chosen from one or more of chronic lymphocytic leukemia (CLL), acute leukemias, acute lymphoid leukemia (ALL), B-cell acute lymphoid leukemia (B-ALL), T-cell acute lymphoid leukemia (T-ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, myelodysplasia and myelodysplastic syndrome, non-Hodgkin's lymphoma, Hodgkin's lymphoma, plasmablastic lymphoma, plasmacytoid dendritic cell neoplasm, Waldenstrom macroglobulinemia, or pre-leukemia.

Administering and Pharmaceutical Compositions and Formulations

Administering can comprise aerosol delivery, nasal delivery, vaginal delivery, rectal delivery, buccal delivery, ocular delivery, local delivery, topical delivery, intracisternal delivery, intraperitoneal delivery, oral delivery, intramuscular injection, intravenous injection, subcutaneous injection, intranodal injection, intratumoral injection, intraperitoneal injection, intradermal injection, or any combination thereof. The thermally actuated probiotic cells can be administered at a therapeutically effective amount. For example, a therapeutically effective amount of the thermally actuated probiotic cells can be at least about $10^4$ cells, at least about $10^5$ cells, at least about $10^6$ cells, at least about $10^7$ cells, at least about $10^8$ cells, at least about $10^9$, or at least about $10^{10}$. In another embodiment, the therapeutically effective amount of the thermally actuated probiotic cells is about $10^4$ cells, about $10^5$ cells, about $10^6$ cells, about $10^7$ cells, or about $10^8$ cells. In one particular embodiment, the therapeutically effective amount of the thermally actuated probiotic cells is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg.

The thermally actuated probiotic cells described herein may be included in a composition for therapy. In some embodiments, the composition comprises a population of thermally actuated probiotic cells. The composition may include a pharmaceutical composition and further include a pharmaceutically acceptable carrier. A therapeutically effective amount of the pharmaceutical composition comprising the thermally actuated probiotic cells may be administered. The thermally actuated probiotic cells may be administered either alone, or as a pharmaceutical composition in combination with diluents and/or with other components such as IL-2 or other cytokines or cell populations.

The thermally actuated probiotic cells can be administered in the form of a pharmaceutical composition. The dosage of the pharmaceutical composition and the frequency of administration may be selected based on the severity of the symptoms and the progression of the disease or disorder. The appropriate therapeutically effective dose and the frequency of administration can be selected by a treating clinician.

The pharmaceutical compositions disclosed herein may be formulated in a conventional manner using one or more physiologically acceptable carriers comprising excipients and auxiliaries, which facilitate processing of the active ingredients into compositions for pharmaceutical use. Methods of formulating pharmaceutical compositions are known in the art (see, e.g., "Remington's Pharmaceutical Sciences," Mack Publishing Co., Easton, Pa.). In some embodiments, the pharmaceutical compositions are subjected to tableting, lyophilizing, direct compression, conventional mixing, dissolving, granulating, levigating, emulsifying, encapsulating, entrapping, or spray drying to form tablets, granulates, nanoparticles, nanocapsules, microcapsules, microtablets, pellets, or powders, which may be enterically coated or uncoated. Appropriate formulation depends on the route of administration.

The thermally actuated probiotic cells may be formulated into pharmaceutical compositions in any suitable dosage form (e.g., liquids, capsules, sachet, hard capsules, soft capsules, tablets, enteric coated tablets, suspension powders, granules, or matrix sustained release formations for oral administration) and for any suitable type of administration (e.g., oral, topical, injectable, intravenous, sub-cutaneous, intratumoral, peritumor, immediate-release, pulsatile-release, delayed-release, or sustained release). Suitable dosage amounts for the thermally actuated probiotic cells may range from about $10^4$ to $10^{12}$ bacteria. The composition may be administered once or more daily, weekly, or monthly. The composition may be administered before, during, or following a meal. In one embodiment, the pharmaceutical composition is administered before the subject eats a meal. In one embodiment, the pharmaceutical composition is administered currently with a meal. In on embodiment, the pharmaceutical composition is administered after the subject eats a meal.

The thermally actuated probiotic cells may be formulated into pharmaceutical compositions comprising one or more pharmaceutically acceptable carriers, thickeners, diluents, buffers, buffering agents, surface active agents, neutral or cationic lipids, lipid complexes, liposomes, penetration enhancers, carrier compounds, and other pharmaceutically acceptable carriers or agents. For example, the pharmaceutical composition may include, but is not limited to, the addition of calcium bicarbonate, sodium bicarbonate, calcium phosphate, various sugars and types of starch, cellulose derivatives, gelatin, vegetable oils, polyethylene glycols, and surfactants, including, for example, polysorbate 20. In some embodiments, the thermally actuated probiotic cells of the invention may be formulated in a solution of sodium bicarbonate, e.g., 1 molar solution of sodium bicarbonate (to buffer an acidic cellular environment, such as the stomach, for example). The thermally actuated probiotic cells may be administered and formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

In some embodiments, the thermally actuated probiotic cells are co-administered with a PEGylated form of rHuPH20 (PEGPH20) or other agent in order to destroy the tumor septae in order to enhance penetration of the tumor capsule, collagen, and/or stroma. In some embodiments, the thermally actuated probiotic cells are capable of producing an anti-cancer molecule as well as one or more enzymes that degrade fibrous tissue.

The thermally actuated probiotic cells disclosed herein may be administered orally and formulated as tablets, pills, dragees, capsules, liquids, gels, syrups, slurries, suspensions, etc. Pharmacological compositions for oral use can be made using a solid excipient, optionally grinding the resulting mixture, and processing the mixture of granules, after adding suitable auxiliaries if desired, to obtain tablets or dragee cores. Suitable excipients include, but are not limited to, fillers such as sugars, including lactose, sucrose, mannitol, or sorbitol; cellulose compositions such as maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP) or polyethylene glycol (PEG). Disintegrating agents may also be added, such as cross-linked polyvinylpyrrolidone, agar, alginic acid or a salt thereof such as sodium alginate.

Tablets or capsules can be prepared by conventional means with pharmaceutically acceptable excipients such as binding agents (e.g., pregelatinized maize starch, polyvinylpyrrolidone, hydroxypropyl methylcellulose, carboxymethylcellulose, polyethylene glycol, sucrose, glucose, sorbitol, starch, gum, kaolin, and tragacanth); fillers (e.g., lactose, microcrystalline cellulose, or calcium hydrogen phosphate); lubricants (e.g., calcium, aluminum, zinc, stearic acid, polyethylene glycol, sodium lauryl sulfate, starch, sodium benzoate, L-leucine, magnesium stearate, talc, or silica); disintegrants (e.g., starch, potato starch, sodium starch glycolate, sugars, cellulose derivatives, silica powders); or wetting agents (e.g., sodium lauryl sulphate). The tablets may be coated by methods well known in the art. A coating shell may be present, and common membranes include, but are not limited to, polylactide, polyglycolic acid, polyanhydride, other biodegradable polymers, alginate-polylysine-alginate (APA), alginate-polymethylene-co-guanidine-alginate (A-PMCG-A), hydroymethylacrylate-methyl methacrylate (HEMA-MMA), multilayered HEMA-MMA-MAA, polyacrylonitrilevinylchloride (PAN-PVC), acrylonitrile/sodium methallylsulfonate (AN-69), polyethylene glycol/poly pentamethylcyclopentasiloxane/polydimethylsiloxane (PEG/PD5/PDMS), poly N,N-dimethyl acrylamide (PDMAAm), siliceous encapsulates, cellulose sulphate/sodium alginate/polymethylene-co-guanidine (CS/A/PMCG), cellulose acetate phthalate, calcium alginate, k-carrageenan-locust bean gum gel beads, gellan-xanthan beads, poly(lactide-co-glycolides), carrageenan, starch poly-anhydrides, starch polymethacrylates, polyamino acids, and enteric coating polymers.

In some embodiments, the thermally actuated probiotic cells are enterically coated for release into the gut or a particular region of the gut, for example, the large intestine. The typical pH profile from the stomach to the colon is about 1-4 (stomach), 5.5-6 (duodenum), 7.3-8.0 (ileum), and 5.5-6.5 (colon). In some diseases, the pH profile may be modified. In some embodiments, the coating is degraded in specific pH environments in order to specify the site of release. In some embodiments, at least two coatings are used. In some embodiments, the outside coating and the inside coating are degraded at different pH levels.

Liquid preparations for oral administration may take the form of solutions, syrups, suspensions, or a dry product for constitution with water or other suitable vehicle before use. Such liquid preparations may be prepared by conventional means with pharmaceutically acceptable agents such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of the thermally actuated probiotic cells described herein.

Applying Thermal Energy

In some embodiments, the method comprises: applying thermal energy to a target site of the subject sufficient to increase the local temperature of the target site to an activating temperature, thereby inducing the expression of the payload in thermally actuated probiotic cells at the target site. The activating temperature can be about 37.5° C., about 38.0° C., about 38.5° C., about 39.0° C., about 39.5° C., about 40.0° C., about 40.5° C., about 41.0° C., about 41.5° C., about 42.0° C., about 42.5° C., about 43.0° C., about 43.5° C., about 44.0° C., about 44.5° C., about 45.0° C., about 45.5° C., or about 46.0° C., or a number or a range between any two of these values. In some embodiments, the subject maintains a physiological temperature of about 31.5° C., about 32.0° C., about 32.5° C., about 33.0° C., about 33.5° C., about 34.0° C., about 34.5° C., about 35.0° C., about 35.5° C., about 36.0° C., about 36.5° C., about 37.0° C., about 37.5° C., about 38.0° C., about 38.5° C., about 39.0° C., about 39.5° C., about 40.0° C., or a number or a range between any two of these values.

Applying thermal energy to a target site of the subject can comprise the application of one or more of focused ultrasound (FUS), magnetic hyperthermia, microwaves, infrared irradiation, liquid-based heating, and contact heating. Liquid-based heating can comprise intraperitoneal chemotherapy (HIPEC). The term "applying ultrasound" shall be given its ordinary meaning, and shall also refer to sending ultrasound-range acoustic energy to a target. The sound energy produced by the piezoelectric transducer can be focused by beamforming, through transducer shape, lensing, or use of control pulses. The soundwave formed is transmitted to the body, then partially reflected or scattered by structures within a body; larger structures typically reflecting, and smaller structures typically scattering. The return sound energy reflected/scattered to the transducer vibrates the transducer and turns the return sound energy into electrical signals to be analyzed for imaging. The frequency and pressure of the input sound energy can be controlled and are selected based on the needs of the particular imaging/delivery task The period of time between the administering and applying thermal energy can be about 48 hours, about 44 hours, about 40 hours, about 35 hours, about 30 hours, about 25 hours, 20 hours, 15 hours, 10 hours, about 8 hours, about 8 hours, 8 hours, about 7 hours, about 6 hours, about 5 hours, about 4 hours, about 3 hours, about 2 hours, about 1 hour, about 30 minutes, about 15 minutes, about 10 minutes, about 5 minutes, or a number or a range between any two of these values.

Applying thermal energy to a target site can comprise a continuous application of thermal energy to the target site over a second duration of time. Applying thermal energy to a target site can comprise applying one or more pulses of thermal energy to the target site over a second duration of time. The second duration of time can be about 48 hours, about 44 hours, about 40 hours, about 35 hours, about 30 hours, about 25 hours, 20 hours, 15 hours, 10 hours, about 8 hours, about 8 hours, 8 hours, about 7 hours, about 6 hours, about 5 hours, about 4 hours, about 3 hours, about 2 hours, about 1 hour, about 30 minutes, about 15 minutes, about 10 minutes, about 5 minutes, or a number or a range between any two of these values.

In some embodiments, the one or more pulses have a duty cycle of greater than about 1% and less than about 100%. The one or more pulses have a duty cycle of about 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. In some embodiments, the duty cycle is kept constant at 50% while alternating the temperature between 37° C. and 42° C.

In some embodiments, the one or more pulses each have a pulse duration of about 1 hour, about 30 minutes, about 15 minutes, about 10 minutes, or about 5 minutes, about 1 minute, about 1 second, about 1 millisecond, or a number or a range between any two of these values.

In some embodiments, applying thermal energy to a target site comprises application of FUS for about 1 hour at about 43° C. In some embodiments, applying thermal energy to a target site comprises application of FUS for about 1 hour at about 43° C. with an about 50% duty cycle, optionally with an about 5 minute pulse duration.

In some embodiments, the method comprises: monitoring the temperature of the target region. The monitoring can be performed by magnetic resonance imaging (MM). The application of thermal energy to a target site of the subject can be guided spatially by magnetic resonance imaging (MRI).

Target Sites

The target site can comprise a solid tumor. The target site can comprise a site of disease or disorder or can be proximate to a site of a disease or disorder. The location of the one or more sites of a disease or disorder can be predetermined, can be determined during the method, or both. The target site can be an immunosuppressive environment. The target site can comprise a tissue. The tissue can be inflamed tissue and/or infected tissue. The tissue can comprise adrenal gland tissue, appendix tissue, bladder tissue, bone, bowel tissue, brain tissue, breast tissue, bronchi, coronal tissue, ear tissue, esophagus tissue, eye tissue, gall bladder tissue, genital tissue, heart tissue, hypothalamus tissue, kidney tissue, large intestine tissue, intestinal tissue, larynx tissue, liver tissue, lung tissue, lymph nodes, mouth tissue, nose tissue, pancreatic tissue, parathyroid gland tissue, pituitary gland tissue, prostate tissue, rectal tissue, salivary gland tissue, skeletal muscle tissue, skin tissue, small intestine tissue, spinal cord, spleen tissue, stomach tissue, thymus gland tissue, trachea tissue, thyroid tissue, ureter tissue, urethra tissue, soft and connective tissue, peritoneal tissue, blood vessel tissue and/or fat tissue. In some embodiments, the target site comprises a section or subsection of the GI tract (e.g., stomach, proximal duodenum, distal duodenum, proximal jejunum, distal jejunum, proximal ileum, distal ileum, proximal cecum, distal cecum, proximal ascending colon, distal ascending colon, proximal transverse colon, distal transverse colon, proximal descending colon and distal descending colon, or any combination thereof). In some embodiments, the target site comprises a site of disease or disorder or is proximate to a site of a disease or disorder. In some embodiments, the location of the one or more sites of a disease or disorder is predetermined, is determined during the method, or both. In some embodiments, the target site is an immunosuppressive environment. The tissue can comprise: (i) grade I, grade II, grade III or grade IV cancerous tissue; (ii) metastatic cancerous tissue; (iii) mixed grade cancerous tissue; (iv) a sub-grade cancerous tissue; (v) healthy or normal tissue; and/or (vi) cancerous or abnormal tissue. In some embodiments, at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, or a number or a range between any two of these values, of the thermally actuated probiotic cells at the target site express the payload protein after applying thermal energy to the target site. In some embodiments, less than about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or a number or a range between any two of these values, of the thermally actuated probiotic cells at a site other than the target site express the payload protein. Less than about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, or a number or a range between any two of these values, of the thermally actuated probiotic cells at the target site can express the payload protein before applying thermal energy to the target site.

The ratio of the concentration of payload-expressing thermally actuated probiotic cells at the subject's target site to the concentration of payload-expressing thermally actuated probiotic cells in subject's blood, serum, or plasma can be vary. In some embodiments, the ratio of the concentration of payload-expressing thermally actuated probiotic cells at the subject's target site to the concentration of payload-expressing thermally actuated probiotic cells in subject's blood, serum, or plasma can be, or be about, 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, 10000:1, or a number or a range between any two of the values. In some embodiments, the ratio of the concentration of payload-expressing thermally actuated probiotic cells at the subject's target site to the concentration of payload-expressing thermally actuated probiotic cells in subject's blood, serum, or plasma can be at least, or be at most, 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, or 10000:1.

The ratio of the concentration of payload protein at the subject's target site to the concentration of payload protein in subject's blood, serum, or plasma can be vary. In some embodiments, the ratio of the concentration of payload protein at the subject's target site to the concentration of payload protein in subject's blood, serum, or plasma can be, or be about, 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, 10000:1, or a number or a range between any two of the values. In some embodiments, the ratio of the concentration of payload protein at the subject's target site to the concentration of payload protein in subject's blood, serum, or plasma can be at least, or be at most, 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, or 10000:1. The concentration of payload protein(s) at the subject's target site can be increased by at least about 1.1-fold (e.g., 1.1-fold, 1.3-fold, 1.5-fold, 1.7-fold, 1.9-fold, 2-fold, 3-fold, 4-fold, 5-fold, 6-fold, 7-fold, 8-fold, 9-fold, 10-fold, or a number or a range between any of these values) after the application of thermal energy.

The target site can comprise target cells. The target cells can be tumor cells (e.g., solid tumor cells). In some embodiments, the application of thermal energy to a target site of the subject results in the death of at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, or a number or a range between any two of these values, of the target cells. Non-target cells can comprise cells of the subject other than target cells. The ratio of target cell death to non-target cell death after application of thermal energy can be at least about 2:1. In some embodiments, the ratio of target cell death to non-target cell death after application of thermal energy can be, or be about, 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, 10000:1, or a number or a range between any two of the values. In some embodiments, the ratio of target cell death to non-target cell death after application of thermal energy can be at least, or be at most, 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, or 10000:1. The ratio of target cell death to non-target cell death can be at least about 1.1-fold (e.g., 1.1-fold, 1.3-fold, 1.5-fold, 1.7-fold, 1.9-fold, 2-fold, 3-fold, 4-fold, 5-fold, 6-fold, 7-fold, 8-fold, 9-fold, 10-fold, or a number or a range between any of these values) greater as compared to a method comprising probiotic cells constitutively expressing the payload protein.

The target site can comprise a solid tumor (e.g., a head-and-neck, liver, breast, prostate, ovarian, pancreatic or brain tumor). The tumor can be a metastatic tumor, and wherein the application of thermal energy causes the reduction or elimination of distant tumor lesions (e.g., via an abscopal effect). The disease can be an oligometastatic disease, and wherein the target site can comprise one or more metastases. The one or more metastases can comprise defined liver metastases or brain metastases of tumors other primary tissue origin. The application of thermal energy to a target site of the subject can result in an at least an about 1.1-fold (e.g., 1.1-fold, 1.3-fold, 1.5-fold, 1.7-fold, 1.9-fold, 2-fold, 3-fold, 4-fold, 5-fold, 6-fold, 7-fold, 8-fold, 9-fold, 10-fold, or a number or a range between any of these values) reduction in tumor proliferation, tumor size, tumor volume, and/or tumor weight. The application of thermal energy to a target site of the subject can result in an at least an about 1.1-fold (e.g., 1.1-fold, 1.3-fold, 1.5-fold, 1.7-fold, 1.9-fold, 2-fold, 3-fold, 4-fold, 5-fold, 6-fold, 7-fold, 8-fold, 9-fold, 10-fold, or a number or a range between any of these values) reduction in tumor proliferation, tumor size, tumor volume, and/or tumor weight as compared to a method wherein the subject is administered the payload or administered probiotic bacteria constitutively expressing the payload. After applying thermal energy to the target site, thermally actuated probiotic cells at the target site can express the payload protein for at least about for at least about 2 days, about 4 days, about 7 days, about 10 days, about 20 days, about 40 days, about 80 days, about 80 days, about 100 days, or a number or a range between any two of the values. In some embodiments, upon administration, the thermally actuated probiotic cells accumulate in one or more target sites of the subject(e.g., hypoxic environments and/or immunosuppressive environments (e.g., the necrotic core of a solid tumor)).

Additional Agents

In some embodiments, the method comprises administering one or more additional agents to the subject (e.g., an antibiotic, a prodrug or a pro-death agent). In some embodiments, the one or more additional agents increases the efficacy of the thermally actuated probiotic cells. In some embodiments, the thermally actuated probiotic cells are administered sequentially, simultaneously, or subsequently to dosing with one or more additional agents. The one or more additional agents can comprise a protein phosphatase inhibitor, a kinase inhibitor, a cytokine, an inhibitor of an immune inhibitory molecule, and/or or an agent that decreases the level or activity of a TREG cell. The one or more additional agents can comprise an immune modulator, an anti-metastatic, a chemotherapeutic, a hormone or a growth factor antagonist, an alkylating agent, a TLR agonist, a cytokine antagonist, a cytokine antagonist, or any combination thereof. The one or more additional agents can comprise an agonistic or antagonistic antibody specific to a checkpoint inhibitor or checkpoint stimulator molecule such as PD1, PD-L1, PD-L2, CD27, CD28, CD40, CD137, OX40, GITR, ICOS, A2AR, B7-H3, B7-H4, BTLA, CTLA4, IDO, KIR, LAG3, PD-1, TIM-3.

The one or more additional agents can comprise a therapeutic agent useful for treating a disease of the GI tract (e.g., an inflammatory bowel disease). The therapeutic agent useful for treating inflammatory bowel disease can comprise one of the following classes of compounds: 5-aminosalicyclic acids, corticosteroids, thiopurines, tumor necrosis factor-alpha blockers and JAK inhibitors. The therapeutic agent useful for treating inflammatory bowel disease can comprise one or more of Prednisone, Humira, Lialda, Imuran, Sulfasalazine, Pentasa, Mercaptopurine, Azathioprine, Apriso, Simponi, Enbrel, Humira Crohn's Disease Starter Pack, Colazal, Budesonide, Azulfidine, Purinethol, Proctosol HC, Sulfazine EC, Delzicol, Balsalazide, Hydrocortisone acetate, Infliximab, Mesalamine, Proctozone-HC, Sulfazine, Orapred ODT, Mesalamine, Azasan, Asacol HD, Dipentum, Prednisone Intensol, Anusol-HC, Rowasa, Azulfidine EN-tabs, Veripred 20, Uceris, Adalimumab, Hydrocortisone, Colocort, Pediapred, Millipred, Azathioprine injection, Prednisolone sodium phosphate, Flo-Pred, Aminosalicylic acid, ProctoCream-HC, 5-aminosalicylic acid, Millipred DP, Golimumab, Prednisolone acetate, Rayos, Proctocort, Paser, Olsalazine, Procto-Pak, Purixan, Cortenema, Giazo, Vedolizumab, Entyvio, Micheliolide, and Parthenolide.

The one or more additional agents can be selected from the group consisting of alkylating agents (nitrogen mustards, ethylenimine derivatives, alkyl sulfonates, nitrosoureas and triazenes); uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®); bendamustine (Treakisym®, Ribomustin®, Treanda®); chlormethine (Mustargen®); cyclophosphamide (Cytoxan®, Neosar®, Clafen®, Endoxan®, Procytox®, Revimmune™); ifosfamide (Mitoxana®); melphalan (Alkeran®); Chlorambucil (Leukeran®); pipobroman (Amedel®, Vercyte®); triethylenemelamine (Hemel®, Hexylen®, Hexastat®); triethylenethiophosphoramine; Temozolomide (Temodar®); thiotepa (Thioplex®); busulfan (Busilvex®, Myleran®); carmustine (BiCNU®); lomustine (CeeNU®); streptozocin (Zanosar®); estramustine (Emcyt®, Estracit®); fotemustine; irofulven; mannosulfan; mitobronitol; nimustine; procarbazine; ranimustine; semustine; triaziquone; treosulfan; and Dacarbazine (DTIC-Dome®); anti-EGFR antibodies (e.g., cetuximab (Erbitux®), panitumumab (Vectibix®), and gefitinib (Iressa®)); anti-Her-2 antibodies (e.g., trastuzumab (Herceptin®) and other antibodies from Genentech); antimetabolites (including, without limitation, folic acid antagonists (also referred to herein as antifolates), pyrimidine analogs, purine analogs and adenosine deaminase inhibitors): methotrexate (Rheumatrex®, Trexall®), 5-fluorouracil (Adrucil®, Efudex®, Fluoroplex®), floxuridine (FUDF®), carmofur, cytarabine (Cytosar-U®, Tarabine PFS), 6-mercaptopurine (Puri-Nethol®)), 6-thioguanine (Thioguanine Tabloid®), fludarabine phosphate (Fludara®), pentostatin (Nipent®), pemetrexed (Alimta®), raltitrexed (Tomudex®), cladribine (Leustatin®), clofarabine (Clofarex®, Clolar®), mercaptopurine (Puri-Nethol®), capecitabine (Xeloda®), nelarabine (Arranon®), azacitidine (Vidaza®), decitabine (Dacogen®), enocitabine (Sunrabin®), sapacitabine, tegafur-uracil, tiazofurine, tioguanine, trofosfamide, and gemcitabine (Gemzar®); vinca alkaloids: vinblastine (Velban®, Velsar®), vincristine (Vincasar®, Oncovin®), vindesine (Eldisine®), vinorelbine (Navelbine®), vinflunine (Javlor®); platinum-based agents: carboplatin (Paraplat®, Paraplatin®), cisplatin (Platinol®), oxaliplatin (Eloxatin®), nedaplatin, satraplatin, and triplatin; anthracyclines: daunorubicin (Cerubidine®, Rubidomycin®), doxorubicin (Adriamycin®), epirubicin (Ellence®), idarubicin (Idamycin®), mitoxantrone (Novantrone®), valrubicin (Valstar®), aclarubicin, amrubicin, liposomal doxorubicin, liposomal daunorubicin, pirarubicin, pixantrone, and zorubicin; topoisomerase inhibitors: topotecan (Hycamtin®), irinotecan (Camptosar®), etoposide (Toposar®, VePesid®), teniposide (Vumon®), lamellarin D, SN-38, camptothecin (e.g., IT-101), belotecan, and rubitecan; taxanes: paclitaxel (Taxol®), docetaxel (Taxotere®), larotaxel, cabazitaxel, ortataxel, and tesetaxel; antibiotics: actinomycin (Cosmegen®), bleomycin (Blenoxane®), hydroxyurea (Droxia®, Hydrea®), mitomycin (Mitozytrex®, Mutamycin®); immunomodulators: lenalidomide (Revlimid®), thalidomide (Thalomid®); immune cell antibodies: alemtuzamab (Campath®), gemtuzumab (Myelotarg®), rituximab (Rituxan®), tositumomab (Bexxar®); interferons (e.g., IFN-alpha (Alferon®, Roferon-A®, Intron®-A) or IFN-gamma (Actimmune®)); interleukins: IL-1, IL-2 (Proleukin®), IL-24, IL-6 (Sigosix®), IL-12; HSP90 inhibitors (e.g., geldanamycin or any of its derivatives). In some embodiments, the HSP90 inhibitor is selected from geldanamycin, 17-alkylamino-17-desmethoxygeldanamycin ("17-AAG") or 17-(2-dimethylaminoethyl)amino-17-desmethoxygeldanamycin ("17-DMAG"); anti-androgens which include, without limitation nilutamide (Nilandron®) and bicalutamide (Casodex®); antiestrogens which include, without limitation tamoxifen (Nolvadex®), toremifene (Fareston®), letrozole (Femara®), testolactone (Teslac®), anastrozole (Arimidex®), bicalutamide (Casodex®), exemestane (Aromasin®), flutamide (Eulexin®), fulvestrant (Faslodex®), raloxifene (Evista®, Keoxifene®) and raloxifene hydrochloride; anti-hypercalcaemia agents which include without limitation gallium (III) nitrate hydrate (Ganite®) and pamidronate disodium (Aredia®); apoptosis inducers which include without limitation ethanol, 2-[[3-(2,3-dichlorophenoxy)propyl]amino]-(9Cl), gambogic acid, elesclomol, embelin and arsenic trioxide (Trisenox®); Aurora kinase inhibitors which include without limitation binucleine 2; Bruton's tyrosine kinase inhibitors which include without limitation terreic acid; calcineurin inhibitors which include without limitation cypermethrin, deltamethrin, fenvalerate and tyrphostin 8; CaM kinase II inhibitors which include without limitation 5-Isoquinolinesulfonic acid, 4-[{2S)-2-[(5-isoquinolinylsulfonyl)methylamino]-3-oxo-3-{4-phenyl-1-piperazinyl)propyl]phenyl ester and benzenesulfonamide; CD45 tyrosine phosphatase inhibitors which include without limitation phosphonic acid; CDC25 phosphatase inhibitors which include without limitation 1,4-naphthalene dione, 2,3-bis[(2-hydroxyethyl)thio]-(9Cl); CHK kinase inhibitors which include without limitation debromohymenialdisine; cyclooxygenase inhibitors which include without limitation 1H-indole-3-acetamide, 1-(4-chlorobenzoyl)-5-methoxy-2-methyl-N-(2-phenylethyl)-(9Cl), 5-alkyl substituted 2-arylaminophenylacetic acid and its derivatives (e.g., celecoxib (Celebrex®), rofecoxib (Vioxx®), etoricoxib (Arcoxia®), lumiracoxib (Prexige®), valdecoxib (Bextra®) or 5-alkyl-2-arylaminophenylacetic acid); cRAF kinase inhibitors which include without limitation 3-(3,5-dibromo-4-hydroxybenzylidene)-5-iodo-1,3-dihydroindol-2-one and benzamide, 3-(dimethylamino)-N-[3-[(4-hydroxybenzoyl)amino]-4-methylphenyl]-(9Cl); cyclin dependent kinase inhibitors which include without limitation olomoucine and its derivatives, purvalanol B, roascovitine (Seliciclib®), indirubin, kenpaullone, purvalanol A and indirubin-3'-monooxime; cysteine protease inhibitors which include without limitation 4-morpholinecarboxamide, N-[(1S)-3-fluoro-2-oxo-1-(2-phenylethyl)propyl]amino]-2-oxo-1-(phenylmethyl)ethyl]-(9Cl); DNA intercalators which include without limitation plicamycin (Mithracin®) and daptomycin (Cubicin®); DNA strand breakers which include without limitation bleomycin (Blenoxane®); E3 ligase inhibitors which include without limitation N-((3,3,3-trifluoro-2-trifluoromethyl)propionyl)sulfanilamide; EGF Pathway Inhibitors which include, without limitation tyrphostin 46, EKB-569, erlotinib (Tarceva®), gefitinib (Iressa®), lapatinib (Tykerb®) and those compounds that are generically and specifically disclosed in WO 97/02266, EP 0 564 409, WO 99/03854, EP 0 520 722, EP 0 566 226, EP 0 787 722, EP 0 837 063, U.S. Pat. No. 5,747,498, WO 98/10767, WO 97/30034, WO 97/49688, WO 97/38983 and WO 96/33980; farnesyltransferase inhibitors which include without limitation ahydroxyfarnesylphosphonic acid, butanoic acid, 2-[(2 S)-2-[[(2S,3 S)-2-[[(2R)-2-amino-3-mercaptopropyl]amino]-3-methylpent-yl]oxy]-1-oxo-3-phenylpropyl]amino]-4-(methylsulfonyl)-1-methylethylester (2S)-(9Cl), tipifarnib (Zarnestra®), and manumycin A; Flk-1 kinase inhibitors which include without limitation 2-propenamide, 2-cyano-3-[4-hydroxy-3,5-bis(1-methyl ethyl)phenyl]-N-(3-phenylpropyl)-(2E-)-(9Cl); glycogen synthase kinase-3 (GSK3) inhibitors which include without limitation indirubin-3'-monooxime; histone deacetylase (HDAC) inhibitors which include without limitation suberoylanilide hydroxamic acid (SAHA), [4-(2-amino-phenylcarbamoyl)-benzyl]carbamic acid pyridine-3-ylmethylester and its derivatives, butyric acid, pyroxamide, trichostatin A, oxamflatin, apicidin, depsipeptide, depudecin, trapoxin, vorinostat (Zolinza®), and compounds disclosed in WO 02/22577; I-kappa B-alpha kinase inhibitors (IKK) which include without limitation 2-propenenitrile, 3-[(4-methylphenyl)sulfonyl]-(2E)-(9Cl); imidazotetrazinones which include without limitation temozolomide (Methazolastone®, Temodar® and its derivatives (e.g., as disclosed generically and specifically in U.S. Pat. No. 5,260,291) and Mitozolomide; insulin tyrosine kinase inhibitors which include without limitation hydroxyl-2-naphthalenylmethylphosphonic acid; c-Jun-N-terminal kinase (JNK) inhibitors which include without limitation pyrazoleanthrone and epigallocatechin gallate; mitogen-activated protein kinase (MAP) inhibitors which include without limitation benzenesulfonamide, N-[2-[[[3-(4-chlorophenyl)-2-propenyl]methyl]amino]methyl]phenyl]-N-(2-hy-droxyethyl)-4-methoxy-(9Cl); MDM2 inhibitors which include without limitation trans-4-iodo, 4'-boranyl-chalcone; MEK inhibitors which include without limitation butanedinitrile, bis[amino[2-aminophenyl)thio]methylene]-(9Cl); MMP inhibitors which include without limitation Actinonin, epigallocatechin gallate, collagen peptidomimetic and non-peptidomimetic inhibitors, tetracycline derivatives marimastat (Marimastat®), prinomastat, incyclinide (Metastat®), shark cartilage extract AE-941 (Neovastat®), Tanomastat, TAA211, MMI270B or AAJ996; mTor inhibitors which include without limitation rapamycin (Rapamune®), and analogs and derivatives thereof, AP23573 (also known as ridaforolimus, deforolimus, or MK-8669), CCI-779 (also known as temsirolimus) (Torisel®) and SDZ-RAD; NGFR tyrosine kinase inhibitors which include without limitation tyrphostin AG 879; p38 MAP kinase inhibitors which include without limitation Phenol, 4-[4-(4-fluorophenyl)-5-(4-pyridinyl)-1H-imidazol-2-yl]-(9Cl), and benzamide, 3-(dimethylamino)-N-[3-[(4-hydroxylbenzoyl)amino]-4-methylphenyl]-(9Cl); p56 tyrosine kinase inhibitors which include without limitation damnacanthal and tyrphostin 46; PDGF pathway inhibitors which include without limitation tyrphostin AG 1296, tyrphostin 9, 1,3-butadiene-1,1,3-tricarbonitrile, 2-amino-4-(1H-indol-5-yl)-(9Cl), imatinib (Gleevec®) and gefitinib (Iressa®) and those compounds generically and specifically disclosed in European Patent No.: 0 564 409 and PCT Publication No.: WO 99/03854; phosphatidylinositol 3-kinase inhibitors which include without limitation wortmannin, and quercetin dihydrate; phosphatase inhibitors which include without limitation cantharidic acid, cantharidin, and L-leucinamide; protein phosphatase inhibitors which include without limitation cantharidic acid, cantharidin, L-P-bromotetramisole oxalate, 2(5H)-furanone, 4-hydroxy-5-(hydroxymethyl)-3-(1-oxohexadecyl)-(5R)-(9Cl) and benzylphosphonic acid; PKC inhibitors which include without limitation 1-H-pyrollo-2,5-dione, 3-[1-3-(dimethylamino)propyl]-1H-indol-3-yl]-4-(1H-indol-3-yl)-(9Cl), Bisindolylmaleimide IX, Sphinogosine, staurosporine, and Hypericin; PKC delta kinase inhibitors which include without limitation rottlerin; polyamine synthesis inhibitors which include without limitation DMFO; PTP1B inhibitors which include without limitation L-leucinamide; protein tyrosine kinase inhibitors which include, without limitation tyrphostin Ag 216, tyrphostin Ag 1288, tyrphostin Ag 1295, geldanamycin, genistein and 7H-pyrrolo[2,3-d]pyrimidine derivatives as generically and specifically described in PCT Publication No.: WO 03/013541 and U.S. Publication No.: 2008/0139587; SRC family tyrosine kinase inhibitors which include without limitation PP1 and PP2; Syk tyrosine kinase inhibitors which include without limitation piceatannol; Janus (JAK-2 and/or JAK-3) tyrosine kinase inhibitors which include without limitation tyrphostin AG 490 and 2-naphthyl vinyl ketone; retinoids which include without limitation isotretinoin (Accutane®, Amnesteem®, Cistane®, Claravis®, Sotret®) and tretinoin (Aberel®, Aknoten®, Avita®, Renova®, Retin-A®, Retin-A MICRO®, Vesanoid®); RNA polymerase H elongation inhibitors which include without limitation 5,6-dichloro-1-beta-D-ribofuranosylbenzimidazole; serine/Threonine kinase inhibitors which include without limitation 2-aminopurine; sterol biosynthesis inhibitors which include without limitation squalene epoxidase and CYP2D6; VEGF pathway inhibitors, which include without limitation anti-VEGF antibodies, e.g., bevacizumab, and small molecules, e.g., sunitinib (Sutent®), sorafinib (Nexavar®), ZD6474 (also known as vandetanib) (Zactima™), SU6668, CP-547632 and AZD2171 (also known as cediranib) (Recentin™)

EXAMPLES

Some aspects of the embodiments discussed above are disclosed in further detail in the following examples, which are not in any way intended to limit the scope of the present disclosure.

Example 1

Acoustic Remote Control of Bacterial Cancer Immunotherapy

Introduction

Cell therapies are rapidly emerging as an exciting and effective class of technologies for cancer treatment. Among the cell types being investigated for therapy, immune cells have excelled in the treatment of hematologic malignancies. However, their use in solid tumors has been hampered by their reduced ability to penetrate and function in the tumor's immunosuppressive environment, especially within immune-privileged hypoxic cores. Conversely, the reduced immune activity of some tumor cores creates a favorable microenvironment for the growth of certain bacteria, which can reach the tumors after systemic administration. Capitalizing on their tumor-infiltrating properties, such bacteria can be engineered to function as effective cellular therapies by secreting therapeutic payloads to directly kill tumor cells or remodel the microenvironment to stimulate anti-tumor immunity. However, the benefits of microbial therapy are often counterbalanced by safety concerns accompanying the systemic injection of microbes into patients with limited control over their biodistribution or activity. This is especially important given the well-documented engraftment of circulating bacteria into healthy tissues such as the liver, spleen, and certain hypoxic stem cell niches. To avoid damaging healthy organs, it is crucial that the therapeutic activity of microbes be targeted to tumors.

Among the available mechanisms to regulate microbial function, systemically administered chemical inducers are convenient to apply but incapable of targeting a particular anatomical site. Meanwhile, light-induced control elements provide high spatiotemporal precision, but are constrained by the poor penetration of light into intact tissues. Radiation-induced promoters can be targeted by deeply penetrant energy. However, ionizing radiation carries the risk of damage to host immune cells and engineered microbial cells. Alternatively, temperature-based transcriptional regulators enable spatiotemporal control at depth, since temperature can be elevated precisely within a well-tolerated range in deep tissues using noninvasive methods such as focused ultrasound (FUS).

Indeed, it was recently demonstrated that FUS can be used in conjunction with temperature-dependent repressors to control the expression of bacterial genes. However, these repressors operated in clinically irrelevant cloning strains of bacteria, had non-therapeutic outputs, and produced only transient activation unsuitable for tumor treatment, which typically requires weeks of therapeutic activity.

Described herein is the development of FUS-activated therapeutic bacteria in which a brief thermal stimulus activates sustained release of anti-cancer immunotherapy. These cellular agents were engineered by adapting temperature-sensitive repressors to the tumor-homing probiotic species *E. coli* Nissle 1917 and designing gene circuits in which they control an integrase-based state switch resulting in long-term therapy production. To improve the safety and efficacy of these cells, random and rationally designed libraries of gene circuit variants were screened for constructs with minimal baseline activity and maximal induction upon thermal stimulation. The optimized gene circuits were used to express immune checkpoint inhibitors targeting CTLA-4 and PD-L1. In a mouse cancer model, the resulting engineered microbes were shown to be reliably and chronically activated by a brief, noninvasive FUS treatment after systemic administration to release therapy and successfully suppress tumor growth.

Results

Characterizing Thermal Bioswitches in a Therapeutically Relevant Microbe

To develop a temperature-actuated therapeutic circuit, high-performance temperature-dependent transcriptional repressors were started with, which actuate transient gene expression in response to small changes in temperature around 37° C. Since genetic elements tend to behave differently across cell types due to variations in protein expression and other aspects of the intracellular environment, the performance of these repressors in a chosen therapeutic chassis was first characterized: *E. coli* Nissle 1917 (EcN). This bacterial strain is approved for human probiotic use and is commonly employed in microbial tumor therapy. Three repressor candidates—TlpA39, wild-type TcI, and TcI42—were selected as starting points due to their desirable activation temperature thresholds of 39° C., 38° C., and 42° C., respectively. In its natural host, *Salmonella typhimurium*, TlpA is speculated to be responsible for the regulation of virulence genes upon entry into a warm host organism. Meanwhile, TcI is a temperature-sensitive mutant of the bacteriophage lambda protein "cI". In its native context, cI serves as a transcriptional repressor that allows the bacteriophage lambda virus to establish and maintain latency.

Figure 1B:
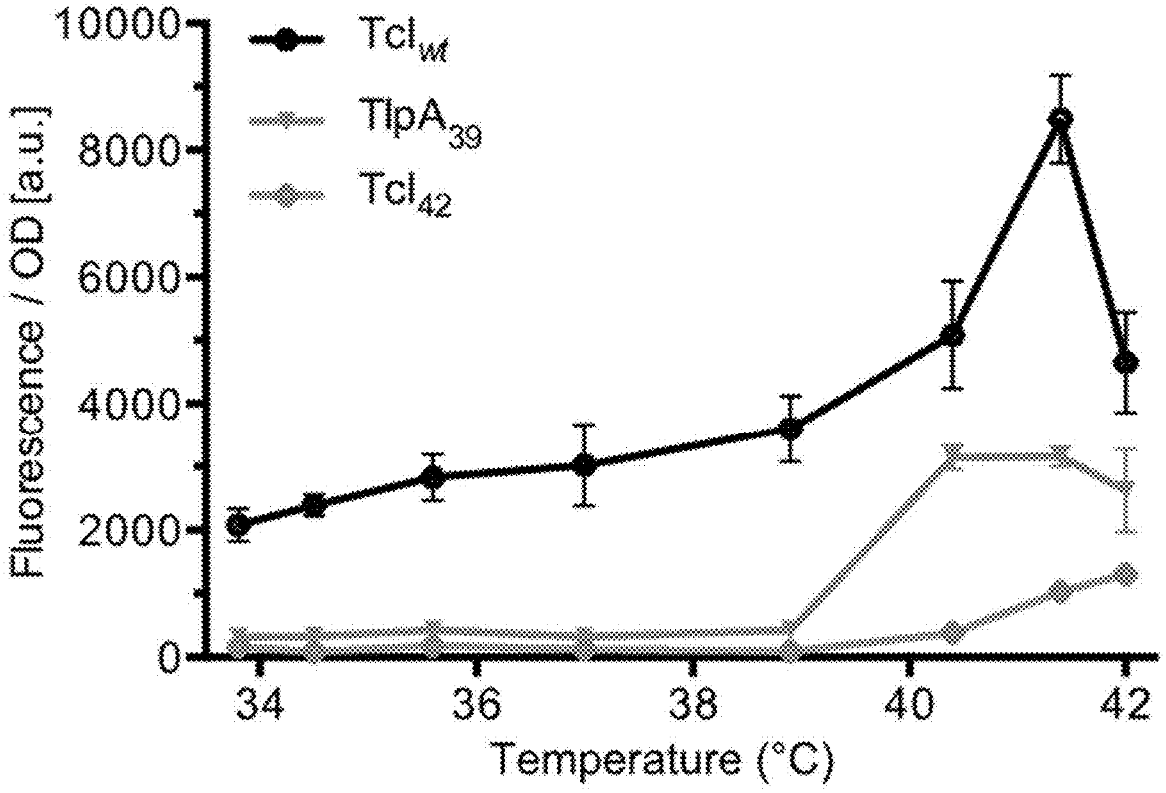
Figure 1C:
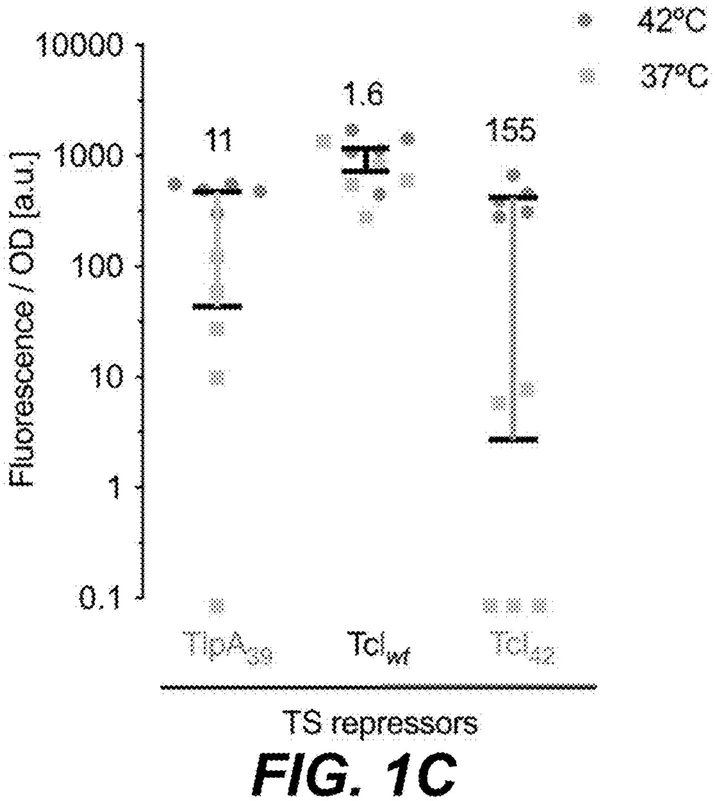

To evaluate the performance of these candidates reporter constructs were designed where they regulate the expression of a green fluorescent protein (GFP) (FIG. 1A), they were transformed into EcN cells, and the corresponding cell density-normalized fluorescence intensity was measured as a function of temperature between 33° C. and 42° C. (FIG. 1B). This construct provided a tractable platform for us to directly evaluate the inducibility of thermally responsive repressors in EcN cells by measuring GFP fluorescence. In view of the interest in using these bioswitches in vivo, the fold-change between the mammalian physiological temperature (37° C.) and an elevated temperature that can be used to trigger activation in vivo while minimizing thermal damage to local tissues (42° C.) was focused on (FIG. 1C). Results from these experiments indicated that TcI42 is the best candidate for integration into the disclosed thermal switch since it exhibits strong induction at 42° C. while maintaining low levels of baseline activity.

Figure 1D:
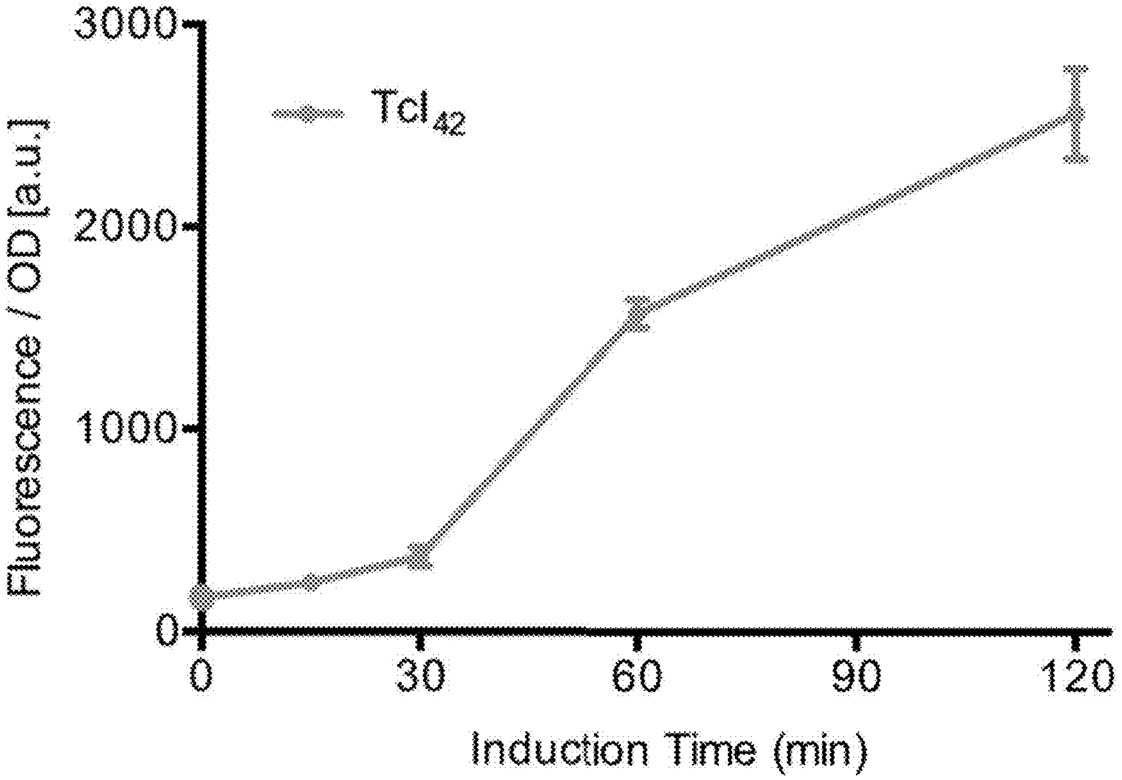
Figure 1E:
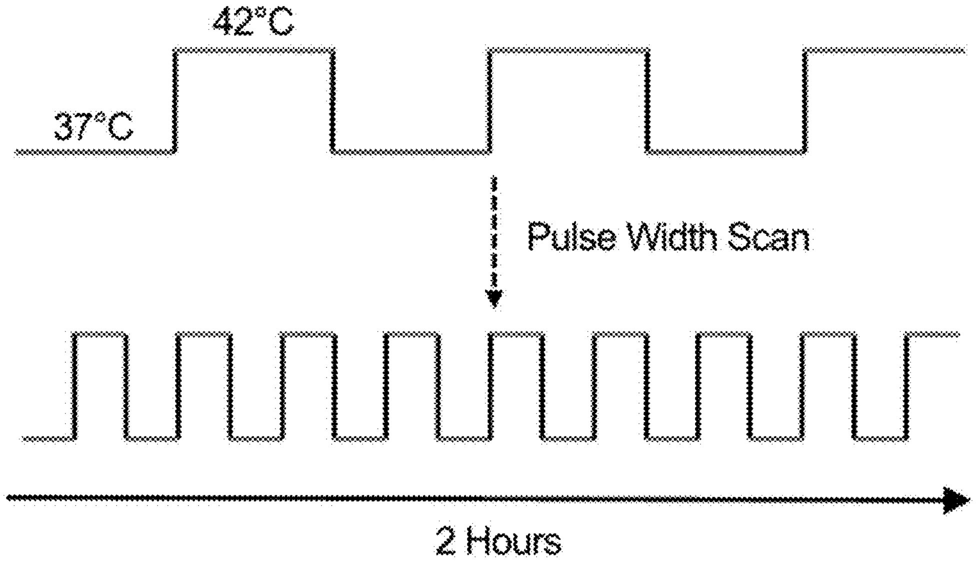
Figure 1F:
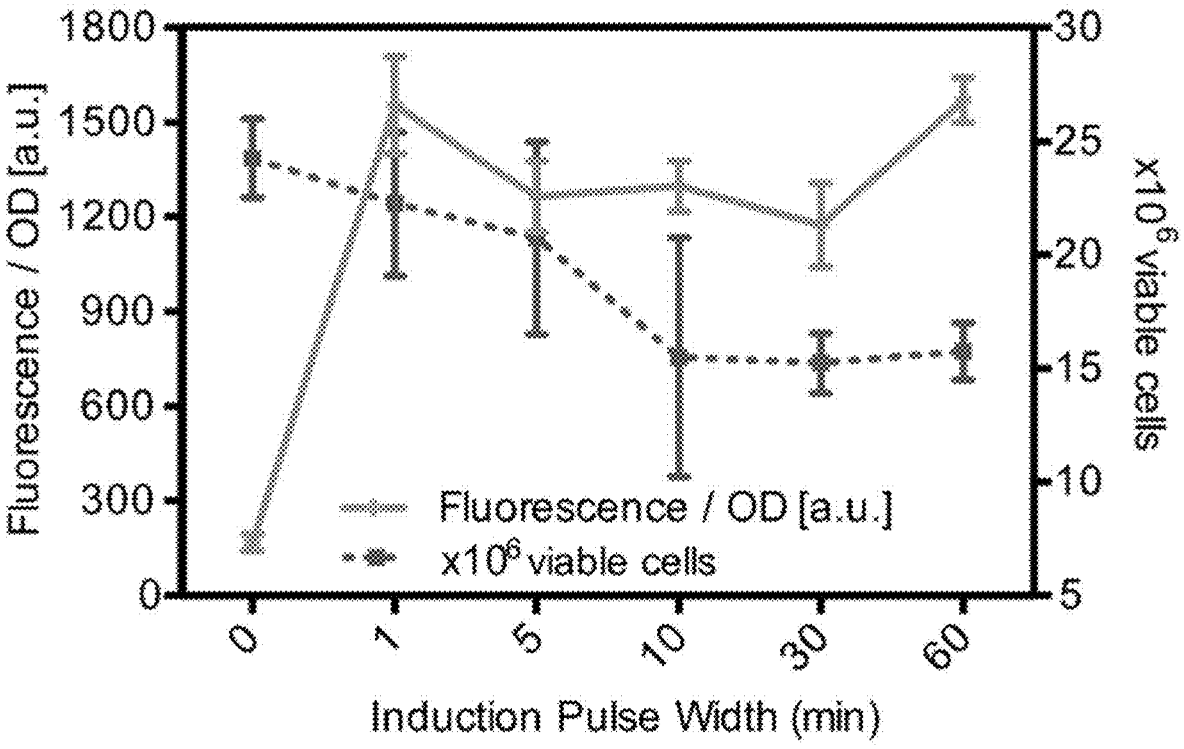
Figure 1G:
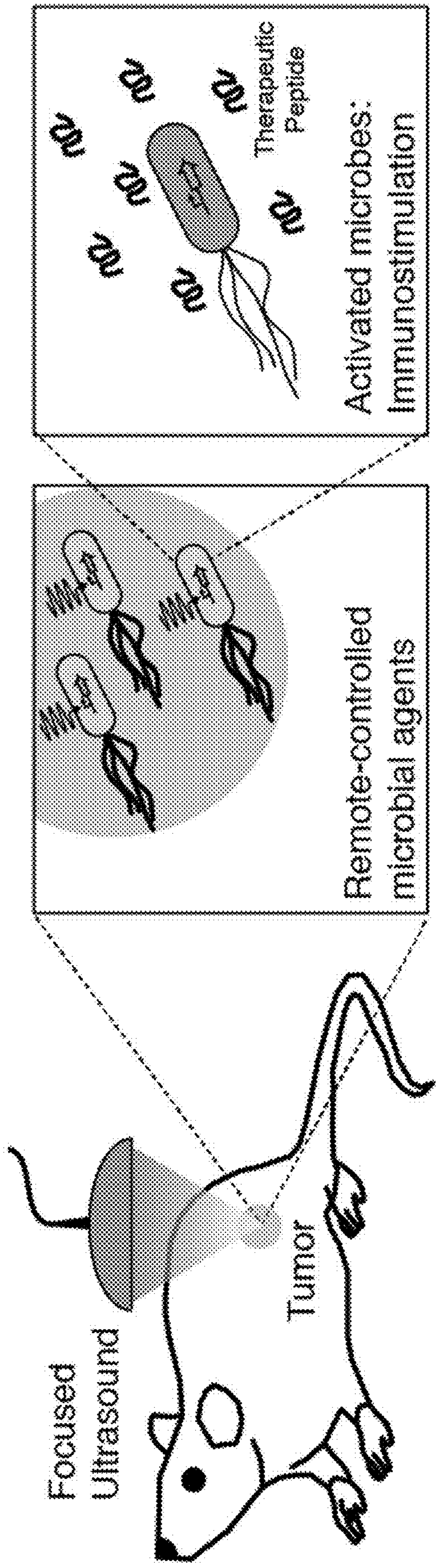

With TcI42 serving as the thermal transducer in the disclosed cells, next it was sought to determine the minimal heating duration and ideal heating parameters required to achieve strong activation while minimizing damage to cells. Cells carrying the circuit described in FIG. 1*a* were stimulated by elevating the temperature to 42° C. for different durations and measured the corresponding fluorescence intensity (FIG. 1D). The results indicated that a minimal heating time of one hour is needed for robust activation. The effect of this thermal dose on microbial cell viability was quantified and a pulsatile heating scheme that was previously shown to enhance viability in mammalian cells was simultaneously tested. For the pulsatile heating scheme, the duty cycle was kept constant at 50% while alternating the temperature between 37° C. and 42° C., resulting in a total of one hour at 42° C. over a two-hour period, with pulse duration varying between 1 and 60 minutes (FIG. 1E). As hypothesized, cell viability decreased as the pulse duration increased, while induction levels did not significantly vary (FIG. 1F). Based on these results, a five-minute pulse duration for subsequent applications was selected, as this heating paradigm enhanced cell viability while being readily achievable with a focused ultrasound setup. Collectively, these experiments identified and characterized TcI42 as an effective thermal transducer to control gene expression in the therapeutically relevant EcN strain.

Constructing a Thermally Actuated State Switch

On its own, the TcI42 switch is not sufficient for microbial cancer therapy. This switch is transiently activated for the duration of heating, while tumor therapy requires weeks to effectively suppress tumor growth. Since daily FUS application over this period is infeasible in a clinical setting, a gene circuit that maintains a prolonged therapeutic response following a single, brief thermal activation was engineered.

Figure 2A:
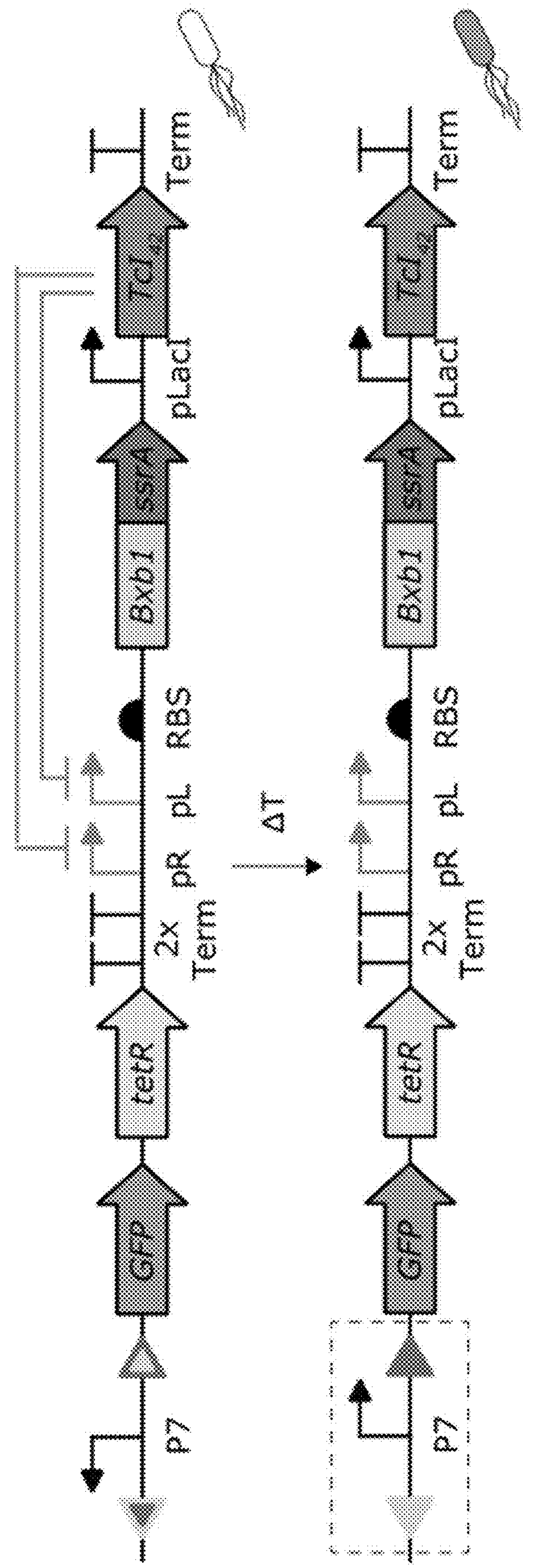
FIGS. 2A-2F depict data related to construction and optimization of a temperature responsive state switch.

To enable stable thermal switching, the expression of Bxb1, a serine integrase, was placed under the control of the pL/pR phage lambda thermally inducible promoters, whose activity is regulated by the TcI42 repressor (FIG. 2A). Serine integrases such as Bxb1 were initially discovered in bacteriophages as a class of enzymes targeting DNA sequences known as attP and attB sites. In their native context, these sites serve as a hub for the integration of bacteriophage DNA into the genome of target cells. However, these sites can be repurposed to flank an arbitrary DNA sequence and mediate its inversion, resulting in a stable switching functionality. The disclosed design combines the temperature sensitivity of TcI42 with this permanent effector function of the Bxb1 integrase. At physiological temperatures of approximately 37° C., constitutive expression of the TcI42 repressor from the pLacI promoter represses the expression of Bxb1. Upon thermal stimulation, the release of TcI42 repression results in a burst of Bxb1 expression. Thermally derepressed Bxb1 expression then catalyzes the inversion of minimal recognition sites attP and attB flanking the P7 promoter, resulting in its activation and subsequent expression of a fluorescent reporter to monitor the state of the circuit and a tetracycline resistance cassette serving as a placeholder for a therapeutic protein (FIG. 2A). Because the attP and attB recognition sites are modified post-inversion by the Bxb1 enzyme, the inverted DNA sequence is not recognized by a subsequent Bxb1 interaction and is therefore a permanent inversion event. Subsequently, the P7 promoter will continue to drive the expression of its protein payloads even when the temperature stimulus is terminated. The P7 promoter was chosen from a depository of synthetic constitutive bacterial promoters due to its balance of strongly driving the expression of a genetic payload without creating excessive stress on the cell. To avoid unregulated expression of Bxb1 the activity of the temperature-activated promoter was insulated by inserting two strong terminators upstream to block activity from other regions of the plasmid.

Figure 2B:
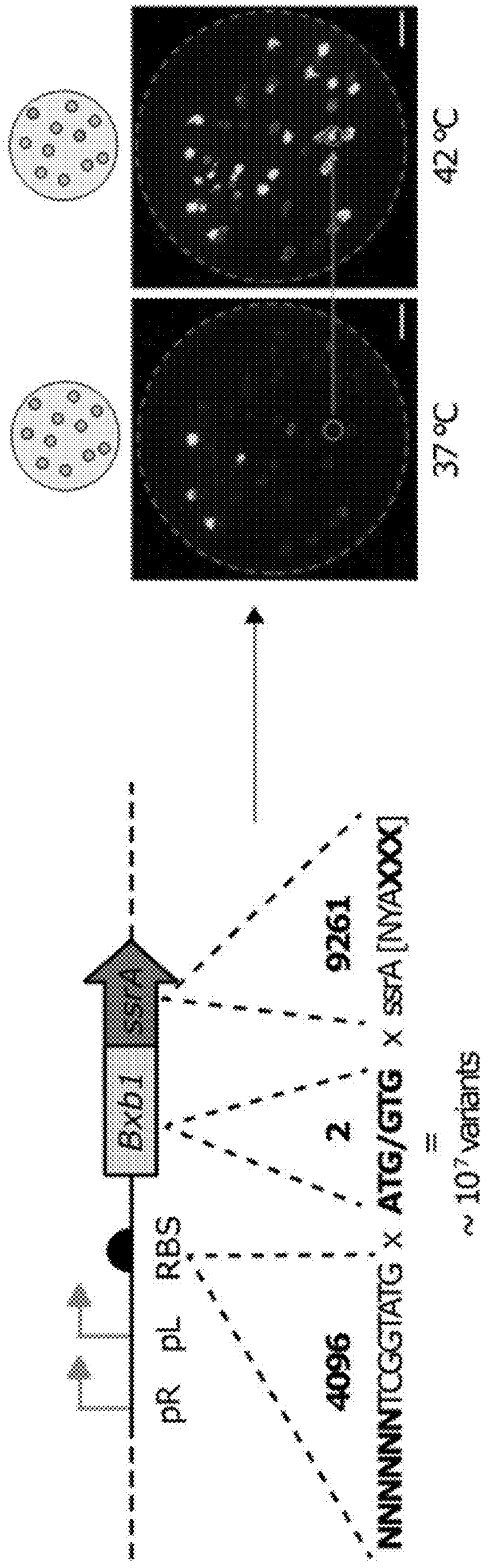
Figure 2C:
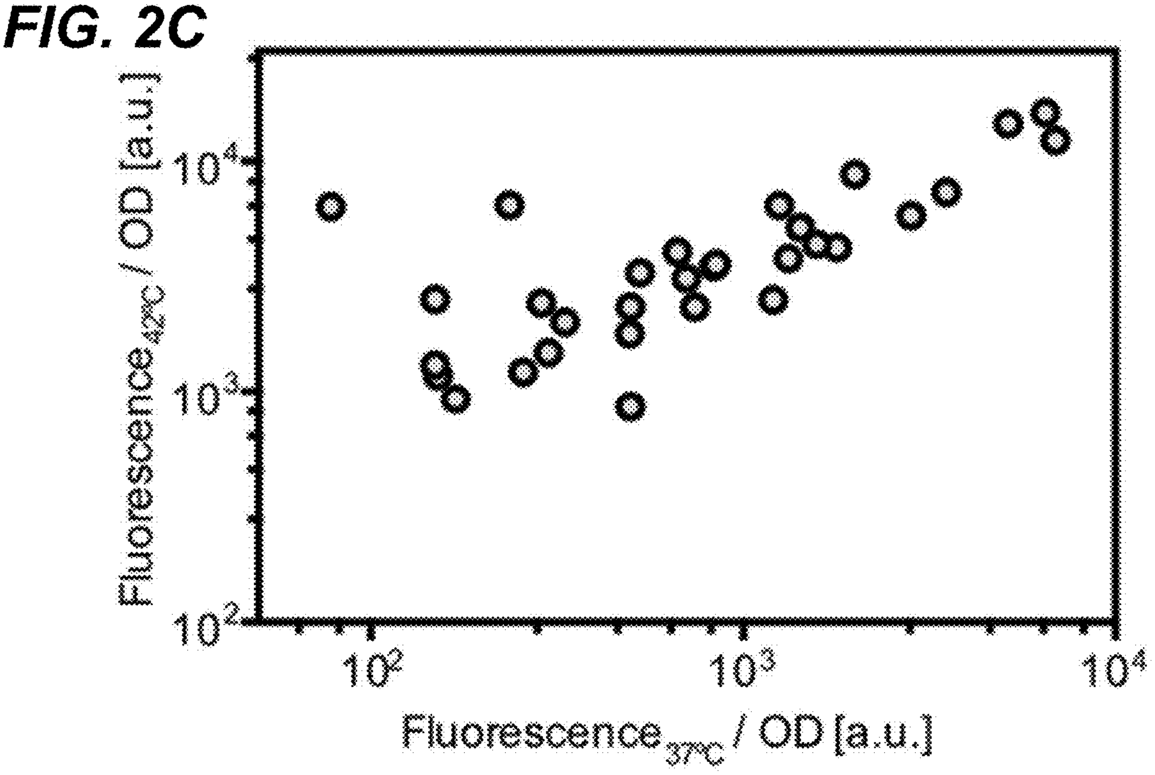
Figure 2D:
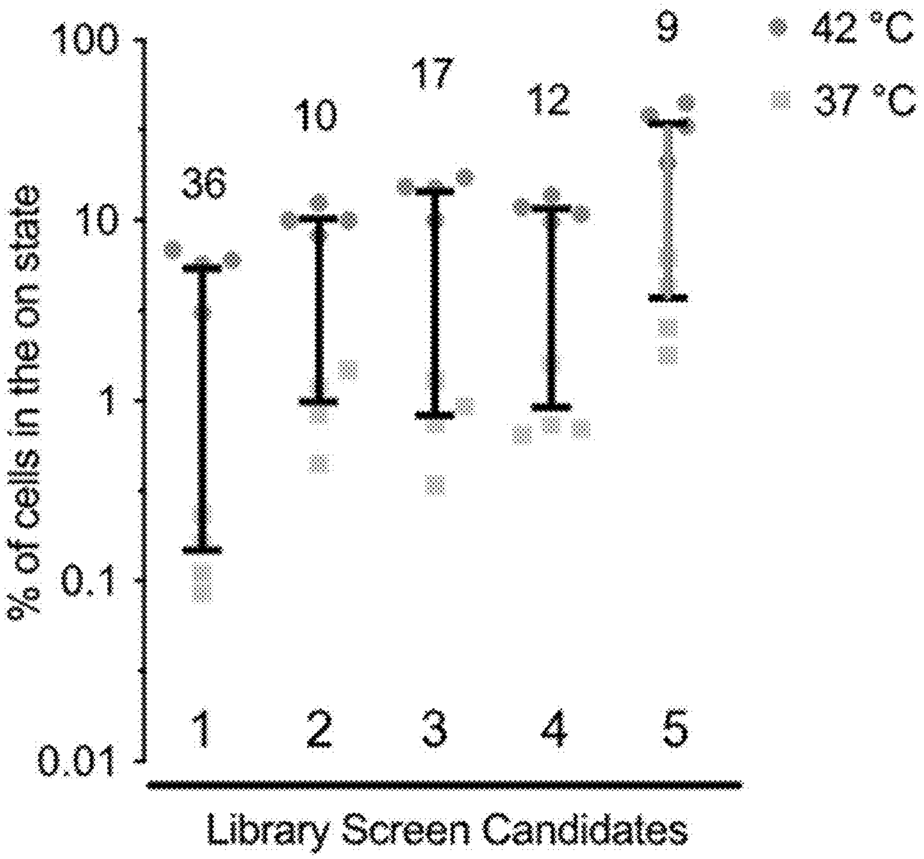

The ideal performance of the circuit described above would maintain low baseline activity at physiological temperature while providing strong and lasting induction once thermally stimulated. To achieve this performance, three key sequence elements affecting Bxb1 translation and stability were tuned: the Bxb1 ribosomal binding sequence (RBS), start codon, and ssrA degradation tag (FIG. 2B). The ssrA tag is a short peptide that naturally gets added to the C terminus of proteins whose translation has stalled. Proteins that carry this sequence as a fusion are targeted for degradation by endogenous bacterial proteases. To efficiently identify the best versions of these elements a library screen was performed that consisted of randomized 6-bp sequences within the Bxb1 RBS, two Bxb1 start codon choices, and randomized terminal tripeptides in the Bxb1 ssrA degradation tag. Two start codons were tested because the non-canonical start codon GUG can down-regulate ribosomal efficiency, and the last three amino acids of the ssrA degradation tag were randomized because they strongly modulate the degradation rate of ssrA-tagged proteins. A total landscape of approximately $10^7$ possible unique variants was sampled using a high-throughput plate-replication assay (FIG. 2B). Agar plates containing colonies of library members were first replicated, and then one plate was incubated at 37° C. to assess baseline expression, while the other plate was stimulated at 42° C. for an hour and returned 37° C. for the rest of the growth period. The temperature-dependent fluorescence of a representative sampling of variants is shown in FIG. 2C. A subset of variants with low leak and high activation were selected to quantify their switching performance with a larger number of replicates (FIG. 2D). Out of these candidates, candidate #5 was selected for further optimization since it activated the largest percentage of the cells upon stimulation, a metric that is important to ensure strong therapeutic activity in vivo, while still retaining a reasonable temperature-dependent fold change (FIG. 2D). (See FIG. 13 and FIGS. 15-16)

Figure 2E:
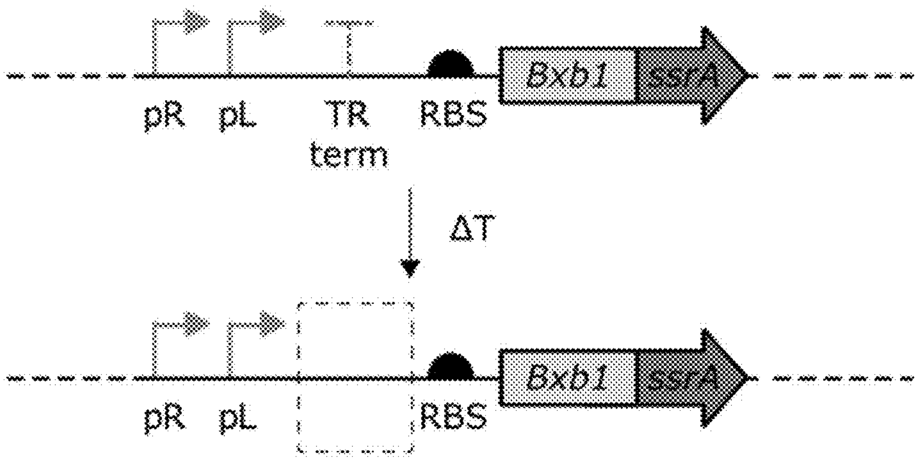
Figure 2F:
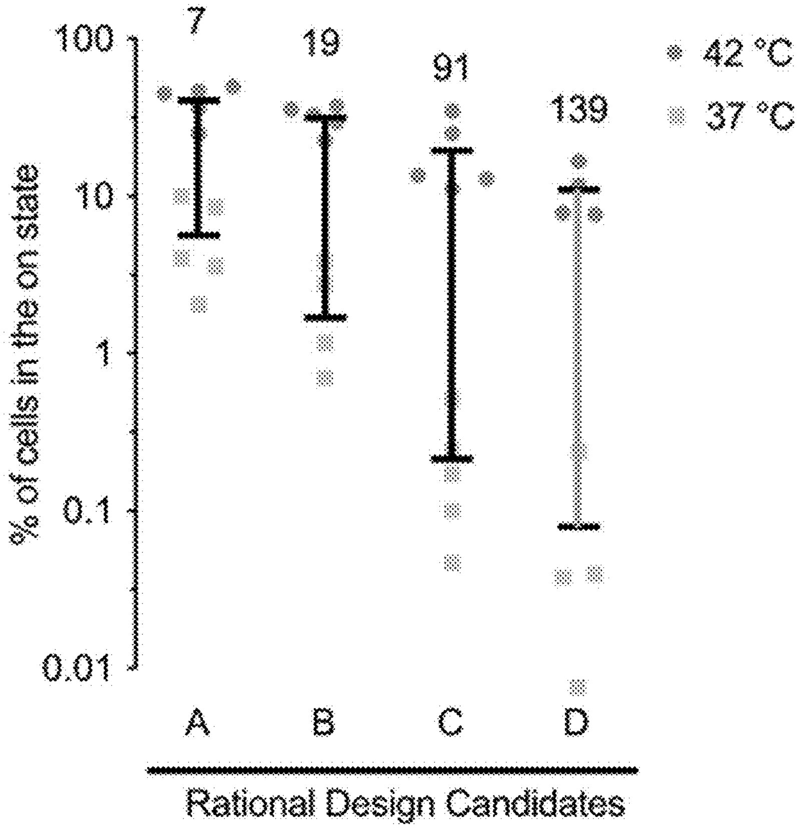

To reduce the baseline activity of candidate #5, two additional circuit components were modified (FIG. 2E). The first modification changed the origin of replication from the low-copy origin pSC101 to the medium-copy origin p15A. The second modification explored the effect of inserting a temperature-sensitive terminator upstream of the Bxb1 coding sequence. This family of terminators have been engineered to mimic temperature-modulated structures known as RNA thermometers that are found in the 5' untranslated region of microbial mRNAs and play an important role in regulating microbial gene expression in response to temperature changes. In the disclosed circuit, this terminator was used to introduce a temperature-sensitive secondary structure in the mRNA transcript that helps terminate protein expression at low temperatures, adding to the control provided by TcI42 to prevent leaky Bxb1 protein production at physiological temperature. At 42° C., this terminator loses its secondary structure and Bxb1 expression is unimpeded. The performance of four constructs with either one or both of these modifications was assessed (FIG. 2F).

Increasing the copy number of the plasmid and inserting the terminator reduced baseline activation independently. When combined together, these modifications resulted in significantly reduced leakage while maintaining a large fold-change in activated cells upon induction. The resulting construct, obtained through a combination of randomized and rational engineering, displayed a more than 100-fold change in activity between 37° C. and 42° C.

Engineering Cells for Thermally Actuated Secretion of Immunotherapy

Figure 3A:
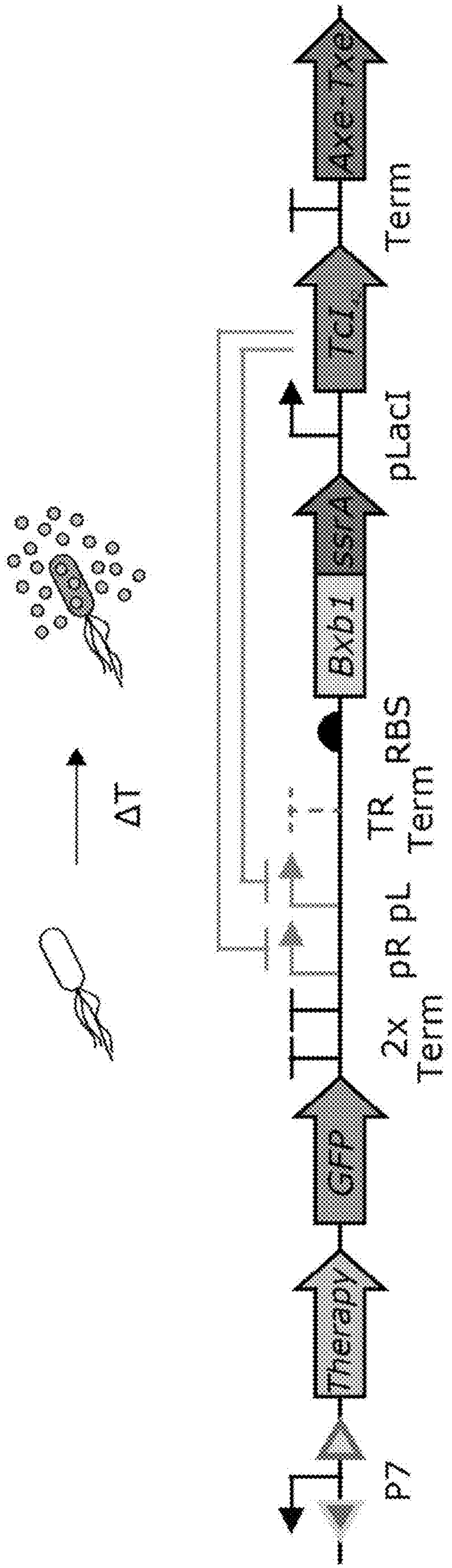
FIGS. 3A-3C depict data related to thermally activated sustained release of a therapeutic payload.

To demonstrate the functionality of the disclosed optimized thermally-actuated cells in a clinically relevant scenario, the output of their gene circuit was modified to express an anti-tumor therapeutic payload (FIG. 3A). αCTLA-4 and αPD-L1 nanobodies were selected, which block signaling through the CTLA-4 and PD-L1 checkpoint receptor pathways, which are heavily implicated in T-cell silencing within immunosuppressive solid tumors. Checkpoint inhibitors such as αCTLA-4 and αPD-L1 have emerged as a major class of cancer therapy, but their therapeutic efficacy is commonly accompanied by the risk of unintentionally activating autoimmunity in bystander tissues when administered systemically. By combining the ability of FUS to target specific areas deep within tissues with the tumor infiltration, thermal response and molecular specificity of the disclosed engineered cells, it was reasoned that the activity of these potent immunomodulators could be targeted to tumors and thereby mitigate the risk of systemic exposure.

αCTLA-4 and αPD-L1 have been shown to produce antitumor effects when released by tumor-injected probiotics. It was hypothesized that local FUS-activated release of these proteins in tumors from systemically administered engineered bacteria would suppress tumor growth. To test this hypothesis, αCTLA-4 and αPD-L1 were fused to a PelB secretion tag to enhance their extracellular release upon activation and cloned each construct in place of the tetracycline cassette in the disclosed optimized switching circuit. The pelB leader peptide, derived from the *Erwinia carotovora* pelB gene, has been previously used to secrete proteins from microbes. In addition, to stabilize the disclosed plasmids for long-term retention in vivo without antibiotic selection, an Axe-Txe toxin-antitoxin stability domain was added, which ensures retention of the plasmid in a cell population by eliminating cells that lose it. The Axe-Txe type II toxin anti-toxin system originates from the Axe-Txe locus of the gram-positive *Enterococcus faecium* plasmid pRUM.

Figure 3B:
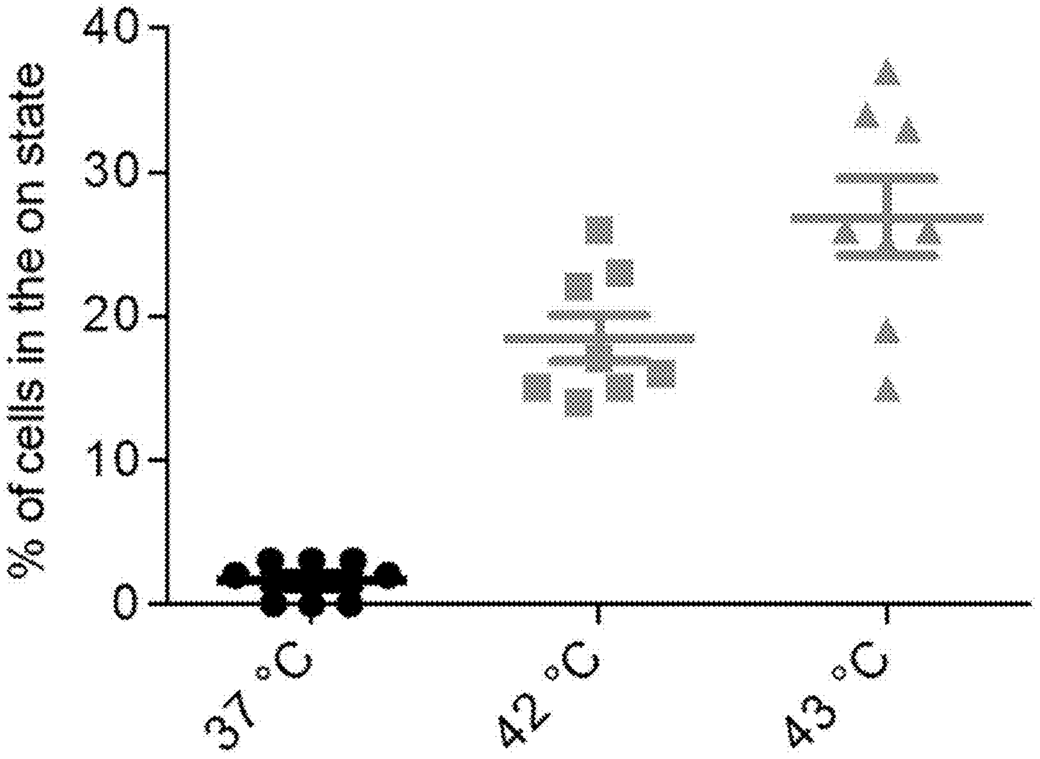
Figure 7:
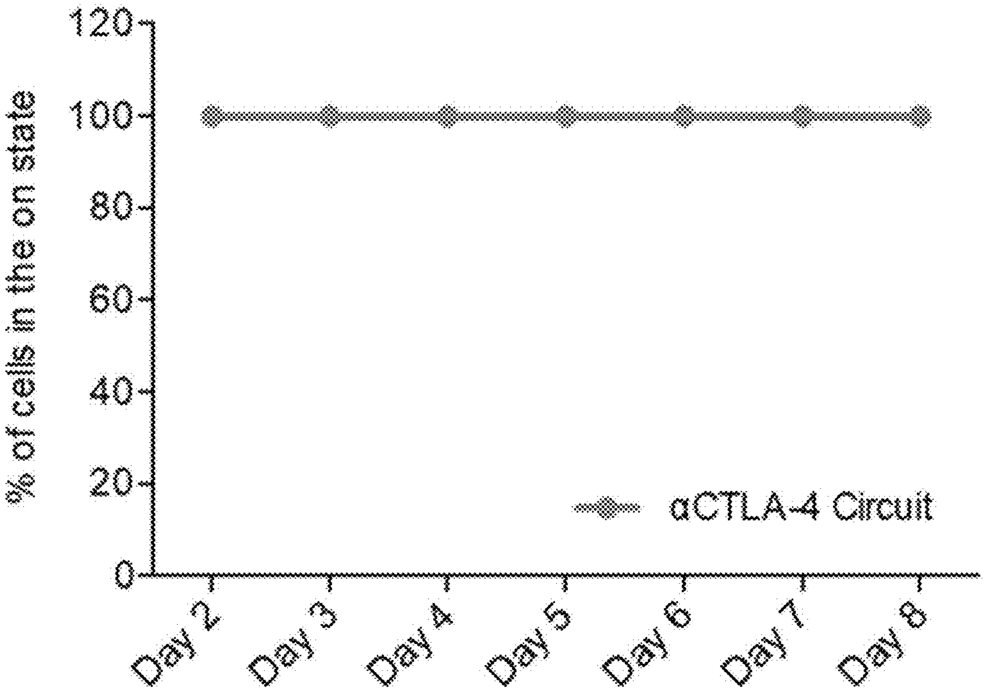
FIG. 7 depicts data related to stability of gene expression in thermally induced circuits. EcN cells were transformed with the αCTLA-4 therapeutic circuit from FIG. 3 and thermally induced at 43° C. for 1 hour with the five-minute pulsing scheme. The following day four colonies were picked and propagated to assess circuit stability. These cells were diluted every day by a factor of 1000× and simultaneously plated to assess the number of cells in the on state from each colony by counting GFP positive cells. No evidence of burden on the cells was found, which is typically reflected in mutational escape. N=4 biological replicates. All data points were 100% GFP positive.

The thermal switching functionality of the disclosed therapeutic circuits closely resembled their non-therapeutic counterpart. The circuit containing αCTLA-4 maintained a tight off-state at 37° C. while exhibiting robust fold-changes upon induction at 42° C. and 43° C. (FIG. 3B). Furthermore, upon tracking induced cells post-induction no evidence of mutational escape was seen, suggesting a tolerable level of burden (FIG. 7).

Figure 3C:
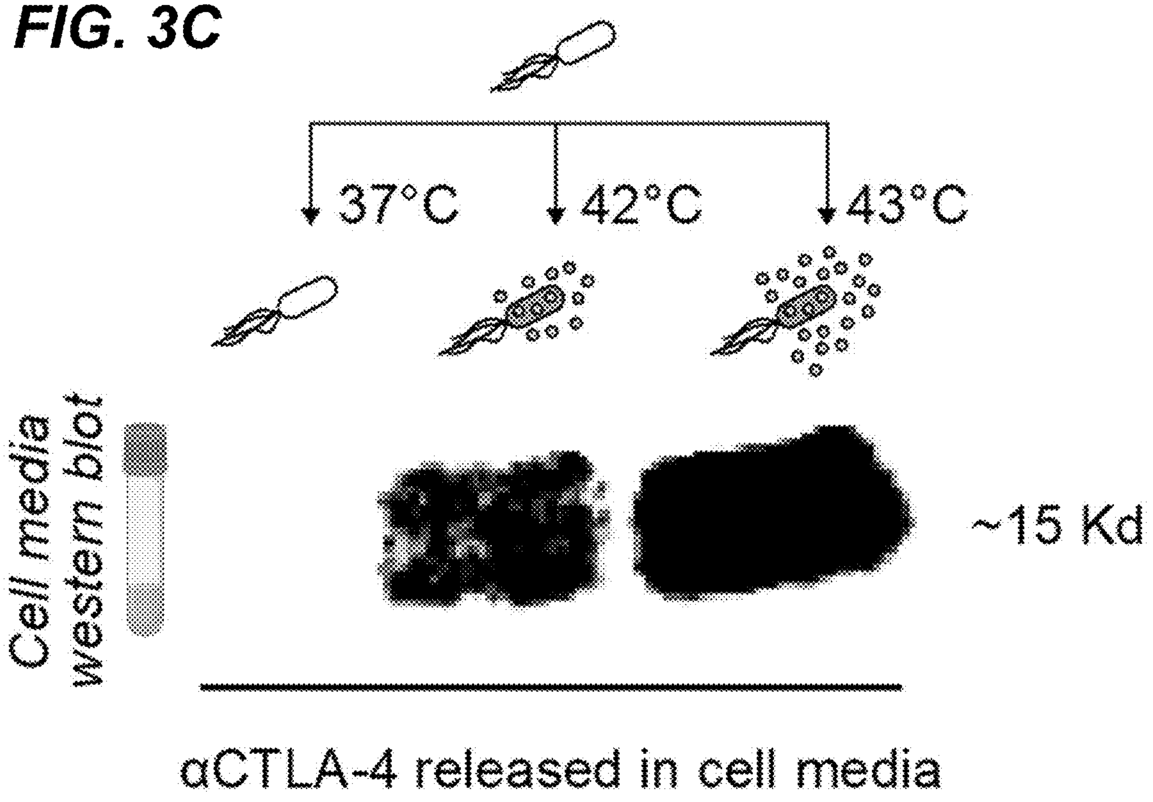

To assess the secretion of therapeutic nanobodies upon activation, the cells were stimulated for one hour at 37° C., 42° C. and 43° C., then cultured them for one day at 37° C. and a Western Blot was performed to evaluate the levels of αCTLA-4 nanobodies released in their media. This experiment demonstrated that αCTLA-4 nanobodies are reliably secreted exclusively upon stimulation at 42° C. and 43° C. (FIG. 3C). There was no detection of any secretion when the cells were incubated at 37° C. Similar characterization was performed for cells expressing αPD-L1.

Focused Ultrasound Activation Elicits In Vivo Tumor Suppression

Figure 4A:
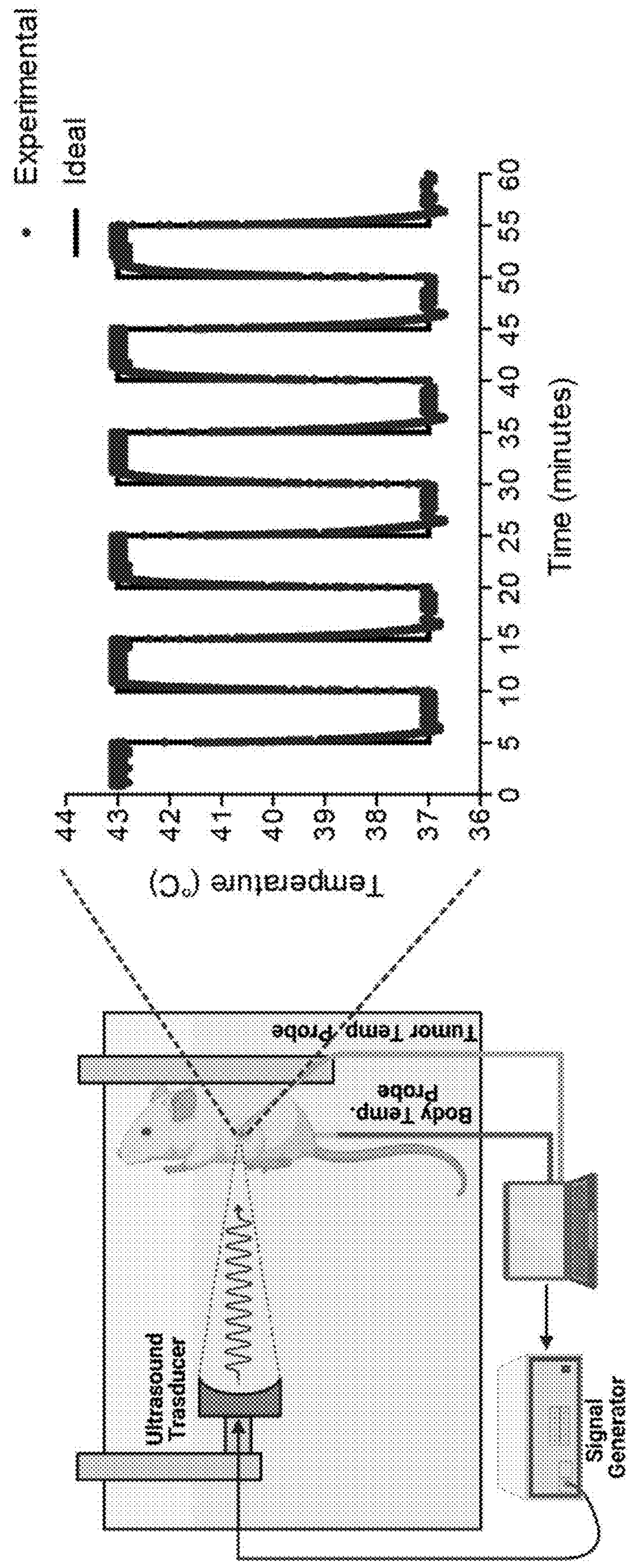
FIGS. 4A-4E depict data related to ultrasound-activated bacterial immunotherapy reducing tumor growth in vivo.

To enable thermal control of engineered therapeutic microbes in vivo a FUS stimulation setup was built providing feedback-controlled pulsatile tumor heating (FIG. 4A), capturing the key features of clinically available instruments. It was demonstrated that the disclosed system is capable of toggling the temperature in the tumor of a live animal between 37° C. and 43° C. every five minutes (FIG. 4A). The focal maximum temperature was set inside the tumor at 43° C. to allow more of the mass to be heated above 42° C. and ensure reliable activation within the context of a mouse. While this could lead to some thermal damage, it was reasoned that such damage within the tumor is acceptable and could synergize with the microbial immunotherapy.

Figure 4B:
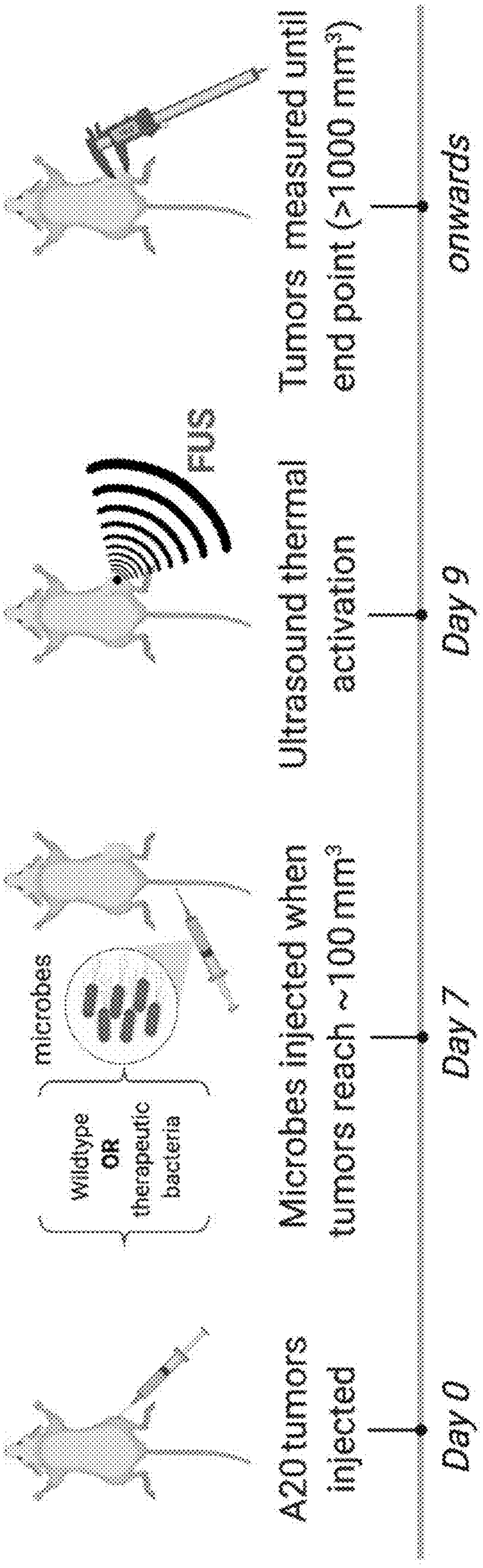
Figure 8:
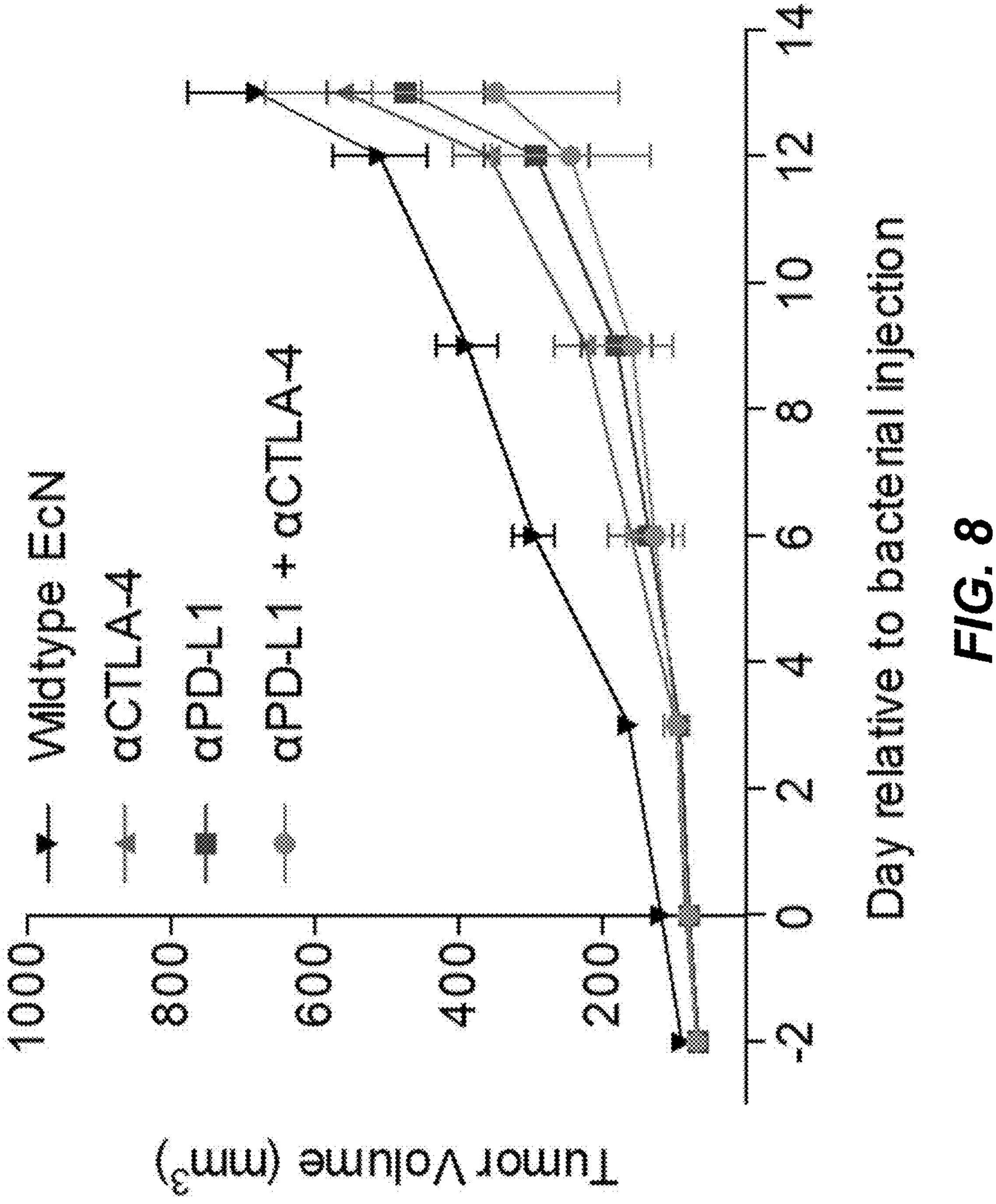
FIG. 8 depicts data related to assessing the effect of combination checkpoint therapy. EcN cells were transformed with the αCTLA-4 or αPD-L1 therapeutic circuit from FIG. 3 and thermally induced at 43° C. for 1 hour with the five-minute pulsing scheme. The following day activated colonies were picked and propagated before being injected into mice bearing A20 tumors. Mice were injected with αCTLA-4 EcN, αPD-L1 EcN, αCTLA-4 and αPD-L1 EcN at 1:1 ratio, and wildtype EcN. Tumor sizes were measured over two weeks. N=4 biological replicates.
Figure 9A:
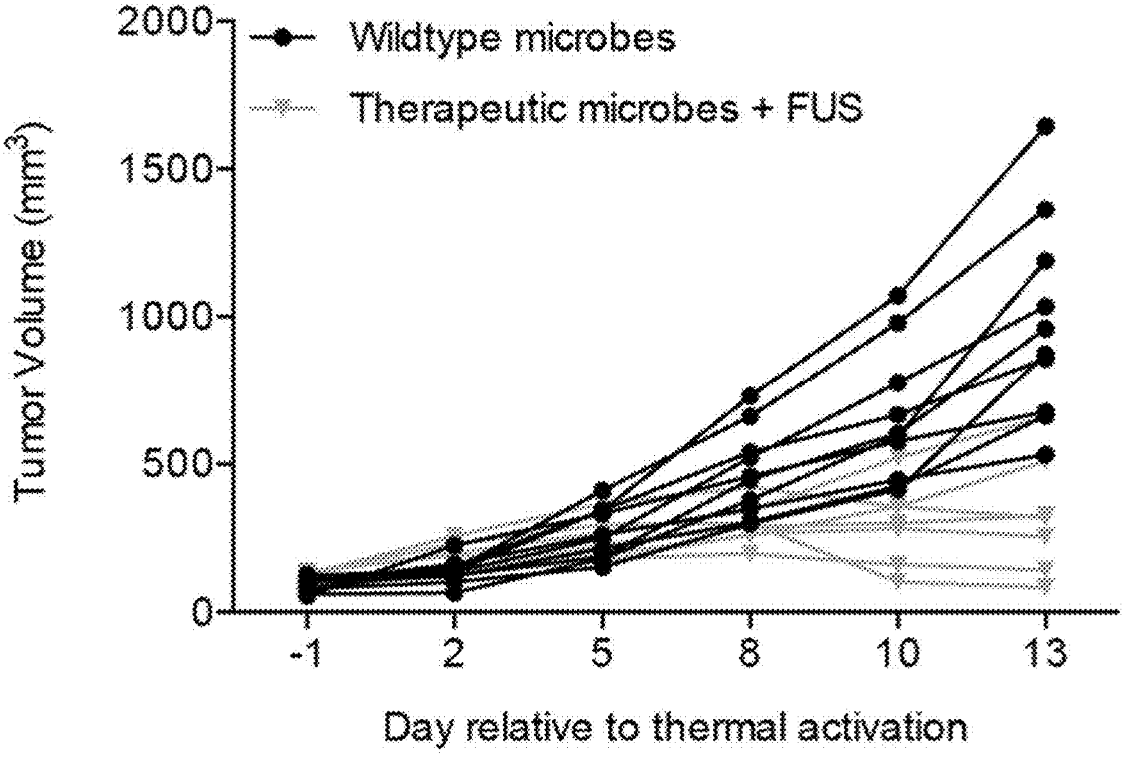
FIGS. 9A-9D depict individual growth curves of tumors analysed in FIG. 4C. Individual growth curves of all the tumors analysed and plotted in FIG. 4C. All conditions plotted relative to animals injected with wildtype microbes.
Figure 9B:
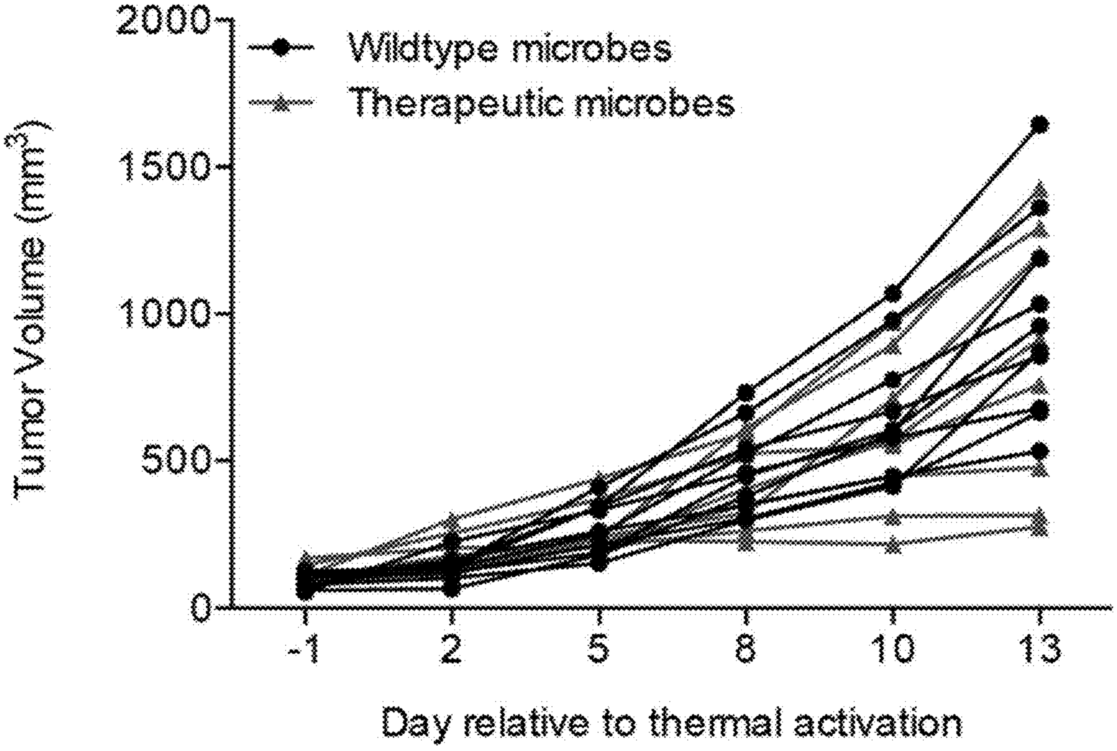
Figure 9C:
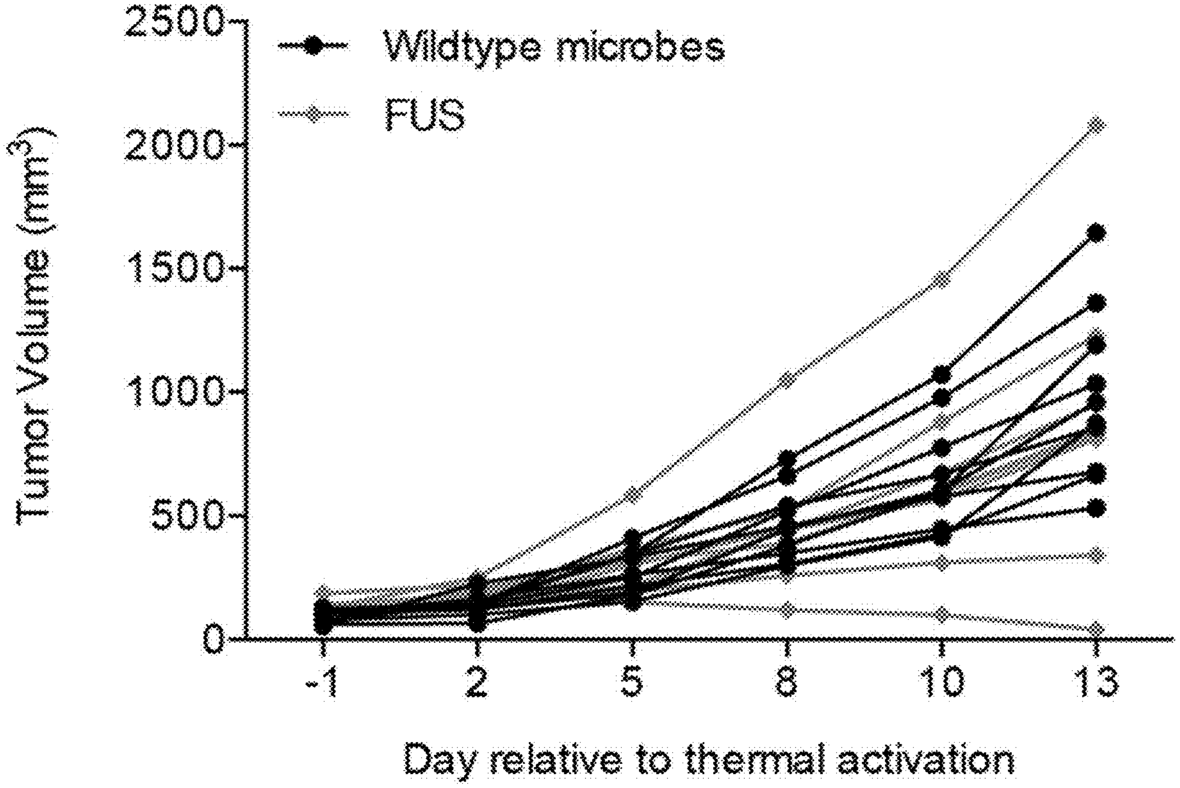
Figure 9D:
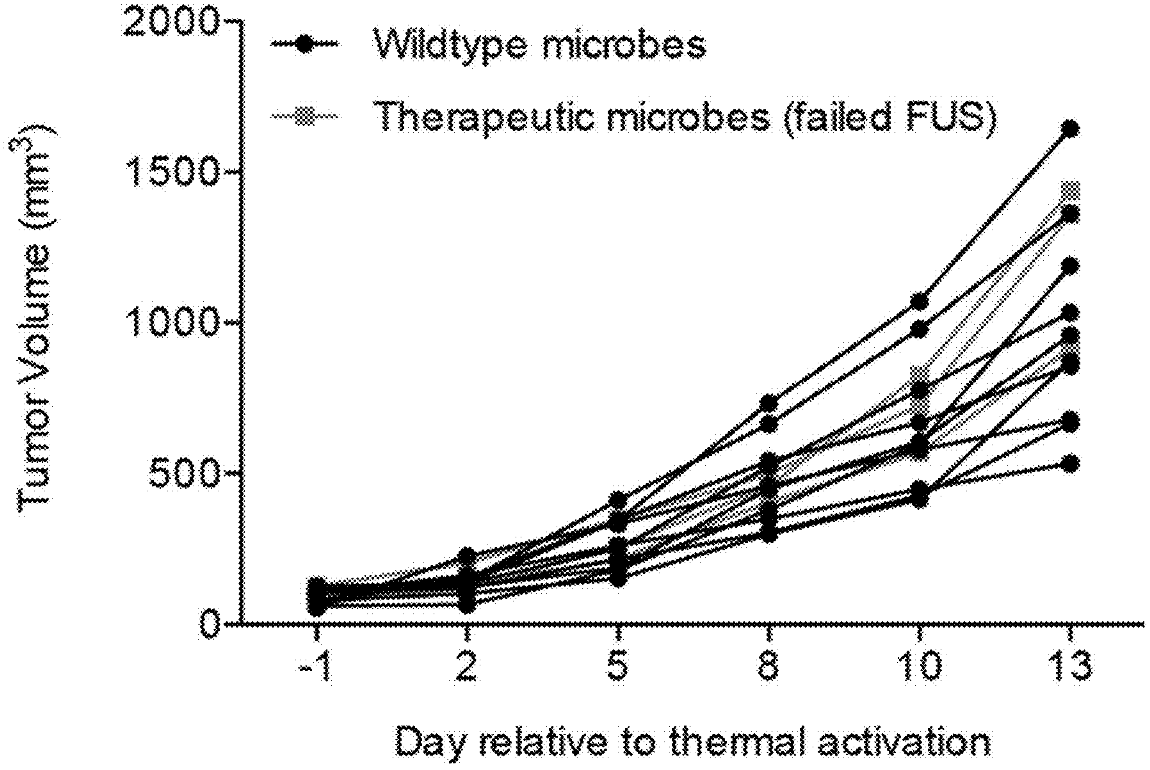

Using this in vivo setup, the ability to locally activate systemically administered therapeutic microbes inside tumors was tested. $5\times10^6$ A20 murine tumor cells were seeded in the right flanks of BALB/c mice (FIG. 4B). Once the tumors grew to approximately 100 $mm^3$, $10^8$ EcN cells comprising a 1:1 mixture of cells engineered for thermally-actuated αCTLA-4 or αPD-L1 (circuits depicted in FIGS. 11-12) secretion were intravenously injected. This combination therapy was chosen because it provides a stronger anti-tumor compared to either therapeutic output on its own (FIG. 8). Injected microbes were given two days to engraft in tumors before they were stimulated with FUS. After FUS activation, tumor growth was monitored to assess therapeutic efficacy.

Figure 4C:
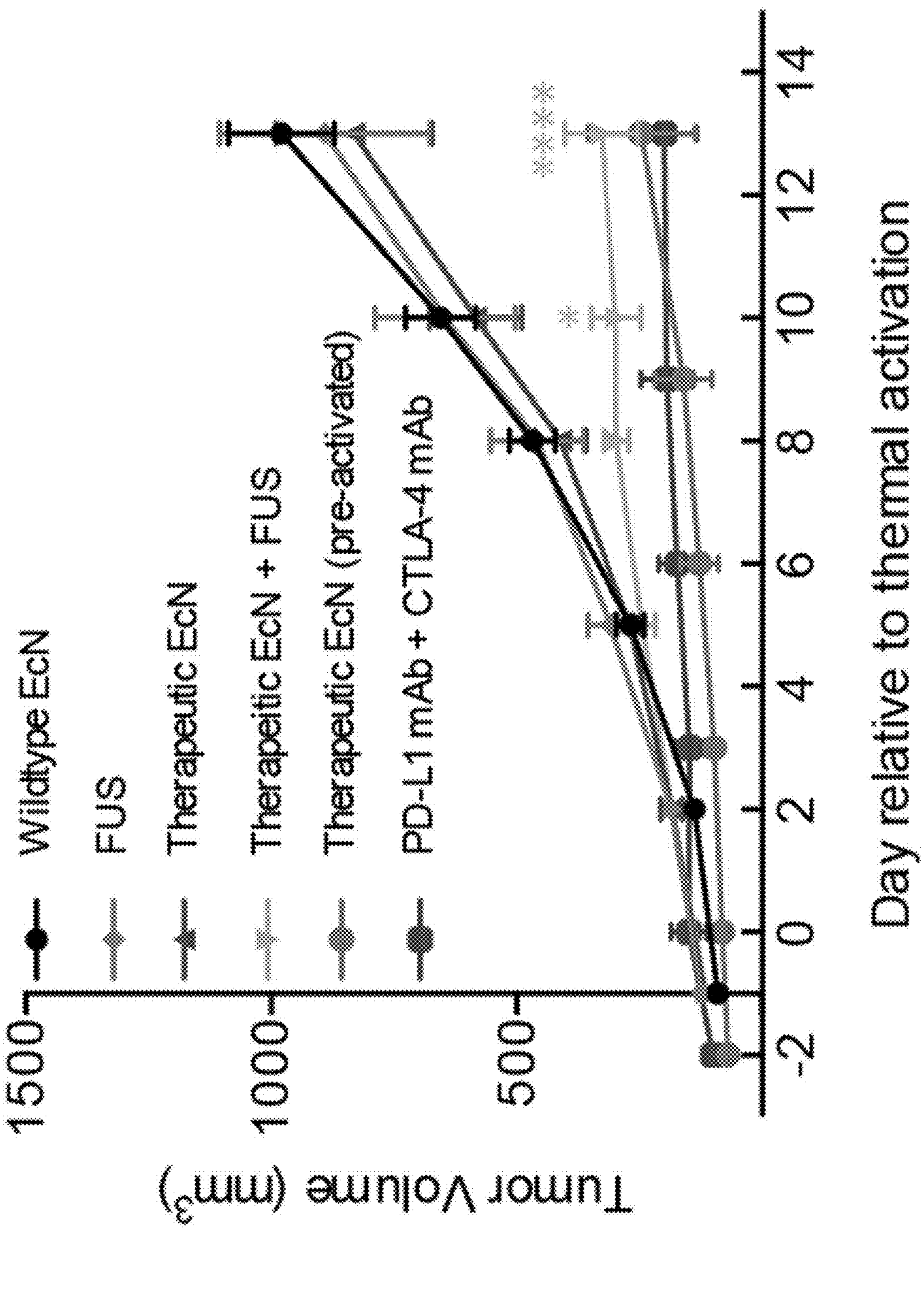
Figure 4D:
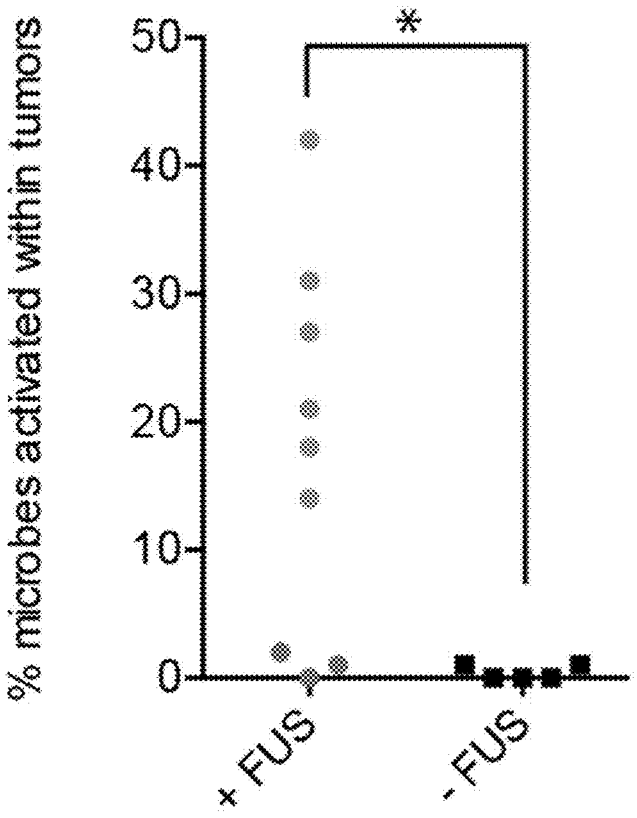
Figure 4E:
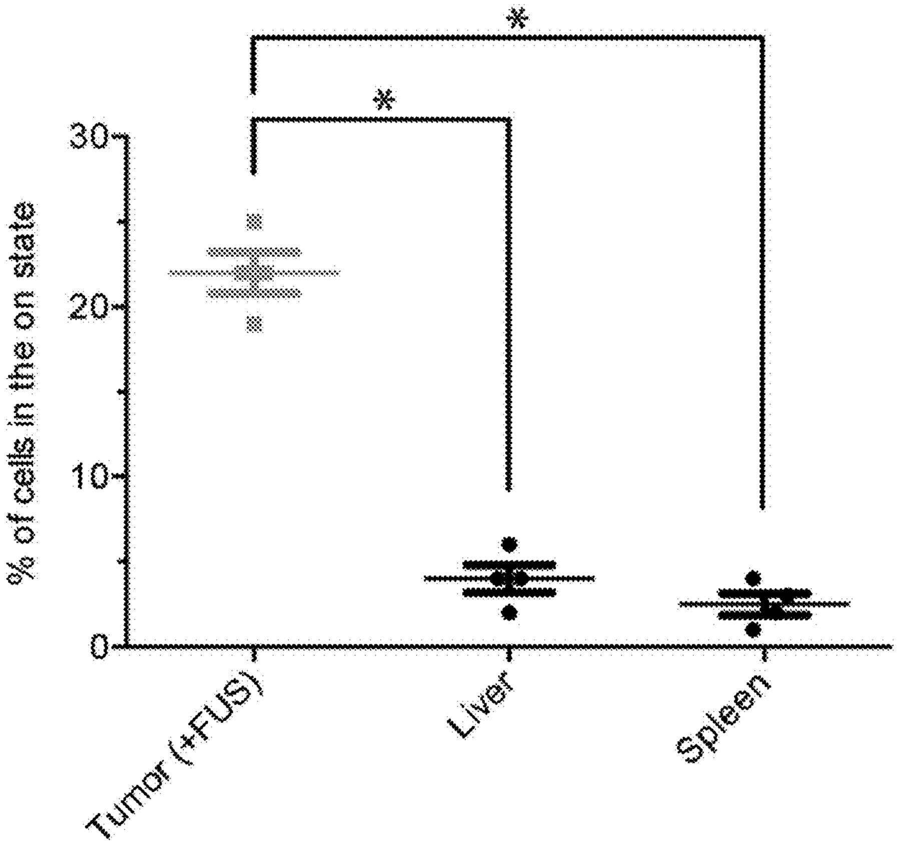
Figure 5A:
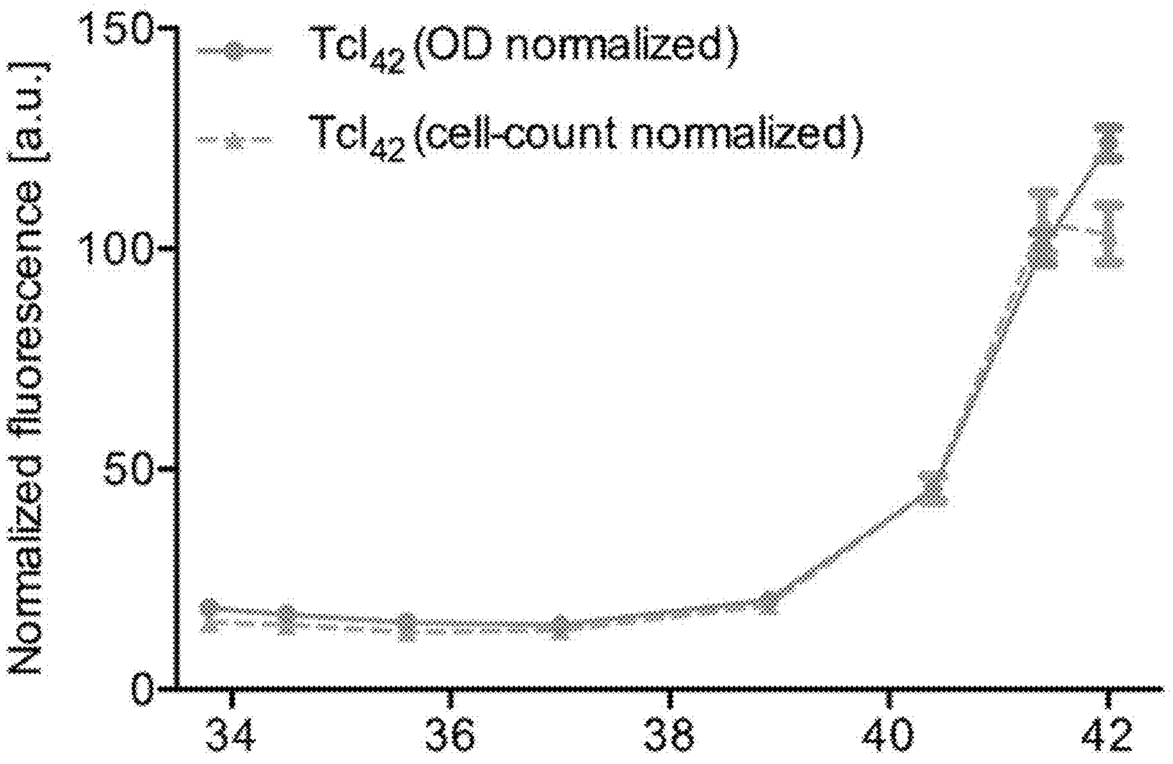
FIGS. 5A-5B depict data related to evaluation of different methods to normalize fluorescence from activated cells.
Figure 5B:
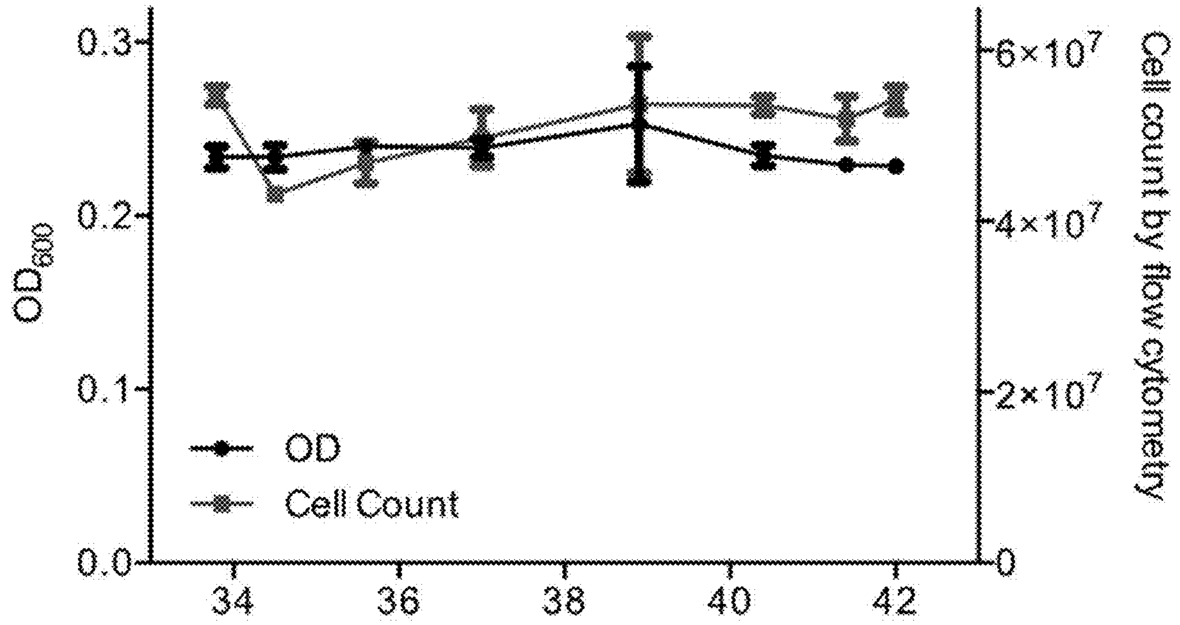
Figure 6:
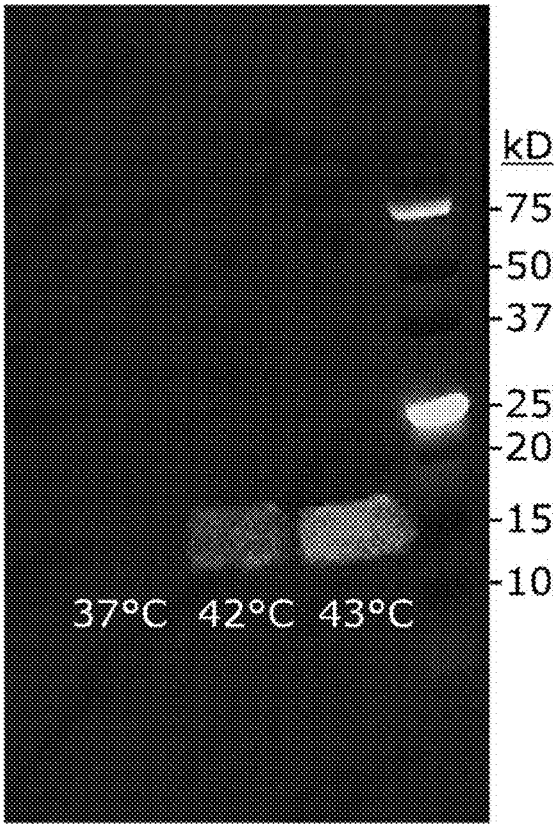
FIG. 6 depicts data related to western blotting to assay for the release of αCTLA-4 upon thermal activation. Unmodified image of the western blot shown in FIG. 3C. The image in FIG. 3C was cropped and inverted to make it fit better into the figure presentation.

A major retardation in tumor growth in FUS-treated tumors colonized by therapeutic cells was observed, while growth rates in controls including non-FUS treated mice, animals treated with only FUS, and subjects injected with wild-type EcN were substantially higher (FIG. 4C, FIG. 9). The observed effect on tumor growth was comparable to that obtained by systemically administering antibody-based immune checkpoint inhibitors against αCTLA-4 and αPD-L1, or by systemically injecting pre-activated therapeutic EcN. However, unlike each of these established treatments, whose activity depends solely on the system biodistribution of the injected agents and thus carries potential for side-effects, FUS-activated bacterial therapy can acts in a spatially localized fashion. To illustrate this localization, after completing this experiment, tumors, livers and spleens were collected, chemically homogenized, and plated the suspension on selective media. By counting the percentage of activated bacteria, it was first demonstrated that the disclosed thermal switch is triggered in targeted tumors and remains active for at least two weeks post-activation (FIG. 4D). The percentage of activated bacterial agents in the tumors, livers and spleens of FUS-treated animals was then examined, which confirmed that the activation is primarily localized to targeted tumors while sparing bystander tissues (FIG. 4E).

One of the six FUS-activated tumors disappeared as a result of the treatment and bacterial activation inside it could not be quantified. This tumor does not represent the typical outcome of this therapy. In three out of nine FUS-treated tumors, ultrasound failed to activate the therapeutic bacterial circuit. This could be due to limitations in the disclosed heating setup, which is currently capable of only partially heating the tumor mass. Clinical FUS systems that use MM feedback and dynamic mechanical or electrical focusing to ensure the precise heating of defined volumes can overcome these limitations by heating the whole tumor. The two non-activated mice were removed from the analysis of tumor growth. Overall, the in vivo experiments demonstrated that EcN cells engineered for thermally controlled checkpoint inhibition are able to home to and engraft in tumors from systemic circulation, become activated specifically in response to FUS, maintain this activity for at least two weeks after a 1-hour FUS treatment and significantly reduce tumor growth.

Figure 10A:
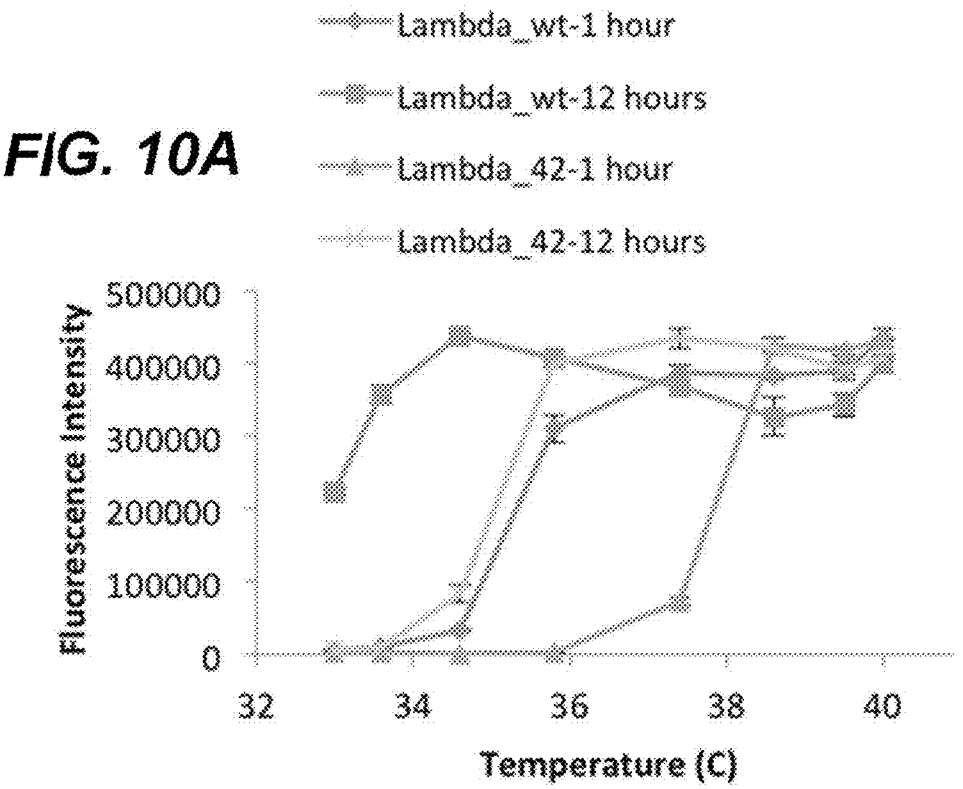
FIGS. 10A-10B depict data relating to testing of therapeutic circuits provided herein in *Salmonella*.
Figure 10B:
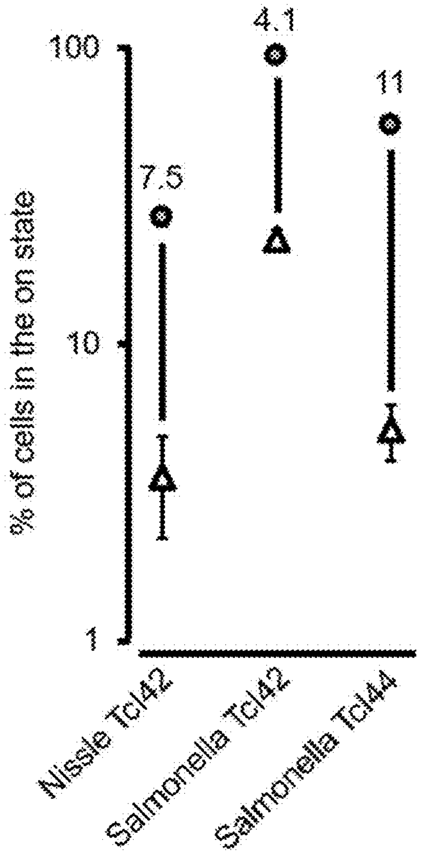
Figure 11:
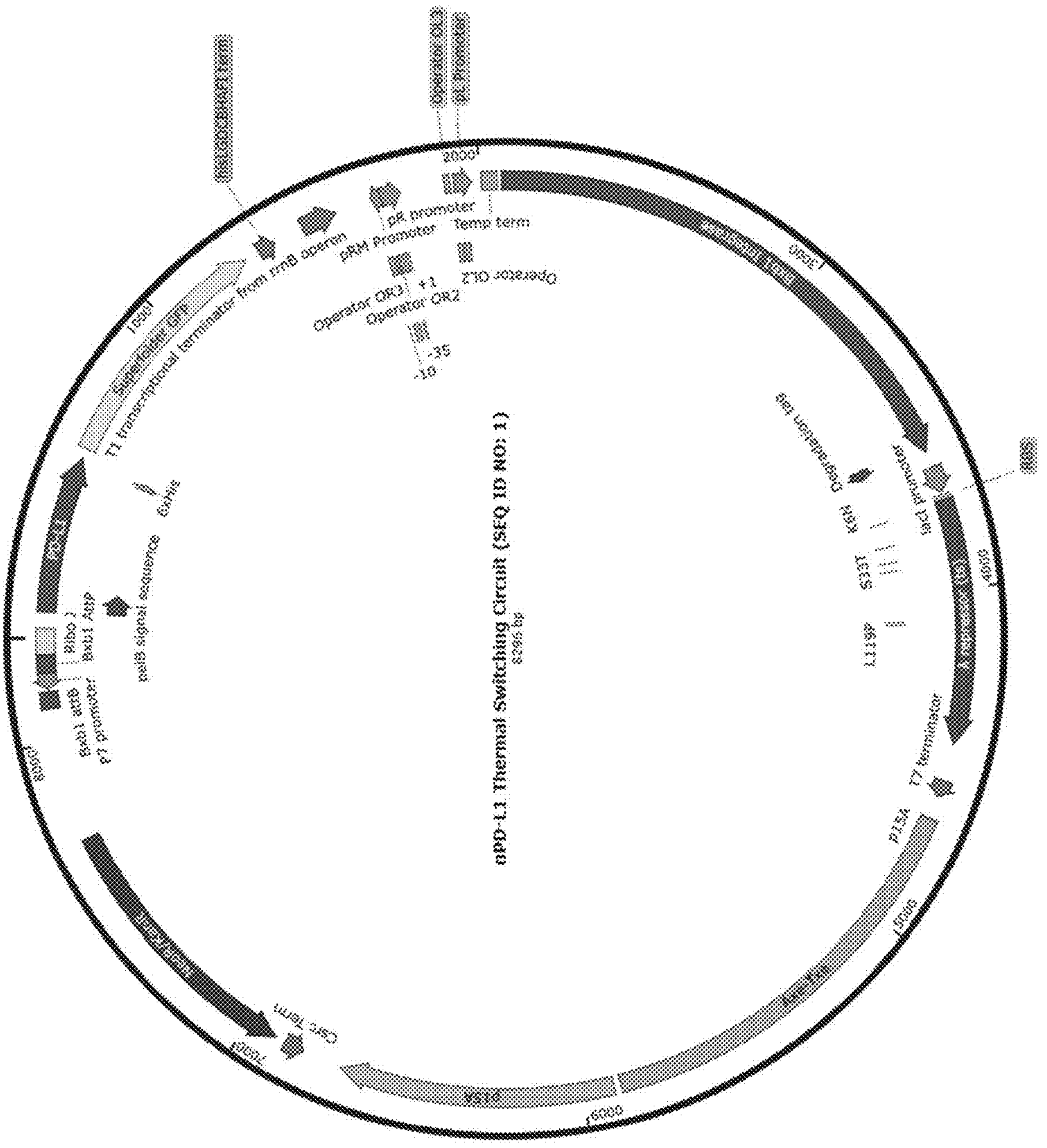
FIG. 11 depicts a map of a plasmid comprising a αPD-L1 Thermal Switching Circuit (SEQ ID NO: 1).
Figure 12:
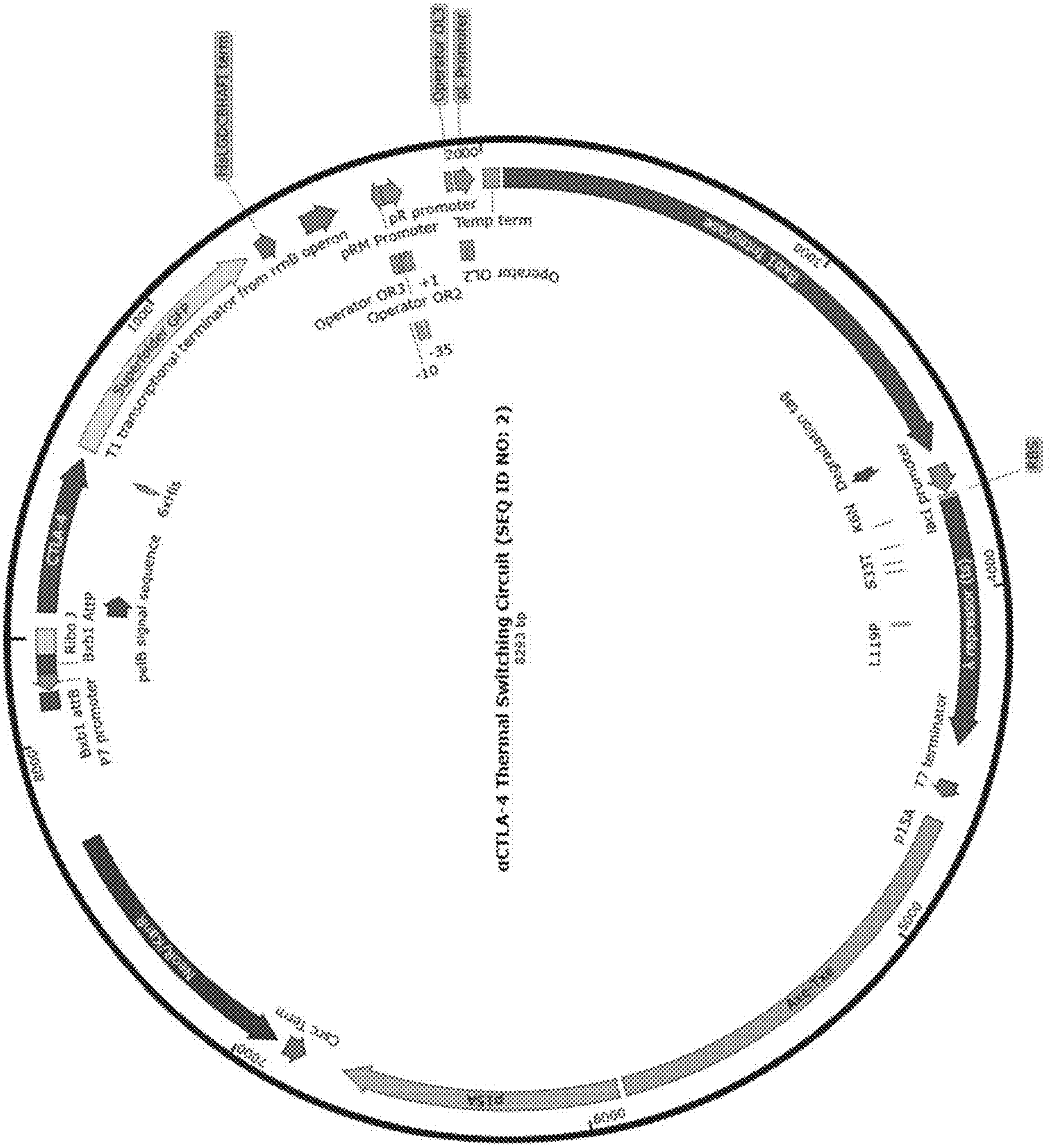
FIG. 12 depicts a map of a plasmid comprising a αCLTA-4 Thermal Switching Circuit (SEQ ID NO: 2).
Figure 13:
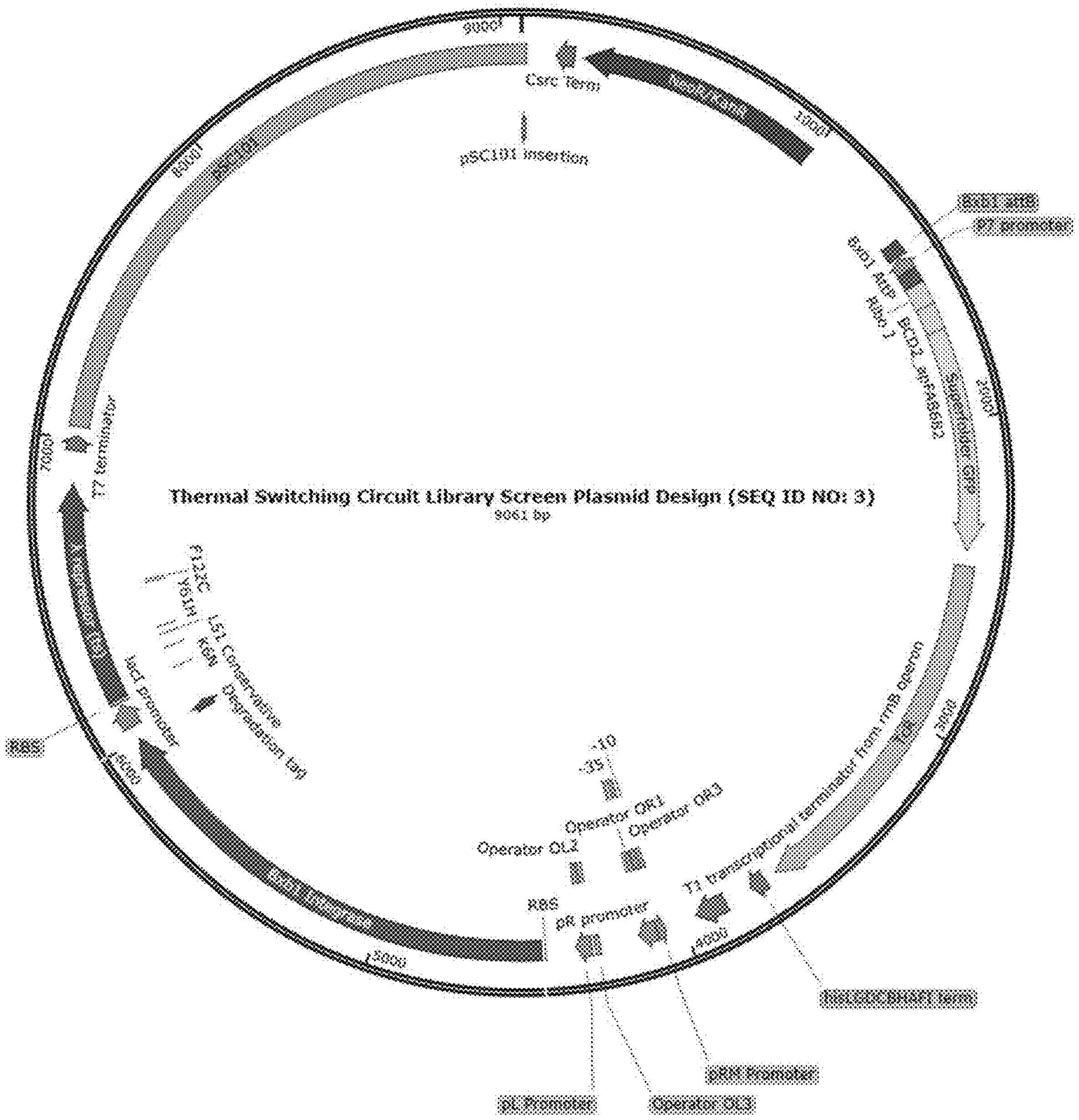
FIG. 13 depicts a map of the Thermal Switching Circuit Library Screen Plasmid Design (SEQ ID NO: 3).
Figure 14:
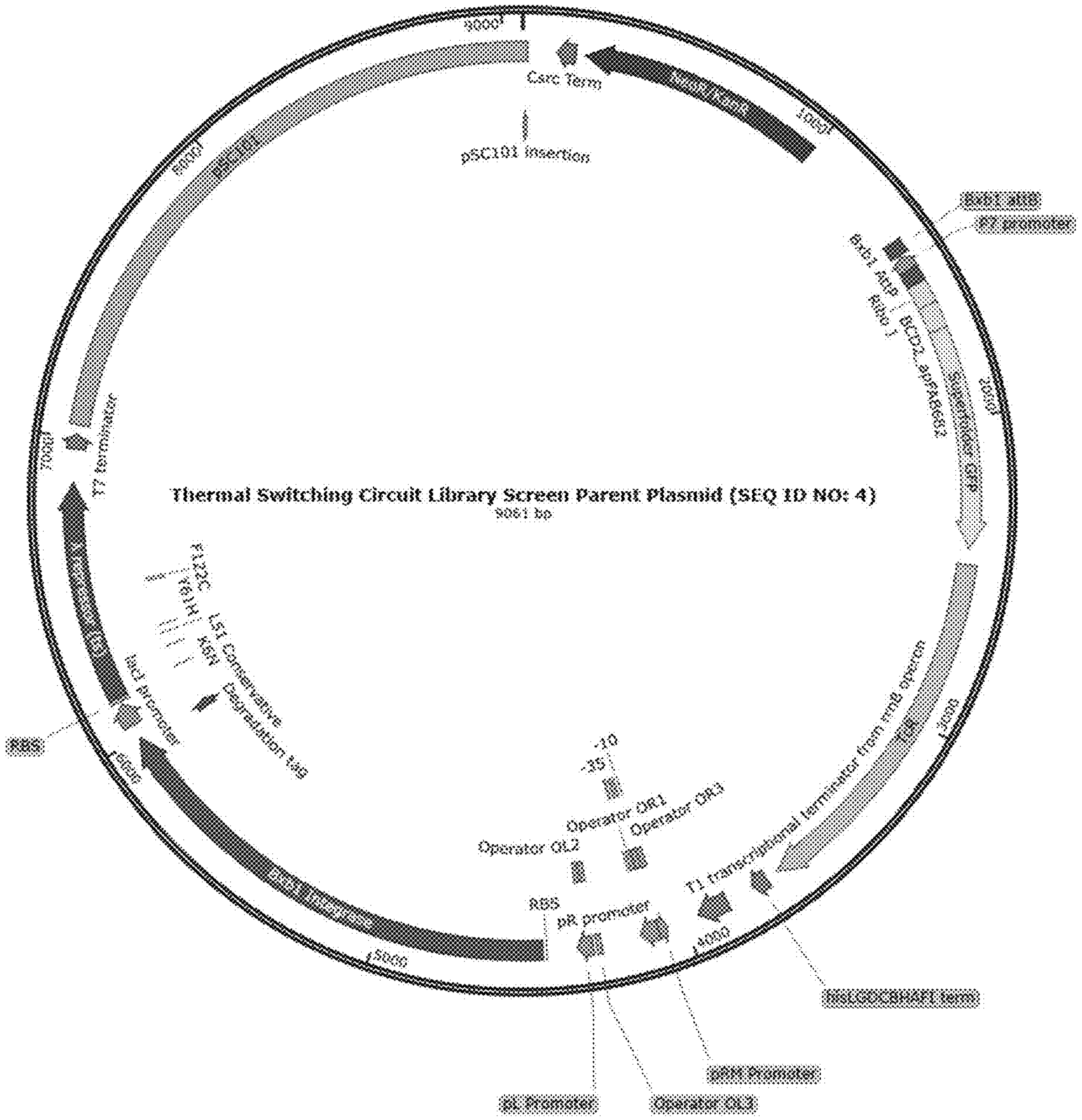
FIG. 14 depicts a map of a Thermal Switching Circuit Library Screen Parent Plasmid (SEQ ID NO: 4).
Figure 15:
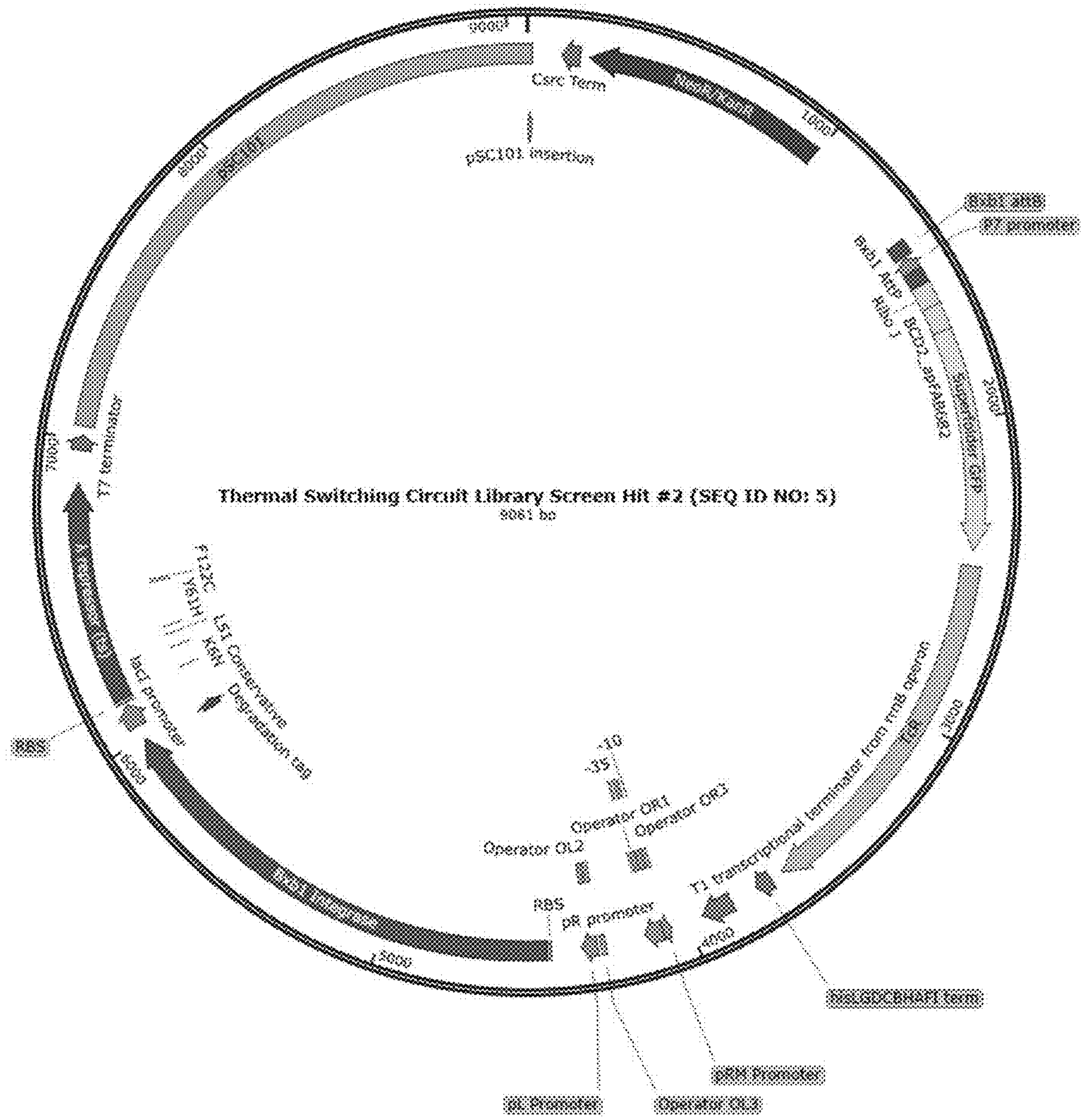
FIG. 15 depicts a map of Thermal Switching Circuit Library Screen Hit #2 plasmid (SEQ ID NO: 5).
Figure 16:
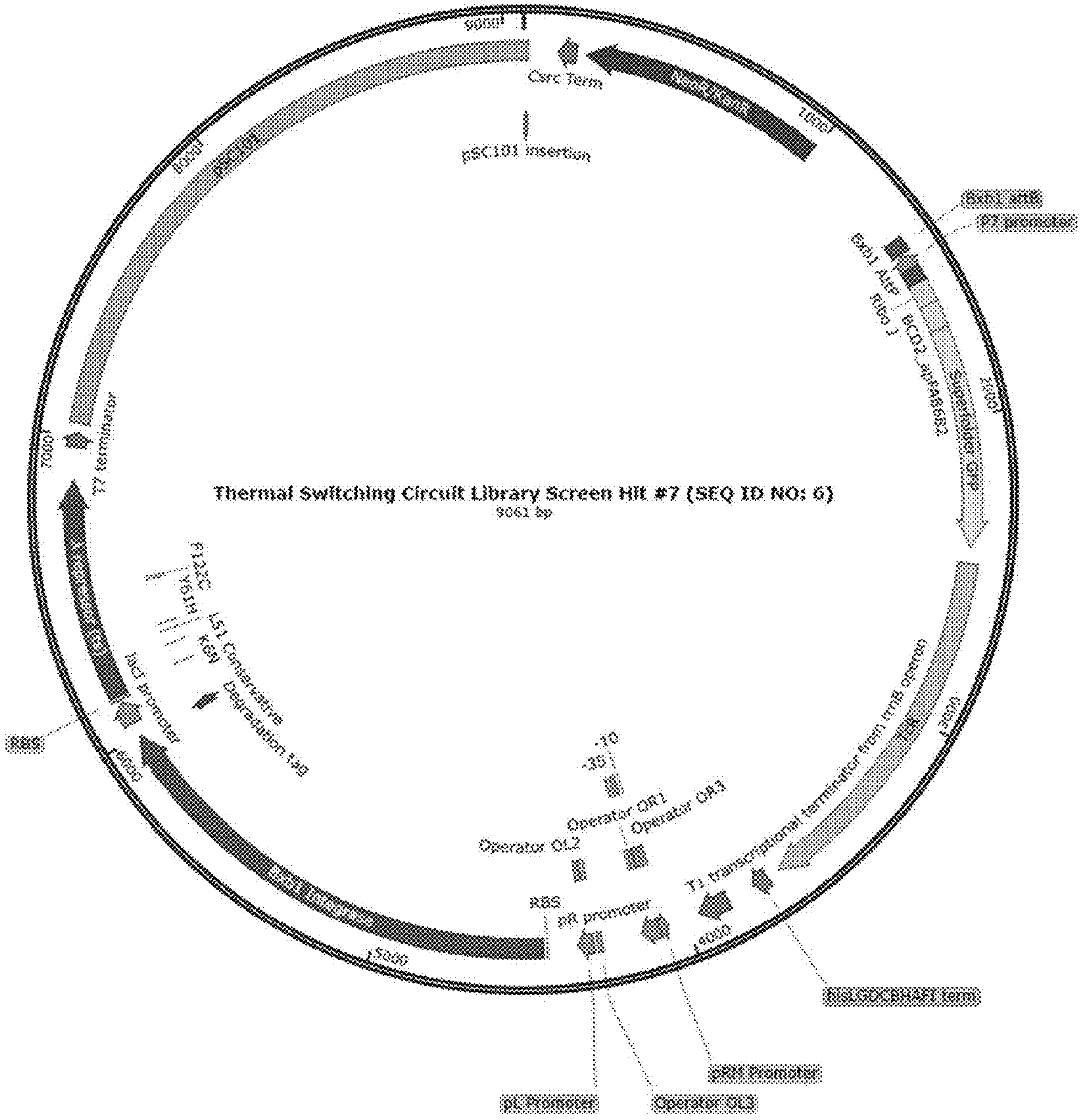
FIG. 16 depicts a map of Thermal Switching Circuit Library Screen Hit #7 plasmid (SEQ ID NO: 6).

As proof of principle for the utility of the thermal circuit design provided herein across other bacterial species, the therapeutic circuits provided herein were tested in *Salmonella* (FIGS. 10A-10B). FIG. 10A depicts the results of testing a thermal switching circuit in *Salmonella* with wild-type lambda (cI) and TcI-42 using the same method as used in FIG. 1B. FIG. 10B depicts the results of testing the thermal switching circuit in *Salmonella* using the same method as used in FIG. 2D. Optimal performance was observed when Tci-44 (a new variant with a higher switching threshold at around 44° C. in Nissle cells but around 42° C. in *Salmonella*) was used.

Discussion

The results provided in this Example establish a system for targeted probiotic immunotherapy that couples the special ability of therapeutic bacteria to home into the necrotic core of solid tumors with the capacity of FUS to locally activate their therapeutic function. The sustained activation of these therapeutic bacteria is enabled by a thermal state switch developed through high throughput genetic engineering to have low baseline activity, rapid induction upon stimulation and sustained activity in situ. When this state switch is used to actuate the release of immune checkpoint inhibitors, the resulting engineered microbes can be activated inside tumors by brief FUS exposure to secrete their therapeutic payload over an extended timeframe and substantially reduce tumor growth.

The growing body of work on bacteria-based therapies and the increasing clinical acceptance of FUS provide FUS-actuated bacterial therapeutics a path to ultimate clinical implementation. Potential disease targets include cancers with readily identified primary masses that are challenging to resect surgically, such as head-and-neck, ovarian, pancreatic or brain tumors. FUS-actuated bacterial therapeutics could be also relevant to metastatic tumors since microbial therapy in a single tumor mass can generate a strong adaptive immune response leading to the elimination of distant tumor lesions through a potent abscopal effect. In some embodiments, to enhance therapeutic efficacy, it may be beneficial to combine FUS-activated bacterial therapeutics with other molecular or cellular therapies. For example, engineered bacteria and immune cells have distinct and often complementary tumor entry and engraftment profiles. Engineering microbes that successfully enter immunosuppressed tumor regions to secrete checkpoint inhibitors or cytokines could help make this environment more accessible to engineered T cells. In this way, the bacteria and T cells can synergistically exert their therapeutic function from the inside-out and from the outside-in, respectively. Beyond tumor therapy, locally activated bacterial agents have potential utility in a wide array of other biomedical applications. For example, in some embodiments, FUS-controlled state switches are useful in controlling the activity of gut microbes in vivo, the function of cell-based living materials in vitro, and in industrial metabolic engineering.

Materials and Methods

Plasmid Construction and Molecular Biology

All plasmids were designed using SnapGene (GSL Biotech) and assembled via reagents from New England Biolabs for KLD mutagenesis (E0554S) or Gibson Assembly (E2621L). After assembly, constructs were transformed into NEB Turbo (C2984I) and NEB Stable (C3040I) *E. coli* for growth and plasmid preparation. The Bxb1 recombinase-encoding gene was a kind gift of Richard Murray (Caltech). Integrated DNA Technologies synthesized other genes and all PCR primers. Plasmids containing the αCTLA-4, αPD-L1, and Axe-Txe genes were kind gifts from of Tal Danino (Columbia University).

Preparation of Cell Lines for In Vitro and In Vivo Experiments

Plasmids containing engineered genetic circuits were transformed into Nissle 1917 *E. coli* (Mutaflor®). Nissle cells were cultured in LB broth (Sigma) and grown on LB agar plates (Sigma) containing appropriate antibiotics. Singular colonies were picked into LB broth and grown overnight in a shaking incubator (30° C., 250 rpm). The next day, optical density measurements ($OD_{600}$) were taken, and the saturated cultures were diluted to 0.1 $OD_{600}$. Diluted cultures were then allowed to grow to exponential phase until they reached 0.6 $OD_{600}$ before starting assays. Optical density measurements were taken using a Nanodrop 2000c (Thermo Scientific) in cuvette mode.

Western Blot

Five milliliters of cell media were collected for each sample and concentrated with an Amicon® Ultra-15 Centrifugal Filter Unit. Concentrated cell media was then mixed with Laemmli loading buffer and BME before loading into a pre-cast polyacrylamide gels SDS-PAGE gel (Bio Rad) and ran at 75 V for 140 minutes. Western blotting was performed using the Transblot Turbo apparatus and nitrocellulose membrane kit (Bio Rad). Transfer was performed at 25 V for 7 minutes. Membranes were blocked with 5% Blotto milk (Santa Cruz Biotechnology) in 0.05% TBS-Tween for 1 hour at room temperature. Primary staining was performed using the mouse anti-His sc-8036 antibody (Santa Cruz Biotech) overnight at 4° C. Blots were then washed three times for 15 minutes at 4° C. with 0.05% TBS-Tween and stained for 4 hours with mouse IgG kappa binding protein (m-IgGκ BP) conjugated to Horseradish Peroxidase (HRP) (Santa Cruz Biotech, sc-516102) at room temperature. After three 15-minute washes, HRP visualization was performed using Super signal west Pico PLUS reagent (Thermo Fisher Scientific). Imaging was performed in a Bio-Rad ChemiDoc MP gel imager. A subsequent epi white light image of the blot under the same magnification was acquired to visualize the stained molecular weight standards.

Thermal Regulation Assay

Once bacterial cell cultures reached approximately 0.6 $OD_{600}$, 50 μL aliquots of each sample was transferred into individual Bio-Rad PCR strips with optically transparent caps and subsequently heated in conditions specific to the experiment using a Bio-Rad C100 Touch thermocycler with the lid set to 50° C. Following heating, cells continued to incubate overnight undisturbed at either 30° C. (FIG. 1) or 37° C. (FIGS. 2-4). The PCR strips were then removed, vortexed, and spun down, and the green fluorescence of each of the samples was measured using the Strategene MX3005p qPCR (Agilent) and an unamplified FAM filter. To measure cell density, the samples were diluted 1:4 with fresh LB media (without antibiotic) and then transferred into individual wells of a 96-well plate (Costar black/clear bottom). Optical density measurements were taken using the SpectraMax M5 plate reader (Molecular Devices). In order to quantify the temperature-dependent gene expression (E) using background-subtracted, OD-normalized fluorescence (FIGS. 1B-1D, 1F, and 2C), Equation (1) was used:

$$E = \frac{F_{sample} - F_{blank}}{OD_{sample} - OD_{blank}}$$

In this equation, F is defined as the raw fluorescence measurement and OD is the $OD_{600}$ measurement of the sample. The value of the blank fluorescence and blank optical density was determined as the average of N=4 samples of untransformed Nissle cells, as opposed to engineered Nissle cells, in LB. Samples with $F_{sample} < F_{blank}$ were recorded as E=0.

Screens to Optimize Circuit Behavior

To improve Bxb1 thermal regulation, a sequence randomized library of the RBS, start codon, and ssrA degradation tag was ordered from Integrated DNA Technologies. PCR products that included the Bxb1 coding region and immediately surrounding sequences were amplified using custom primers and were inserted into the backbone of the rest of the parent plasmid using Gibson Assembly (FIGS. 2B-2D). This library was transformed into EcN and plated on LB Agar plates with antibiotic resistance at a low colony density of approximately 30 colonies per petri dish. Following overnight incubation at 30° C. to allow the colonies to become visible, these plates were then replicated into two daughter petri dishes using a replica-plating tool (VWR 25395-380). The parent petri dish was incubated at 4° C. until the conclusion of the experiment. One daughter plate was grown overnight at the baseline temperature of 37° C., and the other was incubated at 42° C. for 1 hour and then moved to 37° C. overnight. After colonies became visible, the plates were imaged using a 530/28 nm emission filter to determine colonies that were fluorescent at the 'on' temperature but opaque at the 'off' temperature (Bio-Rad ChemiDoc MP imager). Promising library variants were then picked from the corresponding parent petri dish at 4° C. and analysed against the parent plasmid of the library using the liquid culture fluorescence-based assay described above.

Percent Switching Assay

Strips of liquid bacteria samples were prepared and incubated in the Bio-Rad Touch thermocycler. After the prescribed thermal stimulus and incubation at 37° C., PCR strips were removed, vortexed, and spun down on a tabletop centrifuge. Five 1:10 serial dilutions in liquid LB were then performed, transferring 10 μL of sample into 90 μL of LB media sequentially. After thorough mixing, 50 μL of the most diluted samples was plated onto an LB plate and allowed to incubate at 30° C. overnight. Upon the appearance of visible colonies, plates were imaged using the same Bio-Rad ChemiDoc MP imager with both blue epifluorescence illumination and the 530/28 nm emission filters. The percentage of colonies in the 'on state' (P) was determined according to Equation (2):

$$P = \frac{\text{number of } GFP \text{ positive colonies counted on a plate}}{\text{total number of colonies counted on a plate}}$$

Flow Cytometry

EcN cells were incubated for 24 h before assaying with a flow cytometer (MACSQuant VYB) that was thoroughly cleaned to ensure that there are no counts being detected from debris. EcN cells were resuspended in cold PBS+0.5% BSA (filtered with a 0.2 micron filter) to prevent clumping and were run at 3 different dilutions (targeting 1e6, 1e7, and 1e8 cells/mL).

Animal Procedures

All animal procedures were performed under a protocol approved by the California Institute of Technology Institutional Animal Care and Use Committee (IACUC). 8-12 week-old BALB/c female mice were purchased from Jackson Laboratory. To establish A20 tumor models in mice, $5\times10^6$ A20 cells were collected and suspended in 100 μL phosphate buffer saline (PBS) prior to subcutaneous injection into the flank of each mouse. When tumor volumes reached approximately 100 $mm^3$, engineered EcN cells prepared according to the procedure outlined in the section above were then collected by centrifugation (3000 g for 5 min), washed with phosphate buffer saline PBS 3 times, and diluted in PBS to 0.625 $OD_{600}$. 100 μL of the resulting solution was injected into each of the A20 tumor bearing mice via tail vein. For some conditions, mice were injected with a combination of αCTLA-4 (200 μg per mouse) and αPD-L1 (100 μg per mouse) checkpoint inhibitors intraperitoneally. These murine checkpoint inhibitors (αCTLA-4 clone 9D9 and αPD-L1 clone 10F.9G2) were obtained from BioXCell. For thermal actuation using ultrasound, mice were anesthetized using a 2% isoflurane-air mixture and placed on a dedicated animal holder. Anesthesia was maintained over the course of the ultrasound procedure using 1-1.5% isoflurane, adjusted in real-time to maintain the respiration rate at 20-30 breaths per minute. Body temperature was continuously monitored using a fiber optic rectal thermometer (Neoptix). When appropriate, the target flank was thermally activated using the automated FUS setup described below, cycling between the temperatures of 43° C. and 37° C. every 5 minutes for 1 hour of total heating. Following ultrasound treatment, the mouse was returned to its cage and the size of its tumor was measured with a caliper to track the therapeutic efficacy. When the tumors reached ~1000 $mm^3$ mice were culled and the tumors were collected for analysis. Mice that did not have microbial cells in their tumors were excluded from the study.

Tumor and Organ Analysis

Tumors and organs (liver and spleen) were collected and homogenized in ten milliliters of PBS containing 2 mg/ml collagenase and 0.1 mg/ml DNAse for one hour at 37° C. Homogenized tissues were serially diluted and plated onto LB plates to quantify the number of cells colonizing the tissues. The percentage of cells activated within tissues was determined by counting the number of GFP positive cells.

Feedback-Controlled Focused Ultrasound

A closed loop thermal control setup was developed to maintain a specified predetermined temperature within the tumor of a mouse by modulating the intensity of the FUS. This setup includes a water bath filled with pure distilled water that is being actively cleaned and degassed with an AQUAS-10 water conditioner (ONDA) and maintained at 33° C. with a sous vide immersion cooker (InstantPot Accu Slim). A tumor-bearing mouse that has been anesthetized as described above is fastened nose up vertically to an acrylic arm that is connected to a manual 3D positioning system (Thorlabs) to enable 3D motion of the mouse within the water bath. A Velmex BiSlide motorized positioning system is used to submerge and position the 0.67 MHz FUS transducer (Precision Acoustics PA717) such that the focal point of the transducer lies within the tumor of the mouse. A signal generator (B&K #4054B) generates the thermal ultrasound signal which is then amplified (AR #100A250B) and sent to drive the ultrasound transducer. The water in this chamber acts as the coupling medium to transfer the ultrasound wave from the transducer to the tumor. To measure the internal tumor temperature during a heating session a thin fiber optic temperature probe (Neoptix) was temporarily implanted into the tumors. This temperature readout is also used to align the focus of the transducer with the tumor by emitting a constant test thermal ultrasound signal. Once the system is aligned, a Matlab closed loop thermal control script is run that regulates the signal generator output. Feedback for the controller is provided by the temperature measurements acquired with a sampling rate of 4 Hz. The actuator for the controller is the voltage amplitude of the continuous sinusoidal signal at 0.67 MHz used to drive the FUS transducer, where the voltage is adjusted also at 4 Hz. The system uses a PID controller with anti-windup control that modifies the amplitude of the thermal ultrasound waveform to achieve a desired temperature in the targeted tissues. The Kp, Ki, Kd, and Kt parameters for the PID and anti-windup were tuned using Ziegler-Nichols method, and in some cases adjusted further through trial-and-error tuning to achieve effective thermal control.

Statistics and Replicates

Data is plotted and reported in the text as the mean±S.E.M. Sample size is N=4 biological replicates in all in vitro experiments unless otherwise stated. This sample size was chosen based on preliminary experiments indicating that it would be sufficient to detect significant differences in mean values. P values were calculated using a two-tailed unpaired t-test.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms “a,” “an,” and “the” include plural references unless the context clearly dictates otherwise. Any reference to “or” herein is intended to encompass “and/or” unless otherwise stated.

It will be understood by those within the art that, in general, terms used herein, and especially in the appended claims (e.g., bodies of the appended claims) are generally intended as “open” terms (e.g., the term “including” should be interpreted as “including but not limited to,” the term “having” should be interpreted as “having at least,” the term “includes” should be interpreted as “includes but is not limited to,” etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases “at least one” and “one or more” to introduce claim recitations. However, the use of such phrases should not be construed to imply that the introduction of a claim recitation by the indefinite articles “a” or “an” limits any particular claim containing such introduced claim recitation to embodiments containing only one such recitation, even when the same claim includes the introductory phrases “one or more” or “at least one” and indefinite articles such as “a” or “an” (e.g., “a” and/or “an” should be interpreted to mean “at least one” or “one or more”); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of “two recitations,” without other modifiers, means at least two recitations, or two or more recitations). Furthermore, in those instances where a convention analogous to “at least one of A, B, and C, etc.” is used, in general such a construction is intended in the sense one having skill in the art would understand the convention (e.g., “a system having at least one of A, B, and C” would include but not be limited to systems that have A alone, B alone, C alone, A and B together, A and C together, B and C together, and/or A, B, and C together, etc.). In those instances where a convention analogous to “at least one of A, B, or C, etc.” is used, in general such a construction is intended in the sense one having skill in the art would understand the convention (e.g., “a system having at least one of A, B, or C” would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as “up to,” “at least,” “greater than,” “less than,” and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A nucleic acid composition, comprising:

a first promoter operably linked to a first polynucleotide comprising a recombinase gene, wherein the first promoter is capable of inducing transcription of the first polynucleotide to generate a recombinase transcript upon a thermal stimulation in a bacterium, and wherein the recombinase transcript is capable of being translated to generate a recombinase capable of catalyzing a recombination event, wherein the first polynucleotide and/or recombinase transcript comprises one or more elements capable of being tuned to modulate recombinase translation; wherein the one or more elements capable of being tuned to modulate recombinase translation comprise a temperature-sensitive terminator comprising the nucleotide sequence set forth in SEQ ID NO: 11; and a second promoter and a second polynucleotide comprising a therapeutic payload gene, wherein, in the absence of the recombination event, the second promoter and the second polynucleotide are not operably linked, and wherein the second promoter and the second polynucleotide are operably linked after the recombination event such that the second promoter is capable of inducing transcription of the second polynucleotide to generate a therapeutic payload transcript.

2. The nucleic acid composition of claim 1, wherein the thermal stimulation comprises heating to an activating temperature, and wherein the activating temperature is above a physiological temperature.

3. The nucleic acid composition of claim 2, wherein:

the activating temperature is about 37.5° C., about 38.0° C., about 38.5° C., about 39.0° C., about 39.5° C., about 40.0° C., about 40.5° C., about 41.0° C., about 41.5° C., about 42.0° C., about 42.5° C., about 43.0° C., about 43.5° C., about 44.0° C., about 44.5° C., about 45.0° C., about 45.5° C., or about 46.0° C.; and/or the physiological temperature is about 31.5° C., about 32.0° C., about 32.5° C., about 33.0° C., about 33.5° C., about 34.0° C., about 34.5° C., about 35.0° C., about 35.5° C., about 36.0° C., about 36.5° C., about 37.0° C., about 37.5° C., about 38.0° C., about 38.5° C., about 39.0° C., about 39.5° C., or about 40.0° C.

4. The nucleic acid composition of claim 1, wherein, in the absence of the thermal stimulation, the recombinase reaches steady state protein levels in a probiotic cell insufficient to catalyze the recombination event.

5. The nucleic acid composition of claim 1, comprising:

a third promoter operably linked to a third polynucleotide encoding a temperature-sensitive transcription factor, wherein two of the temperature-sensitive transcription factors are capable of associating to generate a temperature-sensitive transcription factor homodimer in the absence of the thermal stimulation, and wherein two of the temperature-sensitive transcription factors are incapable of associating to generate a temperature-sensitive transcription factor homodimer in the presence of the thermal stimulation.

6. The nucleic acid composition of claim 5, wherein the first promoter comprises one or more operators, wherein the temperature-sensitive transcription factor homodimer is capable of binding the one or more operators, and wherein, upon the temperature-sensitive transcription factor homodimer binding the one or more operators, the first promoter is incapable of inducing transcription of the first polynucleotide.

7. The nucleic acid composition of claim 6, wherein the one or more operators are selected from the group comprising TlpA operator/promoter, lambda phage OR1, lambda phage OR2, lambda phage OR3, lambda phage OL1, lambda phage OL2 and lambda phage OL3.

8. The nucleic acid composition of claim 5, wherein the first promoter is incapable of inducing transcription of the first polynucleotide in the absence of the thermal stimulation, and/or wherein the first promoter is capable of inducing transcription of the first polynucleotide in the absence of the temperature-sensitive transcription factor homodimer.

9. The nucleic acid composition of claim 5, wherein temperature-sensitive transcription factor homodimerization occurs with a dissociation constant (Kd) at least 1.1-fold lower in the presence of a physiological temperature as compared to in the presence of the thermal stimulation.

10. The nucleic acid composition of claim 5, wherein the temperature-sensitive transcription factor is or comprises a temperature-sensitive mutant of the bacteriophage lambda cl protein, wild-type TlpA, $TlpA_{36}$, $TlpA_{39}$, TcI, $TcI_{42}$, $TcI_{38}$, or any combination thereof.

11. The nucleic acid composition of claim 1, wherein the second polynucleotide comprises and/or is flanked by recombinase target sites, wherein the recombination event comprises removal of a sequence flanked by recombinase target sites or an inversion of a sequence flanked by recombinase target sites.

12. The nucleic acid composition of claim 11, wherein, after the recombination event, the recombinase target sites are modified such that said modified recombinase target sites are not capable of interacting with the recombinase to yield another recombination event, thereby rendering the recombination event permanent.

13. The nucleic acid composition of claim 1, wherein the one or more elements capable of being tuned to modulate recombinase translation further comprise a ribosomal binding sequence (RBS).

14. The nucleic acid composition of claim 1, wherein the first polynucleotide and/or recombinase transcript comprises the temperature-sensitive terminator upstream of the recombinase coding sequence.

15. The nucleic acid composition of claim 1, wherein the first promoter comprises a TlpA operator/promoter, lambda phage pL, lambda phage pR, lambda phage pRM, or any combination thereof.

16. The nucleic acid composition claim 1, wherein the therapeutic payload transcript is capable of being translated to generate a therapeutic payload protein, and wherein the therapeutic payload protein comprises:

a cytokine selected from the group consisting of interleukin-1 (IL-1), IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, interleukin-1 (IL-1), IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, granulocyte macrophage colony stimulating factor (GM-CSF), M-CSF, SCF, TSLP, oncostatin M, leukemia-inhibitory factor (LIF), CNTF, Cardiotropin-1, NNT-1/BSF-3, growth hormone, Prolactin, Erythropoietin, Thrombopoietin, Leptin, and G-CSF;

a member of the TGF-β/BMP family selected from the group consisting of TGF-β1, TGF-β2, TGF-β3, BMP-2, BMP-3a, BMP-3b, BMP-4, BMP-5, BMP-6, BMP-7, BMP-8a, BMP-8b, BMP-9, BMP-10, BMP-11, BMP-15, BMP-16, endometrial bleeding associated factor (EBAF), growth differentiation factor-1 (GDF-1), GDF-2, GDF-3, GDF-5, GDF-6, GDF-7, GDF-8, GDF-9, GDF-12, GDF-14, mullerian inhibiting substance (MIS), activin-1, activin-2, activin-3, activin-4, and activin-5;

a member of the TNF family of cytokines selected from the group consisting of TNF-alpha, TNF-beta, LT-beta, CD40 ligand, Fas ligand, CD 27 ligand, CD 30 ligand, and 4-1 BBL;

an interferon selected from the group comprising interferon alpha, interferon beta, and interferon gamma;

a chemokine selected from the group comprising CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13, and CXCL15;

an interleukin selected from the group comprising IL-10 IL-12, IL-1, IL-6, IL-7, IL-15, IL-2, IL-18 and IL-21;

an agonistic or antagonistic antibody or antigen-binding fragment thereof specific to a checkpoint inhibitor or checkpoint stimulator molecule selected from the group comprising PD1, PD-L1, PD-L2, CD27, CD28, CD40, CD137, OX40, GITR, ICOS, A2AR, B7-H3, B7-H4, BTLA, CTLA4, IDO, KIR, LAG3, PD-1, and TIM-3; and/or a tumor necrosis factor (TNF) selected from the group comprising TNF-alpha, TNF-beta, TNF-gamma, CD252, CD154, CD178, CD70, CD153, and 4-1BBL.

17. A thermally actuated probiotic cell, comprising:

the nucleic acid composition of claim 1, and wherein the thermally actuated probiotic cell comprises *Escherichia coli* Nissle 1917.

* * * * *

SEQUENCE LISTING

<160> NUMBER OF SEQ ID NOS: 11

<210> SEQ ID NO 1
<211> LENGTH: 8296
<212> TYPE: DNA
<213> ORGANISM: Artificial Sequence
<220> FEATURE:
<223> OTHER INFORMATION: alpha-PD-L1 Thermal Switching Circuit

<400> SEQUENCE: 1
gaaacagcct ctacaaataa ttttgtttaa gggcccaagt tcacgagaac gatatagaaa 60
gttccaggag aaaggtacca tgaaatacct gctgccgacc gctgctgctg gtctgctgct 120
cctcgctgcc cagccggcga tggccgctca agtccagtta gttgaaaccg gagggggatt 180
agttcaacct ggtggatcat tacgcttgtc ctgtacggct tcaggtttca ccttcagcat 240
gcatgcgatg acttggtatc gtcaggctcc cggaaagcaa cgcgagcttg tcgcagtaat 300
tacttcccat ggggatcgcg ccaactatac ggactctgtc cgtggccgct tcacaatctc 360
gcgtgataat actaaaaata tggtttactt gcagatgaac tctttaaaac cagaagatac 420

-continued

```
ggcggtttat tattgtaatg taccgcgcta tgattcttgg ggacagggta cgcaagtcac    480
ggtcagcagt ggtggcttac cagagacggg aggacatcat caccatcatc actaggtaag    540
gcaagctcgt actgggagtt ctaatgcgta aaggcgaaga gctgttcact ggtgtcgtcc    600
ctattctggt ggaactggat ggtgatgtca acggtcataa gttttccgtg cgtggcgagg    660
gtgaaggtga cgcaactaat ggtaaactga cgctgaagtt catctgtact actggtaaac    720
tgccggtacc ttggccgact ctggtaacga cgctgactta tggtgttcag tgctttgctc    780
gttatccgga ccatatgaag cagcatgact tcttcaagtc cgccatgccg gaaggctatg    840
tgcaggaacg cacgatttcc tttaaggatg acggcacgta caaaacgcgt gcggaagtga    900
aatttgaagg cgatactctg gtaaaccgca ttgagctgaa aggcattgac tttaaagaag    960
acggcaatat cctgggccat aagctggaat acaattttaa cagccacaat gtttacatca   1020
ccgccgataa acaaaaaaat ggcactaaag cgaattttaa aattcgccac aacgtggagg   1080
atggcagcgt gcagctggct gatcactacc agcaaaacac tccaatcggt gatggtcctg   1140
ttctgctgcc agacaatcac tatctgagca cgcaaagcgt tctgtctaaa gatccgaacg   1200
agaaacgcga tcatatggtt ctgctggagt tcgtaaccgc agcgggcatc acgcatggta   1260
tggatgaact gtacaaatga tgaactgggc acaacagagt aataattcaa aagagatgtc   1320
ggtttaacgc atgagaaagc cccggaaga tcaccttccg gggcttttt tattgcgccc   1380
caatgataac cccaagggaa gttttagtca aaagcctccg gatgtcactc aatgaagtcg   1440
cagggttgag gcgatgaggg gtccttccag gcatcaaata aaacgaaagg ctcagtcgaa   1500
agactgggcc tttcgtttta tctgttgttt gtcggtgaac gctctcctga gtaggacaaa   1560
tccgccgccc tagacttagg cgttcggctg cggcgagcgg tatcagctca ctcaaagaat   1620
ccttagcttt cgctgaggat gatttctgct agaggcagag gtggttgtgt tgcgatcgag   1680
tatcaccgca agggataaat atctaacacc gtgcgtgttg actattttac ctctggcggt   1740
gataatggtt gcatgtacta aggaggttgt atggaacaac gcataaccct gaaagattat   1800
gcaatgcgct ttgggcaaac caagacagct aaaagatctc tcacctacca aacaatgccc   1860
ccctgcaaaa aataaattca tataaaaaac atacagataa ccatctgcgg tgataaatta   1920
tctctggcgg tgttgacata aataccactg gcggtgatac tgagcacatc agcaggacgc   1980
actgaccacc atgaaggtga cgctcatgac ttacttgctg aatctcagga gtttatgacc   2040
ttttttttt agatcctatc ggtatgagag ccctggtagt catccgcctg tcccgcgtca   2100
ccgatgctac gacttcaccg gagcgtcagc tggagtcttg ccagcagctc tgcgcccagc   2160
gcggctggga cgtcgtcggg gtagcggagg atctggacgt ctccggggcg gtcgatccgt   2220
tcgaccggaa gcgcagaccg aacctggccc ggtggctagc gttcgaggag caaccgtttg   2280
acgtgatcgt ggcgtaccgg gtagatcggt tgacccgatc gatccggcat cttcagcagc   2340
tggtccactg ggccgaggac cacaagaagc tggtcgtctc cgcgaccgaa gcgcacttcg   2400
atacgacgac gccgtttgcg gcggtcgtca tcgcgcttat gggaacggtg gcgcagatgg   2460
aattagaagc gatcaaagag cggaaccgtt cggctgcgca tttcaatatc cgcgccggga   2520
aataccgagg atccctgccg ccgtggggat acctgcctac gcgcgtggac ggggagtggc   2580
ggctggtgcc ggaccctgtg cagcgagagc gcatcctcga ggtgtatcac cgcgtcgtcg   2640
acaaccacga gccgctgcat ctggtggccc acgacctgaa ccggcgtggt gtcctgtcgc   2700
cgaaggacta cttcgcgcag ctgcaaggcc gcgagccgca gggccgggag tggtcggcta   2760
```

```
ccgcgctgaa gcgatcgatg atctccgagg cgatgctcgg gtacgcgact ctgaacggta   2820
agaccgtccg agacgacgac ggagccccgc tggtgcgggc tgagccgatc ctgacccgtg   2880
agcagctgga ggcgctgcgc gccgagctcg tgaagacctc ccgggcgaag cccgcggtgt   2940
ctaccccgtc gctgctgctg cgggtgttgt tctgcgcggt gtgcggggag cccgcgtaca   3000
agttcgccgg gggaggacgt aagcacccgc gctaccgctg ccgctcgatg gggttcccga   3060
agcactgcgg gaacggcacg gtggcgatgg ccgagtggga cgcgttctgc gaggagcagg   3120
tactggatct gctcggggac gcggagcgtc tggagaaagt ctgggtagcg ggctcggact   3180
ccgcggtcga actcgcggag gtgaacgcgg agctggtgga cctgacgtcg ctgatcggct   3240
ccccggccta ccgggcgggc tctccgcagc gagaagcact ggatgcccgt attgcggcgc   3300
tggccgcgcg gcaagaggag ctggagggcc tggaggctcg cccgtctggc tgggagtggc   3360
gcgagaccgg gcagcggttc ggggactggt ggcgggagca ggacaccgcg gcaaagaaca   3420
cctggcttcg gtcgatgaac gttcggctga cgttcgacgt ccgcggcggg ctgactcgca   3480
cgatcgactt cggggatctt caggagtacg agcagcatct caggctcggc agcgtggtcg   3540
aacggctaca caccgggatg tcgggttcag cagcaaacga cgaaaactac gctgcacacc   3600
gatgatgctt aagtcgaaca gaaagtaatc gtatgagctc gacaccatcg aatggcgcaa   3660
aacctttcgc ggtatggcat gatagcgccc ggaagagagt caattcaggg tggtgaatgt   3720
ataagaagga gatatacata tgagcacaaa aaagaatcca ttaacacaag agcagcttga   3780
ggacgcacgt cgccttaaag caatttatga aaaaaagaaa aatgaacttg gcttaaccca   3840
ggaatctgtc gcagacaaga tggggatggg gcagtcaggc gttggtgctc tatttaatgg   3900
catcaatgca ttaaatgctc ataacgccgc attgcttaca aaaattctca aagttagcgt   3960
tgaagaattt agcccttcaa tcgccagaga aatctacgag atgtatgaag cggttagtat   4020
gcagccgtca cttagaagtg agtatgagta ccctgttttt tctcatgttc aggcagggat   4080
gttctcacct gagcctagaa cctgtaccaa aggtgatgcg gagagatggg taagcacaac   4140
caaaaaagcc agtgattctg cattctggct tgaggttgaa ggtaattcca tgaccgcacc   4200
aacaggctcc aagccaagct ttcctgacgg aatgttaatt ctcgttgacc ctgagcaggc   4260
tgttgagcca ggtgatttct gcatagccag acttgggggt gatgagttta ccttcaagaa   4320
actgatcagg gatagcggtc aggtgttttt acaaccacta aacccacagt acccaatgat   4380
cccatgcaat gagagttgtt ccgttgtggg gaaagttatc gctagtcagt ggcctgaaga   4440
gacgtttggc tgactcgagt ctggtaaaga aaccgctgct gcgaaatttg aacgccagca   4500
catggactcg tctactagcg cagcttaatt aacctaggct gctgccaccg ctgagcaata   4560
actagcataa ccccttgggg cctctaaacg ggtcttgagg ggttttttgc tgaaaggagg   4620
aactatatcc ggattggctt cctgagtgat accttaccct gcctatttgc cctctcccag   4680
ggttatttcg atgaaaggag agagtactaa tgccaattgc aataggaaat aaacggttac   4740
ccgttacgtt ggatgaaaag agacaaaaag aattgcagca actaaagcag aagtacggca   4800
aaagtgaatc caggattatg tgtattgcgt tagatttatt gattgcccaa gaaaaagcag   4860
gatttgaggt accagcactc aaaaagtgac gtcacttttt atcctaaaaa ctaaaagtga   4920
tagcactttt aattataaga agttagaata ttaatcattt gcttaattgt acaatataat   4980
gtacaattgt tttatagaaa taaataaggg gtgaaaggaa tggaagcagt agcttattca   5040
aatttccgcc aaaatttacg tagttatatg aaacaagtta atgaggatgc tgaaacactt   5100
attgtaacaa gtaaagatgt agaagataca gttgttgtat tatcaaaaag agattatgat   5160
```

```
tctatgcaag aaacgttgag aacactttct aataattacg tcatggaaaa aattcgtcga   5220
ggagatgaac aattctccaa aggtgcattt aaaacacatg acttaatcga ggttgaatct   5280
gatgattaag gcttggtctg atgatgcttg ggatgattat ctttattggc atgagcaagg   5340
aaacaaaagc aatataaaaa agattaacaa gttaataaaa gatatcgatc gttcccctt   5400
tgctggatta ggaaaacctg agccattaaa gcatgattta tctggaaaat ggtccagaag   5460
aattacagat gaacatagac tgatatatag agttgaaaat gaaacgatat ttatttattc   5520
tgcaaaagat cactattaac caatcggaag taaggaaagg gtcagaaact taaaagtttt   5580
tgatccttat tttatttacc ctagtcattt aaaaagctaa tatagcttag tgttgattgt   5640
tattaatgaa tgtgtttgtt acgcgtatta cggatataag gttagtaaaa tcatttctaa   5700
agttgaggaa aagtaaatat aaatggctta aatttcaaca atttgaagtt gaatagatat   5760
gttataatac tattgtagtg tgggatgtta gttactaaag gatgacgctt atatatatga   5820
ctgaatagaa taagcaatag gtttaatat ctattttaaa ttttttgtac tagttttagt   5880
taattagcgg ctgtcagacc aagtttacgg gatatattcc gcttcctcgc tcactgactc   5940
gctacgctcg gtcgttcgac tgcggcgagc ggaaatggct tacgaacggg gcggagattt   6000
cctggaagat gccaggaaga tacttaacag ggaagtgaga gggccgcggc aaagccgttt   6060
ttccataggc tccgcccccc tgacaagcat cacgaaatct gacgctcaaa tcagtggtgg   6120
cgaaacccga caggactata aagataccag gcgtttcccc ctggcggctc cctcgtgcgc   6180
tctcctgttc ctgcctttcg gtttaccggt gtcattccgc tgttatggcc gcgtttgtct   6240
cattccacgc ctgacactca gttccgggta ggcagttcgc tccaagctgg actgtatgca   6300
cgaacccccc gttcagtccg accgctgcgc cttatccggt aactatcgtc ttgagtccaa   6360
cccggaaaga catgcaaaag caccactggc agcagccact ggtaattgat ttagaggagt   6420
tagtcttgaa gtcatgcgcc ggttaaggct aaactgaaag gacaagtttt ggtgactgcg   6480
ctcctccaag ccagttacct cggttcaaag agttggtagc tcagagaacc ttcgaaaaac   6540
cgccctgcaa ggcggttttt tcgttttcag agcaagagat tacgcgcaga ccaaaacgat   6600
ctcaagaaga tcatcttatt aatcagataa aatatttcta gatttcagtg caatttatct   6660
cttcaaatgt agcacctgaa gtcagcccca tacgatataa gttgttacga acagatcgac   6720
aatgtaacta ctagagcgaa gatcctttga tcttttctac ggggtctgac gctcagtgga   6780
acgaaaactc acgttaaggg atttggtcat ggctagtgct tggaaagcaa gcaaagaaaa   6840
aaggcgacag attactctgt cgcctttttt cctgactcat aaccaagcca attctcgaac   6900
cccagagtcc cgctcagaag aactcgtcaa gaaggcgata gaaggcgatg cgctgcgaat   6960
cgggagcggc gataccgtaa agcacgagga agcggtcagc ccattcgccg ccaagctctt   7020
cagcaatatc acgggtagcc aacgctatgt cctgatagcg gtccgccaca cccagccggc   7080
cacagtcgat gaatccagaa aagcggccat tttccaccat gatattcggc aagcaggcat   7140
cgccgtgggt cacgacgaga tcctcgccgt cgggcatacg cgccttgagc ctggcgaaca   7200
gttcggctgg cgcgagcccc tgatgctctt cgtccagatc atcctgatcg acaagaccgg   7260
cttccatccg agtacgtgct cgctcgatgc gatgtttcgc ttggtggtcg aatgggcagg   7320
tagccggatc aagcgtatgc agccgccgca ttgcatcagc catgatggat actttctcgg   7380
caggagcaag gtgagatgac aggagatcct gccccggcac ttcgcccaat agcagccagt   7440
cccttcccgc ttcagtgaca acgtcgagca cagccgcgca aggaacgccc gtcgtggcca   7500
```

```
gccacgatag ccgcgctgcc tcgtcttgca gttcattcag ggcaccggac aggtcggtct   7560

tgacaaaaag aaccgggcga ccctgcgctg acagccggaa cacggcggca tcagagcagc   7620

cgattgtctg ttgtgcccag tcatagccga atagcctctc cacccaagcc gccggagaac   7680

ctgcgtgcaa tccatcttgt tcaatcatgc gaaacgatcc tcatcctgtc tcttgatcag   7740

atcttgatcc cctgcgccat cagatccttg gcggcaagaa agccatccag tttactttgc   7800

agggcttccc aaccttacca gagggcggcc caactggcaa ttccgacgtc tgtgcaagta   7860

ctactgttct gcagtcactt gcctaagata ctagctccgg caaaaaaacg ggcaaggtgt   7920

caccaccctg cccttttct ttaaaaccga aaagattact tcgcgtttgc cacctgacgt   7980

ctaagaaaag gaatattcag caatttgccc gtgccgaaga aaggcccacc cgtgaaggtg   8040

agccagtgag ttgattgcta cgtaattagt tagttagccc ttagtgactc gaatttcggc   8100

cggcttgtcg acgacggcgg tctccgtcgt caggatcatc cgggcaagct ttccacacat   8160

tataggtaca aaaagatgcg aaagcaaata aattttttgg gtttgtaccg tacaccactg   8220

agaccgcggt ggttgaccag acaaaccacg aagctgtcac cggatgtgct ttccggtctg   8280

atgagtccgt gaggac                                                    8296
```

<210> SEQ ID NO 2
<211> LENGTH: 8293
<212> TYPE: DNA
<213> ORGANISM: Artificial Sequence
<220> FEATURE:
<223> OTHER INFORMATION: alpha-CLTA-4 Thermal Switching Circuit

<400> SEQUENCE: 2

```
gaaacagcct ctacaaataa ttttgtttaa gggcccaagt tcacgagaac gatatagaaa     60

gttccaggag aaaggtacca tgaaatacct gctgccgacc gctgctgctg gtctgctgct    120

cctcgctgcc cagccggcga tggccgcgca ggtgcaactt gttgagtcgg gtggggggct    180

tgcgcagcct ggcggctcct tacgccttag ttgtgccgcg tcagggagta cgatctcttc    240

cgtggccgtt gggtggtatc gtcaaacccc aggcaatcaa cgtgagtggg tggccacttc    300

atctaccagc agtacgacag ctacttacgc ggactcagtg aaggggcgtt tcactattag    360

ccgtgacaac gcgaaaaaca cgatttattt gcagatgaac tcactgaagc ctgaggatac    420

agcggtttac tattgtaaga ctggccttac caactggggg cgtggtacac aagtaacggt    480

gtcatctggc gggttgccag aaactggagg gcatcatcat caccaccact aggtaaggca    540

agctcgtact gggagttcta atgcgtaaag gcgaagagct gttcactggt gtcgtcccta    600

ttctggtgga actggatggt gatgtcaacg gtcataagtt ttccgtgcgt ggcgagggtg    660

aaggtgacgc aactaatggt aaactgacgc tgaagttcat ctgtactact ggtaaactgc    720

cggtaccttg gccgactctg gtaacgacgc tgacttatgg tgttcagtgc tttgctcgtt    780

atccggacca tatgaagcag catgacttct tcaagtccgc catgccggaa ggctatgtgc    840

aggaacgcac gatttccttt aaggatgacg gcacgtacaa aacgcgtgcg gaagtgaaat    900

ttgaaggcga tactctggta aaccgcattg agctgaaagg cattgacttt aaagaagacg    960

gcaatatcct gggccataag ctggaataca attttaacag ccacaatgtt tacatcaccg   1020

ccgataaaca aaaaaatggc actaaagcga attttaaaat tcgccacaac gtggaggatg   1080

gcagcgtgca gctggctgat cactaccagc aaaacactcc aatcggtgat ggtcctgttc   1140

tgctgccaga caatcactat ctgagcacgc aaagcgttct gtctaaagat ccgaacgaga   1200

aacgcgatca tatggttctg ctggagttcg taaccgcagc gggcatcacg catggtatgg   1260
```

-continued

```
atgaactgta caaatgatga actgggcaca acagagtaat aattcaaaag agatgtcggt   1320
ttaacgcatg agaaagcccc cggaagatca ccttccgggg gctttttat tgcgccccaa   1380
tgataacccc aagggaagtt ttagtcaaaa gcctccggat gtcactcaat gaagtcgcag   1440
ggttgaggcg atgaggggtc cttccaggca tcaaataaaa cgaaaggctc agtcgaaaga   1500
ctgggccttt cgttttatct gttgtttgtc ggtgaacgct ctcctgagta ggacaaatcc   1560
gccgccctag acttaggcgt tcggctgcgg cgagcggtat cagctcactc aaagaatcct   1620
tagctttcgc tgaggatgat ttctgctaga ggcagaggtg gttgtgttgc gatcgagtat   1680
caccgcaagg gataaatatc taacaccgtg cgtgttgact attttacctc tggcggtgat   1740
aatggttgca tgtactaagg aggttgtatg gaacaacgca taaccctgaa agattatgca   1800
atgcgctttg ggcaaaccaa gacagctaaa agatctctca cctaccaaac aatgcccccc   1860
tgcaaaaaat aaattcatat aaaaaacata cagataacca tctgcggtga taaattatct   1920
ctggcggtgt tgacataaat accactggcg gtgatactga gcacatcagc aggacgcact   1980
gaccaccatg aaggtgacgc tcatgactta cttgctgaat ctcaggagtt tatgaccttt   2040
ttttttaga tcctatcggt atgagagccc tggtagtcat ccgcctgtcc cgcgtcaccg   2100
atgctacgac ttcaccggag cgtcagctgg agtcttgcca gcagctctgc gcccagcgcg   2160
gctgggacgt cgtcggggta gcggaggatc tggacgtctc cggggcggtc gatccgttcg   2220
accggaagcg cagaccgaac ctggcccggt ggctagcgtt cgaggagcaa ccgtttgacg   2280
tgatcgtggc gtaccgggta gatcggttga cccgatcgat ccggcatctt cagcagctgg   2340
tccactgggc cgaggaccac aagaagctgg tcgtctccgc gaccgaagcg cacttcgata   2400
cgacgacgcc gtttgcggcg gtcgtcatcg cgcttatggg aacggtggcg cagatggaat   2460
tagaagcgat caaagagcgg aaccgttcgg ctgcgcattt caatatccgc gccgggaaat   2520
accgaggatc cctgccgccg tggggatacc tgcctacgcg cgtggacggg gagtggcggc   2580
tggtgccgga ccctgtgcag cgagagcgca tcctcgaggt gtatcaccgc gtcgtcgaca   2640
accacgagcc gctgcatctg gtggcccacg acctgaaccg gcgtggtgtc ctgtcgccga   2700
aggactactt cgcgcagctg caaggccgcg agccgcaggg ccgggagtgg tcggctaccg   2760
cgctgaagcg atcgatgatc tccgaggcga tgctcgggta cgcgactctg aacggtaaga   2820
ccgtccgaga cgacgacgga gccccgctgg tgcgggctga gccgatcctg acccgtgagc   2880
agctggaggc gctgcgcgcc gagctcgtga agacctcccg ggcgaagccc gcggtgtcta   2940
ccccgtcgct gctgctgcgg gtgttgttct gcgcggtgtg cggggagccc gcgtacaagt   3000
tcgccggggg aggacgtaag cacccgcgct accgctgccg ctcgatgggg ttcccgaagc   3060
actgcgggaa cggcacggtg gcgatggccg agtgggacgc gttctgcgag gagcaggtac   3120
tggatctgct cggggacgcg gagcgtctgg agaaagtctg ggtagcgggc tcggactccg   3180
cggtcgaact cgcggaggtg aacgcggagc tggtggacct gacgtcgctg atcggctccc   3240
cggcctaccg ggcgggctct ccgcagcgag aagcactgga tgcccgtatt gcggcgctgg   3300
ccgcgcggca agaggagctg gagggcctgg aggctcgccc gtctggctgg gagtggcgcg   3360
agaccgggca gcggttcggg gactggtggc gggagcagga caccgcggca aagaacacct   3420
ggcttcggtc gatgaacgtt cggctgacgt tcgacgtccg cggcgggctg actcgcacga   3480
tcgacttcgg ggatcttcag gagtacgagc agcatctcag gctcggcagc gtggtcgaac   3540
ggctacacac cgggatgtcg ggttcagcag caaacgacga aaactacgct gcacaccgat   3600
```

```
gatgcttaag tcgaacagaa agtaatcgta tgagctcgac accatcgaat ggcgcaaaac   3660
ctttcgcggt atggcatgat agcgcccgga agagagtcaa ttcagggtgg tgaatgtata   3720
agaaggagat atacatatga gcacaaaaaa gaatccatta acacaagagc agcttgagga   3780
cgcacgtcgc cttaaagcaa tttatgaaaa aaagaaaaat gaacttggct taacccagga   3840
atctgtcgca gacaagatgg ggatggggca gtcaggcgtt ggtgctctat ttaatggcat   3900
caatgcatta aatgctcata acgccgcatt gcttacaaaa attctcaaag ttagcgttga   3960
agaatttagc ccttcaatcg ccagagaaat ctacgagatg tatgaagcgg ttagtatgca   4020
gccgtcactt agaagtgagt atgagtaccc tgttttttct catgttcagg cagggatgtt   4080
ctcacctgag cctagaacct gtaccaaagg tgatgcggag agatgggtaa gcacaaccaa   4140
aaaagccagt gattctgcat tctggcttga ggttgaaggt aattccatga ccgcaccaac   4200
aggctccaag ccaagctttc ctgacggaat gttaattctc gttgaccctg agcaggctgt   4260
tgagccaggt gatttctgca tagccagact tgggggtgat gagtttacct tcaagaaact   4320
gatcagggat agcggtcagg tgtttttaca accactaaac ccacagtacc caatgatccc   4380
atgcaatgag agttgttccg ttgtggggaa agttatcgct agtcagtggc ctgaagagac   4440
gtttggctga ctcgagtctg gtaaagaaac cgctgctgcg aaatttgaac gccagcacat   4500
ggactcgtct actagcgcag cttaattaac ctaggctgct gccaccgctg agcaataact   4560
agcataaccc cttggggcct ctaaacgggt cttgaggggt tttttgctga aaggaggaac   4620
tatatccgga ttggcttcct gagtgatacc ttaccctgcc tatttgccct ctcccagggt   4680
tatttcgatg aaaggagaga gtactaatgc caattgcaat aggaaataaa cggttacccg   4740
ttacgttgga tgaaaagaga caaaaagaat tgcagcaact aaagcagaag tacggcaaaa   4800
gtgaatccag gattatgtgt attgcgttag atttattgat tgcccaagaa aaagcaggat   4860
ttgaggtacc agcactcaaa aagtgacgtc actttttatc ctaaaaacta aaagtgatag   4920
cacttttaat tataagaagt tagaatatta atcatttgct taattgtaca atataatgta   4980
caattgtttt atagaaataa ataaggggtg aaaggaatgg aagcagtagc ttattcaaat   5040
ttccgccaaa atttacgtag ttatatgaaa caagttaatg aggatgctga aacacttatt   5100
gtaacaagta aagatgtaga agatacagtt gttgtattat caaaaagaga ttatgattct   5160
atgcaagaaa cgttgagaac actttctaat aattacgtca tggaaaaaat tcgtcgagga   5220
gatgaacaat tctccaaagg tgcatttaaa acacatgact taatcgaggt tgaatctgat   5280
gattaaggct tggtctgatg atgcttggga tgattatctt tattggcatg agcaaggaaa   5340
caaaagcaat ataaaaaaga ttaacaagtt aataaaagat atcgatcgtt ccccctttgc   5400
tggattagga aaacctgagc cattaaagca tgatttatct ggaaaatggt ccagaagaat   5460
tacagatgaa catagactga tatatagagt tgaaaatgaa acgatattta tttattctgc   5520
aaaagatcac tattaaccaa tcggaagtaa ggaaagggtc agaaacttaa aagtttttga   5580
tccttatttt atttacccta gtcatttaaa aagctaatat agcttagtgt tgattgttat   5640
taatgaatgt gtttgttacg cgtattacgg atataaggtt agtaaaatca tttctaaagt   5700
tgaggaaaag taaatataaa tggcttaaat ttcaacaatt tgaagttgaa tagatatgtt   5760
ataatactat tgtagtgtgg gatgttagtt actaaaggat gacgcttata tatatgactg   5820
aatagaataa gcaataggtt taataatcta ttttaaattt tttgtactag ttttagttaa   5880
ttagcggctg tcagaccaag tttacgggat atattccgct tcctcgctca ctgactcgct   5940
acgctcggtc gttcgactgc ggcgagcgga aatggcttac gaacggggcg gagatttcct   6000
```

ggaagatgcc aggaagatac ttaacaggga agtgagaggg ccgcggcaaa gccgtttttc 6060
cataggctcc gcccccctga caagcatcac gaaatctgac gctcaaatca gtggtggcga 6120
aacccgacag gactataaag ataccaggcg tttccccctg gcggctccct cgtgcgctct 6180
cctgttcctg cctttcggtt taccggtgtc attccgctgt tatggccgcg tttgtctcat 6240
tccacgcctg acactcagtt ccgggtaggc agttcgctcc aagctggact gtatgcacga 6300
accccccgtt cagtccgacc gctgcgcctt atccggtaac tatcgtcttg agtccaaccc 6360
ggaaagacat gcaaaagcac cactggcagc agccactggt aattgattta gaggagttag 6420
tcttgaagtc atgcgccggt taaggctaaa ctgaaaggac aagttttggt gactgcgctc 6480
ctccaagcca gttacctcgg ttcaaagagt tggtagctca gagaaccttc gaaaaaccgc 6540
cctgcaaggc ggttttttcg ttttcagagc aagagattac gcgcagacca aaacgatctc 6600
aagaagatca tcttattaat cagataaaat atttctagat ttcagtgcaa tttatctctt 6660
caaatgtagc acctgaagtc agccccatac gatataagtt gttacgaaca gatcgacaat 6720
gtaactacta gagcgaagat cctttgatct tttctacggg gtctgacgct cagtggaacg 6780
aaaactcacg ttaagggatt tggtcatggc tagtgcttgg aaagcaagca aagaaaaaag 6840
gcgacagatt actctgtcgc ctttttttcct gactcataac caagccaatt ctcgaacccc 6900
agagtcccgc tcagaagaac tcgtcaagaa ggcgatagaa ggcgatgcgc tgcgaatcgg 6960
gagcggcgat accgtaaagc acgaggaagc ggtcagccca ttcgccgcca agctcttcag 7020
caatatcacg ggtagccaac gctatgtcct gatagcggtc cgccacaccc agccggccac 7080
agtcgatgaa tccagaaaag cggccatttt ccaccatgat attcggcaag caggcatcgc 7140
cgtgggtcac gacgagatcc tcgccgtcgg gcatacgcgc cttgagcctg gcgaacagtt 7200
cggctggcgc gagcccctga tgctcttcgt ccagatcatc ctgatcgaca agaccggctt 7260
ccatccgagt acgtgctcgc tcgatgcgat gtttcgcttg gtggtcgaat gggcaggtag 7320
ccggatcaag cgtatgcagc cgccgcattg catcagccat gatggatact ttctcggcag 7380
gagcaaggtg agatgacagg agatcctgcc ccggcacttc gcccaatagc agccagtccc 7440
ttcccgcttc agtgacaacg tcgagcacag ccgcgcaagg aacgcccgtc gtggccagcc 7500
acgatagccg cgctgcctcg tcttgcagtt cattcagggc accggacagg tcggtcttga 7560
caaaaagaac cgggcgaccc tgcgctgaca gccggaacac ggcggcatca gagcagccga 7620
ttgtctgttg tgcccagtca tagccgaata gcctctccac ccaagccgcc ggagaacctg 7680
cgtgcaatcc atcttgttca atcatgcgaa acgatcctca tcctgtctct tgatcagatc 7740
ttgatcccct gcgccatcag atccttggcg gcaagaaagc catccagttt actttgcagg 7800
gcttcccaac cttaccagag ggcggcccaa ctggcaattc cgacgtctgt gcaagtacta 7860
ctgttctgca gtcacttgcc taagatacta gctccggcaa aaaaacgggc aaggtgtcac 7920
caccctgccc tttttcttta aaaccgaaaa gattacttcg cgtttgccac ctgacgtcta 7980
agaaaaggaa tattcagcaa tttgcccgtg ccgaagaaag gcccacccgt gaaggtgagc 8040
cagtgagttg attgctacgt aattagttag ttagccctta gtgactcgaa tttcggccgg 8100
cttgtcgacg acggcggtct ccgtcgtcag gatcatccgg gcaagctttc cacacattat 8160
aggtacaaaa agatgcgaaa gcaaataaat tttttgggtt tgtaccgtac accactgaga 8220
ccgcggtggt tgaccagaca aaccacgaag ctgtcaccgg atgtgctttc cggtctgatg 8280
agtccgtgag gac 8293

<210> SEQ ID NO 3
<211> LENGTH: 9061
<212> TYPE: DNA
<213> ORGANISM: Artificial Sequence
<220> FEATURE:
<223> OTHER INFORMATION: Thermal Switching Circuit Library Screen
Plasmid Design
<220> FEATURE:
<221> NAME/KEY: misc_feature
<222> LOCATION: (4455)..(4460)
<223> OTHER INFORMATION: n is a, c, g, or t
<220> FEATURE:
<221> NAME/KEY: misc_feature
<222> LOCATION: (5999)..(6004)
<223> OTHER INFORMATION: n is a, c, g, or t

<400> SEQUENCE: 3
cagatcgaca atgtaactac tagagcgaag atcctttgat cttttctacg ggtctgacg 60 ctcagtggaa cgaaaactca cgttaaggga tttggtcatg gctagtgctt ggaaagcaag 120
caaagaaaaa aggcgacaga ttactctgtc gcctttttc ctgactcata accaagccaa 180
ttctcgaacc ccagagtccc gctcagaaga actcgtcaag aaggcgatag aaggcgatgc 240
gctgcgaatc gggagcggcg ataccgtaaa gcacgaggaa gcggtcagcc cattcgccgc 300
caagctcttc agcaatatca cgggtagcca acgctatgtc ctgatagcgg tccgccacac 360
ccagccggcc acagtcgatg aatccagaaa agcggccatt ttccaccatg atattcggca 420
agcaggcatc gccgtgggtc acgacgagat cctcgccgtc gggcatacgc gccttgagcc 480
tggcgaacag ttcggctggc gcgagcccct gatgctcttc gtccagatca tcctgatcga 540
caagaccggc ttccatccga gtacgtgctc gctcgatgcg atgtttcgct tggtggtcga 600
atgggcaggt agccggatca agcgtatgca gccgccgcat tgcatcagcc atgatggata 660
ctttctcggc aggagcaagg tgagatgaca ggagatcctg ccccggcact tcgcccaata 720
gcagccagtc ccttcccgct tcagtgacaa cgtcgagcac agccgcgcaa ggaacgcccg 780
tcgtggccag ccacgatagc cgcgctgcct cgtcttgcag ttcattcagg gcaccggaca 840
ggtcggtctt gacaaaaaga accgggcgac cctgcgctga cagccggaac acggcggcat 900
cagagcagcc gattgtctgt tgtgcccagt catagccgaa tagcctctcc acccaagccg 960
ccggagaacc tgcgtgcaat ccatcttgtt caatcatgcg aaacgatcct catcctgtct 1020
cttgatcaga tcttgatccc ctgcgccatc agatccttgg cggcaagaaa gccatccagt 1080
ttactttgca gggcttccca accttaccag agggcggccc aactggcaat tccgacgtct 1140
gtgcaagtac tactgttctg cagtcacttg cctaagatac tagctccggc aaaaaaacgg 1200
gcaaggtgtc accaccctgc cctttttctt taaaaccgaa aagattactt cgcgtttgcc 1260
acctgacgtc taagaaaagg aatattcagc aatttgcccg tgccgaagaa aggcccaccc 1320
gtgaaggtga gccagtgagt tgattgctac gtaattagtt agttagccct tagtgactcg 1380
aatttcggcc ggcttgtcga cgacggcggt ctccgtcgtc aggatcatcc gggcaagctt 1440
tccacacatt ataggtacaa aaagatgcga aagcaaataa attttttggg tttgtaccgt 1500
acaccactga gaccgcggtg gttgaccaga caaaccacga agctgtcacc ggatgtgctt 1560
tccggtctga tgagtccgtg aggacgaaac agcctctaca aataattttg tttaagggcc 1620
caagttcact taaaaaggag atcaacaatg aaagcaattt tcgtactgaa acatcttaat 1680
catgctaagg aggttttcta atgcgtaaag gcgaagagct gttcactggt gtcgtcccta 1740
ttctggtgga actggatggt gatgtcaacg gtcataagtt ttccgtgcgt ggcgagggtg 1800

-continued

```
aaggtgacgc aactaatggt aaactgacgc tgaagttcat ctgtactact ggtaaactgc   1860
cggtaccttg gccgactctg gtaacgacgc tgacttatgg tgttcagtgc tttgctcgtt   1920
atccggacca tatgaagcag catgacttct tcaagtccgc catgccggaa ggctatgtgc   1980
aggaacgcac gatttccttt aaggatgacg gcacgtacaa aacgcgtgcg gaagtgaaat   2040
ttgaaggcga tactctggta aaccgcattg agctgaaagg cattgacttt aaagaagacg   2100
gcaatatcct gggccataag ctggaataca attttaacag ccacaatgtt tacatcaccg   2160
ccgataaaca aaaaaatggc actaaagcga attttaaaat tcgccacaac gtggaggatg   2220
gcagcgtgca gctggctgat cactaccagc aaaacactcc aatcggtgat ggtcctgttc   2280
tgctgccaga caatcactat ctgagcacgc aaagcgttct gtctaaagat ccgaacgaga   2340
aacgcgatca tatggttctg ctggagttcg taaccgcagc gggcatcacg catggtatgg   2400
atgaactgta caaatgatga tacgcggtag tttatcacag ttaaattgct aacgcagtca   2460
ggcaccgtgt atgaaatcta acaatgcgct catcgtcatc ctcggcaccg tcaccctgga   2520
tgctgtaggc ataggcttgg ttatgccggt actgccgggc ctcttgcggg atatcgtcca   2580
ttccgacagc atcgccagtc actatggcgt gctgctagcg ctatatgcgt tgatgcaatt   2640
tctatgcgca cccgttctcg gagcactgtc cgaccgcttt ggccgccgcc cagtcctgct   2700
cgcttcgcta cttggagcca ctatcgacta cgcgatcatg gcgaccacac ccgtcctgtg   2760
gatcctctac gccggacgca tcgtggccgg catcaccggc gccacaggtg cggttgctgg   2820
cgcctatatc gccgacatca ccgatgggga agatcgggct cgccacttcg ggctcatgag   2880
cgcttgtttc ggcgtgggta tggtggcagg ccccgtggcc gggggactgt tgggcgccat   2940
ctccttgcat gcaccattcc ttgcggcggc ggtgctcaac ggcctcaacc tactactggg   3000
ctgcttccta atgcaggagt cgcataaggg agagcgtcga ccgatgccct tgagagcctt   3060
caacccagtc agctccttcc ggtgggcgcg gggcatgact atcgtcgccg cacttatgac   3120
tgtcttcttt atcatgcaac tcgtaggaca ggtgccggca gcgctctggg tcattttcgg   3180
cgaggaccgc tttcgctgga gcgcgacgat gatcggcctg tcgcttgcgg tattcggaat   3240
cttgcacgcc ctcgctcaag ccttcgtcac tggtcccgcc accaaacgtt tcggcgagaa   3300
gcaggccatt atcgccggca tggcggccga cgcgctgggc tacgtcttgc tggcgttcgc   3360
gacgcgaggc tggatggcct tccccattat gattcttctc gcttccggcg gcatcgggat   3420
gcccgcgttg caggccatgc tgtccaggca ggtagatgac gaccatcagg gacagcttca   3480
aggatcgctc gcggctctta ccagcctaac ttcgatcatt ggaccgctga tcgtcacggc   3540
gatttatgcc gcctcggcga gcacatggaa cgggttggca tggattgtag gcgccgccct   3600
ataccttgtc tgcctccccg cgttgcgtcg cggtgcatgg agccgggcca cctcgacctg   3660
aactgggcac aacagagtaa taattcaaaa gagatgtcgg tttaacgcat gagaaagccc   3720
ccggaagatc accttccggg ggcttttta ttgcgcccca atgataaccc caagggaagt   3780
tttagtcaaa agcctccgga tgtcactcaa tgaagtcgca gggttgaggc gatgaggggt   3840
ccttccaggc atcaaataaa acgaaaggct cagtcgaaag actgggcctt tcgttttatc   3900
tgttgtttgt cggtgaacgc tctcctgagt aggacaaatc cgccgcccta gacttaggcg   3960
ttcggctgcg gcgagcggta tcagctcact caaagaatcc ttagctttcg ctgaggatga   4020
tttctgctag aggcagaggt ggttgtgttg cgatcgagta tcaccgcaag ggataaatat   4080
ctaacaccgt gcgtgttgac tattttacct ctggcggtga taatggttgc atgtactaag   4140
gaggttgtat ggaacaacgc ataaccctga aagattatgc aatgcgcttt gggcaaacca   4200
```

agacagctaa aagatctctc acctaccaaa caatgccccc ctgcaaaaaa taaattcata 4260
taaaaaacat acagataacc atctgcggtg ataaattatc tctggcggtg ttgacataaa 4320
taccactggc ggtgatactg agcacatcag caggacgcac tgaccaccat gaaggtgacg 4380
ctcttaaaaa ttaagccctg aagaagggca gcattcaaag cagaaggctt tggggtgtgt 4440
gatacgaaac gaagnnnnnn tcggtrtgag agccctggta gtcatccgcc tgtcccgcgt 4500
caccgatgct acgacttcac cggagcgtca gctggagtct tgccagcagc tctgcgccca 4560
gcgcggctgg gacgtcgtcg gggtagcgga ggatctggac gtctccgggg cggtcgatcc 4620
gttcgaccgg aagcgcagac cgaacctggc ccggtggcta gcgttcgagg agcaaccgtt 4680
tgacgtgatc gtggcgtacc gggtagatcg gttgacccga tcgatccggc atcttcagca 4740
gctggtccac tgggccgagg accacaagaa gctggtcgtc tccgcgaccg aagcgcactt 4800
cgatacgacg acgccgtttg cggcggtcgt catcgcgctt atgggaacgg tggcgcagat 4860
ggaattagaa gcgatcaaag agcggaaccg ttcggctgcg catttcaata tccgcgccgg 4920
gaaataccga ggatccctgc cgccgtgggg atacctgcct acgcgcgtgg acggggagtg 4980
gcggctggtg ccggaccctg tgcagcgaga gcgcatcctc gaggtgtatc accgcgtcgt 5040
cgacaaccac gagccgctgc atctggtggc ccacgacctg aaccggcgtg gtgtcctgtc 5100
gccgaaggac tacttcgcgc agctgcaagg ccgcgagccg cagggccggg agtggtcggc 5160
taccgcgctg aagcgatcga tgatctccga ggcgatgctc gggtacgcga ctctgaacgg 5220
taagaccgtc cgagacgacg acggagcccc gctggtgcgg gctgagccga tcctgacccg 5280
tgagcagctg gaggcgctgc gcgccgagct cgtgaagacc tcccgggcga agcccgcggt 5340
gtctaccccg tcgctgctgc tgcgggtgtt gttctgcgcg gtgtgcgggg agcccgcgta 5400
caagttcgcc gggggaggac gtaagcaccc gcgctaccgc tgccgctcga tggggttccc 5460
gaagcactgc gggaacggca cggtggcgat ggccgagtgg gacgcgttct gcgaggagca 5520
ggtactggat ctgctcgggg acgcggagcg tctggagaaa gtctgggtag cgggctcgga 5580
ctccgcggtc gaactcgcgg aggtgaacgc ggagctggtg gacctgacgt cgctgatcgg 5640
ctccccggcc taccgggcgg gctctccgca gcgagaagca ctggatgccc gtattgcggc 5700
gctggccgcg cggcaagagg agctggaggg cctggaggct cgcccgtctg gctgggagtg 5760
gcgcgagacc gggcagcggt tcggggactg gtggcgggag caggacaccg cggcaaagaa 5820
cacctggctt cggtcgatga acgttcggct gacgttcgac gtccgcggcg ggctgactcg 5880
cacgatcgac ttcggggatc ttcaggagta cgagcagcat ctcaggctcg gcagcgtggt 5940
cgaacggcta cacaccggga tgtcgggttc agcagcaaac gacgaaaact acgctgcann 6000
nnnntgatgc ttaagtcgaa cagaaagtaa tcgtatgagc tcgacaccat cgaatggcgc 6060
aaaacctttc gcggtatggc atgatagcgc ccggaagaga gtcaattcag ggtggtgaat 6120
gtataagaag gagatataca tatgagcaca aaaaagaatc cattaacaca agagcagctt 6180
gaggacgcac gtcgccttaa agcaatttat gaaaaaaaga aaaatgaact tggcttaacc 6240
caggaatctg tcgcagacaa gatggggatg gggcagtcag gcgttggtgc tctatttaat 6300
ggcatcaatg cattaaatgc tcataacgcc gcattgctta caaaaattct caaagttagc 6360
gttgaagaat ttagcccttc aatcgccaga gaaatctacg agatgtatga agcggttagt 6420
atgcagccgt cacttagaag tgagtatgag taccctgttt tttctcatgt tcaggcaggg 6480
atgttctcac ctgagcctag aacctgtacc aaaggtgatg cggagagatg ggtaagcaca 6540

```
accaaaaaag ccagtgattc tgcattctgg cttgaggttg aaggtaattc catgaccgca   6600
ccaacaggct ccaagccaag ctttcctgac ggaatgttaa ttctcgttga ccctgagcag   6660
gctgttgagc caggtgattt ctgcatagcc agacttgggg gtgatgagtt taccttcaag   6720
aaactgatca gggatagcgg tcaggtgttt ttacaaccac taaacccaca gtacccaatg   6780
atcccatgca atgagagttg ttccgttgtg ggaaaagtta tcgctagtca gtggcctgaa   6840
gagacgtttg gctgactcga gtctggtaaa gaaaccgctg ctgcgaaatt tgaacgccag   6900
cacatggact cgtctactag cgcagcttaa ttaacctagg ctgctgccac cgctgagcaa   6960
taactagcat aaccccttgg ggcctctaaa cgggtcttga ggggtttttt gctgaaagga   7020
ggaactatat ccggattggc tctgtcagac caagtttacg agctcgcttg gactcctgtt   7080
gatagatcca gtaatgacct cagaactcca tctggatttg ttcagaacgc tcggttgccg   7140
ccgggcgttt tttattggtg agaatccaag cactagggac agtaagacgg gtaagcctgt   7200
tgatgatacc gctgccttac tgggtgcatt agccagtctg aatgacctgt cacgggataa   7260
tccgaagtgg tcagactgga aatcagaggg gcaggaactg ctgaacagca aaaagtcaga   7320
tagcaccaca tagcagaccc gccataaaac gccctgagaa gcccgtgacg ggcttttctt   7380
gtattatggg tagtttcctt gcatgaatcc ataaaaggcg cctgtagtgc catttacccc   7440
cattcactgc cagagccgtg agcgcagcga actgaatgtc acgaaaaaga cagcgactca   7500
ggtgcctgat ggtcggagac aaaaggaata ttcagcgatt tgcccgagct tgcgagggtg   7560
ctacttaagc ctttagggtt ttaaggtctg ttttgtagag gagcaaacag cgtttgcgac   7620
atccttttgt aatactgcgg aactgactaa agtagtgagt tatacacagg gctgggatct   7680
attcttttta tcttttttta ttctttcttt attctataaa ttataaccac ttgaatataa   7740
acaaaaaaaa cacacaaagg tctagcggaa tttacagagg gtctagcaga atttacaagt   7800
tttccagcaa aggtctagca gaatttacag atacccacaa ctcaaaggaa aaggacatgt   7860
aattatcatt gactagccca tctcaattgg tatagtgatt aaaatcacct agaccaattg   7920
agatgtatgt ctgaattagt tgttttcaaa gcaaatgaac tagcgattag tcgctatgac   7980
ttaacggagc atgaaaccaa gctaatttta tgctgtgtgg cactactcaa ccccacgatt   8040
gaaaacccta caaggaaaga acggacggta tcgttcactt ataaccaata cgctcagatg   8100
atgaacatca gtagggaaaa tgcttatggt gtattagcta aagcaaccag agagctgatg   8160
acgagaactg tggaaatcag gaatcctttg gttaaaggct ttgagatttt ccagtggaca   8220
aactatgcca agttctcaag cgaaaaatta gaattagttt ttagtgaaga gatattgcct   8280
tatcttttcc agttaaaaaa attcataaaa tataatctgg aacatgttaa gtcttttgaa   8340
aacaaatact ctatgaggat ttatgagtgg ttattaaaag aactaacaca aaagaaaact   8400
cacaaggcaa atatagagat tagccttgat gaatttaagt tcatgttaat gcttgaaaat   8460
aactaccatg agtttaaaag gcttaaccaa tgggttttga aaccaataag taaagattta   8520
aacacttaca gcaatatgaa attggtggtt gataagcgag gccgcccgac tgatacgttg   8580
attttccaag ttgaactaga tagacaaatg gatctcgtaa ccgaacttga gaacaaccag   8640
ataaaaatga atggtgacaa aataccaaca accattacat cagattccta cctacgtaac   8700
ggactaagaa aaacactaca cgatgcttta actgcaaaaa ttcagctcac cagttttgag   8760
gcaaaatttt tgagtgacat gcaaagtaag catgatctca atggttcgtt ctcatggctc   8820
acgcaaaaac aacgaaccac actagagaac atactggcta aatacggaag gatctgaggt   8880
tcttatggct cttgtatcta tcagtgaagc atcaagacta acaaacaaaa gtagaacaac   8940
```

```
tgttcaccgt tagatatcaa agggaaaact gtccatatgc acagatgaaa acggtgtaaa   9000

aaagatagat acatcagagc ttttacgagt ttttggtgca tttaaagctg ttcaccatga   9060

a                                                                   9061
```

<210> SEQ ID NO 4
<211> LENGTH: 9061
<212> TYPE: DNA
<213> ORGANISM: Artificial Sequence
<220> FEATURE:
<223> OTHER INFORMATION: Thermal Switching Circuit Library Screen Parent Plasmid

<400> SEQUENCE: 4

```
cagatcgaca atgtaactac tagagcgaag atcctttgat cttttctacg ggtctgacg     60

ctcagtggaa cgaaaactca cgttaaggga tttggtcatg gctagtgctt ggaaagcaag    120

caaagaaaaa aggcgacaga ttactctgtc gcctttttc ctgactcata accaagccaa    180

ttctcgaacc ccagagtccc gctcagaaga actcgtcaag aaggcgatag aaggcgatgc    240

gctgcgaatc gggagcggcg ataccgtaaa gcacgaggaa gcggtcagcc cattcgccgc    300

caagctcttc agcaatatca cgggtagcca acgctatgtc ctgatagcgg tccgccacac    360

ccagccggcc acagtcgatg aatccagaaa agcggccatt ttccaccatg atattcggca    420

agcaggcatc gccgtgggtc acgacgagat cctcgccgtc gggcatacgc gccttgagcc    480

tggcgaacag ttcggctggc gcgagcccct gatgctcttc gtccagatca tcctgatcga    540

caagaccggc ttccatccga gtacgtgctc gctcgatgcg atgtttcgct tggtggtcga    600

atgggcaggt agccggatca agcgtatgca gccgccgcat tgcatcagcc atgatggata    660

ctttctcggc aggagcaagg tgagatgaca ggagatcctg ccccggcact tcgcccaata    720

gcagccagtc ccttcccgct tcagtgacaa cgtcgagcac agccgcgcaa ggaacgcccg    780

tcgtggccag ccacgatagc cgcgctgcct cgtcttgcag ttcattcagg gcaccggaca    840

ggtcggtctt gacaaaaaga accgggcgac cctgcgctga cagccggaac acggcggcat    900

cagagcagcc gattgtctgt tgtgcccagt catagccgaa tagcctctcc acccaagccg    960

ccggagaacc tgcgtgcaat ccatcttgtt caatcatgcg aaacgatcct catcctgtct   1020

cttgatcaga tcttgatccc ctgcgccatc agatccttgg cggcaagaaa gccatccagt   1080

ttactttgca gggcttccca accttaccag agggcggccc aactggcaat tccgacgtct   1140

gtgcaagtac tactgttctg cagtcacttg cctaagatac tagctccggc aaaaaaacgg   1200

gcaaggtgtc accaccctgc cctttttctt taaaaccgaa aagattactt cgcgtttgcc   1260

acctgacgtc taagaaaagg aatattcagc aatttgcccg tgccgaagaa aggcccaccc   1320

gtgaaggtga gccagtgagt tgattgctac gtaattagtt agttagccct tagtgactcg   1380

aatttcggcc ggcttgtcga cgacggcggt ctccgtcgtc aggatcatcc gggcaagctt   1440

tccacacatt ataggtacaa aaagatgcga aagcaaataa attttttggg tttgtaccgt   1500

acaccactga gaccgcggtg gttgaccaga caaaccacga agctgtcacc ggatgtgctt   1560

tccggtctga tgagtccgtg aggacgaaac agcctctaca aataattttg tttaagggcc   1620

caagttcact taaaaaggag atcaacaatg aaagcaattt tcgtactgaa acatcttaat   1680

catgctaagg aggttttcta atgcgtaaag gcgaagagct gttcactggt gtcgtcccta   1740

ttctggtgga actggatggt gatgtcaacg gtcataagtt ttccgtgcgt ggcgagggtg   1800

aaggtgacgc aactaatggt aaactgacgc tgaagttcat ctgtactact ggtaaactgc   1860
```

```
cggtaccttg gccgactctg gtaacgacgc tgacttatgg tgttcagtgc tttgctcgtt   1920

atccggacca tatgaagcag catgacttct tcaagtccgc catgccggaa ggctatgtgc   1980

aggaacgcac gatttccttt aaggatgacg gcacgtacaa aacgcgtgcg gaagtgaaat   2040

ttgaaggcga tactctggta aaccgcattg agctgaaagg cattgacttt aaagaagacg   2100

gcaatatcct gggccataag ctggaataca attttaacag ccacaatgtt tacatcaccg   2160

ccgataaaca aaaaaatggc actaaagcga attttaaaat tcgccacaac gtggaggatg   2220

gcagcgtgca gctggctgat cactaccagc aaaacactcc aatcggtgat ggtcctgttc   2280

tgctgccaga caatcactat ctgagcacgc aaagcgttct gtctaaagat ccgaacgaga   2340

aacgcgatca tatggttctg ctggagttcg taaccgcagc gggcatcacg catggtatgg   2400

atgaactgta caaatgatga tacgcggtag tttatcacag ttaaattgct aacgcagtca   2460

ggcaccgtgt atgaaatcta acaatgcgct catcgtcatc ctcggcaccg tcaccctgga   2520

tgctgtaggc ataggcttgg ttatgccggt actgccgggc ctcttgcggg atatcgtcca   2580

ttccgacagc atcgccagtc actatggcgt gctgctagcg ctatatgcgt tgatgcaatt   2640

tctatgcgca cccgttctcg gagcactgtc cgaccgcttt ggccgccgcc cagtcctgct   2700

cgcttcgcta cttggagcca ctatcgacta cgcgatcatg gcgaccacac ccgtcctgtg   2760

gatcctctac gccggacgca tcgtggccgg catcaccggc gccacaggtg cggttgctgg   2820

cgcctatatc gccgacatca ccgatgggga agatcgggct cgccacttcg ggctcatgag   2880

cgcttgtttc ggcgtgggta tggtggcagg ccccgtggcc gggggactgt tgggcgccat   2940

ctccttgcat gcaccattcc ttgcggcggc ggtgctcaac ggcctcaacc tactactggg   3000

ctgcttccta atgcaggagt cgcataaggg agagcgtcga ccgatgccct tgagagcctt   3060

caacccagtc agctccttcc ggtgggcgcg gggcatgact atcgtcgccg cacttatgac   3120

tgtcttcttt atcatgcaac tcgtaggaca ggtgccggca gcgctctggg tcattttcgg   3180

cgaggaccgc tttcgctgga gcgcgacgat gatcggcctg tcgcttgcgg tattcggaat   3240

cttgcacgcc ctcgctcaag ccttcgtcac tggtcccgcc accaaacgtt tcggcgagaa   3300

gcaggccatt atcgccggca tggcggccga cgcgctgggc tacgtcttgc tggcgttcgc   3360

gacgcgaggc tggatggcct tccccattat gattcttctc gcttccggcg gcatcgggat   3420

gcccgcgttg caggccatgc tgtccaggca ggtagatgac gaccatcagg gacagcttca   3480

aggatcgctc gcggctctta ccagcctaac ttcgatcatt ggaccgctga tcgtcacggc   3540

gatttatgcc gcctcggcga gcacatggaa cgggttggca tggattgtag gcgccgccct   3600

ataccttgtc tgcctccccg cgttgcgtcg cggtgcatgg agccgggcca cctcgacctg   3660

aactgggcac aacagagtaa taattcaaaa gagatgtcgg tttaacgcat gagaaagccc   3720

ccggaagatc accttccggg ggcttttttta ttgcgcccca atgataaccc caagggaagt   3780

tttagtcaaa agcctccgga tgtcactcaa tgaagtcgca gggttgaggc gatgaggggt   3840

ccttccaggc atcaaataaa acgaaaggct cagtcgaaag actgggcctt tcgttttatc   3900

tgttgtttgt cggtgaacgc tctcctgagt aggacaaatc cgccgcccta gacttaggcg   3960

ttcggctgcg gcgagcggta tcagctcact caaagaatcc ttagctttcg ctgaggatga   4020

tttctgctag aggcagaggt ggttgtgttg cgatcgagta tcaccgcaag ggataaatat   4080

ctaacaccgt gcgtgttgac tattttacct ctggcggtga taatggttgc atgtactaag   4140

gaggttgtat ggaacaacgc ataaccctga aagattatgc aatgcgcttt gggcaaacca   4200
```

-continued

```
agacagctaa aagatctctc acctaccaaa caatgccccc ctgcaaaaaa taaattcata   4260
taaaaaacat acagataacc atctgcggtg ataaattatc tctggcggtg ttgacataaa   4320
taccactggc ggtgatactg agcacatcag caggacgcac tgaccaccat gaaggtgacg   4380
ctcttaaaaa ttaagccctg aagaagggca gcattcaaag cagaaggctt tggggtgtgt   4440
gatacgaaac gaaggggata tcggtatgag agccctggta gtcatccgcc tgtcccgcgt   4500
caccgatgct acgacttcac cggagcgtca gctggagtct tgccagcagc tctgcgccca   4560
gcgcggctgg gacgtcgtcg gggtagcgga ggatctggac gtctccgggg cggtcgatcc   4620
gttcgaccgg aagcgcagac cgaacctggc ccggtggcta gcgttcgagg agcaaccgtt   4680
tgacgtgatc gtggcgtacc gggtagatcg gttgacccga tcgatccggc atcttcagca   4740
gctggtccac tgggccgagg accacaagaa gctggtcgtc tccgcgaccg aagcgcactt   4800
cgatacgacg acgccgtttg cggcggtcgt catcgcgctt atgggaacgg tggcgcagat   4860
ggaattagaa gcgatcaaag agcggaaccg ttcggctgcg catttcaata tccgcgccgg   4920
gaaataccga ggatccctgc cgccgtgggg atacctgcct acgcgcgtgg acggggagtg   4980
gcggctggtg ccggaccctg tgcagcgaga gcgcatcctc gaggtgtatc accgcgtcgt   5040
cgacaaccac gagccgctgc atctggtggc ccacgacctg aaccggcgtg gtgtcctgtc   5100
gccgaaggac tacttcgcgc agctgcaagg ccgcgagccg cagggccggg agtggtcggc   5160
taccgcgctg aagcgatcga tgatctccga ggcgatgctc gggtacgcga ctctgaacgg   5220
taagaccgtc cgagacgacg acggagcccc gctggtgcgg gctgagccga tcctgacccg   5280
tgagcagctg gaggcgctgc gcgccgagct cgtgaagacc tcccgggcga agcccgcggt   5340
gtctaccccg tcgctgctgc tgcgggtgtt gttctgcgcg gtgtgcgggg agcccgcgta   5400
caagttcgcc gggggaggac gtaagcaccc gcgctaccgc tgccgctcga tggggttccc   5460
gaagcactgc gggaacggca cggtggcgat ggccgagtgg gacgcgttct gcgaggagca   5520
ggtactggat ctgctcgggg acgcggagcg tctggagaaa gtctgggtag cgggctcgga   5580
ctccgcggtc gaactcgcgg aggtgaacgc ggagctggtg gacctgacgt cgctgatcgg   5640
ctccccggcc taccgggcgg gctctccgca gcgagaagca ctggatgccc gtattgcggc   5700
gctggccgcg cggcaagagg agctggaggg cctggaggct cgcccgtctg gctgggagtg   5760
gcgcgagacc gggcagcggt tcggggactg gtggcgggag caggacaccg cggcaaagaa   5820
cacctggctt cggtcgatga acgttcggct gacgttcgac gtccgcggcg ggctgactcg   5880
cacgatcgac ttcggggatc ttcaggagta cgagcagcat ctcaggctcg gcagcgtggt   5940
cgaacggcta cacaccggga tgtcgggttc agcagcaaac gacgaaaact acgctgcatc   6000
ggtttgatgc ttaagtcgaa cagaaagtaa tcgtatgagc tcgacaccat cgaatggcgc   6060
aaaacctttc gcggtatggc atgatagcgc ccggaagaga gtcaattcag ggtggtgaat   6120
gtataagaag gagatataca tatgagcaca aaaaagaatc cattaacaca agagcagctt   6180
gaggacgcac gtcgccttaa agcaatttat gaaaaaaaga aaaatgaact tggcttaacc   6240
caggaatctg tcgcagacaa gatggggatg gggcagtcag gcgttggtgc tctatttaat   6300
ggcatcaatg cattaaatgc tcataacgcc gcattgctta caaaaattct caaagttagc   6360
gttgaagaat ttagcccttc aatcgccaga gaaatctacg agatgtatga agcggttagt   6420
atgcagccgt cacttagaag tgagtatgag taccctgttt tttctcatgt tcaggcaggg   6480
atgttctcac ctgagcctag aacctgtacc aaaggtgatg cggagagatg ggtaagcaca   6540
accaaaaaag ccagtgattc tgcattctgg cttgaggttg aaggtaattc catgaccgca   6600
```

-continued

```
ccaacaggct ccaagccaag ctttcctgac ggaatgttaa ttctcgttga ccctgagcag   6660
gctgttgagc caggtgattt ctgcatagcc agacttgggg gtgatgagtt taccttcaag   6720
aaactgatca gggatagcgg tcaggtgttt ttacaaccac taaacccaca gtacccaatg   6780
atcccatgca atgagagttg ttccgttgtg ggaaaagtta tcgctagtca gtggcctgaa   6840
gagacgtttg gctgactcga gtctggtaaa gaaaccgctg ctgcgaaatt tgaacgccag   6900
cacatggact cgtctactag cgcagcttaa ttaacctagg ctgctgccac cgctgagcaa   6960
taactagcat aaccccttgg ggcctctaaa cgggtcttga ggggtttttt gctgaaagga   7020
ggaactatat ccggattggc tctgtcagac caagtttacg agctcgcttg gactcctgtt   7080
gatagatcca gtaatgacct cagaactcca tctggatttg ttcagaacgc tcggttgccg   7140
ccgggcgttt tttattggtg agaatccaag cactagggac agtaagacgg gtaagcctgt   7200
tgatgatacc gctgccttac tgggtgcatt agccagtctg aatgacctgt cacgggataa   7260
tccgaagtgg tcagactgga aaatcagagg gcaggaactg ctgaacagca aaaagtcaga   7320
tagcaccaca tagcagaccc gccataaaac gccctgagaa gcccgtgacg ggcttttctt   7380
gtattatggg tagtttcctt gcatgaatcc ataaaaggcg cctgtagtgc catttacccc   7440
cattcactgc cagagccgtg agcgcagcga actgaatgtc acgaaaaaga cagcgactca   7500
ggtgcctgat ggtcggagac aaaaggaata ttcagcgatt tgcccgagct tgcgagggtg   7560
ctacttaagc ctttagggtt ttaaggtctg ttttgtagag gagcaaacag cgtttgcgac   7620
atccttttgt aatactgcgg aactgactaa agtagtgagt tatacacagg gctgggatct   7680
attcttttta tcttttttta ttctttcttt attctataaa ttataaccac ttgaatataa   7740
acaaaaaaaa cacacaaagg tctagcggaa tttacagagg gtctagcaga atttacaagt   7800
tttccagcaa aggtctagca gaatttacag atacccacaa ctcaaaggaa aaggacatgt   7860
aattatcatt gactagccca tctcaattgg tatagtgatt aaaatcacct agaccaattg   7920
agatgtatgt ctgaattagt tgttttcaaa gcaaatgaac tagcgattag tcgctatgac   7980
ttaacggagc atgaaaccaa gctaatttta tgctgtgtgg cactactcaa ccccacgatt   8040
gaaaacccta caaggaaaga acggacggta tcgttcactt ataaccaata cgctcagatg   8100
atgaacatca gtagggaaaa tgcttatggt gtattagcta aagcaaccag agagctgatg   8160
acgagaactg tggaaatcag gaatcctttg gttaaaggct ttgagatttt ccagtggaca   8220
aactatgcca agttctcaag cgaaaaatta gaattagttt ttagtgaaga gatattgcct   8280
tatcttttcc agttaaaaaa attcataaaa tataatctgg aacatgttaa gtcttttgaa   8340
aacaaatact ctatgaggat ttatgagtgg ttattaaaag aactaacaca aaagaaaact   8400
cacaaggcaa atatagagat tagccttgat gaatttaagt tcatgttaat gcttgaaaat   8460
aactaccatg agtttaaaag gcttaaccaa tgggttttga aaccaataag taaagattta   8520
aacacttaca gcaatatgaa attggtggtt gataagcgag gccgcccgac tgatacgttg   8580
attttccaag ttgaactaga tagacaaatg gatctcgtaa ccgaacttga gaacaaccag   8640
ataaaaatga atggtgacaa aataccaaca accattacat cagattccta cctacgtaac   8700
ggactaagaa aaacactaca cgatgcttta actgcaaaaa ttcagctcac cagttttgag   8760
gcaaaatttt tgagtgacat gcaaagtaag catgatctca atggttcgtt ctcatggctc   8820
acgcaaaaac aacgaaccac actagagaac atactggcta aatacggaag gatctgaggt   8880
tcttatggct cttgtatcta tcagtgaagc atcaagacta acaaacaaaa gtagaacaac   8940
```

```
tgttcaccgt tagatatcaa agggaaaact gtccatatgc acagatgaaa acggtgtaaa   9000

aaagatagat acatcagagc ttttacgagt ttttggtgca tttaaagctg ttcaccatga   9060

a                                                                   9061
```

<210> SEQ ID NO 5
<211> LENGTH: 9061
<212> TYPE: DNA
<213> ORGANISM: Artificial Sequence
<220> FEATURE:
<223> OTHER INFORMATION: Thermal Switching Circuit Library Screen Hit #2

<400> SEQUENCE: 5

```
cagatcgaca atgtaactac tagagcgaag atcctttgat cttttctacg gggtctgacg     60

ctcagtggaa cgaaaactca cgttaaggga tttggtcatg gctagtgctt ggaaagcaag    120

caaagaaaaa aggcgacaga ttactctgtc gcctttttc ctgactcata accaagccaa    180

ttctcgaacc ccagagtccc gctcagaaga actcgtcaag aaggcgatag aaggcgatgc    240

gctgcgaatc gggagcggcg ataccgtaaa gcacgaggaa gcggtcagcc cattcgccgc    300

caagctcttc agcaatatca cgggtagcca acgctatgtc ctgatagcgg tccgccacac    360

ccagccggcc acagtcgatg aatccagaaa agcggccatt ttccaccatg atattcggca    420

agcaggcatc gccgtgggtc acgacgagat cctcgccgtc gggcatacgc gccttgagcc    480

tggcgaacag ttcggctggc gcgagcccct gatgctcttc gtccagatca tcctgatcga    540

caagaccggc ttccatccga gtacgtgctc gctcgatgcg atgtttcgct tggtggtcga    600

atgggcaggt agccggatca agcgtatgca gccgccgcat tgcatcagcc atgatggata    660

ctttctcggc aggagcaagg tgagatgaca ggagatcctg ccccggcact tcgcccaata    720

gcagccagtc ccttcccgct tcagtgacaa cgtcgagcac agccgcgcaa ggaacgcccg    780

tcgtggccag ccacgatagc cgcgctgcct cgtcttgcag ttcattcagg gcaccggaca    840

ggtcggtctt gacaaaaaga accgggcgac cctgcgctga cagccggaac acggcggcat    900

cagagcagcc gattgtctgt tgtgcccagt catagccgaa tagcctctcc acccaagccg    960

ccggagaacc tgcgtgcaat ccatcttgtt caatcatgcg aaacgatcct catcctgtct   1020

cttgatcaga tcttgatccc ctgcgccatc agatccttgg cggcaagaaa gccatccagt   1080

ttactttgca gggcttccca accttaccag agggcggccc aactggcaat tccgacgtct   1140

gtgcaagtac tactgttctg cagtcacttg cctaagatac tagctccggc aaaaaaacgg   1200

gcaaggtgtc accaccctgc cctttttctt taaaaccgaa aagattactt cgcgtttgcc   1260

acctgacgtc taagaaaagg aatattcagc aatttgcccg tgccgaagaa aggcccaccc   1320

gtgaaggtga gccagtgagt tgattgctac gtaattagtt agttagccct tagtgactcg   1380

aatttcggcc ggcttgtcga cgacggcggt ctccgtcgtc aggatcatcc gggcaagctt   1440

tccacacatt ataggtacaa aaagatgcga aagcaaataa atttttggg tttgtaccgt    1500

acaccactga gaccgcggtg gttgaccaga caaaccacga agctgtcacc ggatgtgctt   1560

tccggtctga tgagtccgtg aggacgaaac agcctctaca aataattttg tttaagggcc   1620

caagttcact taaaaaggag atcaacaatg aaagcaattt tcgtactgaa acatcttaat   1680

catgctaagg aggttttcta atgcgtaaag gcgaagagct gttcactggt gtcgtcccta   1740

ttctggtgga actggatggt gatgtcaacg gtcataagtt ttccgtgcgt ggcgagggtg   1800

aaggtgacgc aactaatggt aaactgacgc tgaagttcat ctgtactact ggtaaactgc   1860

cggtaccttg gccgactctg gtaacgacgc tgacttatgg tgttcagtgc tttgctcgtt   1920
```

```
atccggacca tatgaagcag catgacttct tcaagtccgc catgccggaa ggctatgtgc   1980
aggaacgcac gatttccttt aaggatgacg gcacgtacaa aacgcgtgcg gaagtgaaat   2040
ttgaaggcga tactctggta aaccgcattg agctgaaagg cattgacttt aaagaagacg   2100
gcaatatcct gggccataag ctggaataca attttaacag ccacaatgtt tacatcaccg   2160
ccgataaaca aaaaaatggc actaaagcga attttaaaat tcgccacaac gtggaggatg   2220
gcagcgtgca gctggctgat cactaccagc aaaacactcc aatcggtgat ggtcctgttc   2280
tgctgccaga caatcactat ctgagcacgc aaagcgttct gtctaaagat ccgaacgaga   2340
aacgcgatca tatggttctg ctggagttcg taaccgcagc gggcatcacg catggtatgg   2400
atgaactgta caaatgatga tacgcggtag tttatcacag ttaaattgct aacgcagtca   2460
ggcaccgtgt atgaaatcta acaatgcgct catcgtcatc ctcggcaccg tcaccctgga   2520
tgctgtaggc ataggcttgg ttatgccggt actgccgggc ctcttgcggg atatcgtcca   2580
ttccgacagc atcgccagtc actatggcgt gctgctagcg ctatatgcgt tgatgcaatt   2640
tctatgcgca cccgttctcg gagcactgtc cgaccgcttt ggccgccgcc cagtcctgct   2700
cgcttcgcta cttggagcca ctatcgacta cgcgatcatg gcgaccacac ccgtcctgtg   2760
gatcctctac gccggacgca tcgtggccgg catcaccggc gccacaggtg cggttgctgg   2820
cgcctatatc gccgacatca ccgatgggga agatcgggct cgccacttcg ggctcatgag   2880
cgcttgtttc ggcgtgggta tggtggcagg ccccgtggcc gggggactgt tgggcgccat   2940
ctccttgcat gcaccattcc ttgcggcggc ggtgctcaac ggcctcaacc tactactggg   3000
ctgcttccta atgcaggagt cgcataaggg agagcgtcga ccgatgccct tgagagcctt   3060
caacccagtc agctccttcc ggtgggcgcg gggcatgact atcgtcgccg cacttatgac   3120
tgtcttcttt atcatgcaac tcgtaggaca ggtgccggca gcgctctggg tcattttcgg   3180
cgaggaccgc tttcgctgga gcgcgacgat gatcggcctg tcgcttgcgg tattcggaat   3240
cttgcacgcc ctcgctcaag ccttcgtcac tggtcccgcc accaaacgtt tcggcgagaa   3300
gcaggccatt atcgccggca tggcggccga cgcgctgggc tacgtcttgc tggcgttcgc   3360
gacgcgaggc tggatggcct tccccattat gattcttctc gcttccggcg gcatcgggat   3420
gcccgcgttg caggccatgc tgtccaggca ggtagatgac gaccatcagg gacagcttca   3480
aggatcgctc gcggctctta ccagcctaac ttcgatcatt ggaccgctga tcgtcacggc   3540
gatttatgcc gcctcggcga gcacatggaa cgggttggca tggattgtag gcgccgccct   3600
ataccttgtc tgcctccccg cgttgcgtcg cggtgcatgg agccgggcca cctcgacctg   3660
aactgggcac aacagagtaa taattcaaaa gagatgtcgg tttaacgcat gagaaagccc   3720
ccggaagatc accttccggg ggcttttttta ttgcgcccca atgataaccc caagggaagt   3780
tttagtcaaa agcctccgga tgtcactcaa tgaagtcgca gggttgaggc gatgaggggt   3840
ccttccaggc atcaaataaa acgaaaggct cagtcgaaag actgggcctt tcgttttatc   3900
tgttgtttgt cggtgaacgc tctcctgagt aggacaaatc cgccgcccta gacttaggcg   3960
ttcggctgcg gcgagcggta tcagctcact caaagaatcc ttagctttcg ctgaggatga   4020
tttctgctag aggcagaggt ggttgtgttg cgatcgagta tcaccgcaag ggataaatat   4080
ctaacaccgt gcgtgttgac tattttacct ctggcggtga taatggttgc atgtactaag   4140
gaggttgtat ggaacaacgc ataaccctga aagattatgc aatgcgcttt gggcaaacca   4200
agacagctaa aagatctctc acctaccaaa caatgccccc ctgcaaaaaa taaattcata   4260
```

taaaaaacat acagataacc atctgcggtg ataaattatc tctggcggtg ttgacataaa 4320
taccactggc ggtgatactg agcacatcag caggacgcac tgaccaccat gaaggtgacg 4380
ctcttaaaaa ttaagccctg aagaagggca gcattcaaag cagaaggctt tggggtgtgt 4440
gatacgaaac gaagatccta tcggtatgag agccctggta gtcatccgcc tgtcccgcgt 4500
caccgatgct acgacttcac cggagcgtca gctggagtct tgccagcagc tctgcgccca 4560
gcgcggctgg gacgtcgtcg gggtagcgga ggatctggac gtctccgggg cggtcgatcc 4620
gttcgaccgg aagcgcagac cgaacctggc ccggtggcta gcgttcgagg agcaaccgtt 4680
tgacgtgatc gtggcgtacc gggtagatcg gttgacccga tcgatccggc atcttcagca 4740
gctggtccac tgggccgagg accacaagaa gctggtcgtc tccgcgaccg aagcgcactt 4800
cgatacgacg acgccgtttg cggcggtcgt catcgcgctt atgggaacgg tggcgcagat 4860
ggaattagaa gcgatcaaag agcggaaccg ttcggctgcg catttcaata tccgcgccgg 4920
gaaataccga ggatccctgc cgccgtgggg atacctgcct acgcgcgtgg acggggagtg 4980
gcggctggtg ccggaccctg tgcagcgaga gcgcatcctc gaggtgtatc accgcgtcgt 5040
cgacaaccac gagccgctgc atctggtggc ccacgacctg aaccggcgtg gtgtcctgtc 5100
gccgaaggac tacttcgcgc agctgcaagg ccgcgagccg cagggccggg agtggtcggc 5160
taccgcgctg aagcgatcga tgatctccga ggcgatgctc gggtacgcga ctctgaacgg 5220
taagaccgtc cgagacgacg acggagcccc gctggtgcgg gctgagccga tcctgacccg 5280
tgagcagctg gaggcgctgc gcgccgagct cgtgaagacc tcccgggcga agcccgcggt 5340
gtctaccccg tcgctgctgc tgcgggtgtt gttctgcgcg gtgtgcgggg agcccgcgta 5400
caagttcgcc gggggaggac gtaagcaccc gcgctaccgc tgccgctcga tggggttccc 5460
gaagcactgc gggaacggca cggtggcgat ggccgagtgg gacgcgttct gcgaggagca 5520
ggtactggat ctgctcgggg acgcggagcg tctggagaaa gtctgggtag cgggctcgga 5580
ctccgcggtc gaactcgcgg aggtgaacgc ggagctggtg gacctgacgt cgctgatcgg 5640
ctccccggcc taccgggcgg gctctccgca gcgagaagca ctggatgccc gtattgcggc 5700
gctggccgcg cggcaagagg agctggaggg cctggaggct cgcccgtctg gctgggagtg 5760
gcgcgagacc gggcagcggt tcggggactg gtggcgggag caggacaccg cggcaaagaa 5820
cacctggctt cggtcgatga acgttcggct gacgttcgac gtccgcggcg ggctgactcg 5880
cacgatcgac ttcggggatc ttcaggagta cgagcagcat ctcaggctcg gcagcgtggt 5940
cgaacggcta cacaccggga tgtcgggttc agcagcaaac gacgaaaact acgctgcaca 6000
ccgatgatgc ttaagtcgaa cagaaagtaa tcgtatgagc tcgacaccat cgaatggcgc 6060
aaaacctttc gcggtatggc atgatagcgc ccggaagaga gtcaattcag ggtggtgaat 6120
gtataagaag gagatataca tatgagcaca aaaaagaatc cattaacaca agagcagctt 6180
gaggacgcac gtcgccttaa agcaatttat gaaaaaaaga aaaatgaact tggcttaacc 6240
caggaatctg tcgcagacaa gatggggatg gggcagtcag gcgttggtgc tctatttaat 6300
ggcatcaatg cattaaatgc tcataacgcc gcattgctta caaaaattct caaagttagc 6360
gttgaagaat ttagcccttc aatcgccaga gaaatctacg agatgtatga agcggttagt 6420
atgcagccgt cacttagaag tgagtatgag taccctgttt tttctcatgt tcaggcaggg 6480
atgttctcac ctgagcctag aacctgtacc aaaggtgatg cggagagatg ggtaagcaca 6540
accaaaaaag ccagtgattc tgcattctgg cttgaggttg aaggtaattc catgaccgca 6600
ccaacaggct ccaagccaag ctttcctgac ggaatgttaa ttctcgttga ccctgagcag 6660
gctgttgagc caggtgattt ctgcatagcc agacttgggg gtgatgagtt taccttcaag 6720
aaactgatca gggatagcgg tcaggtgttt ttacaaccac taaacccaca gtacccaatg 6780
atcccatgca atgagagttg ttccgttgtg ggaaagttta tcgctagtca gtggcctgaa 6840
gagacgtttg gctgactcga gtctggtaaa gaaaccgctg ctgcgaaatt tgaacgccag 6900
cacatggact cgtctactag cgcagcttaa ttaacctagg ctgctgccac cgctgagcaa 6960
taactagcat aaccccttgg ggcctctaaa cgggtcttga ggggtttttt gctgaaagga 7020
ggaactatat ccggattggc tctgtcagac caagtttacg agctcgcttg gactcctgtt 7080
gatagatcca gtaatgacct cagaactcca tctggatttg ttcagaacgc tcggttgccg 7140
ccgggcgttt tttattggtg agaatccaag cactagggac agtaagacgg gtaagcctgt 7200
tgatgatacc gctgccttac tgggtgcatt agccagtctg aatgacctgt cacgggataa 7260
tccgaagtgg tcagactgga aaatcagagg gcaggaactg ctgaacagca aaaagtcaga 7320
tagcaccaca tagcagaccc gccataaaac gccctgagaa gcccgtgacg ggcttttctt 7380
gtattatggg tagtttcctt gcatgaatcc ataaaaggcg cctgtagtgc catttacccc 7440
cattcactgc cagagccgtg agcgcagcga actgaatgtc acgaaaaaga cagcgactca 7500
ggtgcctgat ggtcggagac aaaaggaata ttcagcgatt tgcccgagct tgcgagggtg 7560
ctacttaagc ctttagggtt ttaaggtctg ttttgtagag gagcaaacag cgtttgcgac 7620
atccttttgt aatactgcgg aactgactaa agtagtgagt tatacacagg gctgggatct 7680
attcttttta tcttttttta ttctttcttt attctataaa ttataaccac ttgaatataa 7740
acaaaaaaaa cacacaaagg tctagcggaa tttacagagg gtctagcaga atttacaagt 7800
tttccagcaa aggtctagca gaatttacag atacccacaa ctcaaaggaa aaggacatgt 7860
aattatcatt gactagccca tctcaattgg tatagtgatt aaaatcacct agaccaattg 7920
agatgtatgt ctgaattagt tgttttcaaa gcaaatgaac tagcgattag tcgctatgac 7980
ttaacggagc atgaaaccaa gctaatttta tgctgtgtgg cactactcaa ccccacgatt 8040
gaaaacccta caaggaaaga acggacggta tcgttcactt ataaccaata cgctcagatg 8100
atgaacatca gtagggaaaa tgcttatggt gtattagcta aagcaaccag agagctgatg 8160
acgagaactg tggaaatcag gaatcctttg gttaaaggct ttgagatttt ccagtggaca 8220
aactatgcca agttctcaag cgaaaaatta gaattagttt ttagtgaaga gatattgcct 8280
tatcttttcc agttaaaaaa attcataaaa tataatctgg aacatgttaa gtcttttgaa 8340
aacaaatact ctatgaggat ttatgagtgg ttattaaaag aactaacaca aaagaaaact 8400
cacaaggcaa atatagagat tagccttgat gaatttaagt tcatgttaat gcttgaaaat 8460
aactaccatg agtttaaaag gcttaaccaa tgggttttga aaccaataag taaagattta 8520
aacacttaca gcaatatgaa attggtggtt gataagcgag gccgcccgac tgatacgttg 8580
attttccaag ttgaactaga tagacaaatg gatctcgtaa ccgaacttga gaacaaccag 8640
ataaaaatga atggtgacaa aataccaaca accattacat cagattccta cctacgtaac 8700
ggactaagaa aaacactaca cgatgcttta actgcaaaaa ttcagctcac cagttttgag 8760
gcaaaatttt tgagtgacat gcaaagtaag catgatctca atggttcgtt ctcatggctc 8820
acgcaaaaac aacgaaccac actagagaac atactggcta aatacggaag gatctgaggt 8880
tcttatggct cttgtatcta tcagtgaagc atcaagacta acaaacaaaa gtagaacaac 8940
tgttcaccgt tagatatcaa agggaaaact gtccatatgc acagatgaaa acggtgtaaa 9000
aaagatagat acatcagagc ttttacgagt ttttggtgca tttaaagctg ttcaccatga 9060
a 9061

<210> SEQ ID NO 6
<211> LENGTH: 9061
<212> TYPE: DNA
<213> ORGANISM: Artificial Sequence
<220> FEATURE:
<223> OTHER INFORMATION: Thermal Switching Circuit Library Screen Hit #7

<400> SEQUENCE: 6
cagatcgaca atgtaactac tagagcgaag atcctttgat cttttctacg gggtctgacg 60
ctcagtggaa cgaaaactca cgttaaggga tttggtcatg gctagtgctt ggaaagcaag 120
caaagaaaaa aggcgacaga ttactctgtc gcctttttc ctgactcata accaagccaa 180
ttctcgaacc ccagagtccc gctcagaaga actcgtcaag aaggcgatag aaggcgatgc 240
gctgcgaatc gggagcggcg ataccgtaaa gcacgaggaa gcggtcagcc cattcgccgc 300
caagctcttc agcaatatca cgggtagcca acgctatgtc ctgatagcgg tccgccacac 360
ccagccggcc acagtcgatg aatccagaaa agcggccatt ttccaccatg atattcggca 420
agcaggcatc gccgtgggtc acgacgagat cctcgccgtc gggcatacgc gccttgagcc 480
tggcgaacag ttcggctggc gcgagcccct gatgctcttc gtccagatca tcctgatcga 540
caagaccggc ttccatccga gtacgtgctc gctcgatgcg atgtttcgct tggtggtcga 600
atgggcaggt agccggatca agcgtatgca gccgccgcat tgcatcagcc atgatggata 660
ctttctcggc aggagcaagg tgagatgaca ggagatcctg ccccggcact tcgcccaata 720
gcagccagtc ccttcccgct tcagtgacaa cgtcgagcac agccgcgcaa ggaacgcccg 780
tcgtggccag ccacgatagc cgcgctgcct cgtcttgcag ttcattcagg gcaccggaca 840
ggtcggtctt gacaaaaaga accgggcgac cctgcgctga cagccggaac acggcggcat 900
cagagcagcc gattgtctgt tgtgcccagt catagccgaa tagcctctcc acccaagccg 960
ccggagaacc tgcgtgcaat ccatcttgtt caatcatgcg aaacgatcct catcctgtct 1020
cttgatcaga tcttgatccc ctgcgccatc agatccttgg cggcaagaaa gccatccagt 1080
ttactttgca gggcttccca accttaccag agggcggccc aactggcaat tccgacgtct 1140
gtgcaagtac tactgttctg cagtcacttg cctaagatac tagctccggc aaaaaaacgg 1200
gcaaggtgtc accaccctgc ccttttcttt taaaaccgaa aagattactt cgcgtttgcc 1260
acctgacgtc taagaaaagg aatattcagc aatttgcccg tgccgaagaa aggcccaccc 1320
gtgaaggtga gccagtgagt tgattgctac gtaattagtt agttagccct tagtgactcg 1380
aatttcggcc ggcttgtcga cgacggcggt ctccgtcgtc aggatcatcc gggcaagctt 1440
tccacacatt ataggtacaa aaagatgcga aagcaaataa attttttggg tttgtaccgt 1500
acaccactga gaccgcggtg gttgaccaga caaaccacga agctgtcacc ggatgtgctt 1560
tccggtctga tgagtccgtg aggacgaaac agcctctaca aataattttg tttaagggcc 1620
caagttcact taaaaaggag atcaacaatg aaagcaattt tcgtactgaa acatcttaat 1680
catgctaagg aggttttcta atgcgtaaag gcgaagagct gttcactggt gtcgtcccta 1740
ttctggtgga actggatggt gatgtcaacg gtcataagtt ttccgtgcgt ggcgagggtg 1800
aaggtgacgc aactaatggt aaactgacgc tgaagttcat ctgtactact ggtaaactgc 1860
cggtaccttg gccgactctg gtaacgacgc tgacttatgg tgttcagtgc tttgctcgtt 1920
atccggacca tatgaagcag catgacttct tcaagtccgc catgccggaa ggctatgtgc 1980
aggaacgcac gatttccttt aaggatgacg gcacgtacaa aacgcgtgcg gaagtgaaat 2040
ttgaaggcga tactctggta aaccgcattg agctgaaagg cattgacttt aaagaagacg 2100
gcaatatcct gggccataag ctggaataca attttaacag ccacaatgtt tacatcaccg 2160
ccgataaaca aaaaaatggc actaaagcga attttaaaat tcgccacaac gtggaggatg 2220
gcagcgtgca gctggctgat cactaccagc aaaacactcc aatcggtgat ggtcctgttc 2280
tgctgccaga caatcactat ctgagcacgc aaagcgttct gtctaaagat ccgaacgaga 2340
aacgcgatca tatggttctg ctggagttcg taaccgcagc gggcatcacg catggtatgg 2400
atgaactgta caaatgatga tacgcggtag tttatcacag ttaaattgct aacgcagtca 2460
ggcaccgtgt atgaaatcta acaatgcgct catcgtcatc ctcggcaccg tcaccctgga 2520
tgctgtaggc ataggcttgg ttatgccggt actgccgggc ctcttgcggg atatcgtcca 2580
ttccgacagc atcgccagtc actatggcgt gctgctagcg ctatatgcgt tgatgcaatt 2640
tctatgcgca cccgttctcg gagcactgtc cgaccgcttt ggccgccgcc cagtcctgct 2700
cgcttcgcta cttggagcca ctatcgacta cgcgatcatg gcgaccacac ccgtcctgtg 2760
gatcctctac gccggacgca tcgtggccgg catcaccggc gccacaggtg cggttgctgg 2820
cgcctatatc gccgacatca ccgatgggga agatcgggct cgccacttcg ggctcatgag 2880
cgcttgtttc ggcgtgggta tggtggcagg ccccgtggcc gggggactgt tgggcgccat 2940
ctccttgcat gcaccattcc ttgcggcggc ggtgctcaac ggcctcaacc tactactggg 3000
ctgcttccta atgcaggagt cgcataaggg agagcgtcga ccgatgccct tgagagcctt 3060
caacccagtc agctccttcc ggtgggcgcg gggcatgact atcgtcgccg cacttatgac 3120
tgtcttcttt atcatgcaac tcgtaggaca ggtgccggca gcgctctggg tcattttcgg 3180
cgaggaccgc tttcgctgga gcgcgacgat gatcggcctg tcgcttgcgg tattcggaat 3240
cttgcacgcc ctcgctcaag ccttcgtcac tggtcccgcc accaaacgtt tcggcgagaa 3300
gcaggccatt atcgccggca tggcggccga cgcgctgggc tacgtcttgc tggcgttcgc 3360
gacgcgaggc tggatggcct tccccattat gattcttctc gcttccggcg gcatcgggat 3420
gcccgcgttg caggccatgc tgtccaggca ggtagatgac gaccatcagg gacagcttca 3480
aggatcgctc gcggctctta ccagcctaac ttcgatcatt ggaccgctga tcgtcacggc 3540
gatttatgcc gcctcggcga gcacatggaa cgggttggca tggattgtag gcgccgccct 3600
ataccttgtc tgcctccccg cgttgcgtcg cggtgcatgg agccgggcca cctcgacctg 3660
aactgggcac aacagagtaa taattcaaaa gagatgtcgg tttaacgcat gagaaagccc 3720
ccggaagatc accttccggg ggcttttta ttgcgcccca atgataaccc caagggaagt 3780
tttagtcaaa agcctccgga tgtcactcaa tgaagtcgca gggttgaggc gatgaggggt 3840
ccttccaggc atcaaataaa acgaaaggct cagtcgaaag actgggcctt tcgttttatc 3900
tgttgtttgt cggtgaacgc tctcctgagt aggacaaatc cgccgcccta gacttaggcg 3960
ttcggctgcg gcgagcggta tcagctcact caaagaatcc ttagctttcg ctgaggatga 4020
tttctgctag aggcagaggt ggttgtgttg cgatcgagta tcaccgcaag ggataaatat 4080
ctaacaccgt gcgtgttgac tattttacct ctggcggtga taatggttgc atgtactaag 4140
gaggttgtat ggaacaacgc ataaccctga aagattatgc aatgcgcttt gggcaaacca 4200
agacagctaa aagatctctc acctaccaaa caatgccccc ctgcaaaaaa taaattcata 4260
taaaaaacat acagataacc atctgcggtg ataaattatc tctggcggtg ttgacataaa 4320

```
taccactggc ggtgatactg agcacatcag caggacgcac tgaccaccat gaaggtgacg   4380
ctcttaaaaa ttaagccctg aagaagggca gcattcaaag cagaaggctt tggggtgtgt   4440
gatacgaaac gaagctacaa tcggtatgag agccctggta gtcatccgcc tgtcccgcgt   4500
caccgatgct acgacttcac cggagcgtca gctggagtct tgccagcagc tctgcgccca   4560
gcgcggctgg gacgtcgtcg ggtagcgga ggatctggac gtctccgggg cggtcgatcc   4620
gttcgaccgg aagcgcagac cgaacctggc ccggtggcta gcgttcgagg agcaaccgtt   4680
tgacgtgatc gtggcgtacc gggtagatcg gttgacccga tcgatccggc atcttcagca   4740
gctggtccac tgggccgagg accacaagaa gctggtcgtc tccgcgaccg aagcgcactt   4800
cgatacgacg acgccgtttg cggcggtcgt catcgcgctt atgggaacgg tggcgcagat   4860
ggaattagaa gcgatcaaag agcggaaccg ttcggctgcg catttcaata tccgcgccgg   4920
gaaataccga ggatccctgc cgccgtgggg atacctgcct acgcgcgtgg acggggagtg   4980
gcggctggtg ccggaccctg tgcagcgaga gcgcatcctc gaggtgtatc accgcgtcgt   5040
cgacaaccac gagccgctgc atctggtggc ccacgacctg aaccggcgtg gtgtcctgtc   5100
gccgaaggac tacttcgcgc agctgcaagg ccgcgagccg cagggccggg agtggtcggc   5160
taccgcgctg aagcgatcga tgatctccga ggcgatgctc gggtacgcga ctctgaacgg   5220
taagaccgtc cgagacgacg acggagcccc gctggtgcgg gctgagccga tcctgacccg   5280
tgagcagctg gaggcgctgc gcgccgagct cgtgaagacc tcccgggcga agcccgcggt   5340
gtctaccccg tcgctgctgc tgcgggtgtt gttctgcgcg gtgtgcgggg agcccgcgta   5400
caagttcgcc gggggaggac gtaagcaccc gcgctaccgc tgccgctcga tggggttccc   5460
gaagcactgc gggaacggca cggtggcgat ggccgagtgg gacgcgttct gcgaggagca   5520
ggtactggat ctgctcgggg acgcggagcg tctggagaaa gtctgggtag cgggctcgga   5580
ctccgcggtc gaactcgcgg aggtgaacgc ggagctggtg gacctgacgt cgctgatcgg   5640
ctccccggcc taccgggcgg gctctccgca gcgagaagca ctggatgccc gtattgcggc   5700
gctggccgcg cggcaagagg agctggaggg cctggaggct cgcccgtctg gctgggagtg   5760
gcgcgagacc gggcagcggt tcggggactg gtggcgggag caggacaccg cggcaaagaa   5820
cacctggctt cggtcgatga acgttcggct gacgttcgac gtccgcggcg ggctgactcg   5880
cacgatcgac ttcggggatc ttcaggagta cgagcagcat ctcaggctcg gcagcgtggt   5940
cgaacggcta cacaccggga tgtcgggttc agcagcaaac gacgaaaact acgctgcacc   6000
ttattgatgc ttaagtcgaa cagaaagtaa tcgtatgagc tcgacaccat cgaatggcgc   6060
aaaacctttc gcggtatggc atgatagcgc ccggaagaga gtcaattcag ggtggtgaat   6120
gtataagaag gagatataca tatgagcaca aaaaagaatc cattaacaca agagcagctt   6180
gaggacgcac gtcgccttaa agcaatttat gaaaaaaaga aaaatgaact tggcttaacc   6240
caggaatctg tcgcagacaa gatggggatg gggcagtcag gcgttggtgc tctatttaat   6300
ggcatcaatg cattaaatgc tcataacgcc gcattgctta caaaaattct caaagttagc   6360
gttgaagaat ttagcccttc aatcgccaga gaaatctacg agatgtatga agcggttagt   6420
atgcagccgt cacttagaag tgagtatgag taccctgttt tttctcatgt tcaggcaggg   6480
atgttctcac ctgagcctag aacctgtacc aaaggtgatg cggagagatg ggtaagcaca   6540
accaaaaaag ccagtgattc tgcattctgg cttgaggttg aaggtaattc catgaccgca   6600
ccaacaggct ccaagccaag ctttcctgac ggaatgttaa ttctcgttga ccctgagcag   6660
gctgttgagc caggtgattt ctgcatagcc agacttgggg gtgatgagtt taccttcaag   6720
```

```
aaactgatca gggatagcgg tcaggtgttt ttacaaccac taaacccaca gtacccaatg   6780
atcccatgca atgagagttg ttccgttgtg gggaaagtta tcgctagtca gtggcctgaa   6840
gagacgtttg gctgactcga gtctggtaaa gaaaccgctg ctgcgaaatt tgaacgccag   6900
cacatggact cgtctactag cgcagcttaa ttaacctagg ctgctgccac cgctgagcaa   6960
taactagcat aaccccttgg ggcctctaaa cgggtcttga ggggtttttt gctgaaagga   7020
ggaactatat ccggattggc tctgtcagac caagtttacg agctcgcttg gactcctgtt   7080
gatagatcca gtaatgacct cagaactcca tctggatttg ttcagaacgc tcggttgccg   7140
ccgggcgttt tttattggtg agaatccaag cactagggac agtaagacgg gtaagcctgt   7200
tgatgatacc gctgccttac tgggtgcatt agccagtctg aatgacctgt cacgggataa   7260
tccgaagtgg tcagactgga aatcagaggg gcaggaactg ctgaacagca aaaagtcaga   7320
tagcaccaca tagcagaccc gccataaaac gccctgagaa gcccgtgacg ggcttttctt   7380
gtattatggg tagtttcctt gcatgaatcc ataaaaggcg cctgtagtgc catttacccc   7440
cattcactgc cagagccgtg agcgcagcga actgaatgtc acgaaaaaga cagcgactca   7500
ggtgcctgat ggtcggagac aaaaggaata ttcagcgatt tgcccgagct tgcgagggtg   7560
ctacttaagc ctttagggtt ttaaggtctg ttttgtagag gagcaaacag cgtttgcgac   7620
atccttttgt aatactgcgg aactgactaa agtagtgagt tatacacagg gctgggatct   7680
attcttttta tcttttttta ttctttcttt attctataaa ttataaccac ttgaatataa   7740
acaaaaaaaa cacacaaagg tctagcggaa tttacagagg gtctagcaga atttacaagt   7800
tttccagcaa aggtctagca gaatttacag atacccacaa ctcaaaggaa aaggacatgt   7860
aattatcatt gactagccca tctcaattgg tatagtgatt aaaatcacct agaccaattg   7920
agatgtatgt ctgaattagt tgttttcaaa gcaaatgaac tagcgattag tcgctatgac   7980
ttaacggagc atgaaaccaa gctaatttta tgctgtgtgg cactactcaa ccccacgatt   8040
gaaaacccta caaggaaaga acggacggta tcgttcactt ataaccaata cgctcagatg   8100
atgaacatca gtagggaaaa tgcttatggt gtattagcta aagcaaccag agagctgatg   8160
acgagaactg tggaaatcag gaatcctttg gttaaaggct ttgagatttt ccagtggaca   8220
aactatgcca agttctcaag cgaaaaatta gaattagttt ttagtgaaga gatattgcct   8280
tatcttttcc agttaaaaaa attcataaaa tataatctgg aacatgttaa gtcttttgaa   8340
aacaaatact ctatgaggat ttatgagtgg ttattaaaag aactaacaca aaagaaaact   8400
cacaaggcaa atatagagat tagccttgat gaatttaagt tcatgttaat gcttgaaaat   8460
aactaccatg agtttaaaag gcttaaccaa tgggttttga aaccaataag taaagattta   8520
aacacttaca gcaatatgaa attggtggtt gataagcgag gccgcccgac tgatacgttg   8580
attttccaag ttgaactaga tagacaaatg gatctcgtaa ccgaacttga gaacaaccag   8640
ataaaaatga atggtgacaa aataccaaca accattacat cagattccta cctacgtaac   8700
ggactaagaa aaacactaca cgatgcttta actgcaaaaa ttcagctcac cagttttgag   8760
gcaaaatttt tgagtgacat gcaaagtaag catgatctca atggttcgtt ctcatggctc   8820
acgcaaaaac aacgaaccac actagagaac atactggcta aatacggaag gatctgaggt   8880
tcttatggct cttgtatcta tcagtgaagc atcaagacta acaaacaaaa gtagaacaac   8940
tgttcaccgt tagatatcaa agggaaaact gtccatatgc acagatgaaa acggtgtaaa   9000
aaagatagat acatcagagc ttttacgagt ttttggtgca tttaaagctg ttcaccatga   9060
```

a 9061

<210> SEQ ID NO 7
<211> LENGTH: 14
<212> TYPE: DNA
<213> ORGANISM: Artificial Sequence
<220> FEATURE:
<223> OTHER INFORMATION: RBS

<400> SEQUENCE: 7
atcctatcgg tatg 14

<210> SEQ ID NO 8
<211> LENGTH: 14
<212> TYPE: DNA
<213> ORGANISM: Artificial Sequence
<220> FEATURE:
<223> OTHER INFORMATION: RBS

<400> SEQUENCE: 8
ctacaatcgg tatg 14

<210> SEQ ID NO 9
<211> LENGTH: 13
<212> TYPE: PRT
<213> ORGANISM: Artificial Sequence
<220> FEATURE:
<223> OTHER INFORMATION: ssrA degradation tag

<400> SEQUENCE: 9

Gly Ser Ala Ala Asn Asp Glu Asn Tyr Ala Ala His Arg
1 5 10

<210> SEQ ID NO 10
<211> LENGTH: 13
<212> TYPE: PRT
<213> ORGANISM: Artificial Sequence
<220> FEATURE:
<223> OTHER INFORMATION: ssrA degradation tag

<400> SEQUENCE: 10

Gly Ser Ala Ala Asn Asp Glu Asn Tyr Ala Ala Pro Tyr
1 5 10

<210> SEQ ID NO 11
<211> LENGTH: 45
<212> TYPE: DNA
<213> ORGANISM: Artificial Sequence
<220> FEATURE:
<223> OTHER INFORMATION: temperature-sensitive terminator

<400> SEQUENCE: 11
atgacttact tgctgaatct caggagttta tgacctttt ttttt 45